(12) United States Patent
Finlay et al.

(10) Patent No.: US 8,889,105 B2
(45) Date of Patent: Nov. 18, 2014

(54) BACTERIOPHAGE COMPOSITIONS FOR TREATMENT OF BACTERIAL INFECTIONS

(76) Inventors: Warren H. Finlay, Edmonton (CA); Jonathan J. Dennis, Edmonton (CA); Helena Orszanska, Edmonton (CA); Kimberley D. Seed, Boston, MA (US); Karlene Heather Lynch, Edmonton (CA)

(*) Notice: Subject to any disclaimer, the term of this patent is extended or adjusted under 35 U.S.C. 154(b) by 632 days.

(21) Appl. No.: 13/131,836

(22) PCT Filed: Nov. 26, 2009

(86) PCT No.: PCT/CA2009/001696
§ 371 (c)(1), (2), (4) Date: Aug. 17, 2011

(87) PCT Pub. No.: WO2010/060200
PCT Pub. Date: Jun. 3, 2010

(65) Prior Publication Data
US 2011/0293671 A1     Dec. 1, 2011

Related U.S. Application Data

(60) Provisional application No. 61/118,545, filed on Nov. 28, 2008.

(51) Int. Cl.
*A61K 35/76* (2006.01)
*A61K 9/00* (2006.01)
*A61K 47/26* (2006.01)

(52) U.S. Cl.
CPC .............. *A61K 35/76* (2013.01); *A61K 9/0075* (2013.01); *C12N 2795/00032* (2013.01); *Y10S 977/704* (2013.01); *Y10S 977/773* (2013.01); *Y10S 977/795* (2013.01); *Y10S 977/904* (2013.01)
USPC ............ 424/46; 424/93.6; 424/489; 424/499; 435/5; 435/6.15; 435/235.1; 435/268; 977/704; 977/773; 977/795; 977/904

(58) Field of Classification Search
USPC .................. 424/46, 94.1, 405, 434, 489, 499; 435/5, 6.15, 42, 235.1, 20.1, 268; 977/704, 773, 795, 904

See application file for complete search history.

(56) References Cited

U.S. PATENT DOCUMENTS

| | | | |
|---|---|---|---|
| 7,007,406 | B2 | 3/2006 | Wang et al. |
| 7,363,726 | B2 | 4/2008 | Wang et al. |

(Continued)

FOREIGN PATENT DOCUMENTS

| | | | |
|---|---|---|---|
| CA | 2435632 | 1/2005 | |
| WO | WO-2004/027020 A2 | 4/2004 | |
| WO | WO2004/062677 A1 * | 7/2004 | ............. A61K 35/76 |

OTHER PUBLICATIONS

Golshahi, L. et al., "Toward modern inhalational bacteriophage therapy: nebulization of bacteriophages of *Burkholderia cepacia* complex," J. Aerosol Med. Pulm. Drug Delivery, Dec. 2008; 21(4):351-360.*

(Continued)

*Primary Examiner* — Jane C Oswecki

(74) *Attorney, Agent, or Firm* — Schwegman Lundberg & Woessner, P.A.

(57) ABSTRACT

A respirable composition for treatment of a bacterial infection includes one or more active bacteriophages in combination with a pharmaceutically acceptable respirable carrier. The composition includes a carbohydrate carrier, and is prepared as fine powder. In another aspect, bacteriophages are provided in a liquid carrier for administration by nebulization. In one aspect, the bacteriophages have anti-bacterial activity against one or more species or strains of *Burkholderia cepacia* complex (BCC) bacteria. The invention further relates to the use of a BCC bacteriophage to treat a BCC infection, in particular in an individual suffering from cystic fibrosis.

24 Claims, 7 Drawing Sheets

(56) References Cited

U.S. PATENT DOCUMENTS

| | | | | |
|---|---|---|---|---|
| 7,402,309 B2 * | 7/2008 | Fischetti et al. | ............. | 424/94.6 |
| 2005/0019270 A1 * | 1/2005 | Finlay et al. | .................... | 424/46 |

OTHER PUBLICATIONS

European Application Serial No. 09828491.2, Supplementary European Search Report mailed Apr. 3, 2014, 7 pgs.

International Application No. PCT/CA2009/001696, International Preliminary Report on Patentability issued May 31, 2011, 10 pgs.

International Application No. PCT/CA2009/001696, International Search Report and Written Opinion mailed Mar. 22, 2010, 15 pgs.

Bradbury, Jane, "My enemy's enemy is my friend: Using phages to fight bacteria", Lancet, 363(9409), (Feb. 21, 2004), 624-5.

Coenye, Tom, et al., "Updated version of the *Burkholderia cepacia complex* experimental strain panel", J Clin Microbiol., 41(6), (Jun. 2003), 2797-8.

Golshahi, L., et al., "In vitro lung delivery of bacteriophages KS4-M and FKZ using dry powder inhalers for treatment of *Burkholderia cepacia complex* and *Pseudomonas aeruginosa* infections in cystic fibrosis", J Appl Microbiol., 110(1), (Jan. 2011), 106-17.

Golshahi, Laleh, et al., "Toward modern inhalational bacteriophage therapy: nebulization of bacteriophages of *Burkholderia cepacia complex*", J Aerosol Med Pulm Drug Deliv., 21(4), (Dec. 2008), 351-60.

Hoe, Susan, et al., "Manufacturing and Device Options for the Delivery of Biotherapeutics", Journal of Aerosol Medicine and Pulmonary Drug Delivery, vol. 27, No. 0, (Oct. 7, 2013), 1-14.

Langley, Ross, et al., "Lysogeny and bacteriophage host range within the *Burkholderia cepacia complex*", J Med Microbiol., 52(Pt 6), (Jun. 2003), 483-90.

Mahenthiralingam, Eshwar, et al., "Diagnostically and experimentally useful panel of strains from the *Burkholderia cepacia complex*", J Clin Microbiol., 38(2), (Feb. 2000), 910-3.

Matinkhoo, Sadaf, et al., "Spray-dried respirable powders containing bacteriophages for the treatment of pulmonary infections", J Pharm Sci., 100(12), (Dec. 2011), 5197-205.

Seed, Kimberley D, et al., "Development of *Galleria mellonella* as an alternative infection model for the *Burkholderia cepacia complex*", Infect Immun., 76(3), (Mar. 2008), 1267-75.

Seed, Kimberley D, et al., "Experimental bacteriophage therapy increases survival of *Galleria mellonella* larvae infected with clinically relevant strains of the *Burkholderia cepacia complex.*", Antimicrob Agents Chemother., 53(5), (May 2009), 2205-8.

Seed, Kimberly D., et al., "Isolation and characterization of bacteriophages of the *Burkholderia cepacia complex*", FEMS Microbiol Lett., 251(2), (Oct. 15, 2005), 273-80.

Summer, Elizabeth J., et al., "*Burkholderia cenocepacia* phage BcepMu and a family of Mu-like phages encoding potential pathogenesis factors", J Mol Biol., 340(1), (Jun. 25, 2004), 49-65.

\* cited by examiner

BACTERIOPHAGE COMPOSITIONS FOR TREATMENT OF BACTERIAL INFECTIONS

CROSS-REFERENCE TO RELATED APPLICATION

This application is a national stage application under 35 U.S.C. §371 of PCT/CA2009/001696, filed Nov. 26, 2009, and published as WO 2010/060200 A1 on Jun. 3, 2010, which claims the benefit of priority to U.S. patent application No. 61/118,545, filed on Nov. 28, 2008, which applications and publication are incorporated herein by reference and made a part hereof in their entirety, and the benefit of priority of each of which is claimed herein.

FIELD OF THE INVENTION

The present invention relates to pharmaceutical formulations, compositions and methods for treatment of individuals with bacterial infections, and more particularly to compositions and methods which comprise respirable bacteriophage-containing formulations. The invention further relates to novel bacteriophages active against *Burkholderia cepacia* complex (BCC) bacteria, and respirable formulations comprising such phage viruses.

BACKGROUND OF THE INVENTION

BCC Infections in Cystic Fibrosis Patients

Cystic fibrosis is the most common fatal genetic disease among the Caucasian population. Inhaled microbes pose a significant threat to these patients as they exhibit impaired pulmonary mucociliary clearance. This deficiency makes cystic fibrosis patients susceptible to repeated and prolonged infections from a relatively narrow spectrum of opportunistic bacterial pathogens. Chronic microbial colonization leading to debilitating pulmonary infection is the major cause of morbidity and mortality in cystic fibrosis patients.

The *Burkholderia cepacia* complex (BCC) is a group of opportunistic pathogens that have considerable impact on the quality of life and mortality of cystic fibrosis patients. The known BCC pathogens currently consist of a total of nine *Burkholderia* species that is expected to soon expand to seventeen species. The nine major species are *B. cepacia, B. multivorans, B. cenocepacia, B. stabilis, B. vietnamiensis, B. dolosa, B. ambifaria, B. anthina*, and *B. pyrrocinia*. The ability of the members of the BCC to cause infections in the cystic fibrosis population is not species dependent, as members of all species have been recovered from infected individuals. However, the vast majority of clinical isolates in North America are *B. cenocepacia* and *B. multivorans*; in Canada, *B. cenocepacia* strains cause approximately 80% of BCC infections in cystic fibrosis patients, although this prevalence varies by region.

Pulmonary infections with members of the BCC can result in variable clinical outcomes, one of which is "cepacia syndrome," a rapidly progressive necrotizing pneumonia and sepsis that occurs in up to 20% of cystic fibrosis patients at particular cystic fibrosis clinics. Both direct transmission (for example, interpersonal contact) and indirect transmission (via shared equipment or by third parties) play a potential role in spreading cross-infection among cystic fibrosis patients.

Evidence shows that BCC bacteria can be transmitted through social contact, such as among siblings and summer camps, leading epidemiologists to employ segregation as a means to control possible outbreaks. Furthermore, BCC bacteria are highly resistant to antibiotics, and even aggressive antibiotic therapy often does not result in improved clinical prognosis or a reduction in bacterial numbers. Increasing resistance to common antibiotic treatments is an escalating concern, and opportunities for developing new effective chemical antibiotic treatments in the future may be limited.

Use of Bacteriophages to Treat Bacterial Infections

Bacteriophages are viruses that specifically attack and kill different types of bacteria. Because bacteria are their "natural" target cells, efforts have been made to enlist bacteriophages to fight bacterial infections of higher organisms. Bacteriophages are harmless to mammalian cells and even to other nontargeted bacteria, and thus, they are more specific than broad-spectrum antibiotics that will kill beneficial bacteria in the human body along with the infectious bacteria.

Bacteriophage therapy has been applied to human beings using nonaerosol delivery routes. Research studies were published on the therapeutic use of bacteriophages in the 1930s and early 1940s (Sulakvelidze A, and Kutter E: *Bacteriophages: Biology and Applications* CRC Press, Boca Raton, Fla., 2005). However, bacteriophage biology was not well understood at the time, resulting in inconsistent data. Moreover, bacteriophages were improperly tested against bacteria insensitive to those particular bacteriophages or even against diseases that were not caused by bacteria. Such missteps, along with the discovery and mass production of antibiotics, led to a reduced interest in bacteriophage therapy (Bradbury J. *Lancet.* 2004, 363, 624-625). Therefore bacteriophage therapy remains relatively unexplored, although it does appear that at least some bacteriophages can be used for treatment of bacterial infections.

An important aspect of bacteriophage treatment is the development of an effective route of administration. For treating respiratory infections, inhalation-based routes have been proposed. There have been previous attempts to nebulize bacteriophages for veterinary medicine, human treatment, and agricultural applications. However, little is known about bacteriophage behavior in the human lung and bacteriophage-derived clearance of bacteria in the lung. In previous investigations, there are no quantitative data regarding the titer used, the inhaled number of bacteriophages, the nebulizer type, or aerosol properties. A number of older studies have indicated that bacteriophages can be inactivated by aerosolization, and that aerosolized bacteriophages are sensitive to the salt content of the nebulized solution.

Compared to the bacteriophages of other high profile bacteria such as *E. coli* and *Streptococci*, relatively little study of bacteriophages active against members of the BCC has been performed. There are no known examples in the prior art of bacteriophage treatment of respiratory infections caused by members of the BCC. It is therefore unknown from the prior art if BCC bacteriophages would provide useful therapeutic agents for treatment of BCC infections such as those suffered by individuals with cystic fibrosis.

SUMMARY OF THE INVENTION

It is an object of the invention to provide bacteriophages active against species or strains of members of the *Burkholderia cepacia* complex (BCC) for treatment of BCC infections.

It is a further object to provide respirable compositions for delivery of bacteriophages to the lungs of individuals, for use in treating persons infected with a bacterial infection capable of treatment with bacteriophages. One such viral infection is a BCC infection; however, the invention is not limited to compositions containing such bacteriophages.

It is a further object to provide medical treatments, uses, and uses for preparing medicaments, of compositions comprising multiple bacteriophages active against BCC and other infective bacteria.

One aspect of the invention relates to a respirable composition comprising one or more active bacteriophages in combination with a pharmaceutically acceptable respirable carrier. In another aspect, the bacteriophage is active against one or more strains of the *Burkholderia cepacia* complex.

Lytic bacteriophages are advantageous because they lyse the host bacterium, thereby controlling the infection. Lysogenic bacteriophages may also incorporate their DNA into the chromosome of the host bacterium. While the mechanism of action of lysogenic bacteriophages is more complex than that of the lytic bacteriophages, lysogenic bacteriophages nonetheless may prove useful for development of new therapies.

According to one aspect, a bacteriophage may be delivered in a carrier which comprises water or an aqueous solution having a pH range of about 4.5 to about 8.5, preferably about 6.5 to about 8.5. This aqueous solution may include about 25 to about 75 mM of a buffer system. The buffer system may comprise any suitable buffer such as phosphate (including phosphate buffered saline (PBS). The carrier may also include a salt, for example about 50 mM to about 150 mM NaCl, as well as other excipients known to those with skill in the art, including but not limited to polymers, stabilizers, surfactants, granulating agents and preservatives.

It is advantageous if the composition has an osmolarity between about 110 to about 550 mOsm, preferably about 250 to about 320 mOsm. It is also advantageous if the bacteriophage concentration is about $1.0\times10^8$ to about $3.8\times10^8$ PFU/ml (plaque-forming units per ml) although lower or higher concentrations may also be useful, depending upon the effectiveness of each individual bacteriophage.

According to one aspect of the invention, bacteriophage may be administered with the use of a dry, respirable powder as a carrier. It is advantageous if the powder comprises a carbohydrate such as lactose, trehalose or sucrose or any combination thereof. Advantageously, the bacteriophage concentration in the powder is about $7\times10^5$ to about $1.5\times10^7$ PFU/ml., although both lower and higher concentrations are also contemplated.

Another aspect of the invention relates to a drug delivery system for delivery of a respirable bacteriophage composition such as the compositions described herein. Such a system comprises a nebulizer, dry powder inhaler, or pressured metered dose inhaler configured to deliver the composition to the pulmonary system of human. A nebulizer is defined as a device used for to provide medication in forms of a liquid mist or droplets to the airways. As used herein, a "dry powder inhaler" is a device used to provide medication in the form of solid fine particles. As used herein, the term "pressured metered dose inhaler" refers to a pressurized metal canister containing a mixture of propellants, surfactants, preservatives, and an active ingredient. As used herein, the term "aerosol" means dispersed solid or liquid particles suitable for delivery to the airways of a patient.

Another aspect of the invention is a method of treatment of an individual with a bacterial infection, and a use of a bacteriophage composition for treating a bacterial infection in an individual. The method or use involves administration to the individual of a therapeutically effective amount of a composition containing one or more bacteriophages active against an infective bacterium or bacteria. According to one aspect, the bacterial infection is caused by one or more *Burkholderia cepacia* complex (BCC) strains. Such individuals with BCC infections typically include individuals with cystic fibrosis or chronic granulomatous disease (CGD).

Another aspect of the invention is a method of preparing a powder composition containing one or more active bacteriophages for administration by inhalation. In this method, an aqueous solution which includes one or more active bacteriophages is desiccated to obtain a solid matrix. The solid matrix is then refined into a powder having fine particles. The diameter of such particles may be about 0.1 μm to about 20 μm, preferably about 0.5 μm to about 10 μm and still more preferably about 1 μm to about 5 μm. Alternatively, the desiccation process produces fine particles within these size ranges, and subsequent processing is not required to achieve the desired particle size. Particles within these ranges of diameters provide for sufficient deposition within the lungs. Larger particles tend to deposit within the mouth and throat while smaller particles tend to be too small to contain active bacteriophages. The process of refining the particles into an appropriate range of sizes may be accomplished by a gentle mechanical processing or milling without excessive shear stress. Such milling may be carried out using a drum roller or drum tumbler such as the Turbula™ Roller. Other means of providing gentle mechanical processing or milling without producing excessive shear stress of the matrix may be used for this step. In the above process, it is advantageous if the aqueous solution includes a carbohydrate such as lactose, trehalose or sucrose.

In another method of preparing a powder composition containing one or more active bacteriophages, an aqueous solution including one or more active bacteriophages is obtained. This aqueous solution is then subjected to a process of spray-freeze drying such as the process described in U.S. Pat. Nos. 7,007,406 and 7,363,726, which are incorporated herein in entirety. In these methods, a flow of liquid droplets of the aqueous solution is generated within a chamber and the flow is treated with a flow of coolant inside the chamber to freeze the liquid droplets and produce frozen particles. The frozen particles are then deposited on a collector and dried to form the powder. The powder may be further processed to generate smaller particles if necessary.

In another method of preparing a powder composition containing one or more active bacteriophages, an aqueous solution including one or more active bacteriophages is obtained and subjected to a process of spray-drying. A spray dryer is a device used to separates the solute or suspension as a solid and the solvent into a vapor from a stream of the aqueous solution. The solid is usually collected in a drum or cyclone. The liquid input stream is sprayed through a nozzle into a hot vapor stream and vaporized. Solids form as moisture quickly leaves the droplets.

In preferred embodiments, the bacteriophage used in the above formulations is a BCC bacteriophage. In other aspects, a "cocktail" comprising a combination of bacteriophages may be used. These may comprise a plurality of BCC bacteriophages, and/or other phage types.

In another aspect, the bacteriophage formulation is used to treat bacterial infections which are present in a biofilm. BCC and other bacterial infections tend to grow in biofilms in the lung. Use of the present invention is believed to result in phage lysis of bacteria encased in biofilms, and will tend to degrade the biofilm such that the infection will become easier to clear by traditional antibiotics or the immune system.

In still another aspect, the invention relates to a bacteriophage active against BCC, comprising the gene sequence of SEQ ID NO: 1, SEQ ID NO: 2, SEQ ID NO: 3, or SEQ ID NO:

4. In a further aspect, the bacteriophage comprises a gene sequence having at least 75%, 85%, 90% or 95% identity with SEQ ID NO: 1, SEQ ID NO: 2, SEQ ID NO: 3, or SEQ ID NO: 4.

The term "bacteriophage" as used herein is a virus that infects a bacterium, wherein the bacterium is of a type which causes an infective disease. The bacteriophage may constitute a single or double-stranded DNA or RNA virus. When used in the plural, unless the context otherwise requires, "bacteriophages" refers to a plurality of bacteriophage types, species, or strains.

The term "gene sequence" means the entirety or substantial portion of the genetic sequence of a bacteriophage, and includes single and double-stranded RNA and DNA.

The term "identity" in reference to a percentage identity to a defined gene or genomic sequence refers to deletions, substitutions, or insertions in a gene sequence due to degeneracy or other transcription errors in the gene sequence.

The term "respirable composition" means a composition that is in the form of a nebulizable liquid or a fine powder that is capable of being inhaled by a patient, whether through a mechanical device intended to introduce a composition into the patient's lungs, or otherwise.

DETAILED DESCRIPTION

In Vivo Testing of BCC Bacteriophages

Example 1

Bacteriophage Preparation, Isolation, and Sequencing

Bacteriophage KS4-M is an uncharacterized phenotypic mutant of bacteriophage KS4 (Seed, K. D., and J. J. Dennis. 2005. *FEMS Microbiol. Lett.* 251:273-280), which, unlike its parent, is able to clear liquid cultures of *B. cenocepacia* K56-2, indicating that this bacteriophage is active against *B. cenocepacia* K56-2. High titers of bacteriophage KS4-M were prepared by adding KS4-M bacteriophage to K56-2 (pre-grown for about 3.5 hours at 30° C. in one-half-strength Luria-Bertani (½ LB)), and the mixture was shaken at 30° C. until complete bacterial clearing was observed. These preparations were purified by centrifugation ($1\times10^4$×g for 10 minutes), and supernatant filtration (pore size, 0.45 μm). Bacteriophage KS4 was prepared as previously described (Seed, K. D., and J. J. Dennis. 2005. *FEMS Microbiol. Lett.* 251:273-280). In vitro lytic activity of KS4-M and KS4 was determined by adding 1 mL of bacteriophage ($2\times10^8$ PFU/mL) to 10 mL of K56-2 pre-grown in ½ LB for 3.5 hours at 30° C. Cultures were allowed to incubate at 30° C. with shaking until clearing was observed. $OD_{600}$ values were recorded, and any remaining bacteria were isolated from the resulting samples by serial dilution and plating onto ½ LB plates. A sample containing uninfected *B. cenocepacia* K56-2 served as the uninfected control. To quantify the resulting bacteriophage titer from each sample, $CHCl_3$ was added, the mixture was incubated at room temperature for about 30 min, the sample was centrifuged, the supernatant filter sterilized (pore size, 0.45 μm), and finally, dilutions of supernatant containing bacteriophage were plated with K56-2.

Three additional novel bacteriophages were isolated, KS12 from *Dietes grandiflora* soil and KS14 and DC1 from *Dracaena* sp. soil. KS12 was isolated with *B. cenocepacia* strain K56-2 and of the 27 strains in the BCC panel tested, is only able to form plaques on K56-2 and *B. multivorans* C5274. KS14 was isolated using *B. multivorans* strain C5393 and has a considerably broader host bacterium range, capable of producing plaques on eight of the 27 strains tested. These eight strains are *B. multivorans* strains C5393 and C5274, *B. cenocepacia* strains 7153, C6433, C5424 and PC184, *B. dolosa* strain 21443, and *B. ambifaria* strain 17828. DC1 was isolated using *B. cepacia* strain LMG18821, and this bacteriophage is able to form plaques on *B. cenocepacia* strains K56-2, C6433, PC184 and Cep511, and *B. stabilis* strain LMG18870.

Bacteriophages KS12, DC1 and KS14 were isolated from soil as follows: a 10 g soil sample was added to 15 mL ½ LB broth and 300 μl BCC overnight (ON) liquid culture, and this mixture was shaken for about 24 hours at 30° C. Soil particles and bacteria were removed by centrifugation ($4\times10^3$×g for 20 min), and the supernatant was filter-sterilized (pore size 0.45 μm). 400 μL of filtrate was added to 100 μL of ON bacterial culture and incubated at room temperature for 20 min. Three mL of soft nutrient agar (½ LB broth supplemented with 7 g/L agar) was added and the mixture was overlaid on ½ LB agar and allowed to set. Bacteriophage plaques were identified and prepared after an overnight incubation at 30° C. as previously described (Seed, K. D., and J. J. Dennis. 2005. *FEMS Microbiol. Lett.* 251:273-280). High-titer stocks were prepared to generate plates demonstrating confluent lysis; 3 mL sterile milliQ-$H_2O$ (Milipore, Billirica, Mass.) was then added to these plates and allowed to rock at 4° C. for approximately 4 hrs. The liquid was then collected, centrifuged ($1\times10^4$×g for 10 minutes), and filtered (pore size, 0.45 μm). All bacteriophage preparations were applied to a Detoxi-Gel endotoxin-removing column (Pierce Biotechnology, Rockford, Ill.) and serially diluted in 10 mM $MgSO_4$+1.2 mg/ml ampicillin prior to injection. The host ranges of newly isolated bacteriophages KS12, KS14 and DC1 were determined against a previously utilized bacterial panel comprising 24 BCC strains, representing 9 different species of the BCC (Seed, K. D., and J. J. Dennis. 2005. *FEMS Microbiol. Lett.* 251:273-280). In addition to this strain panel, three additional BCC strains were tested for host range in this study: *B. cenocepacia* PC184 and Cep511 (LMG 18830) and *B. vietnamiensis* DBO1 (ATCC 29424).

Following incubation of liquid *B. cenocepacia* K56-2 with KS4-M the optical density ($OD_{600}$) was 0.09, while the sample inoculated with KS4 had an $OD_{600}$ of 0.44 and the uninfected control had an $OD_{600}$ of 0.48. The concentrations of bacteria remaining in the samples were determined to be $6.9 \times 10^6$ CFU/mL (colony-forming units per ml) for the KS4-M infected culture, $1.6 \times 10^8$ CFU/mL for the KS4 infected culture, and $2.1 \times 10^8$ CFU/mL for the uninfected control. Concomitantly, the KS4-M infected sample produced more bacteriophage having a titer of $2 \times 10^7$ PFU/mL compared to the KS4 infected sample ($2 \times 10^5$ PFU/mL).

Bacteria, Media and Molecular Biology

Figure 1:
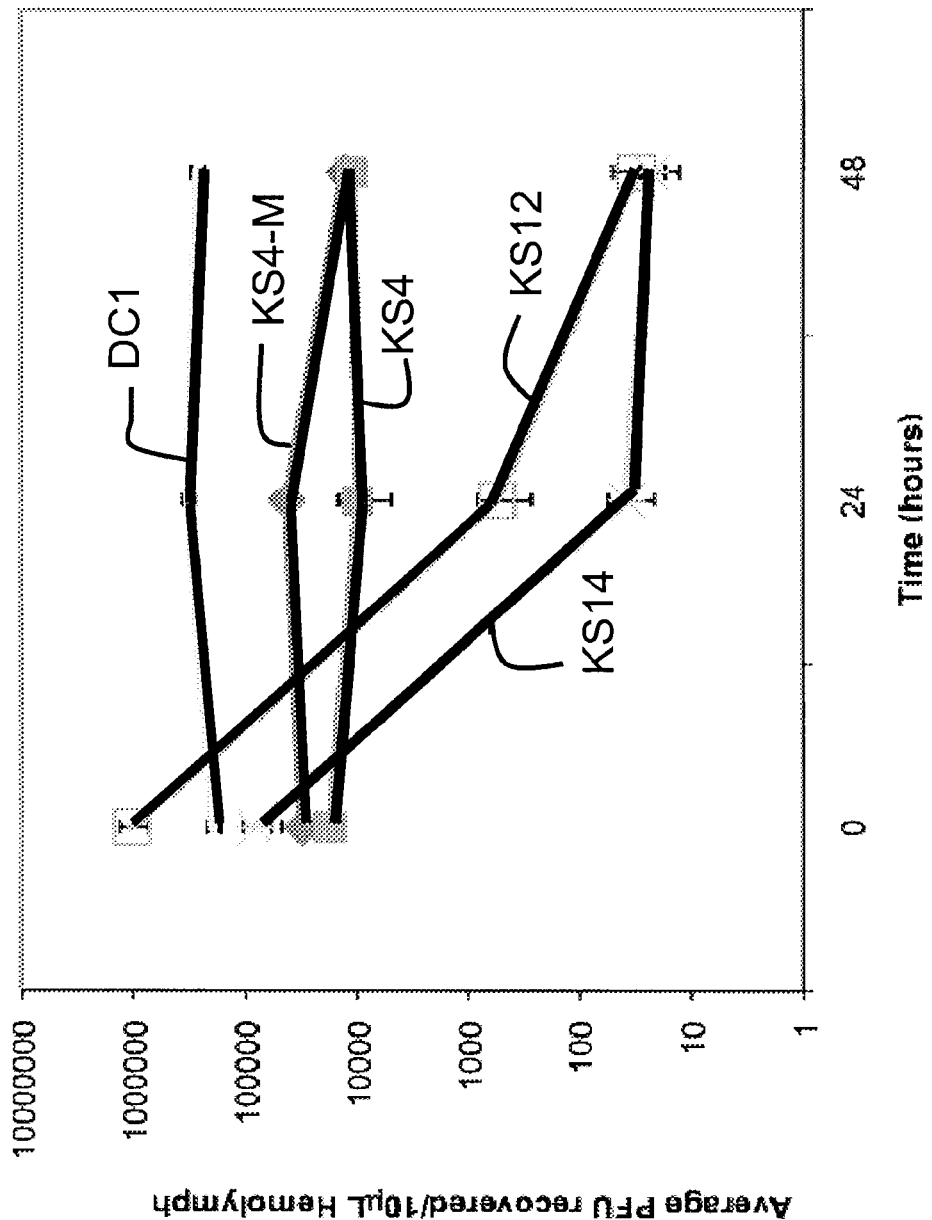
FIG. 1 is a chart indicating bacteriophage persistence in G. mellonella larvae. Uninfected larvae were injected with individual bacteriophages.

The BCC strains of the present invention were collected from the *Burkholderia cepacia* complex experimental strain panel (Mahenthiralingam, E., T. Coenye, J. W. Chung, D. P. Speert, J. R. Govan, P. Taylor, and P. Vandamme. 2000, J. Clin. Microbiol. 38:910-913) and the updated experimental strain panel (Coenye, T., P. Vandamme, J. J. LiPuma, J. R. Govan, and E. Mahenthiralingam 2003, J. Clin. Microbiol. 41, 2797-2798). Bacteria were grown in ½ LB medium at 30° C. Prior to infection with waxworm larvae (see Example 2), overnight cultures were centrifuged (1×104×g for 10 minutes), washed, resuspended and diluted in 10 mM $MgSO_4$ supplemented with 1.2 mg/ml ampicillin. Bacteria collected from the hemolymph of infected larvae were serially diluted in 10 mM $MgSO_4$ and plated onto *B. cepacia* selective agar. Bacterial genomes were isolated from individual colonies using standard procedures. A PCR assay was used to determine the presence of KS4-M within *B. cenocepacia* K56-2 isolates from the hemolymph of larvae undergoing KS4-M bacteriophage therapy. PCR was performed using Taq PCRx DNA polymerase (Invitrogen, Burlington, Ontario, Canada) in 50 μL reactions containing 10 ng of genomic DNA and 50 pmol of primers (Summer, E. J., C. F. Gonzalez, T. Carlisle, L. M. Mebane, A. M. Cass, C. G. Savva, J. LiPuma, and R. Young. 2004, J. Mol. Biol. 340:49-65) using amplification conditions of 96° C. for 2 min for the first cycle, followed by 30 cycles of 96° C. for 1 min, 50° C. for 1 min, and 72° C. for 1 min, with a final extension step of 72° C. for 2 min. PCR products were analyzed by agarose gel electrophoresis.

The BCC bacteriophages of the present invention were isolated as described below and their genomes sequenced using either standard shotgun cloning and Sanger sequencing, or massively parallel pyrosequencing. The present invention relates to bacteriophages comprising these sequences, as well as the sequences in isolated or purified form. Said sequences have uses for preparing bacteriophages for therapeutic and other applications. The following sequences were determined:

DC1(SEQ ID NO:1): vB_BceP-DC1, isolated from *Dracaena* sp. soil (host range includes Bcc LMG 18821, K56-2, C6433, PC184, CEP511 and LMG 18870)

KL3 (SEQ ID NO: 2): vB_BceM-KL3, isolated from Bcc CEP511

KS5 (SEQ ID NO: 3): vB_BceM-K55, isolated from onion soil on Bcc K56-2 (host range includes Bcc LMG 18821, C5393, J2315, 715j, K56-2, C5424, C6433, LMG 19467)

KS14 (SEQ ID NO: 4): vB_BceM-K514, isolated from *Dracaena* sp. soil (host range includes Bcc C5393, C5274, 715J, C6433, C5424, PC184, LMG 21443, LMG 17828)

Example 2

*Galleria mellonella* Assay for In Vivo Analysis of BCC Bacteriophage Activity The waxworm larva *Galleria mellonella* has been developed as an in vivo alternative infection model (Seed and Dennis *Infection and Immunity* Mar. 2008, 1267-1275, incorporated herein by reference in entirety). It has been determined that the innate immune systems of insects such as *G. mellonella* share a high degree of structural and functional homology to the innate immune systems of mammals. Although the immune systems of insects do not display memory or clonal selection mechanisms, they do offer powerful resistance to microbial infections. This defense against microorganisms involves both cellular and humoral defenses. The humoral immune response of insects consists of the processes of melanization, hemolymph clotting, and the production of a number of potent antimicrobial peptides. The cellular reactions include phagocytosis, nodulization, and large-scale encapsulation. Therefore, *G. mellonella* is an attractive alternative infection model for a number of reasons. Analysis of insect responses to pathogens can provide an accurate indication of the mammalian response to that pathogen. Furthermore, substantial correlation between the virulence of certain microbes in mice and the *G. mellonella* model has been established.

While the use of higher animals, such as mice and rats, for the study of the BCC has provided invaluable information, alternative infection models that could provide comparable data but that are more cost-effective, less labor-intensive, and more ethically acceptable would be highly useful. Other alternative infection models have previously been tested with the BCC, including alfalfa seedlings, *Caenorhabditis elegans*, and *Acanthamoeba* species. Unfortunately, all of these models exhibit at least one deficiency in reproducing the virulence observed with BCC in mice and rats.

The use of *G. mellonella* is an alternative infection model for describing BCC virulence is in some cases more quantitative, more accurate, and more robust than other available alternative infection models. Identification of active bacteriophages in the *G. mellonella* assay indicates that these active bacteriophages will be useful as therapeutic agents for treatment of BCC and other bacterial infections in humans.

A 250 μl Hamilton syringe fitted with a reproducibility adapter was used to inject 5 μl aliquots into *G. mellonella*. Initial injections were via the hindmost left proleg and subsequent injections were via the second hindmost left proleg. Following injection, larvae were placed in a static incubator in the dark at 30° C. Larvae were scored as dead or alive 48 hours post-infection at 30° C. Larvae were considered dead when they displayed no movement in response to shaking of the petri dish or touch with a pipette tip. Untreated larvae received a control injection of 10 mM $MgSO_4$+1.2 mg/ml ampicillin in place of bacteriophage, and uninfected larvae received a control injection of 10 mM $MgSO_4$+1.2 mg/ml ampicillin and a subsequent injection of bacteriophage to measure any potentially lethal effects of the physical injection process. Ten larvae were injected in each group, and assays were repeated three times. A 20-G needle was used to withdraw hemolymph from larvae for isolation of bacteriophage and bacteria. In order to quantify the number of bacteriophage in the hemolymph over time, larvae were injected with 5 μl of bacteriophage preparation. At various times thereafter, 10 μl of hemolymph was collected from five larvae and combined. This sample was then serially diluted in suspension media and plated with the appropriate BCC strain for detection and quantification of plaques. For the zero time point, larvae were injected and allowed to sit for 10 minutes before hemolymph collection.

Example 3

Bacteriophage Stability in Hemolymph

Bacteriophages were tested for their ability to persist in the hemolymph of uninfected *G. mellonella* larvae over time.

Equal volumes of hemolymph were collected from five worms at each time point and serially diluted and plated with *B. cenocepacia* K56-2 or *B. cenocepacia* C6433 for quantification. In FIG. 1, each point represents the average of three trials. Larvae injected with bacteriophage KS4-M alone show no decrease in the quantity of bacteriophage collected from the hemolymph over a 48-hour period. These results are also representative for bacteriophages DC1 and KS4, whose bacteriophage titers did not decline in the hemolymph over time. However, not all bacteriophages tested in this study were able to persist in the larval hemolymph. Larvae injected with KS12 or KS14 alone showed a decline in the number of bacteriophages isolated over a 48-hour period (FIG. 1). While both KS14 and KS12 could be isolated from the hemolymph at 48 hours post-injection, their numbers significantly declined over time.

Example 4

KS4-M Bacteriophage Therapy of *B. cenocepacia* K56-2 Infected *G. mellonella* Larvae As with all bacteriophage therapy assays conducted in this study, uninfected larvae that received only bacteriophage had a 100% survival rate and therefore these data are not included in the Figures. Injection of bacteriophage KS4-M which was not purified through the Detoxi-Gel endotoxin-removing column resulted in localized melanization around the injection site as well as a slightly decreased survival rate (about 90% as compared to 100% for endotoxin-free bacteriophages).

Figure 2:
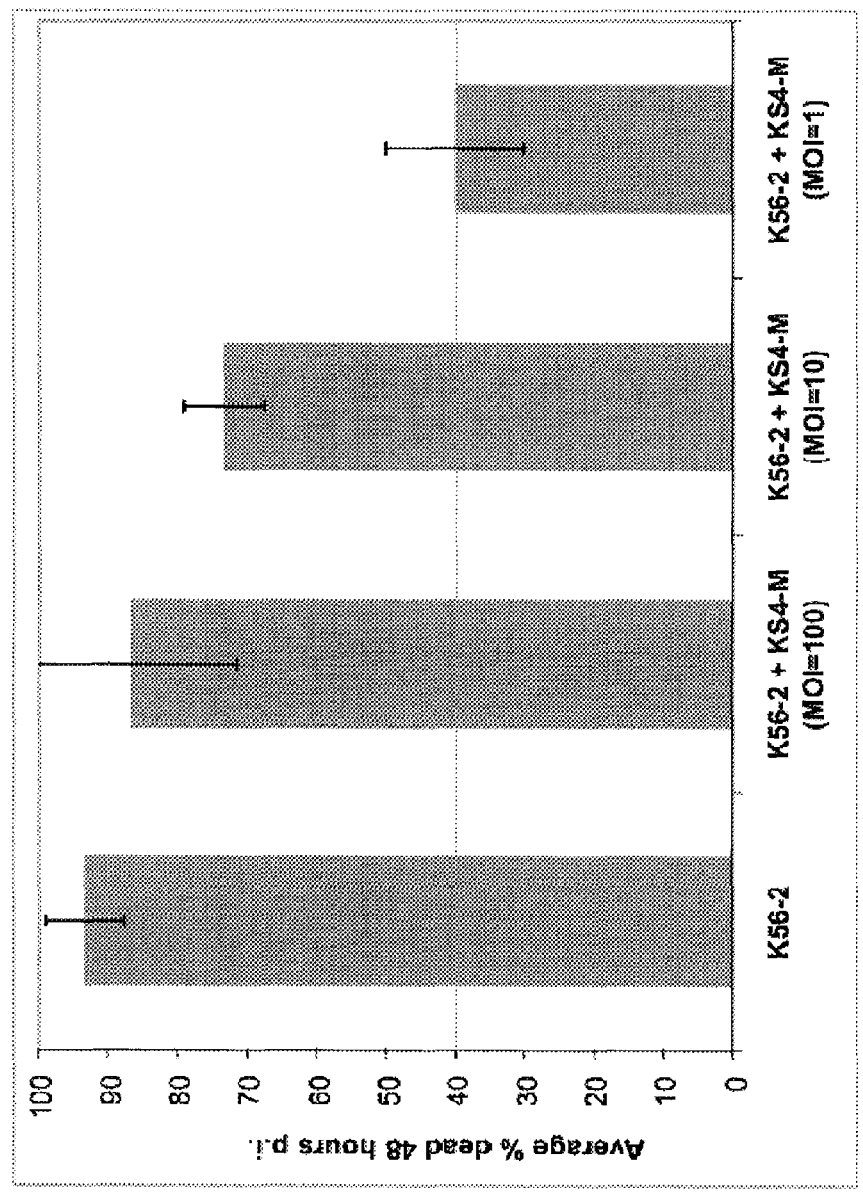
FIG. 2 is a chart indicating the effects of bacteriophage therapy in G. mellonella infected with B. cenocepacia K56-2 or B. cenocepacia C6433 for quantification.

Larvae infected with about $2.5 \times 10^3$ CFU of *B. cenocepacia* K56-2 have nearly a 100% mortality rate 48 hours post-injection. In FIG. 2, each bar represents the average of three trials. Larvae treated with KS4-M immediately following infection show increased survival rates, and this rescue is dependent upon the quantity of bacteriophage used in the therapeutic dose (FIG. 2). The optimal dose of bacteriophage KS4-M used in this experiment was approximately $2.5 \times 10^3$ PFU, resulting in a multiplicity of infection (MOI) of 1. At this dose, 60% of the larvae remained alive 48-hours post-injection, whereas none of the untreated larvae were viable at this time point. Both higher and lower levels of bacteriophage which resulted in higher and lower MOIs were found to be less effective in treating infected larvae (data not shown). *B. cenocepacia* K56-2 isolated from the hemolymph of treated larvae showed resistance to KS4-M infection in vitro (15 of 15 isolates tested). All of these isolates were PCR-positive for KS4-M indicating that lysogeny had occurred in vivo (lysogeny is characterized by integration of the bacteriophage nucleic acid into the host bacterium's genome). Despite in vitro growth differences in liquid culture, bacteriophage KS4 showed results similar to KS4-M in its ability to treat *B. cenocepacia* K56-2 infected larvae with application immediately following infection (data not shown). For this reason, further study of KS4 therapy was not pursued.

Figure 3A:
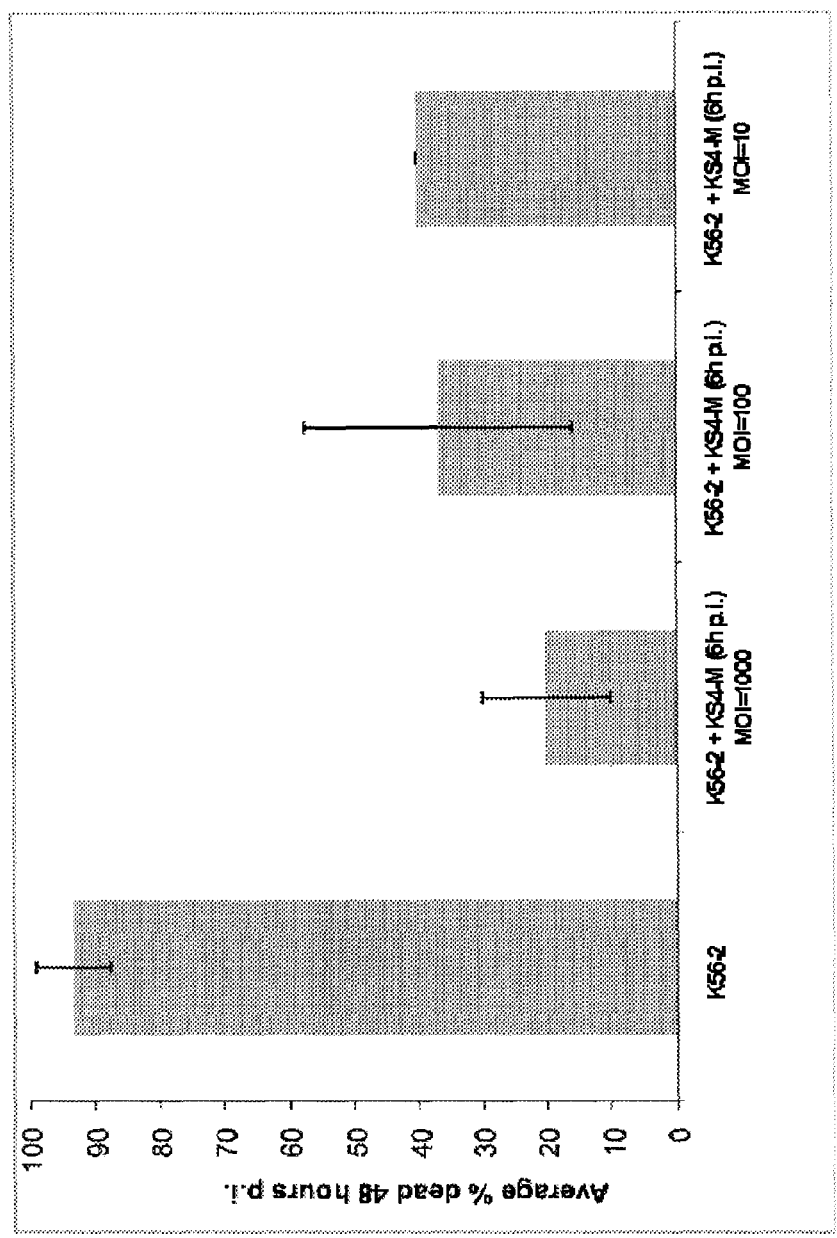
FIG. 3A is a chart indicating the effects of delayed bacteriophage therapy of G. mellonella larvae infected with B. cenocepacia strain K56-2. A single injection of bacteriophage KS4-M (at varying MOI) was administered to larvae at 6 hours after bacterial challenge.
Figure 3B:
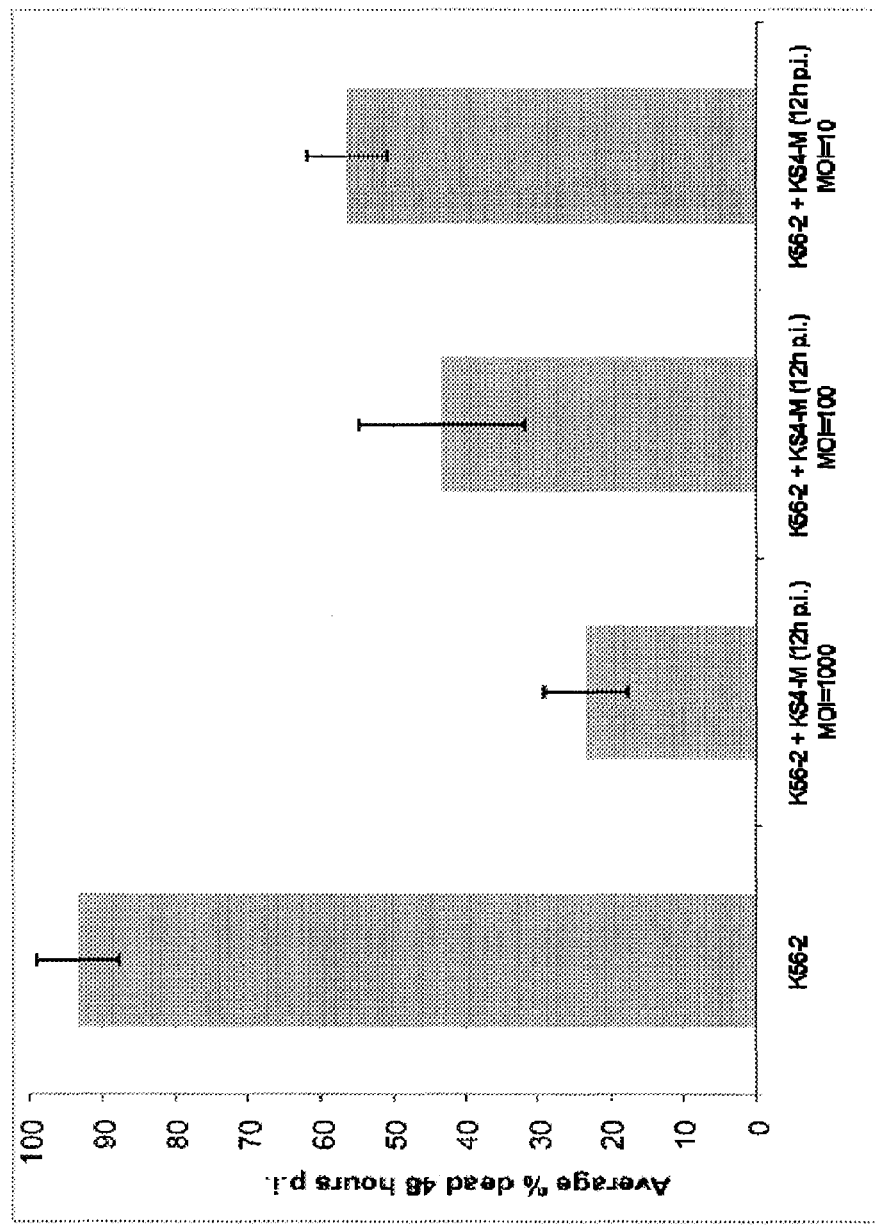
FIG. 3B is a chart indicating the effects of delayed bacteriophage therapy of G. mellonella larvae infected with B. cenocepacia strain K56-2. A single injection of bacteriophage KS4-M (at varying MOI) was administered to larvae at 12 hours after bacterial challenge.

In order to determine whether a delay in treatment altered the ability of bacteriophages to rescue infected larvae, a lethal dose of *B. cenocepacia* K56-2 (about $2.5 \times 10^3$ CFU) was administered and at various intervals thereafter (ranging from 6 to 24 hours). The larvae received a single injection of bacteriophage KS4-M (with MOIs ranging from 10 to 1000). Treatment at either 6 hours (FIG. 3A) or 12 hours (FIG. 3B) post-infection was most effective with the highest dose of bacteriophage and resulted in an MOI of 1000. In FIGS. 3A and 3B, each bar represents the average of three trials. In this experiment, more larvae were found to be viable 48 hours post-injection than when the dose was administered immediately following infection (20% mortality compared to 40% mortality). Although the levels of bacteria are known to remain low in the hemolymph of *G. mellonella* during the first 24 hours, bacteriophages delivered at 24 hours post-injection (irrespective of therapeutic dose) were unable to increase the survivability of infected larvae.

Example 5

Figure 4:
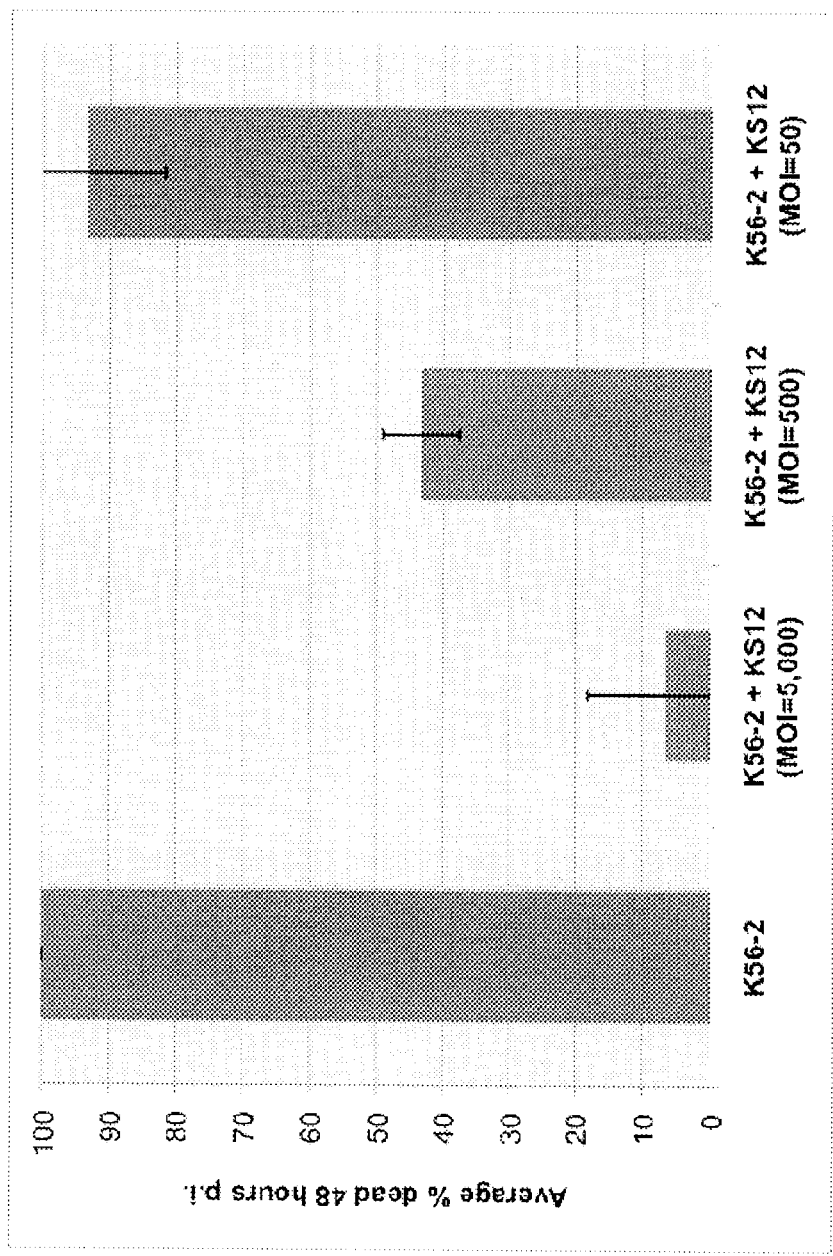
FIG. 4 is a chart indicating KS12 bacteriophage therapy in G. mellonella infected with B. cenocepacia strain K56-2.

KS12 Bacteriophage Therapy of *B. cenocepacia* K56-2 Infected *G. mellonella* Larvae Bacteriophage KS12 was also investigated as a potential candidate for treating *B. cenocepacia* K56-2 infected larvae. As previously observed with KS4-M bacteriophage therapy, immediate therapy of infected larvae with KS12 can increase the survivability of larvae and this effect is dependent on the number of bacteriophage in the therapeutic dose (FIG. 4). At the highest MOI tested, KS12 is able to rescue over 90% of infected larvae. As expected, hemolymph collected from *G. mellonella* larvae infected with K56-2 that received subsequent treatment with KS12 was often completely devoid of bacteria, producing sterile hemolymph. This effect was only observed with bacteriophage KS12. In those instances where bacteria were present in the hemolymph, bacterial isolates recovered from treated larvae were tested for their sensitivity to KS12 in vitro, and both sensitive and resistant isolates were obtained.

In order to determine if the effects observed with bacteriophage therapy were associated with a nonspecific immune activation response, as a control, the effect of heat-inactivated KS12 bacteriophage on the survivability of larvae infected with a lethal dose of K56-2 was determined. This experiment was performed in an attempt to determine whether nonspecific immune response activation was partially (or wholly) responsible for larval survival. KS12 was heat-inactivated for a total of 20 minutes at 80° C. and then cooled prior to being used to treat K56-2 infected *G. mellonella* larvae. Larvae that were treated with heat-inactivated KS12 and untreated larvae had a 100% mortality rate 48 hours post-injection. This sample, in which no viable bacteriophage could be detected by in vitro plating, was used to treat larvae infected with a lethal dose of *B. cenocepacia* K56-2. Ten larvae were injected with a lethal dose of K56-2 (about $2.5 \times 10^3$ CFU) and immediately treated with heat inactivated KS12. Another ten larvae served as a sham control receiving only bacteria and buffer in place of bacteriophage. The quantity of bacteriophages in the sample prior to heat inactivation was calculated to produce a multiplicity of infection (MOI) of approximately 8000. FIG. 4 shows that an experimental KS12-K56-2 MOI of approximately 5,000 results in a *G. mellonella* mortality rate of only about 7% over a similar time period, suggesting that larval survival is entirely due to bacteriophage antibacterial activity rather than host immune stimulation.

Example 6

KS14 Bacteriophage Therapy of *B. cenocepacia* C6433 Infected *G. mellonella* Larvae

Figure 5:
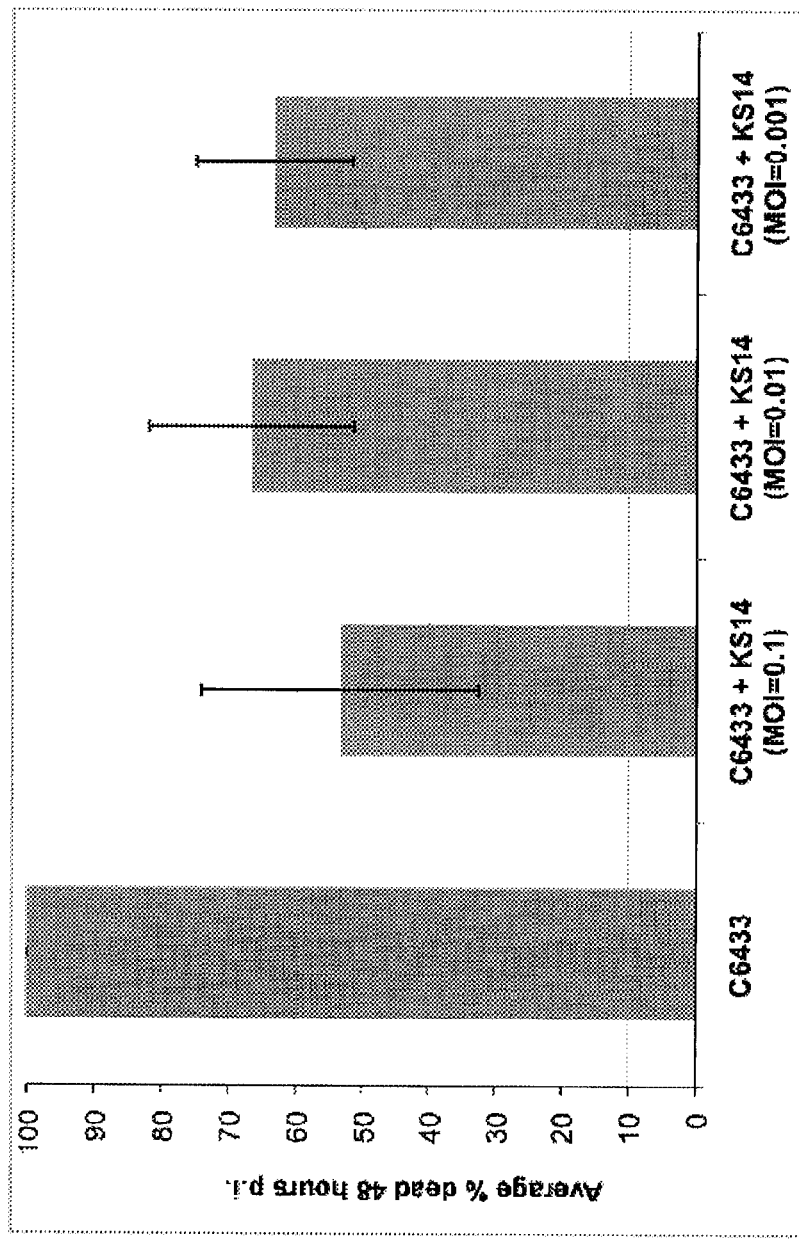
FIG. 5 is a chart indicating KS14 bacteriophage therapy in G. mellonella infected with B. cenocepacia strain C6433.

*G. mellonella* larvae injected with a lethal dose of *B. cenocepacia* C6433 and immediately treated with KS14 show increased survival at the MOIs tested in this study (FIG. 5). The $LD_{50}$ for *B. cenocepacia* C6433 is $3.0 \times 10^4$ CFU in this infection model. Therefore, the investigation was limited to testing the efficacy of low bacteriophage MOIs in evaluating KS14 therapy because in order to reach a lethal dose of *B.* cenocepacia C6433, about $1.0 \times 10^5$ CFU had to be injected. Because of the required small injectable volumes in the *G. mellonella* model, even the highest concentrations of injected bacteriophage only resulted in an MOI of 0.1. However, even at these low levels of bacteriophage, a therapeutic effect was observed. *G. mellonella* larvae treated with the highest dose of bacteriophage (MOI=0.1) had mortality rates of approximately 50%, while untreated infected larvae had a 100% mortality rate at 48 hours post-injection. The amount of KS14 bacteriophage in the therapeutic dose appears to be of lesser importance, with different MOIs ranging from 0.1 to 0.001 all showing rescue of approximately 40% of infected *G. mellonella* larvae (FIG. 5). In vitro evaluation of the sensitivity of *B. cenocepacia* C6433 isolates collected post-infection to subsequent KS14 infection revealed the presence of both sensitive and resistant organisms.

Example 7

DC1 Bacteriophage Therapy of *B. cenocepacia* C6433 Infected *G. mellonella* Larvae

*G. mellonella* larvae were infected with a lethal dose of *B. cenocepacia* C6433 (about $1.0 \times 10^5$ CFU) and immediately treated with bacteriophage DC1 at varying MOIs. Although higher MOIs were achieved in this experiment than with KS14 therapy, at all MOIs tested (ranging from 10 to 0.0001), no therapeutic effect of bacteriophage DC1 was observed (data not shown). *B. cenocepacia* C6433 infected *G. mellonella* larvae either untreated or treated with DC1 all had 100% mortality rates at 48 hours post-injection. Uninfected *G. mellonella* larvae that received a mock injection in place of bacteria and that were subsequently injected with bacteriophage DC1 exhibited no mortality, and therefore no undesirable effects were due to the injection of bacteriophage alone.

The results of this series of in vivo experiments predict that BCC bacteriophage therapy is effective against BCC infections in mammalian, including human subjects, such as individuals with cystic fibrosis and other respiratory tract ailments that can limit the application of other treatments and/or render such subjects more susceptible to respiratory infections.

Inhalational Therapy—Nebulization of BCC Bacteriophages

Example 8

Bacteriophage Preparation

Phage KS4-M was propagated on BCC strain K56-2 using standard liquid propagation techniques. Bacteria were grown at 30° C. in ½ strength Luria-Bertani medium. Prior to aerosolization, bacteriophage preparations were filter sterilized (pore size 0.22 μm) and passed through a Detoxi-Gel Affinitypak™ prepacked column (Pierce Biotechnology, Rockford, Ill.) to remove endotoxins from the solution. Following aerosolization suspension media (SM) (50 mM Tris/HCl pH 7.5, 100 mM NaCl, 10 mM $MgSO_4$, and 0.01% gelatin solution) was used to collect bacteriophage from the filter. The bacteriophages were then quantified by plating serial dilutions with BCC strain K56-2 using the soft overlay agar method for the detection of plaques.

Example 9

Nebulization of Bacteriophage and Measurement of Inhaled Fraction

Nebulization of the BCC bacteriophage was performed with two types of nebulizers each in triplicate, with a total of six tests for each bacteriophage titer. Pari LC Star™ jet nebulizers were used with a Proneb Turbo Compressor model 38B0201 at a flow of 3.6 L/min (Pari Pharma GmbH, Starnberg, Germany). This type of nebulizer is commonly used in cystic fibrosis therapy and has demonstrated good performance in previous nebulization studies. The second tested nebulizer in this study was the recently developed eFlow™ electronic nebulizer (Pari Pharma GmbH). The latter nebulizer has a shorter nebulization time and its gentle aerosol generation has demonstrated the potential to exert less shear on the fluid in the aerosolization of large molecules.

For each test, the nebulizer was filled with 2.5 mL of isotonic (osmolarity of 282-290 mOsm) bacteriophage suspension at an ambient temperature of 21° C. The bacteriophage titer had a mean value (standard deviation) of $2.15 \times 10^8$ ($1.63 \times 10^8$) PFU/mL. To obtain an isotonic suspension of bacteriophages, the derived column eluates were supplemented with 5.25 mg/ml of sodium chloride. In addition, to examine the effect of osmolarity, the nebulizer was filled once with a hypotonic (105 mOsm) suspension of bacteriophages with a titer of $10^8$ PFU/mL. The run time was measured for each test. Nebulization was stopped when there was a pause of more than 15 seconds without aerosol production. The size distribution of nebulizer aerosols can depend on the patient's breathing pattern. Therefore, to simulate the breathing pattern, a computer controlled piston-type breathing machine (Pulmonary Waveform Generator, model: PWG S/N904, MH Custom Design & Mfg. LC, Midvale, Utah) was employed. A tidal volume of 800 mL, with 14 breaths per min, and a duty cycle of 0.5 (i.e., equal inhalation and exhalation with no inspiratory pause) was selected as a breathing pattern for an adult according to previous studies. The size distribution of the nebulizers was characterized by an in-line Phase Doppler Anemometer (PDA) (Dantec Electronics Inc., Mahwah, N.J.), while sampling 10 sec at the beginning of each minute of the run time. For both nebulizers, size measurements were made using a procedure in which the aerosol size distribution is measured at the mouthpiece of the nebulizer connected to the breathing simulator with optical sizing window in place. The refractive index of bacteriophage suspension was measured using a refractometer (Fisher Scientific Economy Refractometers, 13-947 series, Dubuque, Iowa) and found equal to that of pure water, so that the refractive index of water was used for the droplet size measurements by PDA. Also, the solution density of the suspension of bacteriophages (which is clear to the naked eye) is near that of water (1.002 g/cm³). The mass median diameters (MMDs) and geometric standard deviations (GSDs) from the PDA were averaged for each nebulizer and inserted into a mathematical model for deposition calculations.

The total output of the nebulizer was captured on a low resistance filter (Respirgard™ II, Vital Signs Colorado Inc., Totowa, N.J.) in line with the breathing machine. The number of bacteriophages collected on the filter was termed the "inhaled count." The filter collection was performed directly at the exit of the nebulizer mouthpiece, without the sizing region in place, to prevent any loss in the sizing region.

Regional lung deposition of the inhaled bacteriophages was estimated using a numerical lung deposition model based on a one-dimensional Lagrangian approach which has been previously described (Golshani et al., *J. Aerosol. Med. & Pulmonary Drug Delivery* 2008, 21(4), 1-9).

Average values of inhaled counts of bacteriophages, nebulization time, aerosol mass median diameter (MMD), and geometric standard deviation (GSD) of the two types of nebulizers (LC Star™ and eFlow™) are presented in Table 1. It is observed that average nebulization time was longer for the LC Star™ jet nebulizer compared to the eFlow™ electronic nebulizer (p<0.01). The average mass median diameter of the eFlow™ was slightly larger than that of the LC Star™ nebulizer (p>0.01). The polydispersity was similar for the two types of nebulizers, with geometric standard deviation not significantly affected by the type of nebulizer (p>0.01). In Table 1, mean values and standard deviations are given based on six replicates of experiments for each nebulizer (three repeats at two titers). The p-value is a two-tail p value for comparing the two nebulizers using a Students t-test.

TABLE 1

Comparison of Data from LC star ™ and eFlow ™ Nebulizers

| Data | Nebulizer type | | |
|---|---|---|---|
| | LC star ™ Mean ± SD | eFlow ™ Mean ± SD | p-value |
| MMD, (μm) | 4.98 ± 0.06 | 5.83 ± 0.43 | 0.086 |
| GSD (μm) | 1.48 ± 0.01 | 1.44 ± 0.07 | 0.437 |
| Nebulization time (min.) | 7.56 ± 0.59 | 3.09 ± 0.25 | $5.64 \times 10^{-7}$ |
| Inhaled bacteriophages (PFU) | $1.06 \times 10^8 \pm 0.12 \times 10^8$ | $1.15 \times 10^8 \pm 0.14 \times 10^8$ | 0.242 |
| Extrathoracic deposition (PFU) | $2.04 \times 10^7 \pm 0.25 \times 10^7$ | $2.92 \times 10^7 \pm 0.66 \times 10^7$ | 0.023 |
| Tracheobronchial deposition (PFU) | $2.14 \times 10^7 \pm 0.25 \times 10^7$ | $2.58 \times 10^7 \pm 0.33 \times 10^7$ | 0.030 |
| Alveolar deposition (PFU) | $3.02 \times 10^7 \pm 0.35 \times 10^7$ | $2.96 \times 10^7 \pm 0.29 \times 10^7$ | 0.747 |

Average values of the inhaled counts of bacteriophages on the filters are also given in Table 1 for each type of nebulizer. The type of nebulizer did not significantly change the "inhaled count" and regional deposition (p>0.01). Table 1 also shows the quantity of bacteriophages that mathematically were predicted to deposit in different regions of the lung. It is worth mentioning that the quantity of bacteriophages quoted in plaque forming units (PFU) represents the quantity of bacteriophages that survived the nebulization. The extrathoracic deposition obtained with the eFlow is slightly higher, which could be attributed to the larger MMD of that nebulizer. Larger aerosols tend to impact on extrathoracic surfaces. In contrast, the alveolar deposition obtained by the LC Star™ was higher compared to that of the eFlow™. This may be explained by a related argument. The tracheobronchial deposition of LC Star™ and eFlow™ were predicted to be $2.14 \times 10^7$ ($2.5 \times 10^6$) and $2.58 \times 10^7$ ($3.3 \times 10^6$) PFU, respectively.

To assess the effect of osmolarity, one set of experiments was performed with both types of nebulizers filled with 2.5 mL hypotonic suspension (105 mOsm) with titer of $10^8$ PFU/mL ($2.5 \times 10^8$ PFU). The "inhaled count" using LC Star™ and eFlow™ were $1.75 \times 10^7$ ($0.02 \times 10^7$) and $1.8 \times 10^7$ ($0.02 \times 10^7$), respectively. These results revealed that inhaled count was much less than the inhaled count obtained from an isotonic formulation (Table 1). The reduced inhaled count with hypotonic solution is likely due to osmotic pressure sensitivity of bacteriophages during nebulization. This part of the experiment was a preliminary trial. This formulation was abandoned due to concerns that hypotonic formulations can cause patient cough, which makes the drug delivery impractical.

Figure 6:
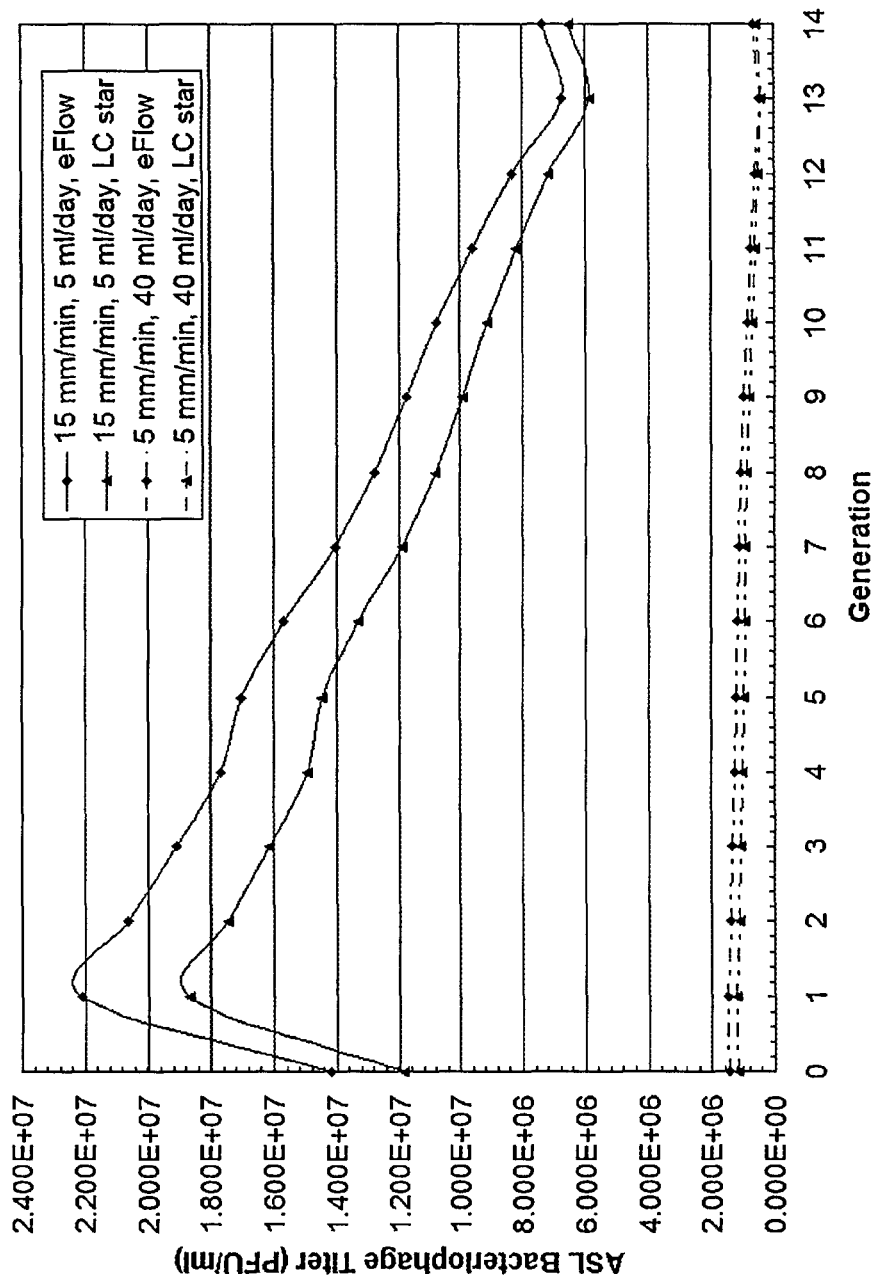
FIG. 6 is a chart indicating generational bacteriophage titer levels in airway surface liquid after nebulization.

Predicted bacteriophage titers in airway surface liquid in different generations of the tracheobronchial region are given in FIG. 6 for two combinations of tracheal mucus velocity-mucus production rates of 5 mm/min:40 mL/day and 15 mm/min:5 mL/day for both LC Star™ and eFlow™ nebulizers. Nebulizing with eFlow™ resulted in higher airway surface liquid concentration in all tracheobronchial generations for both combinations of mucus velocity and mucus production rate. As expected, the largest airway surface liquid concentration was obtained with the largest mucus velocity (15 mm/min) and lowest production rate (5 mL/day), and the lowest airway surface liquid concentration was obtained with the lowest mucus velocity (5 mm/min) and highest production rate (40 mL/day). The nebulization time in the experiment (7.56 and 3.09 min for LC Star™ and eFlow™, respectively) is measured in minutes, while mucociliary clearance occurs on a time scale measured in hours. Therefore, considering a static state for concentration distribution in airway surface liquid is a reasonable approximation. This static state leads to a minimum titer for the low mucus velocity and high production rate because of the higher thickness of airway surface liquid for a given inhaled number of bacteriophages.

These experiments show that BCC bacteriophages survive nebulization both in LC Star™ and eFlow™ nebulizers, and result in good inhaled and deposition titers. Because patients prefer the shortest inhalation time, the eFlow™ is favored in this sense. However, the eFlow™ is currently more expensive, and may be less durable, with the average cycle life of an ultrasonic nebulizer being 600 to 1000 uses, which is reached within a year by a cystic fibrosis patient receiving multiple medications. It is worth noting that imaging lung deposition studies using scintigraphic aerosol have shown good performance of vented jet nebulizers. LC Star™ and eFlow™ both have relatively similar MMD, and the mathematical model predicts similar distribution of bacteriophages in the lungs. This suggests that the LCstar™ and eFlow™ both appear to be suitable for BCC bacteriophage therapy.

These results further demonstrate that bacteriophage therapy delivered by aerosol delivery of an aqueous solution of a bacteriophage has the potential to be effective against bacterial infections, including a BCC infection such as those suffered by individuals with cystic fibrosis.

Respirable Powders Containing Active BCC Bacteriophages

Example 10

Lyophilization of Bacteriophage KS4-M in Carbohydrates

Bacteriophage KS4-M was obtained and purified as described in Example 1. Lactose monohydrate (milk sugar), sucrose, and trehalose were obtained from Sigma-Aldrich Inc., St. Louis Mo., 63103 USA. Lyophilization was done using a Labconco Freeze Dry System, model Freezone™ 4.5 (from Fisher Scientific). Aerolizer inhalers were purchased in a local pharmacy. Hard gelatin capsules #3 were purchased from Capsule Connection, 309 Bloom Pl., Prescott Ariz., 86303 USA. Mixer mill 5100-115 was obtained from ATS Scientific Inc., 4030 Mainway, Burlington, ON, L7M 4B9 Canada (manufactured by SPEX, 203 Norcross Ave, Metuchen N.J., 08840 USA).

Starting concentrations of the carbohydrates lactose, trehalose and sucrose were prepared at 50 mg/ml. Carbohydrate (600 mg) was dissolved in deionized water (6 ml) and filtered through a 0.45 µm filter to give 5 ml of carbohydrate solution (100 mg/ml). Subsequently, the latter was combined with 5 ml of endotoxin-free KS4-M ($1\times10^8$ PFU/ml) in a 300 ml fast freeze flask, frozen in a dry ice/acetone mixture and lyophilized for 30 hours.

The lyophilized material was stored in polypropylene tubes at 4° C. Assuming 100% survivability, in the lyophilized material bacteriophage content should have been about $1\times10^8$ PFU/100 mg. The bacteriophage viability was measured after lyophilization and the following results were obtained with the respective carbohydrates: lactose—$9.4\times10^7$ PFU/100 mg; trehalose—$4.8\times10^7$ PFU/100 mg; and sucrose—$7.8\times10^7$ PFU/100 mg.

Since the difference between ideal and obtained yields is less than 1 log unit, the carbohydrate matrix used to preserve bacteriophage KS4-M in a dry form provides good cryoprotection for this bacteriophage.

In other embodiments, the starting carbohydrate may comprise one or more carbohydrates, such as mannitol, glucose, saccharose or trehalose, in addition to in place of the carbohydrates and sugars mentioned above. It will be seen by those skilled in the art that the carbohydrate component may be selected from a wide range of pharmaceutically acceptable compounds.

The respirable composition of the invention may comprise other active ingredients, such as antibiotics as aminoglycosides, e.g tobramycin, amikacin; fluoroquinolones, eg. ciprofloxacin, levofloxacin; beta lactam and carbapenam antibiotics, cationic peptides, eg. lactoferrin.

The respirable composition may comprise other pharmaceutically acceptable excipients or compounds, such as surfactants eg. poloxamers, Tweens™, phospholipids; polyethylene glycols, glucosinolates, EDTA, amino acids (eg. glycine, leucine) and their polymers (eg. trileucine), and others.

Example 11

Preparation of Respirable Powders Containing BCC Bacteriophages

Upon lyophilization with carbohydrates (and optionally other constituents) as described in Example 10, the bacteriophages become embedded in a solid matrix. This material is not suitable for dry powder inhaler delivery because it is in the form of a porous cake. This product must be further refined by a process of solid particle comminution (fission or erosion of particles to obtain particles of a refined size with a reduced distribution of particle sizes). This process produces a respirable powder suitable for packing into capsules. The refining process must be sufficiently gentle to provide respirable powder particles without destroying the bacteriophages. This is accomplished by minimizing shear forces and other mechanical stresses during the process.

Lyophilized samples prepared as described above were subjected to a milling process. It was found that milling the porous cake described above with a mortar and pestle produces powders without a major loss of bacteriophage titer (see Table 2). Batch L9-BCC also contained 2.5 mg/mg solids of Pluronic F68, a block copolymer surfactant. Batch L7-BCC was first ground using a mortar and then in the mixer mill 5100-115. The recovered concentration indicates recovered quantity of viable bacteriophage from capsule contents, prior to aerosolization.

Preparing powders from lyophilized bacteriophage in solid matrices may be conveniently accomplished on a commercial scale by methods of milling or by any other processes which produce particle diameters of about 1 µm to about 5 µm in diameter, or any other selected particle size or size range, while minimizing shear and other mechanical stresses during the step of reducing the cake to a finely divided powder. Such powders may be obtained on a commercial scale by a variety of known low-stress methods, such as gentle mixing in drum rollers, or tumblers in a manner known to those with skill in the art.

Persons skilled in the relevant art will recognize that the particle size of the preparations of the present invention may be selected from within a wide range. The particle size of the final product may be adjusted to any suitable size or size arrange, according to methods and processes known to the art, and depending on the therapeutic objectives of the formulation. Without limiting the generality of the invention, particle sizes may range, for example, between 0.1 and 100 µm in diameter. Within this exemplary range, one may select narrower ranges, such as 0.5 to 25 µm, 1.0 to 10 µm, or 1.0 to 5 µm in diameter. It will be further understood that within any given range, a small portion of particles may fall outside this range.

TABLE 2

Titer of different preparations of live phages submitted to lyophilization are given as plaque forming units, pfu, per mg powder.

| Batch | Excipient concentration | Workup | Titer prior to lyophilization ($10^6$ pfu/mg solids) | Titer recovered after lyophilization ($10^6$ pfu/mg solids) |
|---|---|---|---|---|
| L3 | Lactose 50 mg/ml | Mortar | 1 | 0.404 (0.046) |
| L4 | Lactose 50 mg/ml | Mortar | 1 | 0.442 (0.0) |
| L7 | Lactose 50 mg/ml | Mortar and mixer | 1 | 0.025 (0.005) |
| L8 | Lactose 50 mg/ml | Mortar | 1 | 0.505 (0.0005) |
| L9 | Lactose 50 mg/ml + Pluronic F68 2.5% wt./wt. solids | Mortar | 1 | 0.206 (0.133) |
| L11 | Lactose 50 mg/ml | Mortar | 1 | 0.064 (0.017) |
| T2 | Trehalose 50 mg/ml | Mortar | 1 | 0.179 (0.083) |
| T3 | Trehalose 100 mg/ml | Mortar | 0.5 | 0.56 (0.07) |

TABLE 2-continued

Titer of different preparations of live phages submitted to lyophilization
are given as plaque forming units, pfu, per mg powder.

| Batch | Excipient concentration | Workup | Titer prior to lyophilization ($10^6$ pfu/mg solids) | Titer recovered after lyophilization ($10^6$ pfu/mg solids) |
|---|---|---|---|---|
| L10 (KS4-M + KS14 phages) | Lactose 50 mg/ml | Mortar | KS4-M: 0.0044 KS14: 0.0044 | KS4-M: 0.00119 (0.00029) KS14: 0.000218 (0.000107) |

All batches except L10 were prepared with KS4-M phages only. Standard deviation is given in brackets (n = 4 for most batches, and n ≥ 2 for all batches).

Example 12

Testing for Viable Bacteriophages in Fine Particle Fractions after Aerosolization Because aerosols must traverse the mouth-throat region before entering the lungs, it is important to be able to mimic aerosol deposition and flow in the human mouth-throat when studying inhaled aerosols. However, there is tremendous variability in the shape and geometry of the human mouth-throat between different individuals. For this reason, a model known as the "Alberta mouth-throat geometry" was developed at the Aerosol Research Laboratory of Alberta. Despite its relative simplicity compared to actual human mouth-throats, the Alberta geometry has been shown to do a remarkable job of mimicking the aerosol and flow motion in the human mouth-throat. For this reason, it has been adopted worldwide by researchers examining and testing aerosols inhaled orally.

Testing for fine particle fraction was performed using the Alberta mouth-throat model and Aerolizer™ inhalers (Novartis). The fractions were collected on 303 Respirgard™ low resistance filters (Vital Signs Inc., Totowa, N.J.) The results of the fine particle fraction testing are shown in Table 3. These results indicate that, while some loss of bacteriophage is incurred during the aerosolization process, in most cases, a quantity is recovered in fine particle fractions, which is predicted to be sufficient for bacteriophage therapy.

Bacteriophage prepared according to the above method or by other methods which achieve a similar result may be delivered as a dry powder in a dry powder inhaler to provide therapeutic benefit to individuals with a bacterial infection, such as a pulmonary BCC infection, including those with BCC infections arising from cystic fibrosis.

TABLE 3

Titer delivered as aerosol distal to the Alberta mouth-throat
is given for different preparations that are listed in Table 2.

| Batch | Capsule load (mg) | Capsule load (pfu) | Delivery distal to mouth-throat (pfu) |
|---|---|---|---|
| L4 | 29.8 (1.6) | 1.32 (0.07) × $10^7$ | 3.23 (1.98) × $10^6$ |
| L7 | 30.4 (2.4) | 7.61 (0.60) × $10^5$ | 6.57 (2.33) × $10^4$ |
| L8 | 22.8 (0.8) | 1.16 (0.04) × $10^7$ | 1.92 (0.57) × $10^5$ |
| L9 | 25.9 (0.7) | 5.34 (0.15) × $10^6$ | 7.63 (3.16) × $10^5$ |
| L11 | 31.3 (0.75) | 6.4 (1.7) × $10^6$ | 9.3 (0.1) × $10^4$ |
| T2 | 30.9 (1.0) | 5.54 (0.17) × $10^6$ | 7.22 (3.22) × $10^5$ |
| T3 | 25.3 (0.40) | 1.42 (0.02) × $10^7$ | 9.62 (0.97) × $10^5$ |
| L10 | 29.7 (0.24) | KS4-M: 6.47 (0.05) × $10^3$ KS14: 3.53 (0.03) × $10^4$ | KS4-M: 2.25 (0.21) × $10^3$ KS14: 3.51 (0.29) × $10^3$ |

Standard deviation is given in brackets (n = 2 for capsule load, and n = 3 for delivery distal to mouth-throat).

TABLE 4

Titer (units of $10^6$ pfu/mg solids) of different preparations that are listed
in Table 2 are given here after storage for the indicated periods of time.

| Batch | 1 week | 2 months | 3 months | 5 months |
|---|---|---|---|---|
| L8 at 0° C. | 0.50 (0.07) | 0.14 (0.2) | 0.19 (0.06) | |
| L9 at 0° C. | 0.08 (0.02) | 0.35 (0.06) | 0.115 (0.007) | 0.125 (0.007) |
| L9 at 22° C. | 0.24 (0.03) | 0.070 (0.03) | | |
| T2 at 0° C. | 0.10 (0.03) | 0.018 (0.002) | | |
| T3 at 0° C. | 0.56 (0.1) | 0.062 (0.002) | | |

It will be seen that the present invention has been described by way of preferred embodiments of various aspects of the invention. However, it will be understood that one skilled in the art may readily depart from the embodiments described in detail herein, while still remaining within the scope of the invention as defined in this patent specification including the statement of invention hereinbelow.

All documents referred to in this patent specification are incorporated herein by reference in their entirety.

We claim:

1. A respirable composition comprising a therapeutically active bacteriophage and a pharmaceutically acceptable respirable carrier, said composition being in the form of a fine powder comprising a desiccated liquid composition of said bacteriophage and a carbohydrate.

2. The composition as defined in claim 1 wherein said powder comprises particles in the size range of 0.1 to 100 μm, 0.5 to 25 μm, 1.0 to 10 μm, or 1.0 to 5 μm in diameter.

3. The composition as defined in claim 1 wherein said carbohydrate comprises lactose, lactose monohydrate, sucrose, trehalose, mannitol, or glucose.

4. The composition of claim 1 wherein said bacteriophage is a lytic bacteriophage, a lysogenic bacteriophage, or a genetically modified lysogenic bacteriophage having lytic activity.

5. The composition of claim 1 wherein said bacteriophage is active against BCC.

6. The composition of claim 1 wherein said bacteriophage comprises a gene sequence of SEQ ID NO: 1, SEQ ID NO: 2, SEQ ID NO: 3, or SEQ ID NO: 4 or a gene sequence having at least 75%, 85%, 90% or 95% identity with SEQ ID NO: 1, SEQ ID NO: 2, SEQ ID NO: 3, or SEQ ID NO: 4.

7. The composition of claim 1 wherein said bacteriophage comprises a mixture of bacteriophages active against a plurality of bacteria species or strains.

8. The composition of claim 1 further comprising an antibiotic compound.

9. A method of preparing a respirable composition comprising a therapeutically active bacteriophage and a pharmaceutically acceptable respirable carrier, comprising the steps of preparing a mixture comprising said carrier and said bacteriophage in a liquid, desiccating said mixture to obtain a matrix, and refining said matrix into fine particles, wherein said step of refining retains the viability of said bacteriophage wherein the step of refining results in the loss of less than one log unit bacteriophage viability.

10. The method of claim 9 wherein said matrix is refined into particle sizes in the range of 0.1 to 100 μm, 0.5 to 25 μm, 1.0 to 10 μm, or 1.0 to 5 μm in diameter.

11. The method of claim 9 wherein said carrier comprises a carbohydrate.

12. The method of claim 9 wherein said bacteriophage is active against BCC.

13. The method of claim 9 wherein said bacteriophage comprises a gene sequence of SEQ ID NO: 1, SEQ ID NO: 2, SEQ ID NO: 3, or SEQ ID NO: 4 or a gene sequence having at least 85%, 90% or 95% identity with SEQ ID NO: 1, SEQ ID NO: 2, SEQ ID NO: 3, or SEQ ID NO: 4.

14. The method of claim 9 wherein said bacteriophage comprises a mixture of bacteriophages active against a plurality of bacteria species or strains.

15. The method of claim 9 further comprising adding an antibiotic compound into said mixture.

16. The method of claim 9 wherein said refining comprises milling.

17. A method of treatment of an individual with a bacterial infection comprising administering to said individual a therapeutically effective amount of the composition of claim 1.

18. The method of treatment of claim 17 wherein said bacteriophage comprises a BCC bacteriophage and said individual has cystic fibrosis or chronic granulomatous disease.

19. The method of treatment of claim 17 wherein said bacterial infection is present in a biofilm within the individual's lung.

20. The composition of claim 1 wherein said dessicated liquid composition comprises an aqueous mixture.

21. The composition of claim 1 wherein said dessicated liquid composition comprises a lyophilized aqueous mixture.

22. The composition of claim 1 wherein said dessicated liquid composition is milled.

23. The method of claim 9 wherein said step of desiccating comprises lyophilizing said liquid mixture.

24. The method of claim 9 wherein said liquid mixture comprises an aqueous mixture.

* * * * *

```
                            SEQUENCE LISTING

<160> NUMBER OF SEQ ID NOS: 4

<210> SEQ ID NO 1
<211> LENGTH: 61847
<212> TYPE: DNA
<213> ORGANISM: Bacteriophage DC1

<400> SEQUENCE: 1
gctgtctcct ccccccttgg caatggggtt gccccggctt cgccgccggg gcttttttc       60 gtctacagga gggacgtgag catgcgcttg aacagcggcg aaggatctgt gccgagctgc     120
ttcagcagcg cctcgagctc gcgcgcgagc acgacgtgcg gctcgggaag cggattccat     180
gcgtccggct cggccgtgtc tgtcgcctcc atcgcttcgc gcatggccgc ctcgctgacc     240
ggttgcccga tcgcctcaga cgcggcgcgc gcgagcacgt cgaggcccga dacgctggcg     300
gcattggcct gcttcagcca ttcgcatagc cggtagaact cgcgcggtgt cagctcagta     360
gcggcggctg tttcggtagg tttcttcata tcgtccttta gtttgacgac cggcggcggc     420
agttccacgg ccggcgggat tggggtgttc tcacgcgcga agcggcgaat cttggcatgc     480
tcgttcaggt cgccgcgggc atcgcccggc cgtagcgaga tggcgaacgt ccgctcgacg     540
ccgttcggcg cgcgcacgtc gacgcatacg cggccggcct tgctgtagtg ctgcacgacc     600
gcgaggccgg cgtccttgac catatcgacg agatcgcgga gacgggattg gctcatacgg     660
ccttccctcg ccgcgtgcag cgcggctcgt ccgcgtcggg cagacggtag agaaaggtcg     720
tgtcgccgac gccgggcttc gcgtagtacg cgcagccctc gcggtcgaac agcacgcggt     780
ggtcgggcat gtcgtcgcgg cacgcggcga gcgccagcac ggcgaggatc agggcggcaa     840
tcttcatgct gcaacctccc ctgcctcgca cgggcccgcg ccgcgcagca cgcgatgcca     900
gttcgcgagc gcggcggccg tcgtgatgac gtggtgctcg gccttgtcct ggtcgcccgc     960
gatcagcgcg ttaagcgcct tgccggccag atagccgacg agccagaacc agtcggcgtg    1020
cgtcttgccg ctgtcgtccc agcgctgccg ctggtgctcg gcctcgatgc tgaccgactt    1080
caggaagtcg tccgtgtgcg gcgtgttgat gatcgcgttc aggcggtcga gctcggcctg    1140
caccttctcg ccccacgatt cctctgtctc gccctcatag cccacgagca ggtaggcgtc    1200
gtgcgccgag cgctcgtcaa acaccttcgg catccagtac gcgagcgcct tctggagggc    1260
ctgaatcacg gccgcgcggt cgtccttctg gcgccgcacc tgcgcaacga tgtcgcagag    1320
cgacgcctgc tttgccgcgc cctcctcgcc gttcagcagc acgtcgagct cgcgcacgag    1380
ccggcggtgg tccgccagca cttcctcgta gtcggccggc gctgctgcgg gcggctcgac    1440
aggggatgct gcggccggcg tcggcggcag cgtcaggacc gtccctaccg ggaaatactc    1500
gtgcggcagc atgccagcga attcgggatt gcacgccagg atgtgccgcc attcgttttc    1560
gttgccgcac tggcgcagcg cgatgcccat gacggactcg ccgggttgcg tcgtgtgcgt    1620
gcgcggctgc gtctcgtagg cttcgagcgc gcggcgcagg cggtaaggt ggcgcggcag     1680 tcccgccgga tcgcccatca gtaacagttc gcgggccgcg tcgataacgg cctgcccggc    1740
agtgccggtc ggtaatgtgc tcactccttt ctccagcgc tcgcgcgcgt taatcgagat     1800
tggattatag agcaatttca gcggattagg ttgatgtagc gaggagtggt gcgaaatcat    1860
```

```
caccgaaaaa gcgcggaggc ggttggtaca tttttgccac atcgccgaca gtgcgccggc    1920
tatcgcgctg aaccttcacg ggaaaatttt gcgtcggtcc aatccatcat gggcgccgtg    1980
cagaaccgcc acttcgaata agatgttgat tttgctgcgc tattggtcat ttcagctcgg    2040
ttagataatc gaaactcggt tcttttttcca caccatttcc ggccgtttcc gcttgttttc    2100
gagggtccgg tggtacatca agtggcacat cggctgtacc actcgacact gaaaggcaat    2160
gtaccaccca tgggcacgat cactacgcgc aaacggcagg acggaacgcc cgcttatatg    2220
gcacgcgtgc gcgtcaagcg cgacggcaag atcgttcaca aggagacgca gaccttcgcc    2280
cgaaagcagg ccgccgaggc gtggatcaag cggcgcgaga cggaactgag cgagcccggc    2340
gcgctggcgt cgatcatcaa tcccgaggcg acccttcgcg agctgaccga gcgctacatc    2400
aaggagctcg aggagatcaa accgatgggg cgttccagaa aggggacgct gaaggcgatc    2460
gccaagggcg agctcggcgc cctgaaggcg tccgaggtcg acgctcaggc gatcgtgaac    2520
tttgcgcgcg agcggatcgc cgaggatggc gtgagtccgg ccacggtact gaacgacttg    2580
gcgttgctga ccggactgtt cgaggttgcg atccccgcct ggggcgccaa gctcgacccg    2640
caggcgatgg agcacgcgaa ggcggtttgc tggaagatgg ggctgatcga ccgggccgag    2700
gaacgcactc gcgtgccgac gatggacgag ctcgagaagc tgatggtcta cttctacgac    2760
atggcgcggc gccggaagtg ggcgacgccg atggtcaaga tcatcgcgtt cgcgatcttc    2820
tcgacgcggc ggcaggagga gatcatcagg atcacgtggg ccgacctcaa cgaggaggag    2880
agcacgcaga tcgtgcgcga cgtgaagcac ccgcgcaaga agatcggcaa cgatcaggaa    2940
tcgcggctca cgcccgaggc gctggcgatc atcaaatcga tgccgcacac gcacgaccgc    3000
atcttcccgt acacgaccga cgcgatcagc gcgcagttca cgcgcgcgtg cgactggctc    3060
gagattgagg acttgcggtt ccacgacctg cgccgggccg cgtgacgcg cctgttcgag    3120 atgggctgga acatccccga cgtggcgaag gtcagtctgc accgcgactg aacatgctg    3180 cgccggtaca ccaacctgaa gggcaagggc gatcggtacg agggctggaa gtggacgcag    3240
atcgcgatcg atcttcctgt cgcgccgccg cggccgaaga agaagggcga gcaggtcagc    3300
gcgaccgtag ctgttgcagc tccttcgccg catcctcgcg ccgcgcatcg agatacgcgg    3360
cgaggtcggc aaggtgcacg cccttcgcgc acttctgcga gcgctccatc cgcacgatcg    3420
gcaaagtgat gtcgccgtcg agtaccttcc gctggagctt ttcggagac aggtgcgcga    3480 agtagtcgcg gcacaccaga tcgagggga tgacggcgcg accgtcgtat tgcgccatca    3540
gaaggaaagc ggtgttcatc tgtatgtctg gttcgatttt gtccgtagcg gtcagataac    3600
cgaaccacga gccggaaatc aacatccccc gcgacttccc cactactctc gttctccctc    3660
tgtccaatac cttgacatag atcaagggcc gcttgtcaat gttccctatc tgttcaggcg    3720
cggcatcgtg cgcgcgatcg cgcgcctacc agagttgatg caggcgggtg acactcaaag    3780
cccggtgatt gggcgttcgc cgtcgaaggg caattgaagc gtctcgccga agcgaggctt    3840
cacgcggtcg agcttctgaa tgaaatcgtc gtagtccgtg cttaactgca tcacggtgac    3900
gaccgaggcc aaatgctcgc gcaagcgcgg atgtccgaaa tcctcgctga gccgacgatg    3960
aagatgatgc ttcaggcgcc cgtccgacgt gcgaggcgtc gcgttttga gctcatcgag    4020 aaccttcgga gccagccgcg catagatgat gtcgttggtc aggtgcccga aatattgcgg    4080
gcgcttcaca gagtcccttg ggaagtcgag cccgcgcaaa cgaaaaagct gggcgtagta    4140
ttcattcgga aaggtctgga cccacggccg cagctcctcc gcgatgaatt tttcgaggat    4200
ttcggcgagc gccgttgcgg cccggtcgcg ctggaagccg gtggcttcat cgaccagggc    4260
```

```
gatgataccg acgttggcga gcgcccggat cagaatatcg gccgcgccga tcatccgctc    4320
atagcgagcg ggtatttcct tcccttcccg caaggtcgcg tcgcggaatc tcaggtaaac    4380
ctccgcgacc tgcggcagga gccgcgcgtc gtagcctacc cctttgccgc ccgatttcgt    4440
gcggtaaaag atcgggttgg tcgacatagc caactcttcg gaaataaagg ctttagggc     4500 atccgcctgt aagaagaagg gtagttcgtc gaccgtggac aaaacgcccg ttccggcctt    4560
cggcgatcgt gagcgcccca atacccggag aaacgccgcc tgcgtgatga tccgcgtgcc    4620
attgggcaaa actgcgcacg caatctgcgc gtcgccgagg gcaaattcgc cctcgtaatc    4680
ggcctggggc aaatccttgt tccagcgcgc aacggctccc gctcgcgcga tttctgactt    4740
cctctccggc ggcaggagca ccgcgcggcg ggctccccct attttgccgg ccttctgctt    4800
gtccatgaac tacctccatg cttggcaatt cgccttacct aatgcttagc attaaatatg    4860
tcaagcatcg catcgacgcc tgccaagcag cgcctcggtt tcgtccgggc cgctgccctt    4920
gggcaggtca ttcggcggcc tgcagaggaa gttgactgtc ctcccgaagc agcccccgat    4980
cgtcggccgg cgcccgatcg gcgggcagac ccgcggcggc ggcgcgcgcg ctcgcggccg    5040
gcgcctgcgg cgcggccact ggctcggcgg cgcgcgcctt gctcacgatg ccggccatgc    5100
gcgaggggcg gcgctgatcc tgctcggcgc gctggtcggt gacggcgggc gtcgcgggcg    5160
cggcaggctc ggccggcgcc acgatcgcgg gcgcgtcgtc gacacgcggg ccgaagtcga    5220
agcccatcgc ctcgttgtca tgctggatca cgcgttccag gcgctcgctg ctggtcggca    5280
agagcttcga gccgcgcttg atgaccgact tgattgcagc ttggtcgtag aaggttcccc    5340
acatgaggcc gttcggctgc ttcgacttac ttttcacctt ctcgatgtcg cggcggtaca    5400
tgacttcgcg ctgcacttcg ccgctcgcca gcttgacgat catgtatgcg gccttgactt    5460
ggcccggatc atcggggccg tcgtagggct catgctcgat acgtggatcg tcgccgcgca    5520
cgaacttgaa gtgatccttt tcgtacacgg ctgcggcatc gatgctcacg acctcgcccg    5580
agttgcgcat caccttgatg atgcccctca ccatcggcag gtattgcacc atcggtatcc    5640
agcgctcgac cttgcggttg ccctcctgaa cctcgacctt ggtgttgtag acgttcagca    5700
ccgcctcgcg cccatccggg aacaggccat cttgcgctgc gcgcatgcac gcgttcatga    5760
gggactggcg gtttgcgtag agcaaatcgg ggttcatctg cacgctggtc agcaccgtgc    5820
ggatgaagcg gtcgacgtcg atgtcaggcg gcagcgcctt ctcgatctcg acgcggatac    5880
cgcggttcag tttctcgcga aactcgtggt acggggtgac ttgctgttgc tgctgctcgt    5940
tactcatctt ctcgtccatt tttcgctcgg atggtcgtgc agtgcggcac cgtgccgcac    6000
tgctggttca cgtcaggcgg cggccttctt ctccgtgatc cgcacgtcgc ggtacggcgg    6060
aacggtcgcc tcgatataggccgccgggac tttgctgatc gtgatcgtca cgcgctcgcc    6120
ggcctcgcgg tcgtatgcct tgaacgtctc cttgcgcgtg ccggccgaga tattgaaccc    6180
ggccgcgcgc acggtcttgg ccgctcgat gatcgtcagc agctcggcct tcgcggcttt    6240
cttccgctcg acggccgcct tctcctcggc gccggccgcc ttgtagtcgc ggcagagctc    6300
gaacacgcgc ggattgtcgg tcaggtcgat cgtgttgccg tcgttttcga ggtacagctt    6360
gccgatcgtg tccgcgtcct tcgtgtagtt cggctctggc gacacgccgg cgtcgatgcg    6420
cgcccagaag ttcgcgacgc gctcgacgat cagcgcgccg acctcgccgt cgcgctcgcg    6480
gatcacgggc ttcggcgtgt tgccgccgac gagtggcgcg atcaggctcc agttcaggtc    6540
cgcgacctcg agctggtgct gcacctggaa ttcgatgtgc ggcggcgcct cgatcacgtc    6600
```

```
gccgtcgtcg atccacgcgc ggcggaactg aaggccgtcg acgttcttca cttccatgat    6660
gccgggcccg tggcggtcga acatctcgcg cgcgtcgttg tgctcgtggc cgggcacgat    6720
gctgacgatc ttgaagtcga acgacgagcc catgcgcagc gacggcatgc gcatgtagac    6780
cttgaagggc tcgacgatca ggccgtagtc ctctgcgatg ccggcggcga tcgcgttttc    6840
gagccgcgtg ccccacttca tccgctcgtt ctcctcgaac tccttggaga ggcggccggt    6900
cttgagctgg tgcagctcga actggtgaa gtacggcgac gcgtcgaaca gcgcggcggc    6960
ctcggtcgac gtcaggtctt tggcgcgcat cgcgagccat tcgcgctcgc tgttgaaagt    7020
cagggtttcg cggatcatct gcatatctgc tcctcggtat ggtgtcgtgc ggcactgtgc    7080
agtgctgcgc cgtgcagctc aaatgccgcg taatcgcggc acgattgcat tgtaagaccg    7140
agtggttaga ttttgcaacc gtgttttttcg gtcgcaggca gatcaaaagc gacaaatcaa    7200
caggggactt gaccagtcga gcggtgcgtt ctcgcgcgca tacgggcccg acaggttgaa    7260
cgtgccatcg cggtagccgc gcttgggcgt ggcgacgacg atcgggccgt ccgtgatctt    7320
gcacatgctg aaccggccgt aggattcggg cgacaccgag tcggtctgct ggccgaacgc    7380
gacccagccg tccatccact ccagcggcga ttcggtagtg cggaactgga tcgcgacact    7440
gccatccggc aggttcggcg gggcgtccgc gcgctcgacc agctccttcg ggttcagcgt    7500
cagcgtgcca tccttgccga taaagccgat cacgtcgacg cgcttgccgg acgtcggccg    7560
gacctctacg ccggcggcta ccgctatctc ggcaagcggg cgcccgaaga tctgtgacag    7620
cttggcagcc tcgtcgagct gcatcttgcg ctggccgctc agggttaaac tgagctgcga    7680
gtgctgcatg tccatcttct gcgcgagcgc gcggagcgat agcttccgcc cctccatcag    7740
gtcgaggaaa tacttctttt tcactttcga catccactca gttcccttct ggtctgcatt    7800
ctgcaacatt ccaatgcttt tgcaaacgga gttccttgac attgtggttc gatagtcgca    7860
ccatacgcac aatccaacca tgaaatcagc cggaaacatg gacatcacca ctgaaaagga    7920
catcacgccg gaagcggcga agcagctccg catggcgtca ggactgacgc agcgcgcgtt    7980
ctggaccagc gtggggagca atcaggcatc ggggcactgg ttcgaagtcg gcaagcgcaa    8040
gagcatcccg cgcccgatcc gcactttgat cttcctgcgc tatgtggcaa agatcgacct    8100
ggacgtcagc acgccggaag gcgcgagcgc gatggtccgc gcggggctgg aactctcggc    8160
gaagctggaa gcggatcgcg cgaaggcgg agccgaagca gcggcccgca tcgctcgcga    8220
ggcagccaag aaggtgaaga agatcgcagc ttgacgaaca tggaggcgtg gcagagtggt    8280
ctaatgcagc ggatttgaaa tccgtcatac gtgcgagcgt atcgtgagtt cgaatctcac    8340
cgcctccgcc agttttttac ccccgtcgcg acacccgcgg cggggttttt tgatgcagta    8400
ccacgttcaa ggagagagca tcatggcagg tccgaagccg ttcaatgaca cgctcgtcca    8460
gctccgtttc ggcgagctgc atagcgagct caccgacgcg atcaacgaga tcgtccacaa    8520
ggtcgcgagc acccagaagg ccggcaagct gacgctgacc ctcgggttta aggccgggaa    8580
aggcggccag atcgagatcg tcgacgagat gaaggtcacg ctgccgaagg aggagaaggg    8640
cagcacaatc atgttcgcga cgccggaagg caacttgcag cgccaagacc cgcggcagca    8700
gacgttcgaa ggtatccgct cggtcgatca ggaattgcag gcgcgcaagg aagccgcaac    8760
cgacgcaccg ctcacgccgc gcgcagccgc cgcgggcggc tgatcctcgc agtagcgcag    8820
cacccgtagt tccgaccaac ccactttaag acgacaccaa catggaaaac ctgaatgcag    8880
aaaccattct gaaggccggc acggctcctcg ccgacatcaa ggaagtcgaa ggcgtgcccg    8940
tcgccatcgt gccggaaggc tacgaggtcc gcgagctggc ccacctgctc gaacaggagc    9000
```

```
gcccgcgccg ccatcgcggc aacctgaaac tgctcgatgc tgacagcttc gtccgctacg    9060
tcgagccgca cgtggccgcc ggccgcaacg tgaacctgct gtaccgcatc gagccggcgc    9120
cggtgttcaa ggccgtgctg aacgcagcca cgcccgagtg gccggcgcac gaggatcaca    9180
ccgccacgta tgacgcgccg ctgtccaagg aatggaaaac gtggacgcag aacgacggcg    9240
aagcgatgag tcaggaaaag ttcgctctgt tcatcgagcg caacctgctg gacatcgcgg    9300
cgccgaccgg cgcggaaatg ctggagctcg caacgagctt ccaggcgaag aagggcgtca    9360
acttcgcgtc gggcacgaag ctccagaacg gtcagaccca gctcgtctac gaggagacga    9420
ttcaggcaaa ggccggcgaa aaggggcagc tcacggtgcc cgacgagatc aagctgcgcc    9480
tgccggtgtt cgagggctcg acgatcgcgg acgagctggt cgcgaagttc cgttaccgta    9540
tcgacggcgg caagctcttt atgtggtacg agctggtgcg cccgcacaag gtgctcgaga    9600
tcgccaccaa agacctgctg aagcagatcg aggaaggcac gggcctgact ggcttcaagg    9660
cgcacatcta agcaaaaccc acgcgcggct cggccgcgct taaatcggcc gcacgatcgg    9720
gcggacgccg gaacccgtaa ccggcacctt cacacatgcg tctggatata gcgcggcggc    9780
atccgcccaa tcagcccatg ccggggcacc ctcgcggaga gggccggacg cagttgtgag    9840
gggcaaccct ctggcacggc accgtgctgc acggtatggt gccgtttccg caccactggt    9900
gcgatcttgc ggcccgaccg cttttgagag tgcgcggcgg gcttaacctt caaggagctc    9960
gacatggcat ccgtcaacaa agtcatcctc gtcggcaatc tcggcgccga cccggaaacc   10020
cgctacctcc cgagcggcga cgcaatctcc aacatccgcc tcgctacgac cgatcgctac   10080
aaggacaagg cgagcggcga gatgaaggaa tcgaccgaat ggcaccgcgt cagcttcttc   10140
ggccgcctcg ccgagatcgt cgacgagtac ctgcgcaagg gcgcgccggt ctacatcgag   10200
ggccgcatcc gcacgcggaa gtggcaggat aacgccggcc aggatcgcta cacgaccgag   10260
atcgtcgccg agaagatgca gatgctcggc gaccgccgcg acggcggcga gcggcagcag   10320
cgcgcacccc agcagcaaca gcagcgcacc cagcgcaacg gatacgccga cgcgactggt   10380
cgtgcgcagc cgtcgcagcg tccgcgggcc ggcggcggct tcgacgaaat ggacgacgac   10440
attcccttct gaggttcatc atgcccgacg aaatcgatct tggtaacgag caagcccagc   10500
gcatgctcga cgcggcgatc gccgccgcac gtgtccgccc ggctatcccg gaaaatctca   10560
ccgaatgcct gaacggttgc ggcgatccgc cggcggccgg cgcacgctac tgctgtcccg   10620
agtgcgcgac ggatcacgag cagcgcatgc tcgttcgcca gcggcaggtg gacgatgag   10680 cgagatcacc cctacctttc acggcgagat gcagctcgcc ggctggtcgg agacacacac   10740
cggcggctgc aaggtcacgt tctggctgcc cgacccggcc gacctcgacg cgttccgcgc   10800
gctgaccgtg cgcaagggca acgtggccgg gcatcgcttc atggtcgcga tggtcgagat   10860
cggcgacgac gagcagcccg ttcagcagcc ggccgggccc aggcccgagc cggagcccga   10920
gaagccgaag ggcggcgcgc tcgcgcggct cgccggcatg tggtgcaacg acccggactt   10980
ctgggcgtgg ctccggtcgc aagggaataa gtgcgccagc gccgaggacg cggcagcgat   11040
cgtgcgcgac atctgcgaca tcgatagccg tgccgagctc gacagcagcg cggacgccga   11100
gcgcgcgttt caggagagca tccgcagccc attcatgctc tggcgtcgcc gggaggcgcg   11160
gtgaagaaat cgcccctcct ccgcaagacg ccgatcgcgc gcggcacgtc gacgctgaag   11220
cgcacggcgt tcgcgcgcag caccacgccg aagccgcgcc gcaccaggcc gccgaaggtg   11280
cgcgatacgc cgcgcccgcg cgtggtgccg tcgtcgctcg gcctgatcca catggggcgc   11340
```

```
gtcgccgagc tcggctgcat cgtgtgcctg aacctccggc tcggccgatc gccggccgag   11400
tgccatcacg cgcgctgctt cgccggcggc ggccagcgct cgaccgactt ccacgcgatt   11460
ccgctctgcc ccctgcacca tcggctcggc ggtgccggcg tcgccctgca cgccgggcgg   11520
cagagcttcg cgcggaactt cggcaccgag cctgagctgc tgttgcaggt gttgcggatg   11580
ctcggcttcg acatcgagcc cgaacagctc gcgcggcctg acctgggcgc gctgctgtat   11640
ccggcgcagg tagcagcatg agcgcgccat ccctcgccgc cgcgctcgcc ggcgcgccgc   11700
ggcgccgcgc gaagaagcca cgtgcgcagc ccgagttcga gatgcagaag gcgcttttcg   11760
agtgggcgcg catgccgtcc gtcgtgcgct cgatgccggg catcgacctg ctggaaggat   11820
cgatgaacgg cgtgaagctg acgacggcgc aggcgggcaa ggcgaaggca gccggcatgc   11880
tgaagggttc gcacgacgtt cgcctgcctg tcgcgcgcgg ccgctggatc ggcctatcga   11940
tcgagctgaa gcacggcgac aacatgccga ccgacgaaca gctcgcgatc ggcgcgcggc   12000
tcgaggcgga aggctggcga gtgcacttcg tctgggattg gctcgacgcc gtgaagatca   12060
tcacggagta cctgagcctg ccccgcccga atgtgattgc tttgtcctag tcggttcgat   12120
cacgatgcca tgtttcgaaa ttcgcaccac tcgcagccga atcatggcat acttcatcgc   12180
gccgcgcccg atgggggcggc gcaactcctt ggcgggagtt cattgagcaa ggctttgtct   12240
gaccccgtgc gcgctgctct gcgcgtccgc caacgcccga aagggtgacg gggcagacaa   12300
agccttttct gtttctggag gcagcatgga tgcgcaatcc caaaaccgca tcatcctcga   12360
ccacctgaaa gaggtcggcc cgatcacccc tctcgaagcg ctgcgcctgc acggcatcat   12420
gcggctgggc gcgcgcgttc acgagctgcg cgagggcggg cacaacatcg tcaccgaaat   12480
tgtcaaggtg aaggggcgca agggctcgaa gccagcgcgc gtcgcgcgct actcgctggt   12540
gaaggcagca gcatgaggcc gtccgagcat ctgctggact tcggccgtcc agtcgcgttc   12600
taccccggcc tggttaaaca cttcggcagc gtcaacgccg tgctgttctt ctgtcagatt   12660
ttctactggc gcgaccgcac gtcatcggag ctggcgtct acaaatcggt cgaggacatc   12720
gaggctgaaa ccgggctcac gtaccgcgaa caggtgacgg cgcgcaagtt gctggtcgag   12780
cgcggcgtgc tgatcgagac gccgaagcgg ctggagcacc gcatctattt ccgcatcgac   12840
gaggaccgtc tggatgcgtt gctcgcgaac tgcgaaaccc gcaattcccg aactgcggaa   12900
agcgcatttc gggaggagcg gaatccgcaa tccgataata gaacagagat tactacagag   12960
actacagcag agagacataa gcgcgcgcgc gcggctgaag gctcgccgga gttcgagcag   13020
gcatggtcgc tgtatccgaa gcgcgccggc ggcaactcga aggccgatgc gctgaaggcg   13080
tggaacgcgc ggatcgcggc cggcgtcgag tcggcgcgga tgctggacgg cgtgcagcgg   13140
tacgcggcgt tctgcaaggc gaccaacaag atcggcaccg agtacgtgaa gcaggcggcg   13200
acgttcttcg ggcccggcct gcacttcgac gcggaatgga cgctgcccgt cgtcgactcg   13260
ccgcgcatgg gcgggcgccc gtcgatgaac agcttcgacc agtcgcagcc ggacgactac   13320
gacgactttt tcgaccatcg ccgggggttt gatcgatgag gcaggctact gagctgatcg   13380
ggggcagcat caaccccccag acctacgagc gcgcgtcgac gtgcgagaag cacggcgcgt   13440
acaccgagcg cggcggctcg ctcacgggcg agctgcacaa ggcgatgtgg ttcggctgcc   13500
cgcagtgcaa tcgcgagcag cgcgagcagg aggagcggga ggaacgcgcg cgccaggagc   13560 ggtgcggca ggcgcggatc gaggcgcggc tgaaccagtc gggcattccc ctcgccttcc   13620
gcgatcgcac gttcgacaac ttcgtcgccg agacggacga gcagcgcaat gcgctcgacg   13680
tggcgcgcgc gttcgctgag aacttctgga cgaagcacct gcccgccggc gactttctcg   13740
```

```
tgttcggcgg caatccgggc accggcaaga gccatctcgc gctcgcgatc atgcaacacg   13800
tcatgcggca ctcgacggcc atgtacatcg acgcgatggc gctgatccgt cgcgtgcgcg   13860
caacgtggcg ccgcgattcc gagcagagcg aggaggacgt gctgcacatg ctcggcttca   13920
ccgtcgacct gctggcgatc gacgagatcg gcgtgcagcg cggcaccgac gacgagcagg   13980
cgatcgtgtt cgagatcatc aatcgccgct atcgcgacct gcggccgacg atcctgatga   14040
cgaacctcga cggcaagggc atgaaggaat tcctcggcgc gcgcacgatg gatcgcctgt   14100
acgagcgcgg gacgatggtg ccgttttgt ggggcagtca ccgtcgcaaa taaattccct   14160
tgccattttc ggaatatggt tagataatca caccatgttt cggaaattgt gagaggggtg   14220
ttatgcgtaa gatcatctgc gccgccgtgg cggcgcttgc ggcgaccgcc gcgcacgctg   14280
acaccggcgt gctcatcttc ggcaagagcc accatttcaa cacgcacggc cgcgcctaca   14340
acgagctgaa cgtcggcggc ggcgtcgagt ggtcgccgga tggttcgggc tggctggtcg   14400
gcggcttcgc gctgaaagac tcgttgaccc ggctcggcgc ggcggcatac ggcggctacc   14460
gcgtgcgctg cgagctcggc ggcggcttcc acgtcgaggc gaccgtgcgc gccggcttcc   14520
tgaaggatgc cgactacatc ggcccggccg ccctgcccgc gatcggcatc ggctaccgga   14580
acgtgaccgt cgaggcgacg tacatcccgg cgatcggcgg caacaaggtg cccgctgccg   14640
tggtgtgggc gcgcatcaac ttctgaggac gccatgcaca cgacctctt gcgcgatgcg   14700 ctcgagcgag acggctaccg ctacggccgc cggctcgtgc tgctcgcgat cgcaatcgcc   14760
gcgctcggcg cgctgatcgg cgccgccgtg ttcggcaatc cgtaagcaac accgttaccc   14820
ggccggctgc cgggaatttt ctgcgccgca aggcgcgcaa ggagagaacg ttggaaaaga   14880
agaaagtcga aatcgcccgt atcccgctgc ccgacgagct gggcgaggcg cttgctggcg   14940
cgctgggttt gacgccgggc gccgaacagg agccgatgcc gctcccgttc acggcggcgg   15000
attcccatca cgctcgcgcg ctgatcgagg ccgcgcgtca accgcgtttc gagctcggcg   15060
atgtcgtcgt gctgcgcccg catgcgcacg actccttcaa gtggccgcag cccggcgaga   15120
agtgcatcgt cacgcaggtg cttgagactc cggtgcgcac cgggcagcac ggctccgcga   15180
tgtttgcgaa accgggcgat tttgcgatcg cgatgatcag cccggacggc gagctcatgg   15240
agttcatgca cgacagccgc gacttcgaga aggtcggttc gatcaacaac tgacgctgat   15300
gcccggcttc gcgccgggcc cgtcgctttc tggcaaggag aaaggagtga acgaaaccat   15360
caacatagcc gatctggtga agccgaagtt cgaggtcggt cagacgctct gggaggttga   15420
tagccgcgcc ggccgcgtcc agcgcatcca gcccgtccgg atcacgtcca tcagctacac   15480
ggtcgtcatc acggacaaag gccgcgaggc ggcgctgcgc tacttctcgg acttcgccga   15540
gcacaatccc gacacgctct acacgagcct cgacgagatt ccgcaggaag atcgcgttcc   15600
gcgcgtgagg agctgaccat gctggccgcc ctgttcgcgc gcatccgcgc gcttctgcac   15660
atcgagccgc gcctgcgctt ctactggatc ggcgaggaga cggaaatctt cgtcgcccgc   15720
agcctggagg aagcgctgga agcgttcgcc cagcccgagg acatcgccga gcaggcatac   15780
ggcgaagtct cgccctaccg caccgtctgc taccgcgtcg aggaaacagg cgagacgcgg   15840
atcgagacgc tggaggagat ggcgcgcggg tgcgtcgtcc ccaacctgct gctgtcccaa   15900
tactgctgac caacagcccg gccgcgcgcc gggcgcaaag gagagagagc aatgtctgac   15960
aaccaaccca ccgcgcaggc caccgatatt gccctgcttc cgccggccga gcgcgcgctg   16020
gtcgtgctga agtcgacgga aacggaaaag cagctccgcg agctggtcgc gcgcacgtcg   16080
```

```
ccgatcagcg cgcccgtcga cgcggcgggc cgcgaggagg ttcaccgcgc cgcgatggac    16140
cacaagaacg cgcgcgtcgc gatcgagaag gccggcaagg ccgcgcgcga ggacgcgacc    16200
gcgttcagca aagccgtcat caaggaggaa cagcggctcg tcgcaatcac cgccgaggag    16260
gaaacccgcc tgttcgagct gcgcgacact tacgacgcca aggtgaagca ggagaaggag    16320
gaagcggagc gcaaggagcg cgagcgtgtg gcggcgatcc gcgagaagat cgacgcgatc    16380
aagaacctgc cgatcgactc ggcgaccgac aacgccgaga cgctcgccgc cacgctggac    16440
gacctgcgcg gtttcgagat cacgttcgag gacttcgccg agttccagga cgaagcgcgc    16500
gccgcgcgcg acgcgtcgat cggcagcctc acgaccatgc acacggcggc agcggcgcgc    16560
gaggcggccg aagcggcagc gcgcgaagcc gaggcgaagc tggccgagca gcgcgcggag    16620
ctggagcgcc agcagcgcga gctcgccgag cagcaggcag aaatcgcgcg gcagcgcgcc    16680
gagctggaag cggcgaagaa gccggccgtc gtcgccggcc cgaacgagcc cccgccggaa    16740
gtgctggacg agtgcgcgca cgactacctg cgctcggacg gcgtgtgcac ggaatgcggc    16800
acgcagtgcg cgctcccgcc tgtcggcgac gctatcccg atgcagcgat ggaacaggcg    16860
gtgctcacgg gcaccggcgc atggcggatc gatgctgacg ccagcggcga gccggcggtc    16920
gagcacgtcg acacgatgag cctcacggcg ctcgaccagc cgcgcagcg tgcggagaac    16980 gcggccgtcg cctacattct ggacaacacg ccgccgtcgc cgctgccgga gagcgaacgc    17040
cgcgtcatcg ttgagcccga gttcgcaggc ttcgacatgg cgggcggccc cgacgtgcac    17100
gtcgagatgg tgacgatcac ccgcgacgag tacgacagcc tgctgacgcg ctcgcgctgg    17160
ctcgaatgcc tggaggcggc cggcgtcgac aattgggagg gcatcgacga ggcgctgcgc    17220
atcaatcggg agcgcgtgcc ggcctgatcg ccgggccctc gaaagcagaa agccgggcat    17280
tgcccggctt tccctttttc aaccgtggtc gttctcgacc ccgcactggc acggcgatgc    17340
gtgctcgatc gcttccgcct tggatgggta gatcaggtcg ttccagaacg actgaaacgg    17400
gctcggaagg gttatcgcca gcagcagcca cgccgcgaca acagcgccc tgcgcgccgc    17460 cgggctgcgc cgcaggcagc caataacccg catcacgccc gccggcacgc tgcccgcggc    17520
gttctcacag atccacgcga acttatgcgt ctcgtcgccg atgtcgtagg cgcagccgct    17580
cacgacggca tcgatcggca gctcaaccgc tgcccgctcg aacgccagcg tcacaatgtc    17640
gcgcacgcgc acatcatcca tatcgagcag ccgcgcgtgc gcggggaacg tcgtcgcgcg    17700
cggcactttc tcgatcagct tcaggctgtc caccccgttc ctctgccgct tgatgacgac    17760
atgcaccatc tccccgccgc tcgcggcaaa gcgcagggag cttgatgatg acggaataga    17820
ttcgcccatg atcttatta cctctgcccg tagttttgtt gtattttcag caccatgata    17880
cgattttcgc accagcgctc aggcgtgcga tgacgaccgg ccatcccttc ctgcggggga    17940
ttttgcagcg ccgcacgccg aattcaagac acattctagg aaaaattggc atgtccaccg    18000
accaaaaagc cacatcacaa agtcgtcatg gggcggcaga gatcacgccg aagcagcagg    18060
cattcgtcga cgaatatctg atcgacctga acgccacgaa ggccgcgatc cgcgccggct    18120
acagccccaa gacggcacag gaacaatcct ctcgcctgct gtcgaagccg cacgtgcagg    18180
ccgcgatcgc cgaggcgaag gcgcgccgcg ccgagcgcac cgagatcgac caggatcgga    18240
tcgtgcgcga gctctggaac gtgctgaccg ccgacgcgaa cggcctgatc gagtatcgcc    18300
gcacgtgctg tcgctactgc tacgcaaggg atcaccggtt ccagcgcacg gccggtgaga    18360
tggagcgcgc gaagatcgag caccgcgcct tcgtgctgaa gtgcaagcag gagggcgtca    18420
agctgaccgt cgccgagcag acgttcgacg agcaaggcgg catcggctac gacccgcgca    18480
```

```
agccgcccgt cgacgattgc ccggagtgct tcggcgaggg ctacggcgac gtgttcgtga   18540
aggacacgcg caacctgtcg ccggagctgc gcagcctgta cgccggcgtg aagcgcacga   18600
aggaaggcat cgaggtcaag atgcacgaca agcaggggtt cgtgcagctc ctcatgcgcc   18660
acgcgggcat gctcaacgac aagctgaagc tgcaaggcga cccggagaat ccgatcgcgc   18720
tgctgctgaa gcaggtgcag ggctcggcgc tgaagccgac cgcgcagccc gatgacgacg   18780
aagaataaaa ttactttgta atttctccgg gatggttcta taatcgaacc gtgcgttaag   18840
gaaacgcgac caccaaggag aaaggacatg aaccgcaccg agtatcgcag cgcccgccga   18900
ctgatccgcg acaacggccg cttcgcgctg cgctggctgc cggccgagca gcgcgacgcg   18960
atggaccgca tcatcaccga gcgcgacagc accgacccgc tcgccgagcg cgccgacatc   19020
atcgcctact gcgcgcgcga gggcatcgcg tgcaacgtcc gccacaccgc gccgcgccgc   19080
gcgctcgacg agtacatcgt cggcggcgcg gtactgaccc gcgacgagta tctggcgcag   19140
accgcgcgcg agtacgacgg ccgcgagacg cactgaccaa cccagccagc tacggcgggc   19200
actcaccacc taccacgacc atgaaacagc tctacaccaa ggccggcctg cggatcgtcg   19260
gcacgaagga agtcatcaac gccacggcgc tcgtgtccgg gttcgacgac cacggccagc   19320
cgatctacgc cggcagcacg gacctcgatt gggacagcca gctctcggaa accgacgaaa   19380
agggcaacta catcctgatc gacgaggacg gcgaggagca ttcgcccgac gagtgcgagc   19440
tgcgcgacgc ctgaccaccc cgcccgcccc gcgcgggcac ccaccccaag gagaaaggag   19500
atggaactga aagacgcctt caacggcgac aacgcggcgc tgatccgcag catcaaggcg   19560
ctgttggagc tggacgcggc cggcgtgctt cggacgcacg gcatcggaga gcacgcgcgc   19620
agcctgctcg cggcagccgc agagcagctc gagacggcag cgggcgagca cgatgaactg   19680
gtcaagctcc gcgccgccac gttcatgccg ccgcccgcgc aggatggcct catcatcacg   19740
cgtgccgagc acactaccga cgacgcgaag ggctatcagc actaccacgt cgagctcaac   19800
ggtcgcgacg gaggccggtt gccgcacttc tacgccctgc gcgtcgtcaa gacgctcaac   19860
gcgggcagcc tggacgcacg cacggccgat cacttcgccg cgatcgagcg ccgcctgctc   19920
gccggcaacc cggtggaggc atgatggaca cgaccaagac cggcgggccg gcgttcccga   19980
tcgcggaccc gttcgcattg cgcccgcgcg acgagacgga gctggagcgc atcgcgtccg   20040
gcatgtcgct ccgcgactac ttcgcggcga aggcgctcgc tggctggatc gcctcgactg   20100
aaccgcagcg caatccggtt gaggtcgctg acaggatcgc ggccggctgc tacgcgctcg   20160
ccgacgccat gctccgcgcg agggaggcgt gatgctgcac atcgaccact ccctgacgct   20220
tcgcggcaac aggacgccga cgcagagcgc atgcgactgg aacgacgagt cgcccgcga   20280 cgcgggctac tgcatcgacg cgccgctgtt ccttcccgga ggctcgacgc ttcgcttcga   20340
cccggagaag gacgacctgt tctcgcccct tcgccgcgacg agcatcgcgc atcgctgatc   20400
gattacattg ttattgaaag ttatccacaa ccccggccaa aggccggact tatccacaag   20460
gagcaaagag catgaagcga attctttccg ctgccgcatc ccttgcgcgg cgagcgcttc   20520
cgtacgttgc gccgtctctg tcggcctaca ctgagtgccc ccgcgcggcg ccccgaaga   20580 accgcatctc ggtcgcgcag ggcaagcgcg cagccgcgaa ggcgcgcaac gtgaagcgcc   20640
acaaggcggc gatgcggcgg gcagcatgag ccgcgtgatc gagccgtccg acgactggcg   20700
cacgcgcggc ctgacgaat ggctgggcga ggttcgcccg ctgacgcccg aggagctgcg   20760
ccagcaggaa gaagcgcggg aggaccgcgt agactgacca catgcccgcc tcgcgcgggc   20820
```

```
gcaggagatc gccgtgaaaa ccgagttgaa gctgctgcac gtcatcattc cgctgctgac   20880
cgcgtacctc gaatacacct gcgtgaatcc gtggatgccg cccgagcggc ggatttgggt   20940
ctaccggcgc acgtcgacc acgcggcgat caccctgctt tgaccaacct gcccgcctcg   21000
cgcgggcttt ttcgctcacg ggcgcgcggg cgccgagcag attcttgcga tgcgccgcgc   21060
tgccgagaga aatgatcttg ctgagaatga ggagaaagga gtgaaactgt tcgcactgat   21120
cggcatggct gccgtgttca tccaccttgc cgccgcgttc ggcctgatcg acgtgcgcct   21180
gtgcatcggc gcggtcggca cctgcaaccc ggtcgacgcc aagccggcgg cgcagaagcc   21240
cgcgaaggtg acggtatgac ggtctacgtc gacgacatgt acctgtaccc gatcggcgag   21300
tacaaggcgc cgttctccgg ccgcaccatg aagatgtcgc acatgatcgc ggacacgcat   21360
gaggagctgg tcgagatggc acgcgccatc ggcctgaacc cgcgccatat ccagaagcgc   21420
gacacgcacg gcgagcactt cgacatctgc ctgagctatc gcaagcgggc gatcgcggcc   21480
ggcgccgtgc agatcaccat gcgccagtgc tcggcgatgt gcatccgccg gcgcgtcgca   21540
ggcgagctcg ccagccgga ggacgccgag gcatggcgtg aggcgcatgc tgccatgcgc   21600
cgtgccgccg catagccccc acccgaatcg gtaagttccc agcaacccccg aatcagctag   21660 tctcgccgcc cgttggggag agactagcaa tgaaaaacgg tgcggttcgg cggctacagt   21720
cggatgccaa ggcgactatg gcctgtcagg acaatttggc gttcatgcgt ccgctcaaga   21780
gcggctcgat gcagctcgtc gtgacgtcgc caccctacaa catcggcaag aggtacgaaa   21840
agcggtcgcc gctggacgcc tacgtgcagg cccaggcgca ggtcatctcc gagtgcgtgc   21900
ggcttctcag cccgcacggc tcgctctgct ggcaggtcgg caatcacgtg cagaaaggcg   21960
agatattccc gctcgacacc gtgctctatc cggtctttcg cgagcacggc ctgaagctac   22020
ggaatcgcgt ggtgtggcat ttcgagcacg gcctgcactg ttcgaaccgc ctgtccggcc   22080
gctacgagac gatcctctgg ttcaccaaga ccgacgacta cgttttcaac ctcgacccga   22140
tccgggtgcc atcgaaatac cccggaaaga aatacttcaa agggccgaag gctggtcagc   22200
tctcctgcaa tccgctggga aaaaacccag gcgacgtgtg gattttcccc aacgtcaaga   22260
acaaccacgt cgaaaagacc gaccatccat gccagttccc ggtcgagctg gtcgagcggt   22320
tggtgctgtc gctgaccgag cccggtgacg cggtgctcga cccgtacatg ggcgtgggct   22380
cgtcggtcgt cgctgccctc aagcacgacc gcctcgggta cggctgcgac gtcgtgaagg   22440
agtacgtcga tgccgcctgg gagcgcgtgc accggcttcg cgccggcaca ctccagacgc   22500
gccccatgca caagcccgtc tatgacccga cgcagcccta tggtgggcac cgcagggttg   22560
gccgccggcc agagcgcggc agcgctccgg agctcgcgct gctctcaccc cagcgggatt   22620
gaggtcgtgc ggatcgtcga gcactactcg catctcaacg gcctcgagtt cctgctggtg   22680
cacaagccga agctctggaa agagattcag gaggtcatca agaacgtcga cgcgacaaag   22740
ttgcggacaa agcagtcgaa agaaacgcgg tcgatgggcg aaatgctcta ttcgccccga   22800
gcgatgaaca aggcgatcga cgagggcttc gcgcggcata agtggggcga gcggcgcatc   22860
tcgtattggg tcacgtccga cgcccgcctg atccgcaaga ctctgttcat gggaccggat   22920
cagcaaaagg ccgagatcga aggcgccgga aagaagccgc tggcgtccta caaccagacc   22980
gatttcgtga aggagcgcgt cgccgtcgag gtgcagttcg gcaagtacgc cttcgtcgcc   23040
tacgacctgt tcgtgaagca tctggcgttc tacgtcggcg acgtgatcga cgtcggcgtg   23100
gaaatcctgc cgatgaagga gctccagcag cagatgtcat cgggcgtcgg ctactacgag   23160
ggcgagctgt acaacctgat ccgcgaaggc cgcggcgtgc cggccgtgcc actcatcgtg   23220
```

```
atcgggatcg ctccgtaacc tgcccccaat cctctgtcgc ctcgcggttc actgcgaggc    23280
tcaggggatt ctttgttttc cgccagtcgt cggacggccc cgagcggtac gtcgagccgc    23340
gtcgcttcga cacgacgccc tcggcgccca gcgcgcaggc atgccggaag atggtcgggc    23400
cgtccccgat caggtgctcg ttgaaccgga tgccgtgcgg cgcgcgcgca agcagccgct    23460
tcaggcggtc cttgcgctcc tccagctcga cgcggcgcag gtccgtgcca tccagttcca    23520
tcaggtcgaa cgcgtacagg agcgcctcgc cgtcgtgccg gcgcgagcgc agcagctcga    23580
acacggccag cccgtcgcca tcgcagcaga cgacctcgcc atcgaggacg aacgaccggg    23640
cgcgcagcgc ggcggcgcac gcgaggatct gtggataccg cttcgaccag tcgtgcccgt    23700
tgcgcgtcag cagccgcacg cgctcggcat cgcgggcgac ctgaaggcgg aacccatcgt    23760
gcttgagctc gtgcagccag tcgggccggg ccggcggtgc gctggcgggt ttcggctggc    23820 agggggataat gaagcccgaa gtacgccggg cggaacgctg gagcatgcca gcgagatagt    23880
gacgcggacg cgctgatgcc agtggcgccc gccgggcgct ggccgggctc ttctcagtgc    23940
tgtacagtgc gacacaacac cgtatagcac tgccgccgat gaccaccgca tcaaccctcg    24000
aacacgacga cgcgccgctc accgaggagg agctggcgcg ctgcctgtcc gaccctatgt    24060
ggcgcatctg ctcggggcgc ctgtacaaga tcatcatcaa gggcgacgac caggacgacg    24120
acgacgggct cgtgctgccc ttccggccga accgcgcgca cgccggctc ctgcgccgcc    24180 tctggcaccg caacgtcatc ctgaaggccc gccagctcgg ctttaccacg ctcatctgca    24240
tcatctggct cgaccacgcg ctgttcaacg ccaacagccg gtgcggcatc atcgcgcagg    24300
accgcgagac ggccgaggcg atctttcgcg acaaggtgaa gttcgcctac gacaacctgc    24360
ccgaggcgct gcgcgaggcg atgccgctcg ccaactgcac gaagtctgag atgttgttcg    24420
gccacaacaa cagcagcatc cgcgtcgcga cgtccgtgcg cggcggcacg atccaccgcc    24480
tgcacatctc cgagttcgga aagatctgtg cgaagtaccc ggacaaggcc aaggaggtcg    24540
tgaccggctc catcccggcc gtgccgaagt cgggcattct ggtcatcgag tcgacggccg    24600
agggccgcga gggcgagttc tacgagatca cgaagcgggc cgaggcgctc gaccagcaga    24660
aggaccggcc gctgtcgccg cgcgactacc ggttccactt ttatccgtgg ttcgaggagc    24720
cgaactaccg catggacccc gccggcgtcg tcgtgaccga aaggacgcc gagtatttca    24780 cgcaggtcga ggcgcgcatg ggcgtgacgc tcgatgccga gcagcgtgct tggtacgtcg    24840
ccacgcgcga cgcagactt tccggcagcg aggagcgtat gtggcaggaa tacccgtcca    24900 ccctgaaga accgttcatg gtgtcgaccg agggcaccta ctacgcgcag cagctcgccg    24960
cggcgcgcaa gcaaggccgc atcaagccgt ccctgccgt gctgttcaac gtgccgtgct    25020
tcacgttctg ggacatcggc aacagcgacg gcacggcgat ctgggtgttc cagcgcatcg    25080
agcacgagtg gcgctgcatc cgattcaagg agggctgggg cgagccgtac agcttctacg    25140
tgaagtggct ccaggagctc ggcctcgtgt gggacacgat gttcctgccg cacgacgccg    25200
accacgtgcg tcagggtcag acgaccaaca agagcccgaa gcagatgctc gaggagctga    25260
tgccgggcgt gcgcttcgag gtcgtgccgc gcatcgagga cgtgaattgg ggcatccagc    25320
agacgcgcga cgtgttcccg ctgatctggt tcgacgagac ggaatgcaag gacggtatca    25380
tccacgtcga gagctaccgc cggaagtgga acgagcgtca gcagacgtgg ggcagcgagc    25440
cggacaagac cggcggccac tccgaagcgg ccgacgcgct gcgccagttc gcgcaggcgt    25500
acaccggcgg cctcatcaac gtgcgcaagc ccgcatcgaa gaagcgccga cagggtagct    25560
```

-continued

```
ggcgcgtagc ctaaccaacc gaaggagaga gcatgaccat cgaagcagcc cgccccgcca   25620
tcgacctcac gcgctacgcg ttcgtgcgcg agctcggcga catccgcctc tacggcacct   25680
ggttctacga cgcggagctg gacgacgacg agccgtgtct ggtactggtg ccggcattcc   25740
ggtcgcacgg tgtcgtgccg tgctgtgtag cactgtcggc cgctttccga tacactgatc   25800
cgcgccatct ggcggcggtt tcgctgcaat tcgcgaagga cttggggttc gacggcaaca   25860
tcatgagcgc ggcacacaag atcggcggca tcatccacga ccacctgctc gacctcatca   25920
agatgccgga gaacccgacc gaggcagtcg tcggcgcaac ggcgaacgtg gacttcggca   25980
acgggcgcaa gcgcacggtc gagattctgg accatgtacc cgtcaagcaa gcctgacatc   26040
gccaagcgcg ccgagtgcgc cgccgccgtg gtgatcctcg tgatcgtcgc ggcggtctttt  26100
ctcgtccgct gggcggcatt cacggcccctt tacgcactgc gcgacgcgcg cgatcggagt   26160
gacacttgtt caacctgaat gacagcgaca gcacgcagct cgtgccggcg cgcaccgacg   26220
agcgcgatcc gagccccggc gagcaagcgc cggcccagcc cgccgacgag ctcgacagcg   26280
agaaagcggt cgagctgcac gggcgcctcc tctcctacta ccggcaagag ctttcgcgac   26340
aggaacctaa tcgggccgag atggcaaccg atgaggacta ctatgacaat atccagtgga   26400
cgcaggacga gatcgaggag ctgaaggagc gcggacaggc gccgaccgtc tacaacgtca   26460
tcgcgcagag cgtgaactgg atcatcggca gcgagaagcg cggccgatcc gacttcaagg   26520
tgctgccgcg ccggaaggat ggcggcaagg ccgccgagcg caagaccgcc ctgctcaagt   26580
acctgtcgga cgtgaaccac ctgcccttcg agcgctcgat ggcgttcgag gatgccgtga   26640
aggccggcat cggctggctg gaatcgcagg tgcaggacga gaacgacggc gagccgctgt   26700
atgccggcgc cgaaagctgg cgcaacatcc tctgggacag cacctaccgg cgcctcgaca   26760
tggacgactg ccggtacatc ttccgcgtga agtgggtcga cctcgacgtt gcggtcgcca   26820
tcttcccgaa ccgccgggcg cagctcgagg cggcggccgt cgacaactac gagacgtggg   26880
gcgcggacga catcgacggc gacgacgcga tggattcgag cgagtacgag cgctcgatga   26940
acaacgtcgc ggcgggcgcc gtgacctacg cgcgcaagcg cgtgcgcatg atcgaggcat   27000
ggttccgcat gcccgtgcgc gtgcagcgcc tgcgcgggcc gcgctccgac ttccgcggcg   27060
aaatctacga tccgaacgac gagcggcatc aggccgagat cgcgtccggc cgcgccgtgc   27120
tcgccgtgtc gccgatgatg cgcatgcact gcgcgatcat gaccacgcgt gacctgatct   27180
gggcgggccc gagcccctac cggcataacc gctacccgtt cacgccgatc tggggcttcc   27240
gccgcgcgcg cgacggcatg ccctacggcg tgatccgctt catgcgcggc atgcaggacg   27300
acgtgaacaa gcgcctgtcg aaggcgctct acatcctgtc gaccaacaag gtcatcatgg   27360
acgagggcgc ggtcgacgac atcgaggagt tccggcgcga gcggcgcggg ccggacgccg   27420
tgatccagaa gaagcagggc aagcagctcg agctcaacgt cgaccgcgac ctcgcgccag   27480
cgcatctgga gctggcgtcg cgctcgatgc agatgattca gcaggtcggc ggcgtcacgg   27540
acgagctgct gggccggtcg acgaacgcgg tgtcgggcgt cgcgatccag gcacggcagg   27600
aacagggcag cgtcgcgacg aacaagctgt tcgacaacct gcgcctcgcc ttccagcagc   27660
acggcgagaa ggaactgagc ctcatcgagc agtacatgac cgaggagaag cagttccgca   27720
tcacgaacag ccgcggcaac ccggaatacg tgacgatcaa cagcggcctg cccgaggacg   27780
acatcacgcg cacgaaagcc gacttcatca tcgatgaagc cgagtggcgc gcgaccatgc   27840
gtcaggcggc cgtcgccgag ctgttggagc tgatcggcaa gatgccgccg cagatcgcga   27900
tcgccatgct cgacctgctg gtcgaaaaca tggacatccc gaaccgcgac gagctcgtga   27960
```

```
agcgcatccg cgcgatcaac ggccagaaag acccggacca ggacgaaccg acgcccgagg    28020
aaatccagcg cgagcaggcg cagcagcagg aacagcagta tcaggatgct atggcgctcg    28080
ccgcgctgcg cgaggcagag gcgaaggccg cacgcgccga ggcggaagcg atcaagaccc    28140
gcgcatctgc gcagcacatc cagaagcaga ccgtgcgcga aggcgttggc gccatcaagg    28200
acgcaaccga cgcagccacg gcgatcgctt ttatgccaga attggcatcg ttgtcggacg    28260
gcattctgag ggaatccggt tgggatgacc cgaacacgcc gcaaccggca gcagcagcga    28320
gcggcacgcc gcccgcgtcg gcgcagcccg cccaacccgc gaatcctgcg caaccgcccg    28380
caccgggcca agcagcatcc gaagcgcagc cggcgctccc ggctaacccg cctcaaccgc    28440
ccggccctgt cttgccggac ggcgcggcac cccagcaacc cctgcaacag tgaggatcga    28500
atgagcggcg aacacagcga agaacttttg agcggcctga ccgacgagga gcgtgcggcg    28560
cttcaggagg acgacggcgc ggacgataag accacgctcg gcgacagcct gcgcgggaac    28620
gaaggtgcca attctggcac caacgacgac gacgacgacg cgaacaaggg cggcgacgac    28680
ggcaagggcg gcaagacgga cgacgcggcc acgacgggca agaccgacga cgccgctgcc    28740
gctgctgctg ccgcgccga cgacgcggct ggcaagaagg gcgaaggcga aggcaacgac    28800
gatgcggcgg ccgacacggg cgcgaagccg atcgtgccgc tgctcgtcgc cgacgcaccg    28860
gccgatgccg acgcgaagct gaaggagatc ggcgacaaga aggccgagct cgtcgagcag    28920
ttcgacaacg gcgacatcac ggccaaggag taccagaccc agctcgacgc gctcggccgg    28980
caggagcgtg agctggagcg cgcgatcgac aaggccaaga tcgcgaccga gatgaagcag    29040
cagcaggaga tgaacgcgtg gctcggcgag gtcaacgact tcacgcacaa ggatcaccc    29100 gagtacagca agagccgcgt gcgctggacc gcgctcgaca cgttcgtgaa ggagattgcc    29160
gcgaagcccg agaacgccgg cctgtcgggc aagcagattc tcgcgaaggc gcacgagatg    29220
gtcgtcgcgg acctcggcga tgcgccggcg ccgcgcgcgg acgccggcgg gaagaaggac    29280
gagaaggacg gcaagccgct gaagggctcg aagatcgagc cgccgcctac cctcgccaag    29340
gtgccggcgg ccgagaatca ggacgtggag ggcggacgct gggctgcgct cgatcgcctt    29400
gccgaaaccg acccgctcga gctcgaggag aagctgatga agatgtcggc tgacgatcgg    29460
gacgcctacc tcgccgcgcg cgccgcgtaa ggagccatca tggggaacta cactttcagc    29520
atcacggccg catcgaaagc ggacgcaaag accgcaatcg cggccgagtt cgaccggaag    29580
gtcggcgccg atccgctcgt ctcgcgggcc cgcgcagccg tggtcgcgaa cgcgggcgcg    29640
gtcatcgacc tgcttggcga cgacgacaat gccgacgtca ccgtgcagtg ctcggtgttc    29700
aactacgcgg cggatgacgg cgaaggcggc cagatcgcgc gctcgggcgg tgtgagtgcg    29760
ttcgccaatc atgtcgcgcg gccggtcgtc gtgctgaccg aagccgactc gctggccgac    29820
ctgaacggca cgccgcggcc ggacaatccg accgtctaac caacagggga ccgcatgctg    29880
aagctggaca tcaaaccggg cgagagcgtg aagatcggcg acatcgccgt gattacgctc    29940
gaggacaagt caggcaaggt cgcccggctg tccatccagg cggacaagtc ggtccccatc    30000
acgcgcaccg ctccatccac ggcagcgcag atcgcggcga aggtcggcct gtcggccgac    30060
gccgcgtagt caccagaccc cgaagccgcg caacgcggcg aagatcagga tcgcaaccat    30120
tccgaatagg gcaagtcgca cgtgcacggt tggcttcatg gctggttgcc ttttctaacc    30180
acctgttcga taatcgggcc aactgcgcg caggaggtgc caaggtgatc gttcaacaac    30240
tttcatcgag gccctactat gccgcaaacc gtcatcccct tcggcgatcc gaaagccgtc    30300
```

```
aagcgttggt ctgccgacct cgcggtcgac gtccgcaaga agtcgtattt cgaacagcgc   30360
ttcatcggca cgtccgagaa cagcgtcatc cagcgtaaga ccgagctgga atccgacgcc   30420
ggcgacacca tctcgttcga cctctccgtc cacctgcgcg gcaagccgac ctacggcgat   30480
aaccgcacgg aaggcacgga agaaaacctg cgcttctata ccgatcaggt gaagatcgac   30540
caagtgcgtc accggtttc ggccggcggt cgcatgtcgc gcaagcgcac gatccacaac   30600
atccgccgca tcgctcgcga tcgcctcggc gactacttct acaagttcac ggacgagctg   30660
ctgttcatct acctgtcggg cgctcgcggc atcaacctgg acttcgtgga aacgccggac   30720
ttcaagggct cgccggcaa cccgctggaa gccccggacg tcgaccacct gctgtacggc   30780
ggcgccgcga cgagcaagcc gagcctgacc gccaacgaca tcatggaccc gatggtgatc   30840
gagaaggcgg tcgaaaaggc gtcgatgatg caggccgaga acccggaagt cgccaacatg   30900
gtgccggtca gcatcgacgg cgacgaccac tacgtctgcg tcatgtcgga gtatcaggcg   30960
accgacatgc gcacgcgac gggcgggcgc tggatcgact tccagaaggc agcggcggcg   31020
gccgaaggtc ggaacaaccc gatcttcaag ggcggcctcg gcatgatcaa caacgtcgtg   31080
ctgcacaagc accgcaacgt gatccgcttc aacgattacg gcgcgggcgc caacgtcgag   31140
gcggcgcgtg cgctgttcat gggccgtcag gctggcgtga tcgcctacgg caccgcgaac   31200
ggcctgcgct tcgattggga agaaacggtg aaggactacg ggaacgaacc cgccatctgc   31260
gcaggcttca tcgccggcat gaagaaggct cgtttcaaca acaaggactt cggcgtcatc   31320
tcgatcgaca ccgcggcgaa gaagcacagc taatcgctgg ccggcacggg ccgccttcgg   31380
gcggctcacc cttaccaccc tgactgaacg aggtatccat catgtctctg ctgcaaagcc   31440
tttgggcgac cggccagcgc aacacgccgt atggcgactg cgcgggcgat gaagtcgtgc   31500
aggtgttcga gttcacgatg ccggcgaccg cgccggccgc gggcgacatc atcgaactcg   31560
ccgtcctccc ggcgacgcac acgccgaccg acgcgattct cgtgtcggat gcgctcgaca   31620
cgctcgctgt cgacgtcggc atcatgtccg gcgaggtcgg cgacaaggac gcggcgcgca   31680
cgtgcggcaa ggaaattttc gccgctcagg ccgtcgacgg caccgtcgtg cgcacgacgc   31740
tcgcgtccgc cttcacgatc ccgccgaccg acaatcaccg ctcgatcggc gcgaaggtga   31800
cgaccgcacc gggcgcctcg gtcgcgggca agaagctgcg cctgctgctg aagtacgtgc   31860
cggcgtaagt cggcgtccca cgccggggc ttcggccccc ggactgcctt tgaggagagg   31920
agttcatgaa gatcgaatgt atcttgcatc gcaagggcgg caccttcgtt gagatgccgg   31980
gcaagaccta ccatttcgcg ccgacgccgg acgatgaacg ccatctcgcc gacgtcgaca   32040
acgatgcgca catcgagcgt ttcctgtcga tccgcgaggc ataccgcatc gcgcgcacgc   32100
cgggcgcgga agccgtcgag acggacgcga ccgcactgct cgcggcacc gtgccgccga   32160
tcgatagccc gccggccgtg accgtcgacc cgagccagct caaggtcgcg ggcgccacgt   32220
tcccgccgtc gttcaacatc aacggcaaga cctactcgct caccgacgtc acgctgcgcg   32280
cgtttcagga ttccggcctg acggtcgagg actggaacgg cctggacgac gagcaccgcg   32340
cgaccaagac ggaaatcgtg ctcgacgcgc tcgaggacgg cgagatcacg atggagccga   32400
gcgcaccgat cgaggcgccg acgccgggcc ggtcgacga gcgcgccgcg ctggtcgccg   32460
cgtacaccgc gaagttcggc cataagccgg cggcgaacat caagatcgag acgctgaagg   32520
cgaagctcgc cgaggctgcc gagtaacgcc atgccgatcg ctgccgccga cctgatcgca   32580
cgcgccgggg aaatcctcca ggacgaggat cacatccgct gggaagtgcc cgagctgctg   32640
cgttggatca acgacgccgc gcgcgagacg atcgtgcgtc ggccggcggc gcggtcggtc   32700
```

```
gcgacggtgc tgccgctcgc ggcgggcacg cggcaggaga ttccggcgcg cggcgtcgag   32760
ctgctggacg tcgtgcgcaa catcggcgcg gacggcacga cgcccggccg catcgtgcgc   32820
cgcgtcgatc ggcacctgct cgacgaccag aacccggatt ggcacgcggc gcggccgaaa   32880
aacgtggtga agcacttcac gttcgacgag cgcgcaccgc gcatcttcta cgtctacccg   32940
ccggcggtcg ccggcacgaa ggtcgaaacg ctccattcgg agctgccgcc cgacgtcaag   33000
gaggacaccg actcgctcga catgggcgcc gagtacgtga acgtgctcgt ctcgtacatc   33060
tgctaccgcg cgctgtcgaa ggacagcgag ttcgcgaacg gcacggtcgc cgccctgcac   33120
tatcaggcgt tcgtcgacgc ggtgtcggac aacaaccagc agaccaccgc taactcgccg   33180
aacgcgaacc acgtatgacc gacctcgacg acttcctcac gaaggttctg ccgttcgctc   33240
cgggctgccc ggagccgact gcgtttgagc acatccgcgc ggcggcgcgc gacttctgcg   33300
agacgacccg gctgtggcgt ttcgacgaca cgttcgagct cggcgacgat ccgaacgtga   33360
tgtgcacgcc gcaggatgcc gtgatccacg agattgagcg gtgcgacttc aacggcaaga   33420
agctcgaccc cgcttcgctc gactggctcg acgaccgcta tcccgactgg cgttcggaaa   33480
cccagctctg gaccggtcag ccgcaattct tcacgcaggt gtgcccggac acggttcgcg   33540
tcgtgcccgc gccgctcgag caaggatctg tgaaggtctg gttgcgcctg aagccgtccg   33600
aggactgcga gcagcttcct gacttcctgt tccgcgagca cggcacgctc atctcgtggg   33660
gcgcgctcgg cagcatcctg atgcttccga accagacgtt ctccaacccg aaccaagccg   33720
tgttctttca gggaaaattc gacaacgccc tcgggcggaa atcgaagctc caggcagccg   33780
ggcagcagcg cgcgcccgtt cgtaccaagg cgactttctt ctaaggaggc atcatgtccg   33840
ccgcatccga ctacaccgaa aataacgtca tcaacgcgct gctgcgcggg acggcatttc   33900
cgctgccgaa caagacgttt ctgtcgctgc acactgccaa tccgggcgag acgggcggca   33960
atgaagtctc gacgagcgta tggccgtcct acgtccgcaa ggatgccgag gtcggcggcg   34020
cgatcggctc gggctgggcg ccgccgaaca acggcacgac cacgaacgcg aagcaggtgc   34080
tctacccgtc gcacaacggc acgtcggcgg tcacgatcac gcactttgcg atctacgacg   34140
ctgtaaccgg cggcaacatg ctctgctacg ccgcgctcaa cacgccgcgc acgctccagc   34200
ccggcgacgt gttcgtgttc gacgtcggtt cgctgaccgt ccagatgctc taagcgcatg   34260
aacctctacg cgctcaacga aaccccgatc aacgggtggg ccacgcagca gggcttcggc   34320
caagctgcga tgtcgctcgc cggatcgggc gtgagcgcga atgtggctct cggcggcggg   34380
tttccgtcgc ttattcttca gtcgagcggc aacgggacgc ggcgcgcgat gggcggcggc   34440
ttcccgtcgc tcgtgcttca ggtggccggt gacggcacgc ggcgcgttcc cgcggacggc   34500
attgccgtgc tcgagctggg cggcgatggc gacggcaaga tcgcgaaggg cactggcggc   34560
cacgcgacga tgatgctgac gtggccttac ggtcagggcg gcatcatcgc gcacgctggc   34620
ggcgccgcga cgctcgagct aaatgcgacg gctgaaggcc gcgcggcggc agggcggcac   34680
ggcttcgcgg acacgtacat gatgctgttc gccgatgggc gggcccggaa cgtccagcct   34740
gtcaaaggcg gcgccctcgc cgaaatgtgg ctgtacccgc gcggcgtgcc gcatctggtc   34800
acgcagaacg gcggcgagat cgagatgatg ctgcgcgcgg cctcgcgcga gcgcgtcggc   34860
aatcacgtgc atggcgatgg cgcgatcgtc atggcgctgg agctgctgcg cgacgaggcg   34920
cggcagtatc ggctcgtcga gggctccggc tcgctcgcga tggcgttggc cctcgccgcc   34980
cgcgacgcgc gcgtcgtcgt cgtgccgtcg accatctacc cggcgccccg tgcgcgcggc   35040
```

```
atgcgcgtcg accatgaaaa ccgtgcgctg cgcgtgcccc gcccgcagcg cgagctcgat    35100
atcgcggagg cataatgctt ggcatcttca tgaagcgtcc ggtcgatcag ctcgactacg    35160
acatcgattt ttcgcgctgg ctcgcggacg gcgacacgat cgcgagcgcg acggccgccg    35220
tgcagccggc cgacagcatg gtcagcgccg cgcaggtcat caccgagctg gaaaccgtca    35280
aggtgtggct cgtcgacggc gtgagcggca agaccgcatc catcatcgtg accgcgacca    35340
cggcccagcg ccgtgtgaag caggtcgagt ttcagcttcg agtgcgcgac tgatatgagc    35400
ctgaaactga ccaacaacgc cgtgagcaag ctggcgtcat cagttgcggc agacgccacg    35460
actgtcgctg ttctccccgg cgatggcacg aagtttcctg cgctcgccgc gggcgactgg    35520
ttccccggca cgctcatcaa ggtcgacggc tcatcagaga tcgtcaaggt tacggcgcga    35580
gctatcgact cattcacggt cgttcgcgct caggagggta cggcggccct cgacttcaac    35640
gcaggtgatc gcttcgagct ccgcatcacc gctttcgccg cccagaacac cagcgatatc    35700
gcgccatccc tggcgaacct ggatcgcacc gtcaatctcc gctcgctgta ccagattttc    35760
gacctgctcg agccgatcgg gaccgtgaag tattgggaca cgacgcgcc gccccgccc    35820 ggctacttca tctgtaacgg ccagaacggc acgcccgact ggcgcgaccg cttcatcgtc    35880
gtcgcaggcg ccagctacgc gcgcggcgcg accggcggcg cgaacaccgt gacgctcgcg    35940
cccgagcaga tgcctgtcca caatcacggg ctgcacgatc cgggccacgc gcacggcgtc    36000
gccgatccgg gccacaatca ctacgtcaac gatccgggcc atgcgcacgg cttcaaggtc    36060
gtcgcataca gcattgacgg cggcggttcg gggcaactca ccggcggcgg ctaccagtcc    36120
ccgaacgatg gcgaattcaa cggcgtcacg aacggcagcg gcacgggcat ctggctcaat    36180
ggttcgggga ccggcatcag catctacggc tccggcaccg gcatctggct cgacaacgcg    36240
ggcggcgggc aggcgcacga gaaccggccg ccctacgtcg caatcccgat catccgcaag    36300
atggtcactg ctctcagcac tctggggtaa cttatggcac tgaaactcgc gaacaacgca    36360
gtcagcaagc tcgccggtgc ggtcgcgcg aacgcgacga gcattgcggt cacgcccgga    36420
gacggcgcga agtatccgac gcttagcgcc ggcgactggt ttccgctcac cgtggtcaag    36480
agcgacggtt cgctcgaggt catgcgctgc acggcacgca cgacggacac gctgactgtc    36540
tcacgtgcgc aggaaggcac ggccgcgctt gcgttcgcag ccggcgatcg cgtcgagctg    36600
cggttcaccg cggcggcggc aatgtcgttc gcgtcgctca ccggcgccca atttactggc    36660
gacgtgtctg tctactcgca ggcgaacgat actgtcggcg cgatctcggc gagttcgtac    36720
agcggcggcc tgtcgatcga ggcgttcaac agcggcaata cggcaaagaa gaacatcgtt    36780
atcgccggct ggggcgggcg cgtgctcgtc ggcaatggcg ttactgacga cggggccagc    36840
aagctgcaag tcaatgggga catcacgaac gccaagggct cgttttattg cgcaaaagat    36900
ggagccactg tgcgccggct gatcggcttg gaggctggtt ccagccacgt cgacattcag    36960
aactcggccg ggcagcgtat ccggtttatc aatcaggcgt acaacgcaga gctcggctgg    37020
atcgacaacg gcggaaactt ctggaccgct ggcaatatga gcgcgttttc cgaccgtcgc    37080
gtgaagtcga acatcaagcg gatcaagggc gcgatggcga aggtgcgcga gctggtcggc    37140
gtgacgttca cgcggcgccg ctcgaaggac aagagccggc atatgggatt catcgcccag    37200
gacgtcgagc cgatcgtgcc cgaggtcgtg cgcaccgacg agaagggcat gaagtcgatc    37260
gcgtacccga acctgaccgc gctcctcgcc gaagcgctga aggagctcga cgatcgcgtc    37320
gcggcgctga agtccaacca atgaccatcc ccacgtctgg agggctcgac ctcgctcgca    37380
tcaagttcga gctcgcaatg gacgggctca acccgcctgc caacgacatc aacaacggct    37440
```

```
ggtttcgctt gctggcaaat cgccaaggcg atcggcagcc gatcgacttc ggcgcgttcc    37500
gcgggcgcgg ctgccgtttc gacggctacg cgggcgtcta cgatccgaca ggcggcgggg    37560
gcgagatgtg gcaattcgac ccgcgcatgc cgttctttaa tgccacgctc gcctctgtcc    37620
agatggtgtt tcagcggcag gcgcggcgct acgacgcgct catcgaaatg tggggcgatc    37680
cgggatcgcg ggtgccgatc ttcgttcaaa atggcacgac cggtatcgcg tatcggttca    37740
cctattcggc cgacggcacc tactactaca tgaacaacat cgacgccaat ttcatgcgct    37800
atggtagcgg cgactggttc atgatcgtcc cggatatgcg gtaagatacg ggcgtgccgc    37860
accgggattc tctcctctct ccttgcgccc gccggcaccc atgatgacca ccccctcgca    37920
catcgtccgc tcatcacgct gaagcctccc gctcaaggct tccgtgtggt ttcgacgatt    37980
gcgagggatt catggctctc aagctctcca acaatgcggt cggcattctc gccggcacgc    38040
ttgaccccga cagtacgatg ctcgcgctgc aacccggaca gggtgccgcg tttcccgttc    38100
tttccgctgg cgactggtgc cccggaacac tggtgcactc gacgggtggt gtcgaggtcg    38160
tgcgcgtgac cgcgcgcagc aacgacagct ttaccatcga gcgtgcgcag gaaggcaccg    38220
cgccgcagca gttcaacccc ggcgaccgct tcgagcatcg gctcacggcg ggcgcgctga    38280
tgtcgatcgt cggcgacgtc gacggcctgt cggccgcgtt cgcgcggatc aagccgcgcg    38340
tcggcgacct gaaaatgtgg tcgggcgcta tcgccgacat cgcggccgtg catggtccgg    38400
gctggtatct ggcagacggg cagaacggca ccatcgacct gcgcgacaag ttcatcgtcg    38460
cggcgggcgg ctcttacgca ccgggcaaca ccggcggcgc cgcaaccgtc gcgctgaccg    38520
cggcgcagat gccgcagcac aatcacggcg tcaacgatcc cggccacgcg cacggcgtga    38580
gcgacccgac gcacgcgcac agtgtctacg atccgggaca cacgcacggc cacaacacgg    38640
cggcgctgac gccctcgagc acgggcggcg gtgcattcca gatcaacggc tatgccggcg    38700
gcacgatcaa cgcggcagct accgggatca gcatctacgg cgccggcacg ggcatcagca    38760
ttcagggctc gggaacgggc atcagcacgc aaaatgccgg cagcggcgcc gcgcacgaaa    38820
accgcccgcc ctactacgcc ctcgccatca tccagtacgt gggagcctga ctatggctct    38880
caagctctcg aacaacggcg tcgggtttct ggctgccgcg ctggccgcca acggcgatac    38940
gatcgcgctt cagcccggac aaggcgaggc gttcccggtc cttgccgccg gcgactggtg    39000
ccccggcacg ctcgtcaacg cggccggcca cgtcgagatc gtgcgcgtca cggcgcgctc    39060
cgacgacacg ttcacggtgc tgcgcgcgca ggaaggcacc caggcgcttc cgttcgttcc    39120
gggcgatcgc ttcgagcacc gcctgaccgc cggcacgctc acggcgatgt caacgcccct    39180
gacggcggct atcaagcaga ttcggccgcg cgtgggtgac atcaaggtgt ggcgtggcgc    39240
gatcgcggac atcgcggcgg tgcacggcgc cggctggcag ctcgcagacg gcacgaacgg    39300
cacgaccgac ctacgcgacc ggttcatcgt gggcgccggc acatcgtatg cgccgggcac    39360
gacgggcggc gccaatacgg tcgtgctcgc gcgacccag atgccggcgc acaatcacgc    39420
ggtatccgat ccgggccatg ctcacggggt aagcgatccg agccacgcgc atagcgtcta    39480
tgacccccgg cacgcccaca acacgtactc gaactactat aaccttggcg ctcagggcag    39540
cggaacggtg acgccgtaca acgggagtgg tcaggtcgtg tccggcggcg ccgtgctcac    39600
cggctacacc ggcatcggca tctatggcgc ctacaccggc atcgcgatcc aaggcgctta    39660
caccggcgtc agcacccaga acgcgggcgg cggggcagcg cacagaaacc ggccgccgta    39720
ttacgcgctg gcgttcatcg agtacaccgg gattggagcg gccgaccctc tggcatcttg    39780
```

-continued

```
acaggctgac gcccttggtg tcgcactgtg ccgcactgta caatgcggca gacgcgttcg    39840
catcgagggg tttgcatgac catcatcaag atcaccgggt tctcgggaga atcccgcgc    39900
cttgtgccgc gtctgctgcc cgacaccgcc gcgcagaacg cgaccaatgc acgcctggaa    39960
tccggcggcc tctcgcccta ccggaaaccg aagttcaccg cgcggatcag cgacatcccg    40020
gccggccaga tcaagaccat ctaccgcgac ggcccgacgt ggctggcgtg ggataagccg    40080
gtctacgttg cgccgggccc ggtcgcgacc gatcgcctct acatcttcgg cgacgggccg    40140
cccaagatga aggtcggcgc gatgacctat cccctcgccg tcccgatgcc gagcgccgcg    40200
ctgaacgccg cgacgagcgg cacgggcacg ggcgacgtgt tcacgcgcgt ctacgtctac    40260
accttcgtga ccggcttcgg cgaggagtcg gaaccctcgc ccatctccaa tcaggtgaac    40320
tggcaggccg acagaccgt caccctctcc ggctttcagg cgccgccggc cggccgcaac    40380
atcacgaagc agcgcatcta ccgctcgcaa acgagcctgt cgggcacgga tctctatttc    40440
atcgccgaac gtgacgcatc tgcggctaac ttcgtcgata atgtgccatt gacccagcaa    40500
aacgagccgc ttccgtcgct ggagtggaac gcgccgcccg acgacctgac cggccttatc    40560
tcgctgccga acggcatgat ggccgcgttc cgcggcaagg agctctggct ctgcgagccg    40620
tggcgcccgc acgcgtggcc cgaaaagtac gtgctgacga tggattacaa catcgtcgcg    40680
ctcggcgcct acggcacgac gatcgtggtc gcgacggacg gccagcccta catcgtctcc    40740
ggagcgtcgc cggacaccat gtcgcaggaa aagctcgagc tcaacctgcc gtgcatcaac    40800
gcgcgcgggc tcgtcgacct cggctatgcg atcgcctacc cgtcgcacga cggcctggtt    40860
gtcgcctcgt ccgccggcgc gcgcgtcgtg accgaccagc tcatgacgcg caacgactgg    40920
ctgaaaaccg cgcccgaccg gttcgtgtcg ggccagttct tcggccgcta tctcgccagc    40980
tacgagtaca tcgacccgtc cgggcaggcg cggcgcggca gcttcatcat cgacctgacc    41040
ggtcaggagg cgttcctgca ccgcacgaac tacaaggcgg atgccacgtg gtacgacatc    41100
agcgacggca agctgtacct ctgcatgggg caggacatct acgagtggga tgcgctggac    41160
agtgaaaacg aaatcctcgt ctggcgctcg aagcagtacg tcatccagaa gccgaccaac    41220
ttcggcgtga tcctgatcga aggatctgtg ctgctgacgc ccgaggaaga agcggccgaa    41280
caggcggcgg ccgaggcggc caaggcgtac aacgaaagca tcttcggcga cgccagcatc    41340
ggcggcgagc tcaacggcgc cgcgctcaac gtctatccga tcaacggcga cgcgctgaag    41400
cggctcgaaa ccagccgttt cgtgtcggcg accgtctacg cggacggcaa accggtcgcg    41460
accgtgagca agctcaaccg gatggcccgg ctgccgtccg gcttcctcgc gcagacgtgg    41520
gaggtcgagg taagcgcgaa gcggacatc gcgcaggtga cgctcgccgg caccggcgca    41580
gaactggcag gagtgtgaca tggcacgtgg cgacctcaac gcaagtcaga ccggcccgaa    41640
ttcgcgcggc gacgcgctga ccgaccgcct cgtcgaaacc tcgatcattc gggtgctcgt    41700
caacaagttc ggcctgtccg agcgtaccgt gcagtcgatt caggagctcg ccggcctgcg    41760
cggtcagctc acgacggat cgcgcccgcg cgaggccgtg cggcacgagg acttaggcgc    41820
cgtctcgcgc atgagcgaga tgaagtcgaa gcaggtcagc gggccgccga ccgcggccga    41880
cttcaacgcg ctgcgcgacg acgtgcgcat gctgtacgag gcgatgcgca cgatcgccca    41940
gcgtctttaa tcgtgtccgc agtggtgcga aaaagctaga atggtgcgaa tttcttaccg    42000
cgacgcgcta tgaaccgact gatctacgac gacgaggaca ggctgctcgc atgggcgaag    42060
gatcgcattg gcgtgccggc gttccggccg gatgcgcgcg cgatcggtca ggagcgcaac    42120
ggcgagctga atgcggtcgt ggtgttcgac ggcttctcga ccgtcgactg caacatccac    42180
```

```
atcgccagcg acggctcgcg ccactggctg acgcgtgagc ttctggccgc cgcgttcgcc    42240
tacccgttca tccagtgcgg attgcggcgc gtcaccggtc tggtgccggc gcggaacgtc    42300
gaagcgctga agttcgacga gcaccttggt ttccggcgcg agggataccg cccgcgcgcc    42360
gctcacgatg gcgacctcgt gtcgctcggc atgctgcgag agtggtgccg cttcatcccc    42420
ccggagtccc gacatgcttg aaaatgccat ctgggccggc ctgatcgccg cgctgatcgt    42480
ctacctgctg ccgttcctgt tcccgccgat cgacacgcag gctgtcacgg tcgacgggtt    42540
cgagctgccc gtcgagcgcg agaagcccgc gcgcaaggca tgggaggagt acgttttctt    42600
caagaaggac gccggcgacg cgccgccgcc cgacccgaac atcggcaagg ccgcgctcga    42660
ggaaatgcag ctcggccgcg acttcctcga cttctcgaag tctcagttcg acgtcgcgag    42720
cgcgcggcag gccgagctcg acgagctgac gaggaaggtc acggaccagc agctcgcgac    42780
gcaggatcag gcgaatgcgt gggcccgcga ggaccgccag cggtacaagg acgtgttcca    42840
gccgctccag gaccagttca tcgacacggc caaaaactac gacagccccg agcgtcagga    42900
gcagatggcc gccgaggcgc aggcggacgt gcagcaggcc gcgaagcagg cgaacgaagc    42960
caacacgcgg cagatggcga gcatgggtat caacccggcg agcggccgat tccagggcgt    43020
cacgcgcgca caggacacgt tgacggcgct caactcggcg ggcgcagcaa acaccgcacg    43080
tcagaacgtt cgctcgacaa ggcgctcgct ct gcgggcggac gcgatcaata tgggcaacgg    43140
cctgccgtcg caggcagcat cgtccgcggg gctcggcctg aacgccggca actcggcgac    43200 cggcaaccttt ggcgcatcga acgcgaactt ccgcgcgaac gtcggcatca tgggacaggg    43260
ctacaccggc gcgatgcaag gtctgcaagg cggcgcgggc gtcctcaacc agcagtacag    43320
cacccaaggc agcatctggg ccgcgcagca gcaggcagcc gcacaaaact cggcggggct    43380
tatgggcggg ctcggcacca tcgcaggtgc gggcatcatg gcttttaag gagagagaac    43440 gtgaaagaga tcatcgagcg gcacgagcgc atcgcactgc aattttccgg cggcaaggat    43500
tcactcgcgc tgctgtactt catgcggccg tattgggacc gcctcaccgt ctactggctg    43560
gacaccggcg acagcttccc ggaaacgcgc gagctcgtcg agcagatcga gcgcacggtt    43620
ccgcgcttcg agcgcatcga gggctgccag ccggccgtga tcgagcagtt cggcatcccg    43680
tccgacatcg tgccggcgaa cgcaacgccg atcggcatcg cggcgaaggg ctcgcgcgtg    43740
ctgatccagg accgctactc gtgctgcatg cgctcgctga tgctgccgat gcacgagcgg    43800
atgaaggcgg acggcatcac cctcgtgatc cgcgggcaga aggcgtccga caagatgcgc    43860
gcgccgatca agtcggggca cgtcgaggac ggcatcgagt acctgttccc gctcgagggc    43920
tgggacgaca gccgcgtgtt cgcgtttctg cacgaacagg gcgtcgcgct gccgcgctac    43980
tacgaggtca tgcgcgcgtc gccggactgc atgacgtgct ccgcgtattg ggaggacggc    44040
cgcgccgcgt acctgaagca ctaccatccc gaggcgtatg aggagtacca gcggcgcctc    44100
aacgcgatca gcgacgccac ggccgaggcg atcgtgcact tcaacatgga aatcggtggg    44160
taatcatggc gaactacggc atcggtatcg gcgcgttcgc gcaagggctc gtgcagggca    44220
tggcgctcgg caagcagttc gcgacgcgca agaagcaatg ggacgcggaa tcggcgacca    44280
aggacgcgat ggacgccgcg aaagctgaac gcgaggacga gatcaaggcc gaacaggcgc    44340
gcatcatcgg gttgggaccg caaggtccgc aaggcccggc cgcgccgccg gcgccggacc    44400
ctgctgccgc gccggccacg acgcagcccg tagacatgag cacgccgacc gcgacgcccc    44460
tgcccgcgca gcagcccggc gcggcgccgg ccgccgcacc tgccacgctc gagccgacgc    44520
```

```
ccgcgcccgc gcaatcccca cagatccctc ccgaggcgac gcagggcacg ccgatggccg   44580
acagcggcag catggcgccg cgccgacgc ccgccgcggc ggtcagcgcg gcgcgcgcga   44640
tggacgcgcc cgcgcgcggc ggcacgaccg catcgatcgc ctcctcgccc gccgtcgcgg   44700
cggcgacgcg cggcatcaac ggtggcgagc cgatgacgga cgcgcaggcc cgcgcgctcg   44760
ccgagaagaa ggcgccgagc gtgatggact tcttccgcaa gaagggcgtg ccgaagatcg   44820
ccgaaacgta cctcgctcag ggcgacccgg ctaaggcgca ggcgtggatg gattgggccg   44880
agcagcagga cagcaagcgc aacatggcgc tgtgggcgaa ggcatggcgc gcgacgcaga   44940
tgggcgacct cgagggcgcg gccgatcact tcatggacct gtacaagagc tacgacgacg   45000
gcgtgacgcc cgtgtccaag gaggtcgtga aggacaagga gggcaacatc accggcttca   45060
acgtcaagct caaggtcgac tcgacgggcg aggagcgcac cagcttcatc gaccgcaatc   45120
agatgctcga aatgggggctc gccgcgctgt cgccgccgca gatgttcgag atggcgtgga   45180
agcgccagca ggagcaggac aaggtgaagg cgcaagccgc ggcagaggtc ggcaaggcaa   45240
agctgaagct ggcgaccgac acggcgctgg agggcgtgcg ccagaagggc cgcgaacggc   45300
tcgaggacaa gcgcgcggag aacaacctgg accgcgacgc gcaaaaggcc aagctcgacg   45360
cggagacgcg ccggaacaag gtgcaggagg agctcgacgc gaagatcgcc gcactgaaga   45420
acggtgggta ttcggaccag ttcatcaacg acgcgctgcc ctcgatcctc ggcatcaacg   45480
agtacaagcg ctcgacgtcg ccggaggagg caaagcgcct cgccttcgct gaccggatga   45540
agaacgaccc cggattctcc cgcaagagcg tcgacgagca gcgcgcgctg atcgatcagg   45600
atatggcgat catctacggc gggatgaagc cgaccgatgc gccgcgcggc gcgcccgctg   45660
cgcccgccgg tgcatccggc gccggcgcga agcccgccgc gcgcggcctg cccgtgctcg   45720
acacgaaaac cggaaagatc gtctaccgat aagccccttt ccctctggtt tgatcgtcgc   45780
accattcgtt atagaatcga accactgcgc cgattgatac cagaggggag ctcgtggcta   45840
aaaatctgtt cctgcaaacg ccgtccgccg gcgacatcga agatttgttc accgaaggcg   45900
cgaacgacat ttcgcgcctt tctctgccga gcttccccgg tgctcccgcg accagcacca   45960
cccctgcccc gcaacaaacc gccgcgccgg cggcgcctga cactgctgcg cctgcgccgg   46020
ccgcacccgc cgcgccgggc cgcgccgcgc cgacgcgcga tgacctgatc cgccgcgcgc   46080
agcagctcgg catcgacccg aagctcgcgc tcgagattca cgggctggag tcgtcgagca   46140
actggaacag caaggacagc aacaagggcg cggtcggcgg catgcaggtg atgcccgaca   46200
cgtacaagat gatgatgggc acctatgccg gtcagcgcga tccgtggaac aacatggagg   46260
ccggcctgcg ctacatcgcc tacggcatga agaagctggg gacgtccgac ccggcgctgc   46320
tggcggccgg ctatcagtcg ggctacgacc gcgcctcgct gaagcgcggc gaaatcccga   46380
atacgacgga cggcggcatg acgacgcgcg cgtatgcggc gcggatcgcg agccgcgtcg   46440
gcacgggcgg cggcacgggt aacagcgcgc tcgacctgca atcgcgcctc gatgcgcagg   46500
agccgggccg ctacaaggtg ctcgactcga ccgaggcaag ccggctcgac ctgcaatcgc   46560
agctcgacca ggaggagccc ggccgcttca aggtgctgac gcagcaggag ctcgacaagc   46620
tgccggccag cgcgttcacc gaccttgcca aggacgagac gccgaaagac gcatcgctct   46680
ggggcgacgt taccgacgtc gccaagaacc tgaaggtcgg cttcaacatg gccgcgcagg   46740
acgtgcgcga gctcacgagc cgcgttccgg tcgtcggcaa gccgtcgtg cgggctatgg   46800 acgccgttga ccgctggacg cacccgcaaa acacgggcga cctcatcacc ggcaaggcac   46860
cgatcaagga ttccgacgac ctgctgaagc gcgataccgc cgccgtcgtc gcgggcatga   46920
```

```
cgccgcagat gcgcggcgcg ctcgagaaga agtggtggga cgacgagaaa ggcaccttcg   46980
ggcccgcctg gaaggactgg cgcagctacg cgggcggcct gctgcaatcg ctgcccgagc   47040
aggccgtcac gatggcgccg ggcatggtgc tcgcgaaggc cgcctatctc gcgaaggtcg   47100
gtcaggtagg cgtgcaggcc gcatcggcgg cagcggcgcg cacggcgatg atctccggca   47160
tgctggccga gggcagcctt ggcggcgcgc agtccgcgcg cgaggtccgc gaccagatca   47220
atgaactgaa gcctgaagtg ctggcgtcgt ccgaggcgtt ccagcagctc aaggctcagg   47280
gcatgaccga cgagcaggca cgcaccgcgc tcgccgatga catgtcgacc cgcgcgttcg   47340
tcaccgctgg cgttgcgacc ggcctgttcg gcggcatggg cgaccgcgcg ctcgcgaaga   47400
tcgtcaccga gaaggtcagc aagagcacgt tgaagcgcgc attctctggc gccgcgcgca   47460
gcgcggttgc agagggcgtg ctcgaggagc tgccgcagag cgcgctccag caggtcgcgc   47520
agaacgaggc cgtgcagcac gccgataaga atgtgtcgct cggccgcgac gtcgcgaacc   47580
aggcgctcgg cggcctcgcg atcggcgcc tgcaaggtgg cggcatgggc gctgtcggcg   47640
gcgcgcgcaa cctgaaccgc ggcggcgtgc cgggtggcga cccgtggcc gaagcggcgc   47700
cgcagccggc cgcgcccgcg cccgccgcgc cgaccggccc gatcggccgc gcgatggagc   47760
gcgccgccgg cgccgcgccg gagcagcaag ccgcgcaacc tgccgcgccc gccgcagagc   47820
gtgtcgtcgt cggcgacgac ggccagcaat accgcctgac gaccggcgag gacggcgtga   47880
cgttcgagcc gatcgccgag gaggcggcag cgcccgacgc gcaacagccg gcagcgaccg   47940
cgccggccgc tgaagccgcg ccggcgcag ccgaggagcg cgcgcccact gtcaaggaag   48000
cgatggacgg catgggcggc ggcatcgtcg atgccctcta cgatcatctc tggcagcgcg   48060
tcgaagccgg caagaccaac gagcaggatg gctgggcgcc ctcgcccgtg ctccaggcgg   48120
cgaaggtgct gcgcaatcag ggcgtcgagc tcacgcgcga cgttccccc gacttcgcgc   48180
ggaagctcga caacgcgatc gagggcaaga agggcgccga gtatcaggcc gcgatccgcg   48240
gcgtgatggc cgagtacgcg ccgaagaatg ccgcgcccgc gccggccgcg cccgagacga   48300
agccggaaac gaaggccgcc gcgcccagcc ccccgcgcc gaaggctgcc gagcgcccga   48360
tgaccgactg gagcgagacg gagctgcgcg accgcctgcg ctacctgacg aagcaggcca   48420
agacgaacgg cggctggaac aagatgctca cggccgagcg cgccaaggtg tcgcgcgaga   48480
tcgaccgccg caacgagggc gcgcccgcgc cggccgagcc cgtgaccgcc gcgccgatcg   48540
agcagccggc cgaagaagcg ccgccgacga ccgcgagcgg cgcgtatctg gatcgcggcg   48600
acgcgaaccg cgcggcgatc agccgccgcc agcgcgaggg ccgcgtgttc acggtcgtgc   48660
cccgcgagga ggacggccgc accgttttcg acatcaaacc gcaggaggcc gccaatgctg   48720
gaaccgatgc aggtgcaaat cgggctggtg ctgatgcaca ggctcgcgca tccgttcaat   48780
cggagcccga gcccgctgcc gctcaacccg gtagcgcgag cgcttcggct gaacctgctg   48840
ctggagctgt caccgccggt gagcaatcgg ctccagtaaa ggacgcgtat gccggcaagt   48900
ggttcggctc gcgcgagaag gcgcaagcct tcctggacaa gaagaaggcc ggcgcgacgc   48960
acgagatcgt gcagacgggc aaggtgcggt tcgagatcaa gccgaaggtc gccgaaggca   49020
tggagcgctt cccggccgag tccggcacgc tcggcattcc gcgcgatcag atgccgcagg   49080
tgccgacgca atcgcacggc gggctcgtca atcacctgaa cgcgcagggc atcgagcacg   49140
aaacgaagat ggtgccggcg gccgacctga agccgacgca ggccgagttc tcgcccggga   49200
aggtcgcgca ggccaaggaa gcgaccggcg accgcgccgt gatcgtgtcg aacgacgggc   49260
```

```
acatcatcga cggacaccat caggcgctcg ccgcggccga ggaaggcaag gacgtcaagg      49320
cgatcgtgct cgacgcaccc gtcgaccagg cgctcgaggc ggtgaagaat tcgccgagcg      49380
cccagcaggc ggcagacgat gccgcgggcc gctggagccg cgcgaccgac accgagcgaa      49440
cggcattcct cgcgcgcgcc ggctacgtca acgacggcaa gctgaacctc gccggccgcc      49500
ggctgctgcg cacgccgctc gaccagatgc gcccgtcgac gcgcggcaag atcgagtccg      49560
ccatgcagat cggcgccgcg ccggccgaag ccaatgcgcc gcgtgccgca acgccgggcc      49620
ccgacacgat cggccgcatg aatgcggttg tgcgcgcgaa atccgtgtcg gagctcgacg      49680
agatcgcccg cgcggaggaa gccgcgtgga acgcgaccga gaagcccgca gcctcgcacg      49740
aggccgcgca tgcggagctg atgcgccgca tcgagcggaa gcgcgagacg ttgcaggaag      49800
ccgaaccggc ggccgagcgc gacaacagtt cggccgcgaa acaagccgcc gcgcgcgact      49860
tcgtgcgcgc cgctcgcgag aatggcgcga agaagatcgc ggacatcatg ccgggcatca      49920
aggatggtcg gacgttccag accggcgccc cgttcgtaaa gcccggtttc atcatggtgg      49980
acggcccgaa gggcgagcaa ttccgccttg ccgatctgtg gaaagcgacc gagccggcgc      50040
cccgcgcaga ggccgccaac gacgccgcgc cgaccgagcc gacgccgccg accggcaccg      50100
accggttcgc cggcaacaag ctgttcacgt cggacaaggt ggaagcggcc cgcgcgcgcc      50160
tgcgctcgaa gctctccggt gcccagctca acagcggcat tgatcccgaa gttgtgatgg      50220
acggcatgac gatcgccggc gcctacatcg aggccgcgt gcgtgatttt gccgcatacg      50280
ccaaggcgat gaccgacgac ctcggcgacg ccgtgaagcc ctacctgctg tcgttctggg      50340
aggcggcccg caactacccc ggcctcgaaa ccgaggcat gaccagcgtg caggagtcga      50400
agcgcctgca cgacgagctc attgcgtcgc aatcggcatc gtctacaatg caatcgaagg      50460
aggttgctca aaatgacgga aacgcaactg ctggagctgc tgacgaaagc tctccagaac      50520
aaggcgccgg acgcgtatcg ccggatgaag gcggacggga cgctggacgc gttcctgagc      50580
aaccttctgg cgacgacgct ggaggcgatc agcgaggcgc ggcaaagcgc gatcggcagt      50640
ctcgtgacgc agggaagccc gcagttcgag gagcaacccc tgaaacggac gcaggcgatc      50700
aacatggccg agaagtcggc cgaggagatc gcgctggcg aggcgatgga aacgatcgag      50760
gcgctgtcag ccgagtcggc gacgactacc gcgtaaagcc gggcgagctg aagcgcaccg      50820
gctcgtggcg ctcgaccgcc gagcagaacg tgcgcatcgt cgagctcgtg aagcagctcg      50880
agcaggaagg ccgccggccg acgccggacg aggccgcgct gctgacgaag ttcacgggct      50940
ggggcgcatc cgagatcgcc aacggcatct tccccgaccg gtacggccgc tacaaggatg      51000
cggcatggca ggcgctcggc gagcggctga aggccgcgct cacgcctgag cagtacgaac      51060
aggcgaagcg caccacgcag tacgcgcact acaccagcga gggcgtgatc cggtcgatct      51120
acgacggcat gcgccgcctg ggcttcgccg gcggaaaggt gctcgagccg ggcatgggta      51180
tcggcctgtt caaggggctg atgcccgaaa gcatggccgc gaccagccag tacaccggcg      51240
tcgagtacga cccgctgacc ggcgcgatcg cgaagctgct gtatccgcag agcaacatca      51300
tcgtcggcga cttcacgaaa accgcgatgc cgcgcgagtt cttcgacgcg gcgatcggca      51360
acccgccctt cgcgtccgtc gttgtgacca atgaccccga gtacaagaaa caggggttca      51420
tgcttcacga ctacttcttc gccaagacca tcgaccgcgt gaagccgggc ggcatgctcg      51480
tgttcgtcac cagcaagggc acgatggata aggcgagcga ccgggcacgc aagtacctcg      51540
ccgaccgcgc caacctgatc ggcgccgtgc ggctgccgca gaccgcgttc aaagacaacg      51600
ccggcacgga agtcgtgacc gacgtgctgt tcctccagaa gcgcgggccc ggcgtggccg      51660
```

-continued

```
acaacggcgt gaagtggctc ggcacggccg aagtgcagac gccgcagggg ccggcccaga   51720
ttaacgagta tttcgccgcg cacccggaaa tggtgctcgg cgcgcacgct ctgaccggca   51780
gcatgtaccg cgccaacgag tacacggtcg tgcccgagcc gggcgtcgac atggacgcgg   51840
cgttcgcgaa ggcgatcgcc aacctgcccg agggcgtcta tcagccgggc gcgcagaacc   51900
cggccgcctc gaaggctgtc gcgctcgaac gcgacttcaa cccgacccac aagaaggagg   51960
gcgggctgta cgtcggcgat aacggcacgc tgatgcaggt cgacagcggc accggcgtcg   52020
agctgacgca ccgccgcggc gcggacggca agcagatcgc gctcaagccg gccgacaagg   52080
cgttcctgaa atcgtgggtg ggcctgcgcg acgcgctgaa gcaggcgcag ctcgaccagc   52140
tctcggacgg cgcatgggaa cagtcgctca aggcgctgtc tgacgcctac gacggtttcg   52200
tggcgaagca cggcaacctc ctcgcctaca gcacgatcga gcgcacggcc gacgacggca   52260
ccgtgaccgt gacgaagcgg ttcaagaacg atccgctact gcgcctggac gtcgacggcg   52320
ccctcgccta ctcgctcgag cacatcaagg agaacggcga gatcgtcaag gcgccggtcc   52380
tgtccgagcg cgtgctgcaa cggccgcgcg agcccgagat caagacgacg cacgacgcga   52440
tgttcgtgtc gctcaacaat aaaggctcgc tcgacctcga cgacgttgcg cgcctgtcga   52500
acatgagccg gcaggaggtc atcgacgcgc tcggcaccgc gatctacgag gacccggcga   52560
agggctggca gacgtccgac gcgtacctgt cgggtaacgt cgtgcgcaaa ctcgccgagg   52620
cgcaggccgc ggcgcgcagc gaccgcaagt accagcgcaa cgtcgaggca ctgctggccg   52680
tgcagccgaa gccgctcggc ccgagcgaca tcacggtgaa gctgggccag aactggattc   52740
cggcggccga cgtcgccgtg ttcgcgagcg aggcgctgaa cgagaacatc gacgtcacct   52800
acaactcgcg gctcggcaac tggtcggcag agcagaccag ctccaactat tcggagttca   52860
acaccccgaa gatgaacgcc ggccagatcc tcgacgcggt gctgaacaac cgtcagatca   52920
aggtcacgtt ccgcgacgat cagggcaaaa cgcacgtcga cgcggaggcg accgagaagg   52980
ccaacgacgt cgcgcagaag atgcgcgcgg cttcgcgcg ctggatttgg acggacacga   53040
agcgcgccga ccggctcgtc aactactaca acgagaactt caacaacatc gcgccgcgcc   53100
agttcgacgg ctcgcacctg acgctgccgg gcgtatcgct gcgcttcgac ctgcgcgaga   53160
accagaagcg cgccatctgg cgcggcattc aggaaggcga tatgtacctc gcgcacgctg   53220
tcggcgcggg caagacgttc acgatgatcg cgacgggcat ggaggagcgt cggctcggcc   53280
tgtccaacaa gccgatgtac gcggtgccga accacatgct cgcgcaattc gcgcgcgagt   53340
tccttgagct gtacccggcc gcgaacatca tggtcgcgga cgagcagaat ttccacaccc   53400
acaaccgccg ccggttcgtc gcgcaggccg cgctcaacaa cccggacgcg atcatcatca   53460
cgcactcggc gttcggccgc atcggcatgt ccgacgagta cgcctcggcg ttcatccgcg   53520
accagatcga cgagtggaaa gccgcgctcg acgagacgga caagggcgac cgcatcacgc   53580
gcaagcagat cgacgccgc atcgagcagc tcgagcgtcg gctggaggcg aaacagggcg   53640
gcgagaagaa ggacaaggtg ctgtcgttcg aggagctggg cgtcgaccgc ctgttcgtcg   53700
acgagttcca cgagttccga aaactcgact tcgcgacgca gcagagcaac atcaagggca   53760
tcgacccggc gggctcgcag cgcgcgatgg acctgttcat gaaggtccaa tacctgcgca   53820
gcaagaagcc gggccgcgcg ctcgtggccg cgtccggcac gccggtcacg aacacgatgg   53880
gcgagctcta caccgcacaa cgcttcttcc agcccgagca gcttgccgag gatggtctgg   53940
atacgttcga cgcgtgggcc aaccaatacg gtgacatcgt tgcgggcttc gagcagaacg   54000
```

```
ccgccggcgg ctacgaggtc gtgagccggt tcgcgaagtt ccagaacgtg cccgagctga   54060
tgcgccgcgt gcgctcgttc atggacatcc tgacgagcca gcagctctcg cagtacgtgg   54120
atcgtccggc gatcgagggc ggcggccgtc agatcatggt cacgccggag ccgttcggat   54180
acaaggcgta ccagaaggcg ctcgagcagc gcatcaccgc gatccgcaac cgcaaggggc   54240
cgccgcagaa ggggcaggac atcatcctga acgtgatcgc ggacggccgt ttctccgcga   54300
tcgacatgcg cttcgtcgac ccgaccgcgc cgagcgaccc gagcagcaag ctgaaccaga   54360
tgatcgacgc cgtgatcgcc gactaccatg cggcgtccga cttcgagtat cgacgaacg    54420 gcaaggtcga cccgatcaag ggcgcgtcgc acatcatctt taccgacatc gggctcggcg   54480
agcagtcggc gaagaaccgc ggtttcgaca tgaaggcgtg gatcgagaag cgtctggtcg   54540
acggcggcat cccgcgcgag cagatcgcgt tcatgcgcga caacaaggag catgccaaga   54600
aagagcgcct gttcgcggac atgcgcgagg gcaaaaagcg cgtgctgatc ggcggcaagg   54660
acatggaaac cggcgtcaac gtgcagaagc gcctctacac cgaggagcat ctggacgcgc   54720
cgtggttccc ggcatccgtc gagcagcgcg agggccgcat catccgtcag gcaaccaga   54780 acaagcaggt gcgcatccgc gcctgggcga cgaagggcag ctacgactcc accatgtggg   54840
ggatgaacgc ccgcaaggcg cggttcatcg aacaggcgct caacggcgac gacagcgtgc   54900
gctcgctcga ggacgtgtcc gaggcatcgg cattcgacat ggccgccgcg ctggcgtcgg   54960
gcgacgagcg ctacatgaag ctggcgggcc tgaaggccga cgtcgagcgg ctggagcgcc   55020
tgagctacgc gcaccacgac gaccagaaca agcttcggcg tgacaagcat tgggctgaga   55080
cgcagatcga gcgcgacaac acgctcgccg gcgagatcaa ggccgcgctc gaaaagcgca   55140
cgccgatccg cgcgggcgag ttcgccggca tggtgggcaa gacctcctac gacaagcgcg   55200
acgagttctc gaacgcgatc ttcaaccgct tcaaggagct ggccggcaag gaggccgaca   55260
ctgccgagca gatcggcgag atcggtggct tcccgatcat gttccacggc acgcagctca   55320
aaggctccgg cgagtacatc gcggccgtgt cggtcgacat ccccggcgac ccctcgccgc   55380
tcgtgcagct cccgctcgac ccggacctgc cggtcggcgg catcgcgacc cgcgcggcga   55440
atcaggtgaa caacctcgac aatcagctcg cgcagctcac ggcccgcgtg cagcagaacg   55500
agcgccgcgt cgagcagatc ggcaaccgtc tgggcgcacc gttccccgag caggccgagc   55560
tcctggacaa gatggcgcag ctcaacgcgc tggagatcga gctgaccgcc gagaaggcgg   55620
ccgagaacgc gccggcgccg tcgtcggacg ccgcggcggc gacgctcgag gtcgagggcg   55680
agaagccggc cgacgaggcg ccgaagttca gcgtcgccga aggcgccgac cgcaatcagg   55740
tcgtgccggt cacgcagatc gacacgttcg acgtgtcgct cgacgacctc tggcgcaccg   55800
ccaacgagtg gtatcgcgac aacctgaccg atcacccggt ccagaacgaa tcgctcggcg   55860
cgcaggtgca gttctcgaag aacggccgca gcaaggtgct gtcggtcggc cgccgcgatc   55920
cgcgccgcat gagcatcgtg aaggcgctcg cggacatcgc gcgcaacggt gtgctcgtga   55980
acgaggaagg ggataaaaag gagcgcaccg gcatcgcggg ttacgcgacg ctggtggcgc   56040
cggttgaggt cgacggcacg ttatacgccg tttcgatgaa ggtccggcag gaagatcggg   56100
cgcgcaacgc acgctcgatc ttctacacgg ttgaagcatt caacctcgaa aaggtggggg   56160
ccagcagggc gaatacggcg cagcaagggc aggaccatcc ttctactggc tcccgccaag   56220
agatcggttc tgccggaaac gacgctgcac aacgtgcacc tgcctccgct ccggccctct   56280
cccaaggcaa tggcgtaact cttggcgatc ttgtcgacgc gatcaacgaa gcaaatcgcg   56340
cgtttagtgt gaccgcatcg actgcggctg atcgctctaa tgtaattatg ggcgatgcga   56400
```

```
atgcaaatgg caatgtattc tcgtcgactg atcttgcaaa taccgtcaaa tcgggtccgc  56460
tcggcgacac cgtgtcgcag ctcatcgcac aacaccgtgt tgtgctgcac gacactgccg  56520
cgacgctgcc ggtcaaggat gcgccggccg gcgtgcgcgg cgtcacgatg ccggacggct  56580
cgatccatct ggttgcggcg aacctgacgc ccgaaaccgc cctgcccgtg ctgctgcatg  56640
aggcgttcca ccaaggcggc gagaagctga tcggtacggc ggcgtggacc gacctgatgg  56700
gccgcctcga ctcgctgcac cgtcaggcgc ggcagtcgag cggccgggcg cgggaattct  56760
tcgacgcggc gcgggcacgt gttgcgagcg cgcaacgcgc cggcgccatg cctgagacgc  56820
tgacggccga ggagttcggc gcctacacga tcgagaacta cgagcaggcg cccgccgcgt  56880
tccgcaagtg ggtcgacgac gtgatcggca cggtgaaggc gtggctgctg cgccgcttcg  56940
gtaagcagct cggcgccgtc acgcggcgcg agctccgcgc gatcgccgcg gccgcgctgc  57000
gcgaccagac cggcggcccg accgatggcg cccgcttctc ggtcggcgcg ccgcagcccg  57060
gccagccgaa tgccggcctg acgccgcctg ccccgtcgcg cttcgagcgg ctccaggcgg  57120
ccgtgcagga caacatgaac cgcgtgaaga aggttcagga gcgcatcaag gagctgaccg  57180
gcgtgaagga gctcggcacg gccgactact accgcgccga ggcgaaccgg ccgggccgca  57240
tcgcggcgcg cctcgaggat gcgaagaagc agctcacggg cccgctgatg gagcgccttg  57300
cgaagtccgg gcacacgccc gaacagctcg aggagctgct gcacgccgag cacgcgcagg  57360
agcggaacga gcgcgtcgcg ctgatcaacg aggacatgcc ggacggcggc tcgggcatga  57420
ccacggccga cgcgaacgcg atcctcgcga agtacgccgg caacaccgaa cttcaggcgc  57480
tcgcgcagca ggcccgcgac atcgcgaaag caacgctcga cctgaagctg gcctacggcc  57540
tgatcgacca gcagacctat gacaccctga cgaacggcta caagaactac gtgccgctga  57600
agggcgacgg cgagtacggc ccgaaggtca agcgcgcaat gggccacgag gagcgcgacg  57660
agcacatcct ccagaacatc gcgcgcgact acgatcaggc ggtcgtcgtc ggcgaaaaga  57720
acctcgcgcg gcaatcgctg ctcgcgctcg tcgcgcagaa cgacgacccg gacctgtgga  57780
cgattggcgt tccgccgcgc gggcgctacg tcgccggcag ggtgtacaac gtggtcgacg  57840
gcaacggcca aaccatcggc tcgtttatct cgcgctcgca ggtcaacgcc ttcctcgaag  57900
gcgcgggccc gcaggctgcc acgtatcagg tgctcgactc gaacggcgat cgcgtcgccg  57960
agttcgtgaa gccgctccag gacaatgagg tcatggtcta cgtgaagggc gagcccgtgc  58020
gcatccagat caaggacgag gcgctggccc gccagctccg gccgctcgat cagcgccaga  58080
tgcacccgat cctcgaaatg atgcgcggcg tgaaccgcta cctgtcgaag atttacaccg  58140
gctacaaccc ggcgttcatc ctgcgcaacg ccgcgcgcga cgcgctcacc ggcacgatca  58200
acatggtcgg gcacgagggc gcggccgtcg cggcgaaggc atgggcgaaa tacccggtcg  58260
ccgtgaaggc gctgggccag tgggcggcaa ccggtaagga gccggccggc gagatcggca  58320
agctcctgaa ggaataccgc atgcacggcg gcaagaccgg agcatcgtgg atgtccgacc  58380
tcgaggagca aggcaagtcg ctcacgcgca tgtacgagga cgcctacggc gcgagcggct  58440
acctgaagga cggccggaag ctgaaggcgg ccacggtcgc cggccgcaag atcgtcagcg  58500
gcatggcgca cgtcgtcgag atcgccaacc aagcaactga gaacgcgctg cgcctgtcgc  58560
tgtacatgac gctgcgcgat cagggcgtga cgccgggccg cgccgcgcag gccgcgaaga  58620
acgtgacggt cgacttcgac cgcaagggca cgctgacgcc ggcgctcggc gcggtctacc  58680
tgttcttcaa cccggcggtc cagggcacgg cgaatgcgat gcgcacgctc gcgagcggcg  58740
```

```
agcaccgcgg tcaggcgctc gtcgcgctcg gcatgctggc gacgctgggc ttcttcgccg   58800
gcgcctccgg catggacgac gacaaggacc gctggctcgg cgagagctgg gacacgcgca   58860
cgcgcaactt catcttcggc atcggcaatc acacgctgcg cgttccgctg tcgcaggaat   58920
ttgcaccggt ctacgcgttc ggcgtggcga tggccgaggc gatgcgcggc gaaagcgcga   58980
tgaagtcggc cgtgcggatc gtgtcgtcgt tcatcgatgc ctacttcccg ctgcacggcg   59040
cctacaaccc ggacagcgac aaccatacgc tcgacgggtt cctgtcggcc gtgccgaccg   59100
tcatcaagcc gctggccgag acggcggcga accggaacag cttcggcagc cagatcgtgc   59160
cggacacgca gtcgacgaag cccctgcccg ataacctgaa gatgtaccgg gcgacgaagg   59220
gcaccgtcta cgacgcgctc gcgcagcaga tcgcggcggc cggcgagctg gccggcgcgc   59280
ggcggtacga gaacgacctc tcgaaggtca gccccgagac gctgaaatac atctggcgca   59340
cctacgcggg cggtctgggc cagttcgtca ccgactcgat cggcgcggcc ggcatggcgg   59400
ccaccagcgc cggcagcatg acgagcaacg acgtgccgat cgtgaaagac ttctggaagc   59460
agaacgacgt caagccgctg cgcggtcgct actacgacct cgcgcgcgag gcgaaggaag   59520
cggccgagga gttccgcgtg gcgaagaagg ccggggacgg cgaagcgctc gacgacatct   59580
ttgcgcgacc ggaacagggc gagctcgtgt cactcgaccg gatgacgcag cgctacggga   59640
aggcgatcgc ggcgctgcgc gacgagcagg tgatggtgaa cgtcgataag acgctcacca   59700
ccgagcagaa gcgggcccgg ctgaaggagc tcgaagccga ggaggaaacg ctgtatcgcg   59760
gcgcgatcga ggcgttccgc cggtaacgag gaacagggcg cgccgggttc gctcggcgcg   59820
ctctgctcac ttcttcgcgt cgtggatgct ggggtacagg tcgtagcagg cgccgaccga   59880
ccagcgcgtt ttcgcctgcg ccgcgcacgc ttccgcgctc gagtacccga acagatttga   59940
ttgcccgatg aaaatcccga gcgccagcgc gccgacgatc acggcgaacg gatgcttgct   60000
gacgatccgc cgcacgacgg cgccagcgcg ataccaagga tttgcgtctg ctatctcaat   60060
gctgctcata atcttccctc gaacgctttg tagcgacgtt cgcattttat ggcaattacc   60120
gccgtgcgcg gtcctcctcc tcgatgcggc gcatcgcctc ctgcacgcgg cgcagcttgt   60180
ctacctcgcg cgtcgccact tcggcaaccg cgtcgcggat gaatgacagc tttgacccga   60240
tcgcgcggtt cttcacgagg tagtcgagct gcatccaaag cggctcgggg aatgggacgt   60300
tgagcgatcg cgtttcgtg ggatcgccct cggtccacgg agcgtcgtgc tgggtcactt   60360
tctgcctctt tcctgatgag gacggccgcg ggcgcggctt tgtggttgcc atagggtat   60420 ctccgcactg tgccgcacca tgcagctcta cgccgcacaa actggcacgg gattctgttg   60480
tgcagtagcg cgcgcgctcg atttgtggtt ctgataccta accgtggtgc tacaatcgca   60540
ccggtaaaac gggactacgg ggccgcgtcc acatggaaaa ccagactgaa tcgggggcg   60600 tcctgctggc gaaaattgcc agcgtttggg cgatggtggg tatcacgtcc tggtcggagg   60660
cggcgagctt tgccgccttc tgctacacga tgtggttgat gggggcgaag ttctggaagg   60720
aagtccttcg cccgctctgc gagcgtcggg ggtgggtttc agcccgcccg gcggcggcag   60780
ccggggagcg tgacgatggc tagtcgcgca cgcaccctga tcggcgcact gaccgtcagc   60840
gccgcagcat tcgccacgtg ggtcgccagc gagggattcg cgccgaaagc cgaaatcccg   60900
acgaagggcg acgtgccgac gatcggccac ggctcgacgc ggtacgagga tggcacgccc   60960
gtgaagatgg cgacaccat cacccgccag cgcgccgcag aactggcgcg caatctcatg   61020
gcaaaggacg agcgcgattt gcgcgcgtcg cttccgcccg acacgcggct ctatcaggcc   61080
gaatacgacg tgtacctgga ttttgtcggc cagtacggca tcggcaattg gcgcaagtcg   61140
```

```
agcatgcggc gttacgtgat cgccggcgag tatgcggcgg cgtgtaaagc gctgctgaac    61200
taccgttttg ccgccggcta cgattgcagc acgctcgtcg acggcaagcc gaacaagcgt    61260
tgctggggcg tgtggacgcg gcagcagcag cgctacaaca cctgcatggg ggcgcaatga    61320
atccgttgaa cccgtgggca atccttggcg ccttcgtggc ggcggccgct tgcttggccg    61380
ccggctgctg gatcggcgtt gacgtggagc acgcgcgccg cgtcgccgag gtcaacgccc    61440
tcaaagcgga ccatgcactc gaagcgaaac ggctttccga cgcagcaacc gaggcgtcgg    61500
agaaggctcg caaagccgag gcaaccatgc gcgagaaggt cgcgcaaatc gaccaacttg    61560
aaaccgacct caatcatgcg aactctgaaa acgctgatct tcgtggccgt ctcagcagcg    61620
gcactcagcg cgtgtacgtc cgcgcaaaat gtcccgcccc cgccggcggt agcgtgcccg    61680
gttccgccgc ccccgccggc gtggaccatg aagccgaccg agccgaactt gacccagcgt    61740 tgcgggcga gctggctgga atcgccggcg acggcgacga cgcaatccgg cgattgagcg    61800
cgctgcaaag ctacgtgcgc gacgtgtgcc tcgcgccgcg cgaatag                  61847

<210> SEQ ID NO 2
<211> LENGTH: 40555
<212> TYPE: DNA
<213> ORGANISM: Bacteriophage KL3

<400> SEQUENCE: 2
tttgtaatca tcaggtggcg ggttcgagtc ctgcagccgg caccatatcc agcaaggggt      60
tacgcgatgt ttgcgtagcc ccttcgcgtt tccaataccc ccctcacgtt tccaatgcgc     120
gtcagcgaga cggtttaacc ggccgggcgc gcgcacgta acgcgccgtc atgccaggtc     180
cgctgtgacc cgccaggcgc tgtccggcct ccaatccctc atcgatcgtc ttgtgcgtca     240
cgccgcgcgc gcggagatcg cggaactgaa acttcgcctt gtcgataccg gcccgctcgc     300
gtgccttatc gaagcgcgac cgcagcttgc ccttcgtgag tggatagcct tcctcgtcgc     360
gcagcaggta gggcgagacg tcgaccttcg aaccacgcca ggccaacagg cgctcgatca     420
gcgccgcgag gtcgcccgtg atttgtaccg taacgaatgc gcccgtcttc tgcgtgcgga     480
agatgaggtt gccacgcacg atgtttgagc gctgcacgcg caggacgtcc gaaggacgtt     540
gtgcgcagag gtcggccagg tccatcgcgt tgcgtagcgg ctggtcggcc accgtgtaga     600
cggcagcata tagctcgtca tcgatgagga tgtcctggcg cccggtctct ttcttcccgc     660
gcacgccggc gcacgggttc gcgatcgtca tcatgccca cagccgcccg cagttcagaa     720
ccagcgacag cacggccttc gtgcggttcg ctgtcacgac gccgcgcttc tctgccgtcg     780
cgcgccagat cgtggcgacg tcggccggcg tgagcgtgtc gagctcgcga gcgccgatga     840
cggctgtgag cctggagagg aacaggtcgt acatgcgttg cgtcgccgca gatttctgcg     900
gcaactcgcg tatgcggtaa gcctgctcaa gcatggcgaa cgtgtgccgc gtcgtttccg     960
acgacggtgc acgggcgcct tctaactcgg cccaacgttg gagtgcgacg acgcgatcag    1020
tgccgagcgg ctcgagaatg cgccgcccgt ccacctcgcc gtgatcgtag taataacgca    1080
gcgagccgtc cgcgttcttg cgtgaacgga agcgcgggat tgcacctgga gtttgtgctc    1140
tgcccgccat cacactgcgc cgagattgag cgacgtaaga ccggccggct gcggtgtgcg    1200
cccttgttta gattcgatga ttcccatttg cttgtcgtgg taagcgcgtg cgaccaaaac    1260
gcgaccgtgc acatcgacga catgcggcca accctgtcga gcgagccaca ggatttggcg    1320
cgcgcgttgc ggcgtgccgg tcagttcgcg cagttcttgt cggccgaggt acgcgccggt    1380
```

```
gccgcgctgc gagtcgcgac gtgaatattc ttgcatggtg attttcaacg cgtaaagagg    1440
ggacacgcag aacaactggt ggactcgtgg ctaacgcgaa tatcgaccgt aagtcgttga    1500
ttcgtaacgg ttgtgtgtgc cactagttgc catgaaaacc ccgtggcacc cccttccgac    1560
tcgtggccta aaaataggc agcgcccgcg actcgtggca aaacgcgccc gactcgtggc    1620
atggcgtttc ggtcaatttc cgcccctct acgtattctt tcttcttctt tttcaatgaa    1680
ttagagagaa gagaaaaagg gagggcggcg gccggcgcaa aagacggact agtggcaaaa    1740
acgcatcgac tggtggcaat tcgaatgcga ttcatggcgg cactcgcttc aagaatcaaa    1800
gacttacgaa cggacagccc cgaaaaccat gattcgcgtg cgctgcctgc ccgttccccg    1860
tggaaaaaac ggcccgcgcg gccccctttc ctcaaggccc gcgctggcgc ccggccgttt    1920
cgacttgcgg ggggtacggg gggaagcaga cagcacggcg gccgcgtggt gacgcgcgcc    1980
gactgctgcg cgcatcgacg cacgcaccgg aaaaccgaat acagggccgc tgcgcggcgg    2040
gaaggaatga gggaaggggt acggccgcac ggcggccgca tcggctgaga ggcgatcatg    2100
ctcggccccg ctgttcggtc gcgtcggtcg cgaggtcttc gcgaatcgac acgtgcaggc    2160
caaagccggc caggcgatcg agcgaaatcg gcgtgaggta cggcacgcgg cgggtgtaga    2220
tgcgacgctc gacttccttc tcgccgacca cgacgccggc gtgcttgagc tgcgccttga    2280
acacgcgatc ggatttcacg gcaatccgt tccatttgtc gcgtagcgcg ctcgtgtggg    2340
cgatgtggtc catcacgtgg ccggtgcgca gcagtaggca aaactcgccg tcgacggtat    2400
cgaaggtgaa tgggtgcttg tagttgccgc cgtcgatctc cgacagcacc gtttccatga    2460
tccagaccca aggctcgcga tcggcgctcg tctcggcgac gtggccgttc atctcggcga    2520
gcagatcgcg cgggaagtcg ccttcgctcg gtccatgcc ggcgaactcg cacaggtagc    2580
gccaggccag cgcgacggcc gcgtagttgc cggccatgcg cttcgcgccg tgtcctcgc    2640 cgctcgcgat gcatttcccg agcgccttgt cgcgcagcgt ggcgtagtgg tcgtgcacgg    2700
tgcgcttgtc catgccagcg aggaattcga gccactgccg aacgggaag gcggcaggt    2760 cgtcgggcat cagcgggccg cgcttgccgg tcagcgtcgt gcgcacgagc ttgccgagca    2820
ggctgcgcac cggcacatcc tcgccggcca acatcacggg cgcgcacagc aggtattcgg    2880
tcatgtcggt gccgcgccgt gtcacggtgt actggtagtt ctcttgcagt aggcccacgg    2940
ccttgtcgat cacgtcctgc cgtcgcgcgg acagctcttc ccatccgacc gggtggctcg    3000
tgtggctaat gctggtcagc aggcggaact cggtctgcag cgactgcccg gaaaacatcg    3060
tgaacgcgag cgagcgctca agccgtttga tgagcgtcga cttgccggcg cccttgttcg    3120
cctggatcgt gatgtgcggc cagaacccga gcagcgcctt caggtggccg ccgagcgccc    3180
acacgagcgg gatcgtcgcg gcgttctgct tgaacgtcgc ctggtacgca gcgatgacgc    3240
ggcgcgcgtc gctggccggc ccgcttggga acgtcaggtt gtgatacggg cactgcttgt    3300
cggcctcggt gaaatagcag tccggcccct cgttgacgat caggcggccg tcgcgccagg    3360
cgagcccgac gaagttcgcc gcctggcgcg cgccgaggtc ggctccacgc tccaggatgt    3420
tgaccatgcg cttgaacggc gccggcgccc agatcgggcc gaacttgccc cactggtcga    3480
cgttgtgcag ctggtcgtcg agcatcacgc ggcgcacgag ctgcgcgccg tggcggggcg    3540
cctggacgga aacggcgaag tagacggtgg gcgcctgatc ggcgtcgccc gtcatcgtcg    3600
acgtcgcgct cgcgacggac acggcggctga tgccggcgat gcggaagccg cacaggtctg    3660
tcatgacggg cgtttcgacg cctgtttcct cgttgcggtc catcttcgag atgtagctgg    3720
tgaagtcggg ccggacgcgg aagcgccagt actgagcgaa atcgtgcgac ggcaagaaga    3780
```

```
tgcgcggccg gccgcggcgc gtcgcgtcgc cggcgaggcc agcaatcaac cagggttcga   3840
gctggtcgag tgcgcgctgc agctcgacgg ggccgcgcag ttgcaggtag tcgttcacgt   3900
cgttgatagg cttggccgtc ttctcgcccgt cagccaggtc cgcgagccag ccggattggt  3960
cgacgagcaa cgcgctgatg ttcagcgcag tgaggcgttc atacagcgcc cacgccgctt   4020
cagggccagg acggcggccg gcgcgtggat ggccgtccgc gaacggctcg tcgttgtcca   4080
ggcagatcac gacctgtttg ccgcgcagga acgcgaagtc gatgccgtcg acgttcgcca   4140
ggccgcgcag cgcgagcgcg gcggcgccag gcatcgcaca ggtgtcgatc gacagcgcgt   4200
tgatcgcgct ttcgacaatg aacacgcgct tcgccttgtc gagccggcga gcatcggcgg   4260
tccagccgta gccggccttg tcgccctggg tctgcgtctt gacgccgccg ttcagcgccg   4320
gatcgacata gcgcatgtcg acggcgacga cgcggccgtc gcccggtgcg cgcacgatga   4380
acgcggcggc cggcccgccg tggccgactt caccggcggt aaccttcgca ctcgtccagg   4440
tgttgaagcc gagcgtgcgc gcgctgatgg cggcatcgat cgccgtggcg gaaatgccgc   4500
ggccgacgag gtattcgcgc acctggtcgc gctcggcgaa gcagcagtcg gcgatgtatt   4560
cgaacttcgt tttctcgcgg cgctcggccg gcgcctggcg gtcgagcggg atgccgtacg   4620
cgtcgtgcag gtagcgcacc gcgtcggcga ccgtgccgcc gcgcgtgtga atgaccaggt   4680
cgatacacga gccgccgacg tcggcgctgt ggtcgcgcca gccggtgccg tgcttcgggt   4740
ggttcacgta gatcgacagg acgggctct tgtcgtcgtg ctgcggcgag tggtagagcg   4800
cgcggtcgcc gccgcggccg cgcttcaagc cgagacggtc ggcaaggtcg tgcaggtcga   4860
tgcgttgttt cagttcgtcg atcgaagcca tcgttattgc tgttgatgca gagagagggc   4920
ggcagggttg ccgggcgtcg aggggctgtc gacgagcgcg cggagcgcgc cggccgacgc   4980
agggaaggca agggccagtc gatcgccgag gacgctgacg aacagcgcga gcaccgcgac   5040
gcgctggagg ccgccgggtt cgtggtcgaa gcgaagaacg tcggcggccg ccgcgatgga   5100
agccgcgagc gcggcgtcgt gagggagtagt tgtgtccgtc atgctgctgc gcctccgagg   5160
atgtcgtgat ggttctgttg caggcgttga acggcgtgct gcagctcgta gcgcgaggtg   5220
atcgcctggt cgagcatggt gcgcaggcgc ttgcggttgc gttcgagatt cgacgtcgcg   5280
ttcgcgagag ctgcggtacg cgtcgcgccg tggccgatgc ggatgcccga tatcaggtgc   5340
gtgacgacac acttttcggg gtggccgtcg tgcaggtgtg gttcggtgtg gatgccgaac   5400
gtggcgccgg cgtcgttcgg gagagcgacg tgatcgcctg cgacagtgcg caggccggcc   5460
gaagtcagca gctcgtaacg aatggtgggc tcgttcgtca tcgtgtcagc cccgcggcgg   5520
aacggcccag gccagcgctg cgaccaggac gatcattgcg acgacgccga tcacaaaagc   5580
gatcggccgg gcgagccgaa cgtcgaacag gcgcagcacg tcggcggcca gggagtagac   5640
gccggtgagg gagagggaaa gcatcagcag cacgccgatg ctgaaaacgt agggcttcat   5700
ggtgtggttc cagatgaggg cgccggcggc cggcgcggat gggtcagtcg aagtcgttcg   5760
cggcgcggcg tttccgtcg acggccggca attcggcgc gggttttcga tcgcgccata    5820
cgttcgccgt gcattcgaat gcacggcggg cggccgggca cagggcgtcg aaattcccga   5880
ccatgcgcag gcgcgccac atcgcgcgca ggtcgacgtc ggtgagggggc gcgcgcatcg   5940 gatcagtgca ggacgatggg cgtcaggacg ggcatgccgg cctcggcgtc ccaatggcag   6000
cccagcgcgt agccgagccg gcgggcggtg ccgacgaaca cgagcggatc gatgtcggcg   6060
cgccacagtg cgcgcaggta ttcgcggcgt ttgtcgagcg acagacgggt cggatcgaac   6120
```

```
ggcatcacga cagcgataga agcgagagtg gccatgctga tctccttttt tcaggcaaaa   6180
aaagtccctc gcgccggata ggcacgatgc gaggggaaaa caggggga ag gggtttaggg   6240 cgctagacgg gcagttcgag ctgctcgacg agacgctcgc gcacgtttgg cgagagcggc   6300
aggtttagcg acagattcgg ggtcgcggac ggtgacaggg tgcgggcgaa ctccatgttc   6360
acgacgtacg tgtggccgca ctcgacgttg ttgcactggt acgtgacttc ccggaaggtc   6420
tgggacattt cgcggctgct gcgcgcggtt gcgcgcgtgc ggcagtgggg gcagcggttc   6480
aggatgcgca tttcggctta ctccggacga gatacagggc gcggccgcga ccgttcagtt   6540
gcttcgaagt gaggcgcagg cgacgcttca cgagccactc ggcggccgcc tcgatcgacg   6600
ggaggctgta ctgctggcgc acacgttcca gcacgtcgcg gtcggcatcc gagaaagaaa   6660
tctccgtgct ggtttcgggc atcgtaggag ctactcattg ttggcggatc ggtgccttcg   6720
ttcaggcgcc ggcgtggtcc agaatcgtgg cattgcgttc ggcgagcacc gcggtcgctt   6780
cgcgcatgac gatctcgcga atcaacacgg cgagttgctc gccctggtag ttcgcgagag   6840
ccgtcaacac ggcttgctcg tagtcgtcga agcggacggt gtgcttgttg ttgcggatgc   6900
gcttgggatc gggatacatg cgggctcctc aattcacgag cgggcgggac gggaacgagg   6960
gatggtgcga agctggcgcg cgccgattcg gatcagctcg cgcgccatgc tcgaaatcga   7020
gcgattgcgc tgcgcggcga attgttcgag ctcgtcgcgc tcggtggatg tcagccggac   7080
gtatacgggc ttgtccgaca gggtgccgcg tggtgatcgg cgcgggcctt tggcggtagt   7140
catggtcggt atactttgat agttagcctt gcgttacggt aaggctagtg taatggccac   7200
aaaagtacac gtcaacaaga aatacaagaa atgggtacaa atggaaactg taggtaagcg   7260
cctgcgtgaa gagcggctgc gcatcggttt gagccaggac gagttcgctg cgatcggcca   7320
actcggccgg aagacattgg cgttctacga atcggacgaa agagcacctg ataccagctt   7380
tcttttggca ctgcgctcga tcggggtcga catcgtctac gtgctgactg gcgagagatt   7440
ggaggcgggg cgccagagcg atgagcgctc agaaactgat gcagaggagg ccgaactcgt   7500
tgccatatat cggcaactca acgaaacagg caaagccacc ctgcagtcgt tcattggtag   7560
cgttctcaat caggccgtca tgcttaagac tggcacgccg cagcgcgcga agcgcctgcc   7620
cgaaaaccgc cgcgcagcgc tcgacgaacg catggtagag aacgttgatc gtgcgatggc   7680
cgaaatcgaa cgcttgcgtg tcgagcgggc tgcgaaggac ggaaagaagt agtccgggcg   7740
cgtcgccgca caccagccat tcttcacaca aacactgtat atccatccag tattgagtta   7800
gcatcctgaa agccggcgat gctggcgacg tgggagattc cgaggcaacc gcgtcgtgtt   7860
gcgtgtcgtc ggtccatgaa catgtttgtg agggaccaga agaatgagca tcgacatgaa   7920
gcacaacaac ggcacggttg gcatggccgc ccgtcatacg gacgcacgca cccaagcgat   7980
gggcgggggg cgagtccgtt cggacatgac cggcggtgag cgcgatgttg cacgcgcagc   8040
gatcgacgat gccatgcagt cggtcagcca cgtgctcgaa gttgcgattc aggcgatggg   8100
aaatcttcgt gtcgcgcgcg cggcgcttgg gcgttgcgac gacgggccgc caatccgagc   8160
gaatatgaac gatcactaga agtcgcgctg accgactccc atagcaagca acctgaagcc   8220
cgccgcgtgc gggcttttta cttttccgcc ttattgaaat gcgaccggtg ccgctcggtc   8280
gtcggatcgt cgcgcatttc gaggtcgagc ccggttgtga atccgccgtc actgtcgatg   8340
gtgtgcgtgg ccttcttcac gagccacgcg gtctcgtcga tttccggttt gaagccggac   8400
agcgtgaccg gcatttcggg gaacagatcg gcgcggccgc gcgcaagcga atagcgcatc   8460
gtcgcctggc tacgctgcat gcgcttgaac tcggcctgcg cagccgcgcg agcctctgcc   8520
```

```
tccgtcgcgt agtcctccgg caacactttc acattcttgt tgttctcccc accgacaatc    8580
accgacttcc gtttcgcttt gccgttcgaa tggtagtgcg cgcgcacggc tgaatagttc    8640
tcgcgttcgg acacgtggta ggcgtgctgg tcgccactcg cacgcgtcag atttaacact    8700
tggaaatttt tcccgctgac ggtcttgccg gtgccgatgg gagtgaagag caaccgcaaa    8760
tccttgacgt tcatcacggc gtcgtagcgc ttcgccaggc gtgtcagaaa cgacatatcg    8820
ctttcgtgcg tctggtcgat atgagcgatg acgatcttcg cgagcgcgtc ggcgacgggc    8880
ggcgtcagct tgtagcgcgc cgcgatcgcg cgcacgatcg agccgatcgt ctgtttgtgc    8940
cagcttttct cacggcgctc ctgcatgccg ttcgacatcg aggccgagcg tgcgcgcacg    9000
gtcagcgtgt cgggcgcgcc gctgtgctcg aactcggtca cgacgaacgt gcccttgtcg    9060
acgagctgct cgccggccca gccgatcgac accttgatttt cgtcgccgcg cttcggcagc    9120
gccaggtcgc cgcgcgagtc gtcgagcaca aggtcgacgg tatccgcatc gtcagagcga    9180
gattccgtga gggtcaacga ttcgagccgc ggcaggaacc gccgcgagat gtcgcggccg    9240
ccgagcgtga tgcggtagtc ggccatcggc tcaacacgtt cgagccgata cacggccgcg    9300
ttcgagtgtt ccatcgcgcg cgttgtcatg ccttcggctc cgcgtccact tcggcatcgg    9360
tctccgaatc atcggccagc gctgcatcct ggtcgatgcg cagcgcgtcg tcgtcgacgc    9420
attcgagcgt caacgtgaat tcgatccggc gcgcagtgcc ttcgcgggtg aagtaacgtc    9480
gcgtctcgtc gagccccacg atgaggtacg cgccgtagac agtccctaga ccgtcgacca    9540
acacgtacgc ttcgccgatg ttcgccatct ggacgagctg gtcgattgac gcgctcgtgc    9600
cgatttgatc cggcgcaatg aggccgtcga gcgtgatgac atcgtcgccc tggccggtgt    9660
actggcgagc atcgcgtgcg ccgatacgcg atttcttcgg atgcttccag ttccggcgcc    9720
gcttcagctc gtggaagggg gcggtagtca ggctgaacac gaactgatcc agcgacagca    9780
acatgggaca gatcctccgt gaatgtcagt cggacaggcg cgagccggcg cgcgcacgct    9840
gcgcgcgttc gcgacgatcc agctcggcgg ccacggcgcg cgcgatcgca cgcggatcgt    9900
caccggcctg cgggtagatg ttgatgatga tcgacgcggg cgcggcggcc gatgcagacg    9960
acgctgcagc cggacccgac gccgcgatcg gcggccgccg gtcgattggc acgagcggcg   10020
cggccgtcga cagtgcgggc gtaccgaatc cggtcacggc agccgtcgcg agcccgagcg   10080
ccgcgcgcgc gacgctcggc gcttcgcctg ccatgccaag cgccgccccc tcaccgacga   10140
atccgcccag ctcggcgaac acgcggctcg ggctgtgaat gccgagcttt tccttgaacc   10200
acgttacggt cgaggtcgcg acgttcgtga tggcttcctt cacggcgccc aggccgttcg   10260
tgatgccgtt gaccaggccg gatatcaggt tcgccccgaa ttcggccatc ttctcggcga   10320
ccttggcggc cacgacgatg atgttcgcga gccattcgcc aaagccacgg cccgcgttgc   10380
tggccttgtc cagactttcc ttgctcgcgt cgaccggccc cagcagacgg gaaatccagt   10440
cccatacgcc cttgaccgca tccatcagcc agttgaacgc aggtttgagc ggttcgaaca   10500
tcgcgccgag cacgccgaag actcggttga agatcggcgc gagcggttgc agaccttcgg   10560
tcaagccctg ccagaagccc gagaagaacg ccttgatcgg ctcccaatat cgaacgatca   10620
gcagcgcggc cagcgcgatc ccggtgatga cgaggcccac cgggttcatg agcgcgacgc   10680
ggccgacgaa catcagcatt tgcgcgagcc cgccgagcgc tgccgcgacg ccgttgattg   10740
caccgaccgc cccgcccttg atgagaccgc ctgcgccctt gagcgcgtcg accgacattc   10800
cggcgacgcc gcggcggccg gcgtactgcc gggcggcggt ccagcgcgaa gcgacggccg   10860
```

```
cgcgcgatgc ggccgcctgc gcggcgacag cgcgccatac ctgcgccgtg tattgccgag    10920
cagcgaccag accgtctttc atcgacgtgg ctgccgtgcg cccccattgg gcgacggtcg    10980
acacagctgc gcggccggcg gctggaatgc cttcgcgcag cgtccgtgcg taaccgcgca    11040
acgtcgccca ggcggtgcgc ggcgatgatg ccgaccaggc ggcggccagc gcgatgcgca    11100
tgcgagcggc ggtcccgcgt gcagcgttgc cgacaacaga gaactgagaa gccgcacccg    11160
acaatcggcc gaagccggtc gcgctcgcac cgagcgtgcg cgcgaggaag ccgccctgaa    11220
tgccgagcgt cgccatgctg aaccgcacga tcgcgagcgg cccgaggatg cccgcgagca    11280
cgatcgtgaa cgttcccatc acgacgagca gcgcggcgaa cgcggcgagc acggacagaa    11340
tgaccttcgc cgcggcgccg tggcgctgga tcaggccgat gaggccgtcg agaatctcgc    11400
gggtcttgtc gagcgccgcg ttgtacagcg gtgcgatgcg ctcgccgatc tcgcggcgca    11460
agtcgcgccc cttcgcgagc aggtcgtttt ccttgccctg ggtttgcagc gctgcgagct    11520
tcgccgcgtc gtcgatgccg tatgcgccgc gattgagctt ttcattcttg tgaatctggt    11580
cccgctgcat gtacatggtc gtgaacagat tcgatgcagt ccggttggta aagatcgtcg    11640
aaatcatgtc tttcaccttg tccggatcgg tgatccccct tcgcggccagc ttcgggagaa    11700 acaccttttc cagccattcg agcggagacg ccttgaacag atcgccgcca gtgagcgcgc    11760
cgggcttgat ttccttgatc gtgccgattt tcgtgtcgac gaccttttt ctgtcgagca    11820 gaccgagcgc gatcatctgg ttcgccgcac gcttcgttgt cttgccctgg tacgcgttgc    11880
tgtatgcgga catgaggcca gtgccgacgc cgtggccgcc catttcctga atcagcggtt    11940
ccatttggta atagaacgcg tcctggcgca tctgcttcgc ggcgacgccg ccggtctgga    12000
tgaagttgcg ccactcgtcg cctccgacac ggccgccggt tgcggacagc actttctgca    12060
ccatgttcgc ttcgttcttg aacgtcgctt cgtctttcgt gccgccgcgc agctcgatca    12120
ccttcagcat gttcatgaac ttctcttcgt tcgcgtgggc gtcctccgcg ccgaacagtg    12180
cttcgttcgc gaacttcatt tttgcgagcg tcggcatcac catctgcgcg tgatgctcgt    12240
ccgcgaagat cgacagcgcg tcgcgcatca gtgtcatgtt gtcggacgtg ctgacgccca    12300
tcatgttcat cgcgcgcacg tatttctcgg cgtcctgcgt cgcctggtcg ccgaggccga    12360
gcgccgtgat gcgcgctcgc tcgttcgtca tcttcttcgc ttcgtcgagc gtgccgccga    12420
ggccgccgag catccgcatg ccggtcgagc gagcggcgta ccgccgatc gccatcccgc    12480 cggcgacgcc ctgcatcgcc tgcatcttgc cgcgcgccgc agcgagcttg cggtcgcgct    12540
ccgtcagcgc ttcgagctgg cgcgtctgcg cctgcatcgt ggccgtcgtc gacgcgatgc    12600
tcgagcgcag cgtgcgctcg tgctgcgaaa ggttgcgcgt ctcgataccg gcctgagcga    12660 gccgccgcg catctcgtcg acggcggccg tctgtttctt ctgctcggcg cgcaggcgcg    12720
acgctgcctg acgcgcgcgc gccagatcgt cgaccatttt tcgagtgggc gggccgaacg    12780
cgtgcagcga accggcgagc gccttcacat tggattgcgc cgcgccgagc ttcttcgtgg    12840
tgtcagcgag cccggtgcgc atctcgcgga acgaggcgac ggccttctgc tgcttgccga    12900
gttcggccag ctcgccgcgc gtcgccttca acgactgcgc gagcccctttg ttgctgttca    12960 gcatgttccg caagggcttc gtccagttgt cgaccatgtc gaacatgacg cgcagtttca    13020
gggcgttgtc catcgttact cgtgtccgct tcgtatccgg gcgcgctcgc gccaatccat    13080
cagctcagaa agtgaaaagt cgtccatgtc gcgcggtgtc cagccgaaca ccgtcgcgac    13140
gtcggccatc gcgtcttcta cgcgttctgg gattccatgc tcgctttcag cgccttcggc    13200
atcaaaaaac cggcaaaaat accccccaat gccacgaggt cggccgggtc catcaacgtg    13260
```

| | |
|---|---|
| acatccattt cggtcagcgt cggcgtggtg atgcgcggga gtaccttgcg cagcgcgtcc | 13320 |
| acgtcgagat tcacgagcgc cgcgagcgac gtgccgcgca gtgcgccggc ggacggcttc | 13380 |
| gcgagggtca cgtgcgtgat gggctggtcg ccgtgcatga tcggcgtgtc gaaggtgtgc | 13440 |
| gtgttggccg cgatcgcgtc gagtacggcg ccgccggtgg gggcgttgtt ggtgtcgagg | 13500 |
| gtcgtcatat gttgcgtgtc ctgatgatga tttagaggga tgcccgcggc tggcgcgggc | 13560 |
| ggggtgggaa caagcggtta caggccgatc gcctggcgca gaccggcgag caggtcgtta | 13620 |
| ccgttgatct tctcgatcat gttgatgaaa tccatctcga tcagctcctg accgttgatg | 13680 |
| gacagcttgt agtagctggc cgccgtcgtg accttgaaat cggtgtcttc cttcggcttg | 13740 |
| cctgaaccca tgtcgatttc cttgtggcgg ccgcgcacga cgatttcgac cgaatcgtag | 13800 |
| gtcttcgaat cctcgcgctg gtagccgccc gagaaacgaa gttgcacgcc gtcgtgcgtg | 13860 |
| gtgatgccgt acatgcgaac gacatcctcc atgaagccgc cgcacgtcca ttcgagctgg | 13920 |
| atcgcttcct ggccgaagtc gatcgggatc gggccgctca tgccgccgcc ctggtagtcc | 13980 |
| tccatctttc gcgacagctt cgggagctgg atttccttcg tctcgccgac aaagttggtg | 14040 |
| ccgttgtgaa acaggttgaa gcctttcagc ttgcggggca tacccatgtg tgtgactcct | 14100 |
| ggttaggccg acacgcgcga ggcgaaatcg gcgagatagc gatcggtgat gcgctggcgc | 14160 |
| agcttcaggt tttcgagcgg cgggaccggc gtgtagtcgt agtcgatcca tgtaccgccc | 14220 |
| gacgtcagct cgtcggtcgt gttcggctcc gggtcgtacc aggcgccgcc accgatcagc | 14280 |
| tcgccgaccg agacttcgcg gcggaaccac gcgttgatgt tctcgatgat gtcgcgcgcg | 14340 |
| cgcgacgggt tgagcgggcc gtcgacgacg cccatctgtt cctcggcgat cgtgtcagcg | 14400 |
| atcacctgtg ccgaacgcgt gtagttctcg aagaagaact tgccgtccgc gtcgcacgtg | 14460 |
| cgcgagcccc agaaacggaa gccgtttcgg ttgacgagcg tggtgacctg gttctcgttc | 14520 |
| agatagccgg cgtccgttgc cgggtcttgc aaatcccacg acacgtccgc gctgatgccg | 14580 |
| gtcacgccgt tgacgacgac gttcgacagc gtcttgtgcc agccgatgtc gttgtcgatc | 14640 |
| ttcgcgcgca ggcccgccgc gatcgccggc gccgggatgg cgacggtcga gttcgttatg | 14700 |
| tcgtcccagc cgagccaatc cggccagatc accatgattt cgcgctggcc gaactgcttg | 14760 |
| cggtacgcga ccgcctcttc cttcgtcttg cagccgtgcg cggcgacgta caccatcgcg | 14820 |
| cgcagcgatt gcgcgatcgt cgcgaatgct gcggcgacgg gctgcgtgtc gaggccgggc | 14880 |
| gcgaccagga tgcgcggctt cacggcgagc ttcccctgcg cggccagcaa cgccttcatg | 14940 |
| ccggtgtatt tgccgtccgg cgtgacggtg ccgatgacgt tcgcggtcgt ctcggcttcg | 15000 |
| tcctttcctt ccgcgacgcg cacgacgacg gtgacgggct tcgtctgctt gccgatcgcg | 15060 |
| tcgagcgtgc ggcgcagcgt gcccttcgtg ccggccttgc caagcgccgc gatgacgttc | 15120 |
| gtcagcagca ccggcgtgtc gagcgggaac gtcgccgggt cggcgtcggc gccggtgcag | 15180 |
| acgatgccga gcacggccgt ggagaccgtg cgaatcggcc ggccgccttc gttgatttcg | 15240 |
| atgacgcgta cgccgtggtg gtaatcctgc ggcatggtgt gcagctccta taggtgtaca | 15300 |
| ggtgagagga aacgggaaag cccgttgtca ggtcgatgcg acgggggccg ggttttgcgg | 15360 |
| ttcgatcggc tcggcgggtg ccacgtatgg cgcgggcgtc gcgggccacg ccactgccgc | 15420 |
| cggaaatgtg tcggcgttga tcgcggagac gagcgccatc tggtacgcgg accaggcttt | 15480 |
| gaagtagtag gtgccttcgt cgtcgagcag gccggcggcg tacgcgtcgg ccttgccagc | 15540 |
| gttcgctcgg cgtgcgattt ccatcagccg ttcgaactcg gccatcgcgg cgtcacgctt | 15600 |

```
ttcgcgcgcg atcagctcgg gcggaacggt ccatgcgtcg tcgatccacg cgtggcgcgg   15660
cgacggccgc ggctcggtcg tcagctccag atcgtcgggc gtcttgccgg caatcgcgat   15720
ttcgacgggc tcgccggtgt cggtgcggta gcagacgcgc ccgcggaagt caggcagcag   15780
gaaccaagcg ccgtcgcgat agaacggcca ggtggtcggc gtgcgcggcg gcggcgcatc   15840
gatcgtcgcg gacgacggaa tgagccagcg tccgtcattg cgcggatcgg cgtcgggctg   15900
gctgctggtc aagtattcgc cggtcgatgg gctgtagtgg tgaatcagca tgtttcgagg   15960
tccgtaaatt agtaggcgcg gatcatggcg agcagcgcga cgttgcgtgg ccgggcttcg   16020
ttgccgccat ccgcgttgac ggtgatgccg tggctgtgcc gaccagcccc gccgatgccg   16080
acgttgtggc cgtggttgcc ctcgccctcg gtgttgaatt cgtggttgtg gccgcccgca   16140
gggctggtca tgccccatgt gttgtcgccg tcagtgttgt ttgagccggt tttgtcattt   16200 cctcccatg ttccccatgg tggcgcgtaa cgactggagt tttcgcccca cggtgagacg   16260
tgctggtgat cgccgacgcc ggccgtccat ccgtggtggc catgccagcc ttgaacatca   16320
gtccatgccg agtgagcgtg gtcgccaact tcgctggcgc tcgccccgtg cgcgtgcgat   16380
cggttctggt cgctctggta cgagccgatg gcgcgctgcg gatcgatgtc gttacggccg   16440
tccgcccaac agcgaatgaa ctcgccgcgc atctcgggca ggcggaacgt cgtcgtgccg   16500
tcaccggttg agaagcagcc ccagcgaccg ttattccatt cggcttcgga cacgagcgca   16560
ccgctcgcct gggcatatgc ccacagcgcc ggatagtcgg cacgattgac gacaacgcca   16620
ttggctttca ggaagccggc gcgcgccagc gtgcggggct cgaagacaat ctggccgacc   16680
gtcacagtcg aaatggcgga cagcacccat tccgtcgtcg cgaggcgcgt cgagcgatca   16740
ccctgcgggg gcgtcgggcc ctgtaccggc ttttcgaaat tcgttccgtt cggagtaaac   16800
gtcacttggg ggagtgagtt gcacgtaatc ccgaacgagc catctgctat gtgatacaag   16860
cccgtgtctg gcgctccgtc gttttggaac gtgagcgacg gggacccgac actaccttcc   16920
gacagaaaaa tgcgcttacc cggatcgaac cacagatcac ccgccatcga gccgcccttc   16980
gtgcgatcga gcggcgtcac gtttccggcg tgccagaccg gcttgccgtt gatgcggaag   17040
gtgcggtcgt caaagaaata ctgaaacgcg tcggtattcc gccaccaacc aatcgactgg   17100
gcgttgcagt agaaataccc atcgttgggt ccgaggcgca accgtgcttc ctgggcggtg   17160
cgcccgactg aaaagctcgcc gcgcacggtg gcatctcccc cgagcaacgt acccgaaccg   17220
gtgtcgtcga tcgtgacgcg acccgttgcg aaattcagcg tgagcggccg gaatccgttg   17280
aacaagcctt ccggatcacc cttagccgtc gacagcagat agaaatttgt accgtcattg   17340
cgcaagaacg cgccgaagtc gccacaaacg gcccggaaat tcgcaccgcc ggcatcaagt   17400
tcacgcgagg tcacgccacc cttgacggtg acatttccgc ccgcctgaat gacatttcga   17460
ccgtcatcgg acacgtcgcc gacgagcagg cgcttcgcga gcgaaaacac cagcgtgctg   17520
cgattgacgc gaaacaccga gaactgggtg acgccgtcgt cggcgaacgc gttcaatccg   17580
aaatcgttgc ccgcattgcc gcccgtcgca gcgccttccc gcttgaacag cgaccaccgc   17640
accttgccgc catcggcgaa gaacagcgtc gagaagctac cggccccgcc gtcgatcgaa   17700
acagccttcg aatagctcgt gccttcggtg agggtgttgc cgccgacgag aagtcgcgag   17760
ccgccgtcat cattttttcac gtcgccgacg ataacgcggc caccgtatgc gatgcgtacg   17820
gcgcgcgcct ggtacgcgtc ggtctgcgta tcgttgcccg ttttgttgag ccaaatatcg   17880
aggtattcgc gcccccacgc accgttgtcg aaccctgacc ggatggtcgc gaccagacgg   17940
gcgccagtgt cggcgatgtt gccgccgaac gtgccgtaca gtcgaacacg actttcacgg   18000
```

```
ccggtcttgc cggatggcgg gatgaccttg acatgggcgg tgtccgggcc ggcgtcaaac   18060
tccgcgacga tcggtcccgt aaatttcgcg ccagtcagcg cagcataccg ggccgcagcg   18120
gtcttcggcg tgatggcgcg cgtgtcgtcc gcgctggcgt cgacttcggc ctgcgtggcg   18180
agttctacga cgcccttgcg ttcggtcgtc gccggcgggt tcagaaatgt ggccgggccg   18240
aactgaagct gcgccgcatc gatcgacgcg aacacgatgt cgctcgcgag cagcagcatt   18300
gcggccggtg atttttcaag aatcggcgtg ctctgcacat agacgccgaa caacacgccg   18360
ttgtccaggt acaggccgta cgcgtacaac gtgtactggt cgttcgtgtc gtcctggatg   18420
acgacgtgca cggtgtccgg cgcgacgttt tcgccgccga acgtcgtcac gcgcttgcgc   18480
tcgttcggca gggtcttcat gcccttgtcg aaagcgaaag cggcggtgcc gagaccgatt   18540
tcggtgacgc ggtgcgcgac ggtgccggtg tttcccgccg cgacgagcgc cgcgcggccg   18600
gcgtcggtga tttggatcag gtttccagcc atgttcaggt atccgagagg gaaaggcggc   18660
aataggctgc ggcgcgcgcg ccggcgccga cgcgctgcgc gccggtcgcg ccaaagccct   18720
gcttgaaggt gtagtgcgcg gtaccgcgct tcgcgcgatc gacttccgcg cggatatcgg   18780
cgacgtattc ggcggtcaca ggcacaccgt cgcggctgcc gaccgtcagc acaatgtcga   18840
acgttcccgg ccggccgcgc ggcgtcatct cgaaccattc gcgcatcgcc acgttcgcgc   18900
cgaacgacgc gcatacctgg cgcacggctt cggccgtgcc cttgatgcgc gcaatgcgga   18960
tcgcggtttt cacgcgcgca cgcttgacct gctcgggcca gtagtctttc caggtctcga   19020
cgccgacgtg ccaggcgagc cacggcagga acgccagcgg gatcgcgtcc gggtccatca   19080
gcgtgccgat gtcgaccggg atgccgctga ttcgcgcgtt ggtctcggcc aggcgccgct   19140
cgagcgcggt cgcgttcggc ggcagcaacg acggcatcgg cttattcatc cgcgaccccg   19200
ccatcgatca gctcgattcc cgtgcagtac ggcgcctgct cgcccgtcac ggcgacgcca   19260
ccggccggcg agtcgagcaa taccttctgc acgcccgcca cgcgcatcgc cgcgtgcagg   19320
ccgtcgaccg tcacttccat gccgatgcgg tgcatgtcgg cggcgaactt cgccgtgcgc   19380
ttgttcgctt ccgcgagcgc gacggcgcgg tccgggccgg agaagaagcg cagcgtcgag   19440
cggatcgcgt agcgcacaat cttcgcgctc tgcacgatca cttcgtcggt ctgcggccgc   19500
ttgccctcca gactctcttt cacgatctcg atcagctcgt cgctcgctgt gccatcacct   19560
tcgcgcgaca ggatcgtgac gaccatcaca cacggttccg ggctgaacgc agcggcagac   19620
agcacgcggc catcagccga gcgcgcatgg aacacgtacg cttcttcagg gccggcgacg   19680
gagaaaccgc gcggcgcgag ctgcacgcgc tcgcgcaggc tgtcgtcatc ctcgtaaacc   19740
ggatcgacgc cgttctcagg atcgccggcc gagatgacca ggcgctctac atcgaagagg   19800
gcggcgatat gttcgagcgt cgtgccgcgt gcatacgcga gcaggatgct ccgcgccttg   19860
tcgttgatga gctggcgcag cagcacttcg cgataagcgt tctcctgcaa cgatcgcgtc   19920
agcggttcgg attcgagagc gagcgtcgcg gcgatctcgg cacgttggtc ggccgggtac   19980
agggaaatga gccgcgcctt gcgttcagca aagaccgttt cgaagtcgag cgggtcgacg   20040
atatcgggcg ccggcagttg cgacaggtcg atcgggtcg ttctcatgcg ccgactccgt   20100
tcaaaacggg gacgcgcagc gacacgggct cgtcgcgctc gtcggtccat ccttcgatgt   20160
cgacgagctg ctgaccggcg agcgcctcat cggtatccgc cacgagctgc acgcgagtga   20220
cggtcagacg cggttcccag cgcatcagcg cagtcgcggc ggccgcatac aggcgaatgc   20280
gcgtcgcgcc attggtcggt gcgtcgatca ggtcgggcaa ttccgaaccg aacgaacggc   20340
```

```
gctggatgca cgagccgagc ggggtcgtca gaatccggcc gaccgactgc gacaggtggt    20400
cgacgcctga aatcgcgcga ccggtgacag cgttcatgcc cttcatgcac cgctccggat    20460
cggcttcgac gtaatggcga actcccctg cgcctggtgc gggtgattga caaggctgac     20520
gccattggcg agcacgtcgc cggtgaagtc ggcgctgccg tcgatcttca tcacggcgcc    20580
gccgtcgccg cccttgccgg tcataccgga ttcgaacgcg aaagggcctt tcacggtcag    20640
cgatttcgtc acggtcgcgt caccgtcgag cagaatgtgc ttggcctgta ccgtcgcatc    20700
cttcgtctgc acgaccaccg cgcccggcgc gacgatgtgc acggtcgcgc cggccggcag    20760
ctcggccgtc agagcgtgcg ccgcatggtc atagctgacg cgcgcgccgt ccgcgtagac    20820
gcgggtgtgg gtgttcgggg agttgtccgg cgctggcgcg cgtccgagt agaggccgcg     20880 cagcgcgact gcttgcgcga agtcgcccat cgggccgagc agcacgacct gctcgcccctt   20940 cgtcggcgga agccattcgc gcgtgctgcc ggccgcaggg gtgagccagg gaatccagtt    21000
ggtttgcagg ccgtcgtcgt cggactcgcc gactgcgacg cggcaaaggc ccgcgccgtg    21060
gtcgacatcg agaatagagc ccttgcgcac ggcgttgcgt gcctgtcgtt gaatttcgtt    21120
cgcatccatg ccgaccatgt tgccggccgc cctcgcgtga cgcgagcgaa cgcaaatgtc    21180
gtgctcgcgg gtacagcatg ctcgtcgcgc gcgcgagcaa gcgtgcgtcg acaatcgtta    21240
ttgctcgctc gatgacatgc ctcgcacacg tcgcgggtgt cccttttcacg ttgcctcaga   21300 accatgacga ttcacatttc agacgccgtg cccgcggccg acattacccc aatgctcaac    21360
cagctccatc gtgtcgacgc gctcgccctg gcgcgcacac tgccggatca gtccgtcgac    21420
ctggtattca ccgatccccc gtatgcgtcg ggcggcctgc acctgtccgc acgaacgcgc    21480
gcgccgagcc agaagtacat caacagcgac acgaaggcgg tctataccga cttcgaaggc    21540
gacaacatgg atcaacgcgc ctgggcgttc tggtgccacg cctggctgac cgaatgccgc    21600
cgtgcgatga aacccggcgc gctgctcgtt tgctttatcg actggcgcca gctcgcgacg    21660
ttgacggacg tggtgcaggc ggccggcctg acgctccgag gcatcgccgt atgggacaag    21720
acgccaggtc gtacgcggcc gcgtcgaggt ggattcgcgc aacaggccga attcatcgta    21780
tgggcgagcc gcgggccgat gaacgaaagt gaccgtgtacc tgccaggcgt gttcccaaca    21840
cgcctggcgc tgccgaagca acacgtcact gaaaagccga tcgagctggc gcgcgatgtg    21900
gtgcgcctgg tgccggatgg cggcgtcgtg tgtgacctgt tcgctggttc cgggacgttc    21960
ctggtcgccg cgcgcgaagc cggcctgcag tgggtcggat gtgagacgag ccaggcgtat    22020
cacgcgatcg cgtcgacgcg cctggctgcc gtgaacgatt cagcggttga ggtagcgtag    22080
cagccggtcg cgcacgagtt cgcgatcggc cgagctgaag ccgagcacga cgcgcaccgg    22140
atactgtgcg agcgggccgc ccggttcgac ggggccttc tggccttcct ggtgaacgcg     22200
cacgatgcgc gacaggcggt cgtcgaagcc gatcgcgagc ccgtgtcgt cgacatcgat     22260 cctcagatag cgggcggtgc gcagcttgcg aaacatcgcc tgccgcttga tgcggccgac    22320
cttggtgcgc aagcccttgc cgcccttctt gatcttgcgc ggcacgtacg cgctgccgtc    22380
tgggttctgc tgcgcggcga cgcgcgactg ctgcgcgcgg cgcatatcgc gccccagctc    22440
gcgaaacagt cgccggcgag ctgccggcgc cagcttcgcg agcagcccgc cggcccactt    22500
ctcaagcgca cgcagatcgt cgtccatcac gccacccatt gctcggccgc gtcgtcgacg    22560
tgtttgaccg tgcggcggcc gccttcgtct gtaccgacca caacgctttc cgtgagcttc    22620
agtttgatcg cgaggtcgac ggcatcgttc gcgaggatgt cggcgatgaa cgtcatgccg    22680
tcgcggccct ggtcggcatt ggtcacgagg tcgggctggt tcgcgcgcac ccattcgacg    22740
```

```
accgcgatca tcacatcgtc ggcgctgccg atgaagtcgc ggatgagaat ctcgcactcg    22800
taccggtatt cgaacgatgg cgtgcgtgtg ccggtcgcga caatgtggcc gtcgttgatg    22860
aagacgacga gcaggtcggg tgctgcggtg agttgaggga gcgccgcgac gagcgcggcg    22920
cgcaggctgt tcggtttaat catgggcggc cgtctgcggg ttcgtctgac tgcgcgcctg    22980
gcacgcggca atcatgtcga cttcggccgc acagcgcgcc catgccgcgc gcgcgacggt    23040
cagcgcgtcg ctcagatcac cgttcgtctg cggatgcgtc gcgggcaggg tgcagcgcgt    23100
caccgctgcg cacgcgttga gcgtaatcgt cggcgccggc gagggcgggg ctgctatgca    23160
ggcgcacaac atcgtcaggc aggcgagcag cagcccacgt gcgaacggct tcgttctcat    23220
cgatgagtct ccgaagttgc gattgatacg cggcgagcgt cgcgtcgacg gtgccgcgtg    23280
tgcggtcgag ctgcgcgcgc tgctcgtctt tctcgcgggc atccgtgagc agccggccga    23340
tgatcgcgtc gcgcgcgcct acgtcctgtt tcgcctggcg cacggcatcc tgtgctgtgg    23400
cgaggcggcc ctgcagcgcg cgcacatatt gcgcgccggc gaccgccgcg acgagagcag    23460
cgagcgccag ccagaaccga aggctcggca cggtcacgcg gccgccttcg tgccggcgta    23520
gcgttcgtac gcctgggcga gcttcgcgtc gtagaggttg cgggcatagt ccgggccgtt    23580
gtagcccttc gcgaacgcgg cccacttccg gttctttagg gcggacagca gcgacgagtc    23640
ggccgcgacg aagcgcacga acccgtcgag ctggtcgcct tcgctcgttt ccatccgcgc    23700
gacgaactcg tcgatgctcg cgtagccgag gcgcttccag tggtagccca tcacctggaa    23760
cgcgccccag ctcgccgatt cgtaagccga cgccgcgtgg attcgcgcgg cagtgtcgag    23820
tcgcacgtat tcggcgctgc cgccctggta gcctcccggc ttctggttga cgacgttcga    23880
gaacaggagc gagtagtgga cggcgtcgtt cgcgccgatg ctgtcgacga gctgccgata    23940
cataacatgc cgctcgaaca ggatcacggg ccgtccgtcc gccaggaagc ccgagccgcg    24000
cgattcgact tcggtgacag cgcgcacgca cgcgggcgac acgccgagct tgtccgcggc    24060
gcgcgcgatg tccgcttcgg tcaggtgttt gcggtcgcgc tggccggccg acagcacggc    24120
atacgtgttc gggccggcga ggccgtcgac gacgatcccg gcggcggcct ggagcgcctt    24180
aacggcctgc tcggtcgctt cgtcgtacag gtgggacacg tcgagcgcgt agccggcacg    24240
taggagacgt tgctgcagca ggccgacttc ggccgcgcgg tcgttgaagc ggagaatatt    24300
catgattcgg tgctccggag aaggcgcgcg acgttcccgc gcgcgaggta gacgaacagg    24360
gccagcatca cggcctgcac ggcctggaag aagccgaccg gcttcgggtg gatgagcagc    24420
tcgattgccg agccgccgga aatcgcgacg atcaaccaag ccgtccaggc aacgtgcgaa    24480
cggtgccgcg cgccgttctt ccggtaggtc agtacgcgca ggatgacggc gaggtgcgcg    24540
gcgagcgcga ccagggcaaa cgacaggtgc atgtcatttc cccctgcgga tcagcgcgcc    24600
gaagtcgatg tccttcacgc gctccatcag cgtcagcgtg accgtgatga cgagcgcggc    24660
ggcgaagaac gcgcgacgc ccgatgagcg gaccggcaca aggtggttga tttccggcgc    24720
ggccagatag cccatcacga gcgagatgag catgtatgcg gcgcgccggc cgatgccgag    24780
gtctttcgag gtgacgacga cgagcgcggc gcccgcgaac gcgccgatca gcgcatcgcc    24840
gtcgatgccc ggcgcgatgc cggccaggcc gatcgcggcg gcaagcgctg cggcggtagt    24900
ggtgttcggt tcagccattc ggacaattcc aggtcagtca aacagttgca ggagggcttt    24960
cgtctgctcg atcgtgttca gctcgggcat gtcgacgacg gttccatcg gcagcacgac    25020 gcccagctcg gcgaggccgg gattggcttc caggaccgct tcgacggtgc cggccgtgct    25080
```

```
ggcgtagtgc cgccagcaaa gggcgtcgag cgtttcaccc tgaagcgtgg cgaccttcat    25140
cagatcagtt caaccgtcga gcgcgcgacg cccaggatgt cgctgatggc ccaccgtgcg    25200
ttgcggcgcg actcgtcggc ggtcacggcc agctcggccg ccacctggcc tccgctcttc    25260
gtcgagtcga agccgcggta tttctccgtc acatccgcgt gcgccaggtg gtagaccgcg    25320
cgccggtaac ggaacacgtg cacggattcg ccgtcgaccc gctcggccgg cacgtcggca    25380
agcgaacccg cgcccgctgc ccgctgtcgg gcgcgccacg cggccagctc gtcgttcacg    25440
gtcagcatgg cgtcgcgcgc ggcgtggcgc aggcgttcgc gcgtcacggt gccgtccagg    25500
cgcatcgcgt cgcgcagcgc cgacaggtcg atgtccggga agaagccgtc gttcgtcagc    25560
gtgccgtcga tcggggacgc cgcgacggca ggcgcagcag tggcaacgaa actgttcatg    25620
gtcgattcgg ggagtgatgg cggtggaccg aaggtcaggg cctgtgtccg tcaggcgttg    25680
ggccgtgcct tcggtgccgc catgccgggg tgggctcttt acgtgccttc ggttccgtcg    25740
ccctgacggc ccgaggcttc gatcagcttc gagagccgat cgatgtcttt tttcacgccg    25800
acgcgatcgt tcaacgacag cgcgcggcgc agatagtcga gagcgcgcgg cgggtcggcg    25860
tcctgtacgg catagccaag cgccttgcag agctttgcgc gtacctggtc gtgcatgtct    25920
gcgtcggccg tcagctcgtc gaccagctcc aggctggcgg cgtcgaacgt actgcgctca    25980
aggaacgcgg ccagcgcggc atcggcgaac tgctcggcga cgacggaggc gagcgaccgt    26040
tcgaactggt cgggtagcgc gaggccgtgc gtgagcgcgt acgcggcgat cgcgagcgca    26100
ccgtcgtagt cgccggcgtc gatgcgccag accatgatcg tcacgagtac gtcgtcctgg    26160
gcgccgcggc cgccgttcaa cacgcccgcc acgtagtcgg cgtactccgg cagcaacttc    26220
cgcttcagtt cgaccttgcg ggcgaccgac tgcacgccct tcagggcgcg gcggtcggcc    26280
gcgagcttcg cgagcatcag ctcgtagggc gtcgcaccgg ccatcgtctg accgggcgcc    26340
gtcgcggccg ccgcgcgggc ggccgacaca cgcgcgaagt gcgcgcgagc gggcgtgttg    26400
atcgtcatgc cgccaccagc tcgatgtttt ccgcgacgca gccgcaaccg aagtcttcga    26460
cgacatacgc gtcgttcgac gattcgtagt tctcgatttg gtcgcgcttc gggttgtcga    26520
tcagcgagcg acggcgcgca ccttcctgga agtagatcga caggttctcc agcttcgtca    26580
ccatcatcgc gcgcttcggg aagaacggca cacgcacggc cggcaggttg ccgatgcgct    26640
tctggctgac gatcaggtcg gccgcgagct gctcggtcgg tgcctgcgtc gtgttgacga    26700
tcgggaaata cttgtcgtgc agcagctcgc ggccgcagat cacaacgagc cccgtgtctt    26760
cctggaacca cgggtcgatc atcgacgaca cgatgtccat cacgagcgcg tcgaggttca    26820
cgtagtcgcc gcccttaccg acgagcacct tgccggcttc cttcgcacct tcgtgcagca    26880
cgcgatgccc ggcgcggtcg cgatactgtt gcagccaacc gatgttcacg tcctgcaaca    26940
gcgggttcgc tgctttgtcc gtcgacagtg ccgcctttac gccgttccag ccgatcatga    27000
tccggtcgag cgcagactgg ttgaggatca cattgcggat gcgttgctgg aagtcgggga    27060
atttcgccca ggcgtcgagc ttgcggtacg taatggccgt gtcgtagtcg gttttctcgc    27120
agcggtagcg gttgctgtcc agcgccgtcg ggtcgatcgg ctggcgttcg gccttcgtcg    27180
tgtcggtgcg gctcgcgatc ggaccggata ccgacaggcc gagcttttcg ccttccagct    27240
cggtcacggg caggatgttg atgctcttca ggaatgcgct cgattcctgc attttggttt    27300
cgagcgtttg ctggacggac ggctcgacgg cgaatttctg cgatacgtcg tcggtgtcgt    27360
tcagcttggc gatttgcgcg gcgtactttc gatacgcctg gcgcgtttcc ttcttcatga    27420
gttgggttct ccggggtgtg agcgtggaag ggatcagcag tcggtcacga gctcgccggt    27480
```

```
cgaaccggtc gacggctggc gccgcggtgc gccgttatcg gtggccgaca gcttcgcagt   27540
cagtgcttcg acagcggcca tcgcctcgtc ggcgcgcttc ttcgcggcgg ccgcatcgtc   27600
ctgcgcggtg gtgaggtcga cgcgcagcgc ggcgacgtcg cggccctgtt gactggcgaa   27660
gccggcgatt tcttcgactg cgtggcgcac gtcggcgtca cgttgatcgt ccgtcgagcg   27720
attgcgcgcg aacatgccct tcacgatgga cagcaggctc gtcgattcgg gttcgccttc   27780
gaactcgatc gacgtttcgc acgcggccga gaacagattg ttcgaacggc gcgccgcgaa   27840
ttgcagtgct tcggtgccga ggctcgccgg gtcgtcggtc gcggccaggc cgaccagata   27900
cgcttcgccg atgtcggcga agtcgggatt gacttcgatc gacgtgaaaa ccttctggcg   27960
cttcttcgac agcgcgacca gctcgtcggt cggatcgagc tgcgcgtaca gccccatctt   28020
gcctttcagc gggccgtctt cgatctcgga tgccttcagc gcgatcacat cgccatacgc   28080
gccgaacggg ttggttgccg agagcggcgc ccatcccttc aggtgctcga tattgagacg   28140
agcgccgtac agttcgcggt tgtagttctt cgccatctgc gtgagccatt cgcgcttgat   28200
ctcgcgaccg tcgacggtcg caccttcgac tgcgacgcgg aaaaacttcg ttttgttggt   28260
tgccatagag agaggtcgaa ccgtgggtca gtgaatgtgg ttcccatgtt cgaccttcat   28320
gcgccacggc tcaacgagcg gcgtatgttg ctcgcatggg tacgtagtgc tccgcgtgat   28380
cgcgcgcgcg cgtcgcccta cgcttgccgc atgctcgaaa cgacagatcc aattcaacgc   28440
gaagcgaacg tgcgacagat cgcgcgctcg ctctactggc aaggctggcg catctcgtcg   28500
atcgcgcggc atctcgaact gaagcccgcg acggtggcgt cgtggtgccg tcgcgataaa   28560
tggaaagacg cgacgccgat cgagcgcatc gaggcggcgg ccgaaacgcg cctgatggtc   28620
ctgattgcga aggacaagaa ggacggcgcg gactacaagg aaatcgacct gctcggccga   28680
cagatcgagc ggctcgcgcg cgtgcagaaa tacggggaga cggggaagga aggcgacctg   28740
aacccgaaca ttgccgcgcg caatgccggg ccgaagcgca agccgccgaa aaacgaaatc   28800
agcgaggaac aggaagagcg gatcgtgaag gcgttccgcg aatcactgtt cgactaccag   28860
aaggtctggt atcgaaacgg cgatcagcag acgcgcaata tcctgaagtc acggcagatc   28920
ggcgccacct ggtatttcgc acgcgaggca ttcgtcgacg cgctcgatac cggccgcaac   28980 cagattttc tatcggccag caaagcacag gcgcacgtct tcaaacagta catcgtgcag   29040
ttcgctcgtg acgtggccga cgttgagctg acgggcgatc cgatcattct gccgaacggt   29100
gcgacgctgt acttcctagg gacgaactcg cgcaccgcgc agtcgtatca cggcaatctg   29160
tacttcgacg aatatttctg ggtgccgaag ttccgcgagc tgaataccgt tgcgtcgggc   29220
atggcgatgc acaaacgctg gcggctgacc tacttcagca cgccgtcgag tacgacccat   29280
gaagcctacg cgttctggag cggcgccgat gcgaatcgtg ggcgcgcgcc tagcgatcgt   29340
atccagatcg acacgagcca cgaagcgctc gtgcgaggca tgctgggcga ggacgagcag   29400
tggcgtcaga tcgtcaccgt actcgatgcg atcgagggcg gctgcgactt gttcgacctg   29460
gagagacttc ggcgccggta cagtgcagag gctttcgcga acctgctgat gtgccagttc   29520
atcgacgatt cggtgtcggt gttcaagctg gccgagctgc agcgctgcat ggtcgactcg   29580
tgggaggaat gggccgacga cttctcgccg ctgctgctgc gtccgttcgg ctatcgcgag   29640
gtgtgggttg gctacgatcc ggcgctgact ggcgactcag ccggtctcgt tgtcgtggcg   29700
ccgccgcgtg tcgagggtgg gacgttccgc gtgctcgaac gtcaccagtt ccgcggcaac   29760
gacttcgagg aacaggccgc ggcgatcgaa cagatcacgc agcgctacaa cgtcggctat   29820
```

```
atcgcgatcg acacgacggg catggggcag ggcgtctatc agctcgtgcg gaagttctac    29880
ccggcggccg ttgcattgaa ctactcgccc gaggtcaaaa ctcgccttgt gctgaagggg    29940
caatccgtca tccgcaacgg ccgcctgcaa ttcgacgcgg gatggaccga cctggccgcg    30000
gcgttcatgg gaatcaaaca gaccatgacg gcgagcggcc gccacgcaac gtacaccgcc    30060
gaccgcaacg aagagacggg ccacgccgac ctggcatggg cctgcctgca cgcgatcgac    30120
cgcgaaccgc tcgccggcgg cgacatcaat tcttcatctt tcacggagtt ctattcatga    30180
gcaagcgccg atcgcgcgcg ccgcgcacgt tcgcggccgc gccggattcg ggcgccgccg    30240
gcaccgcgcc ggcgcgcgcc gaggtcttca ccttcgacga tcccacgccg gtcatgaacc    30300
gcgccgagat tctcgactac gtcgaatgct ggtcgaacgg cgattggttc gagccgcccg    30360
tcagcttcgc cggcctggcg aaatcgttcc gcgctagcac gcaccacagc tccgcgctgt    30420
acttcaaggc gaacgtgctg cgctcgacgt tccggcctca caggtggcta tcccggcatg    30480
cgttcgagcg atgggcgctc gacttcctga cgttcggcaa cggctacctg gaacgccgcc    30540
gcaatcagct cggcgacacg ctgcggctcg aaccggccct ggccaaatac acgcggcgca    30600
aggccgattt cagtggcttt gtgtacgtga acggctggca ggacaagcac gagttcgagc    30660
cgggcagcgt gttccagctc atgcgaccgg acatcaacca ggaggtgtac ggcctgcccg    30720
aatatctcag ctcgcttcac tcggcctggc tgaacgagtc gtcgacgctg ttccggcgga    30780
agtattacga aaacggtagc cacgccggct tcatcctcta catgaccgac gcggcgcaga    30840
agcaggagga tgtcgacaac atgcgcacgg cgttgaagaa cgcgaagggg ccgggcaatt    30900
tccgcaacgt gttcatgtac gcgccgggcg ggaaaaagga cggtatccag ctcatcccag    30960
tgtccgaggt cgcggcgaag gacgagttct tcaacatcaa gaacgtgacg cgcgacgacc    31020
tgctcgccgc gcatcgcgtg ccgccgcaac tgctcggtat cgtgccgagc aattcgggcg    31080
ggttcggcac gccggacacc gcggcgcgcg tgttcggtcg caacgaaatc aagccgctgc    31140
aggcccgctt cgccgagctg aacgactggc tcggcgaaga ggtcgtgttg ttcgacgatt    31200
acgagattcc gccggcgacc gcgtagcgcc tgcggcgatt cgaagtcatg cggcagggcc    31260
gcgcaccggg aaaccgggcg cggcccttttt cgcgtttggg gccggcgcga ttagaggcgc    31320
tacagcggct tggccggcgc agggtgcgca agggtcggac gccgtgaggc gggagccgta    31380
gcgaggcttt cgtgcggccg tgcagggcat ccggcggggt gggaggggggt aggggaggcc    31440
cccgccgcgt cggccgctgc gcggtcccct ccccgcctgc gggcttcgct tggcgggcag    31500
attttagtgc acttggctga gcggcctggc gccccttgtg gtgtggggtc ccgggcgttt    31560
cgtgacgcgc gaaaatcgtg cgtattgatg cgcgatgatg cgaatcgatg caccatcgcg    31620
cgcggcgatg cctcccggcg cgacggcagt ttcaagcatc tttgtgtatc tgtacaccgt    31680
agccggaaaa gcggcttccg gtgcgccgcg ctgggcgatg gctattgttt aaaggattga    31740
ttgcaatacg gatgggtcag ctggcaatta gtggagtgac ccattcctcc ttcccgtgca    31800
cgaacgatgt gatcatagga tacgatttc tccgtgtcca aatatccatt gcaaagcggg    31860
caacgtattg atgaagccag cgcggtatat atgaagcttt gacttttttac atcgtcggag    31920
aactcttttg gtgcgtggtt gcttgagccg gtaactattt tcccattgag atctgccagc    31980
tcgacaatgt ctgcttcaga tactgacaag tcatcattga tgcgattgat taacccatcc    32040
aaaagatcgg cgtatttgct gacgcgtcta gagctgacgt gcttttgtgt tgccgtcgca    32100
atcaaatctt tatgggttac aagaatctct tcaagcttgg atcgggcttt cgtgaatttg    32160
tggaaaaatt gcttgtcgtt gttggaaatt tttcgcccga tcagcgagac cgtccccatg    32220
```

```
aacatggggc ccgagtgacg ccctgttggt ccgtaaaaat acacggcagg atgcaaacct    32280
aggctgccat cgtcattgcc tgtgatcctt cgagctagcg caagcgtttt ggttagtacc    32340
ttgaccgttt cgcttccgtc gagatcatcg cttgtcgccg taaggtcttt gggggctccg    32400
gcctgatcgc gcgacgcgat tagagccata tcgataagaa cttgcagtgc ggttcggacg    32460
ccttttggtc cgccaagggg gagatcaagc gtcttaatcg gacgttttat ctccggatcg    32520
aataaagtcg agtgcaggtt tttggctatt tgctcgatct ggcttgcctt atctggttca    32580
aacgacgacc aatatcgatg ccccttgcct gctcgaataa ttgctcgagc agcgatcgaa    32640
atcggcttct ttcgactctt aagtaaaagc tcttcaatat cgtccagagg agttcccttg    32700
gtgttgatct tgaaaaatga gctttctgct ttgtctgcgt cgcccttgac ccattgaatg    32760
ggaagtcccc gcgtgatgag cgcgttcagc ctctttcgct cagcagggtc gaggttctca    32820
tcggtagact ttgcttgata gtgcttccag cttccgaccc gcttgttcac cagtgagcgt    32880
actctttccg cgattttctt ctgttcttca gatatctgat acccgaaaaa cgcttgtgag    32940
gtcggaccgt ctccgtaatc atcctcaatc caggctttta gaacgctcag ccgatgtccg    33000
ccgtcgatga caaacagata agtcggtgac tgccacagaa ttaccgaggg aatcaggtct    33060
ccgtttgcaa agcactccag caaagacacg acttgctcag gagcccagtg attcgtttct    33120
cttgaaaaat ctggttttct gagatttggt ccgatgaggc cgccttgtgt gaagtctctc    33180
agtgatattg ttgaaacatt ttcgaaattg gaagactccg catccgatgc ggcgaaatcc    33240
tctctcttaa tcattgcgtc aaggttgact aggttggacc gcaaagccat atgttgcttt    33300
ccccgatatc gtttaataga tccacttttg taaccaacaa agtggcgcca ctatctaaaa    33360
atctaagcca ttccaatcca cggtttcaca cggaagagca gcgtaagaga tgtccgatca    33420
tccgtcgcag ttgttagacg ccgtccagat gagtttatgc ctgccgagcc ctgactaact    33480
ctgtaaagcc ggcaatgtcc atcagccacg cttgctgcgt cacagtgtaa gtttcatgca    33540
gcttgcgcgg cacgacgagt tgcaaacgct tcgctctcat ttcgtctgtt tgatgcgcgg    33600
agatcgccgt ttccagcgtc aacaggtgct tgtccatgat gcgatccgct tcggcaagta    33660
cttgacgcca gcgatccttg caggttgact tcacacccaa catggtgagt ttcatcgggt    33720
cgaatgttgg attgtggtac tcaactacgt cggggaagat aaagtcgggc ttcgccttat    33780
tttcggtgac ggctgtccgt gcgtaccgga cgccacattc agcaaacagc agttcaagat    33840
ggttttctaa ggctagaccg acgcggcttt tgcgacgatt ttgaactgag agtgaaaacg    33900
atagaaagcc gtcaacatcg acgctggatt tcgcggtgtc ggcgaaacct tgagaaaggc    33960
gatcggcgat aaggtagcgt tcaagtgtcc ggaacagaat ttcctcgcgc tccatccatg    34020
ccattaacac taagtctggc gattcatttg ggtcgatatc cttcaacgtc gaacgtgcgt    34080 aggcccgagaa ttcgcgggtt gttggaaagc gaccggagaa gcgctttaac atctcttcga    34140
gatagctgtc ttccgatgtc tctacggcaa tgccgatgtt ttcgagaatg aaacgtgaag    34200
caaactcaat acgatcttgt tcagtttcca gctcggattt tacggagaac cccggatgag    34260
ccagatcgaa aaatccaaac aaccattcaa tctggcggcc gatactcgat ccgttctcgg    34320
caatgatgac aagcaagccg ccatcgcgtt tcttggcaat gaacagtaga tcgccctcgc    34380
ttgcgttcag cgagaccgta gtagtcggaa agtaaaacct gaattctgga cttcgtggtt    34440
ttccctttcg aaattgcccc ttccgacagt tgtacagcgt cagaaaggca tcctcgacga    34500
taggatcggg atcatcgtcg ttaacgtaaa catatcgcgc aggtagacgg gtattctcat    34560
```

```
caggacgccc catgaattcg agcattcgcg cgatggcttg atactcatgc tgattcgagc    34620
gggtttcgtc cgcctctact gcgctcaagc gcttcgcagc gaccccctca aagtactccg    34680
ataaataacc aggcttcatc cccgaagctc cgttgttgat gcgtcgctgt aaagccactg    34740
tccgaggcct gtcgcaacgc tctcgatgtt cttgtttgcg ccacgcaaag cgcactccca    34800
cacaatacca acgcgccacc cttgggtacg tagggccgct agtgccttat gatcattggc    34860
acgatttcga tcaattttt cacgccagaa atccgttcgc gttccgggca acttaaagag    34920
cgagcagtca tgtccatgcc agaagcatcc gtgtacgaat atgaccgcat gatagcgcgg    34980
caacacaata tcgggctttc ccggtaaatc ccggacatgg agacgaaatc gaaagccctg    35040
acgatgtagc agactacgaa tgagaatttc gggtttggta ttacgccccc gtatgccgga    35100
catcattcgg ctacgggtgg cgctgtctac cacgtcaacc atcaggcgaa aagcggaagt    35160
gttgacggag tgccgtcacg ctcctcggca acgagcgtct ggatgtgtgg agtcataatt    35220
ctagcgacct cttcatcac tggcatcacg acgctgttac caaattgccg gtacgcctgc    35280
gtatcactaa cggggattcg gtacgtatcc ggaaagccca taagccgcgc acattcgcga    35340
ggcgtcaggc gccgcggacg cttacctttt ccttggtaga cgagaatttc cgagccgtcc    35400
ttgtggtatc gagccgacag cgtacgcgtt acgctgtccg gataggccat gccaaatcca    35460
aagccgttac ccgccgcgcg atgcttctcg gcatatgctt gtaggtacgt ccagaggttc    35520
ggcgtcaggg tgtacttgga ttggaccttg cgcttttcgt gatcaaaaaa tctctcaccg    35580
tcccacggaa gaactggctc gctgccgtca gtcttgtgca aaatcgaagc gagacgaggc    35640
ccatctgccg gcaagcgcag atcgtcccat gagaagccgg tcttcttccg gaatccgacg    35700
atgacgattc gctcacgatg ctgaggggtg aagtgctggc cgtcgatgat cttgtaatgg    35760
acgtcatact ggagctcgtc acgcaacgtt tgcaagataa cggcaaaagt gttgccttta    35820
tcgtgcgaca acaaattctt cacgttttcc aacacgaagg ccgcaggtcg cttcgctgcg    35880
atgatccggg ctacgtcgaa aaatagagtg ccctgagtag tgcactcgaa gccgtgcggg    35940
cggcccagtg agttcttttt gcttactccc gcgatactaa acggctggca agggaagccg    36000
gcaagcaaga cgtcatgagt tggcacactt tcggccgcga atgggacgat gtcaccgatg    36060
aaaggatgat ggtcgccgaa gttatcgacg tacgtcttct tcgaaaagtc gttccactcg    36120
ctagtgaata cgcattcacc gccatgagcc tcaaaaccaa ggcgaatgcc accgattccg    36180
gcgaacagat cgatgaaacg gaatcggttg ttggccgcac tcgtgccact cggttgcgcg    36240
gtctccagca tatcgcgcaa tgcgggttcc aacatggctg gacagggcgt ttcgcccttt    36300
tcccagcgcc gaacggtctt tgcgtccttg ccgacgtgtt cggcgatctc gcgctgcgtg    36360
aagcggctgc gggcctgttt caatagttcg agtggctggg cctgggtcat atttgctctc    36420
gctgggaatc tcagcggaca ttttgacctt taaacgtccc ttcgtccagg attttacgt    36480 ctcttgtagg ggcgatccgg aagcgttggg atgccccgt cagactgttt cccggcgttg    36540
tcgttatgta atcgggcgt cctagacggc tacgcatcct tatggagttt gggtgttttg    36600
tgcagctcca cccagtaggc gttgagctgg tcatccgaca catcaaagcg gcgcagccat    36660
ccttcggtcg cggcgactgt attgagcagc ggcgcagtgc tatcgagcgt cccgtcctgc    36720
agggtatcgg ccgaatccgc aatgatcggc ttcagcgcgc gattcagaat gacgtacgcg    36780
gccggcggtg agacgggaac tcccggtccg ttggacacgc cggactccgg tgcgacgccg    36840
gccttgatca gtagtccgcc gtcaccgaat ggctggcggg agaaccagtc agggggagc    36900 atgagcgaag ttgcgccgcc agccgcgcga acagatcccc cgtcgagcgc gttcagccag    36960
```

```
tcgacggtct tgatcttcat gtaaagcttg cggacagtcg atcgcatcgg atcgccgacg    37020
tcgatgccag gcccgaagcg gcgcgcgtag aaatactcgc tggcctcgtt cggccgccgc    37080
cccatcggag gcacgttcac ggccaggccg ccgtgtccgt ggacggtcgg tagatccttg    37140
gcgaacgcat tgaacagcgt ttcgaatacc cccggccgct ggacgagaaa cgcgcggggc    37200
accgtgaaag ccaagccgtc gagaccgcgc ctgcgcgctg ctttcccttc gctcagcgcg    37260
aacacggtaa attcgtagaa cccggtggcg agcttgtgcg cggcgctcgt catcgcgacc    37320
gcgagcgttt cgtcggcggg cacgcgcgcc gcgatggtct cgaatcccgg ggccttgtcg    37380
tattgggctg gctcttcgcc ctcggcgtac agccagcgca gcggaacgga tttcgatggc    37440
tgctcgccgg ctgccacctc gagcgcgtgg tgatattccc cgatcgccgc attgtattgc    37500
gtgaagcagt gcaccagggc ttggcggacg gcgggtgtga agccgtcgcg gaagtagagc    37560
acgccccgca caaccaaggc ggcaccggtg atgcccttct ggtgcgcggg ctcgtacagg    37620
ccgaagggca tcgtgtccgc tcggcgcgga tccttggccc aagcagcgat tcgtcgtttt    37680
gtcatagcgt cagcttagac agcagaacct tcgctcgcgc ctagtgctca tatgtgatcc    37740
ggcaacatgc agtcggtatc gagcggtggt gtatgcagca gcttcgcctt gtactcgaca    37800
agctgaccat ccggcacatc gaagcgtcgc aaccagtcat cgctttccgc ggttgtggcg    37860
aaatacggtg aagccgagcc tggctggcca atttgcaact gccacacgga aggaacgcgc    37920
accgatttga gggccgcgtt gaggatcacg tagttgggag gcggaacggg cggcccgttc    37980
tcatcgccgt cggtcgacga gcccgattca gggcgccggc cagcctgtat cacaacgccg    38040
ccgttcagat cgtagagcgc gtaccaggct gggggcagtt cgtttcgcag ggtatcgagc    38100
ccgccggcct tatcgagcag ttccttgtcg agcgcggtaa gccagccgac cgtcttgatg    38160
ccgtcacgca ggcgtgccgc gtgcagtagc ggttcgccaa cgtcaagggc aatcatctgc    38220
tttgcgagct ggtattcggt cggcacgttt gctgctgttt tcgcgagact gagattcact    38280
gcgtatccgg cataccccact gacaactttg agccgacggg cgaagtctac gaacagtttc    38340
tggaacgcag tagggttctc ggcgacgtac agcagcgacg tggaaaatgt cagcgtgttc    38400
agacctgcat gcgggcgaga ttcgcgccag cgttgctgac cgaacacctg aaaatgccag    38460
aacccggcgt cggccgaggc attccctgat gtcacgtatg cggtcagtgc tgccttgtcg    38520
gagtatgacg tgaatgtgcc ggagggaagg tttccgccct tgatcttgac gggctccttc    38580
ccgtcctgcc aaagccattt cagctcgtcc ttcgcgatct cgcgatattg ctcgtagcac    38640
tccgctatcg cccggcgtac ttcagggtcc gcagcgttgc ggaagaacag tgcggcacgc    38700
acaacgacgg cagcaccgac atagtcgtgc ttgtcggtcg gctcgagcgc tccgcccgga    38760
atcagcgctt cgagctgatg tgctttcgcg tattcgatga atgctttgtc ggtcatgtca    38820
attagagaac tggaacgggt acagaaggcg gcatgccgcc tcctggggcg gggccagctc    38880
cggtttggtt gagcagcttc ctcacctgcc ttccaatcga cgaaaaggcg tcgcgcagcg    38940
cgtcggcggt cggactggat gactcttcgc ctccgtcgtc agggcagcca caggtcgcgg    39000
ggtcgagttc ggtgaccttt gcgttcgggc ctgcaatttc ctggtaatcc gctatctgct    39060
cgatgtcacg tttgtctggc gggaatttca tttcgaccac gccggacaga ttatcttgcg    39120
tgggcggctt tccggggtct ttgacgatca cgacatcagg tcgtcggatc cagccaacgc    39180
cagggacgta gccttccggg tagtgcgcct tgatccagtt cggaatgaac ccgtgcggct    39240
cgagcggatt tcgcgacgac atgataggcg ctggcgggta ttcgttcatg ttgtagctga    39300
```

```
tttcgggctt gtagatgcta tcgcccctag catccagcgc gttcagcttt gtcgccacgc    39360
atgcctgctt tagtcgggcg ccgacgatgc tgatgttcgg gcctttcttg cattggcaaa    39420
gcgctccgca gagtactttt ttgtcctgct gatcgagatc gccgccgaga tacaccttag    39480
tcgtcgtacc ttcggtcgac attccgccgg gaacgtcgtg gctcattcag gcttctcccg    39540
gccgaatatc agggaggcag gcgagtcggc gtgatgccac tgggtgtaac cgtcggcatc    39600
ggttgtgccg ctgatggtct ggccctctgg ggtttgcaaa ctgtacgggc tatttgcggc    39660
cggccgcccg tccgcgccga cgacctggaa tcgaccgcga taacgctccg ttgaaccatc    39720
ggcctcatgc cgagccgaca tcgtggtacc accagagccc acgggaacgt tcgcaaccgc    39780
atcgccctgg ctagctatca gcgtcgcgcc acatgcggtc atgtctccct gaaatgccgc    39840
tcgccgaccg tcgaaattca tgccgggatt cctactggtg acgatcggaa atactccctt    39900
gcacttcggg cacgtgacca tcgtgccaac aaacgcaatt ggccgaccgt cgatgaaagt    39960
aatcgctccg gatgacagta cagtgccacc gtggtccgta tgatcgccct ctcgaatgaa    40020
cgcgaatccc atgctgaact cctatgacga aatccgcggg gactgtagca cgcgttattg    40080
acacgtaacc atcctgtcag agttgacggg cgtccggctg aatttgcaac ggcggagaag    40140
gcagcgggcg ctatcacctg cgaccaacaa tctcacgtga gatttcacaa ggagaaatag    40200
catgagcgac ctgcacgaaa attcgcgact ggatcgtccg gagcgcctgc tgcgcttcgc    40260
ggaggtccgc tcacgcattg gtttgtccaa gagcgagata tatcgcagga ttggcgcagg    40320
aacatttccg gctggtgtca agctaggcgc tcgggctgtc gcctggcatg aatccgcagt    40380
cgaggattgg attcgagctc tcaggtagat ttcgcttcga attagtcgcg ggtttcgagg    40440
cgtttccaat ccgaattcga tcgttgccag acaaggctgg gaaggcaacg gataagtgaa    40500
aattggaaac gggaaattgc gctaagttat tgtaatcgtt tgaaatttca actgc        40555

<210> SEQ ID NO 3
<211> LENGTH: 37236
<212> TYPE: DNA
<213> ORGANISM: Bacteriophage KS5

<400> SEQUENCE: 3
gcaagctgcg gagctttgcc gaagtggcgt ttcagtagga aaccattgct gtacaaggct      60
ccccggccgg tccggggagc cgtctcgtct aacatgggcg ccgacgtcta acttgcgcgc     120
gtcaacggaa ccggttggac gcgttctacc tcgcgtgcct tcgtgtagtg tgccgtcatg     180
ctttcggtcg tgtggccggc cagcgattgc gcggcagcgg ctcctcgctg tcgtttcaga     240
tcggtcagcg ccttcgcccg cagatcgtgg aagtgcatac cggtcagata tagcgggttc     300
ggttcaatac ctttctttgc gcactctttc tcgtacgtcg accgtgcgcg ttcgcacgca     360
cgtttccacg cagagtacgc gccgatgtag gtgaagcgcc cgccagtgtg tgtgcagatc     420
acaggcccga ttgcggtgac cttgccgccg cgcgcgcgat ccagtgtttc gcgcaggtcc     480
ggggtcattt cgatcagcag gcgcacgccg ctgctgttga ccgttttgct cggatggaac     540
gaaatccctt catcagacac gttttgccaa ttcagggcga gcaggtcccc aatgcgttga     600
gcggtctggt atgccagatc gaccaggcag agaattgagc gtgcggacga agtcttgtag     660
tcggcaccgg caacgattgc agctcgtact gcgtccaact cgtcgtccgt tatgtagcga     720
tcccgcttcc tttccttggc cgcgccgact tcgcgcgcgg gattgccgtc acagagccct     780
cttcgaactg cgtgcatgaa gatcagcgac agcaatgcct tgtgcttgtt gctgctgctc     840 gcttgtcgt ggaaatgttt atccaggaac cgcgcaacat cggctggcct gacgtcctcg     900
```

```
atcagccatt ggggaccaaa ctcctttcgg atgagtccga tcatcttcac gtagttggca    960
cgagttttcg gagcataggc cggaagcttt tttcgcatcc agtcatcgat gagggccggc   1020
atcgtgttgt cgagcgctgc cgcgctatcg gatgcacgtg tgtactcggc cagtgattcg   1080
tacaggcgga cgatgccgtc tcggacgcgg cagagtttgt gccatttccg attcttatcg   1140
acgaaccacc atgacccatg tttctcgtag acgcgggctg gcaggaaaga ggggcttcgg   1200
cgacgtccga tcattttgtg gtgtccttca tgtcagaggt tagctttggg cgtttccggt   1260
tggttttctt ttcatgagcg gcaaaaccga gcacgtggtg acgccagact ctgacgctgc   1320
cgtcaggtct gcggtcggcc gggatgcctg ccaaagtgag cgcgcgtagt tgccgtgctg   1380
gctgtcggta acccgtcgct tcatagattt cgtgcgcgct cagcgtgagt gcggccgaat   1440
gcgccggctc cgggtgatct gcgttgtcca cgccatgcga ggggatagggg cgcagaacaa   1500
ctcgtggaca cgtggtttgc atcgcgatct gaacttaacg tactgatttt taaaaggtta   1560
ttaagccatc agttgccacg aaaaacccgt ggcgcggtct tccgactcgt ggctcaaaaa   1620
ataggcaacg tccgaaactg atggcaaaac ggacaagact cgtggcgctc gatcccggct   1680
tttgctcgcc tcttcctcgc tttctttctt cttcttttc aatgaattag agagaagaga    1740
gaaaggagca atgggcgccg tcgcgaaaat tggactagtg gcaaaaatgc tccaactagt   1800
ggcaaatgga gggcgacaca tggcggtact cttctcaaca atcaaagact tacgagcgga   1860
cgcccccgaa aaccacgctt cgcgtgcgct gcatgcccgt tccctgcgga aaaatcggcc   1920
cgcgcggccc cgccccgtct cggctcgcgc tgttccccgg ccgtttcgac tcgcgggggg   1980
tacgggggga aacggacagc atggcggccg cgtgatcgcg tgcgccgact gctgcgcgca   2040
tcggcgcacg caccggaaac ccgaatccag ggccgctacg cggccggaag gaatgaggaa   2100
aggggtacgg ccgcgcggtg gccgcatcag ctgagagggc atcatgcgcg gccccgctgc   2160
tcggtcgcgt cggtcgccag atcttcacga atcgacacgt gcagcccgaa gtcgccagg    2220
cgctcgagcg agatcggcgt gaggtacggc acgcggcgcg tgtagatgcg cgctcgacc    2280
tccttctcgc cgacaacgac gccggcgtgc ttgagctgcg ccttgaacac gcggtccgat   2340
ttcacgggca ggccgttcca cttgtcgcgc agcgcgctcg tgtgcgcgat gtggtccatc   2400
acgtgcccgg tgcgcagcag taggcagaac tcgccgtcga ccatgtcgaa cgtgtacggg   2460
tgcttgtagt tgccgccgtc gatttccgac agcacggttt ccatgatcca gacccacggt   2520
tcccgatcgg cgctcgtttc ggcgatgtgg ccgttcattt cagcgagcag atcgcgcggg   2580
aagtcgcctt ccgtcggatc catgccgccg aactcgcaca ggtagcgcca cgcgagcgcg   2640
acggccgcat agttgccggc catgcgtttc gcgccgtcgt cctcaccgct cgcgcggcag   2700
ttggccagcg ccttgtcgcg cagcgtcgcg tactggtcga gcacggcgcg cttgtcgagc   2760
ccggtgagaa attcgagcca ctgccgtacc gggaagcgcg gcaggtcgtc gggcagcagc   2820
gggccgcgct tgccggtgag cgtcgtgcgt acgagcttgc cgagcagact gcgcacgggc   2880
acgtcctcgc cggcgagcat caccggcgcg cacagcaggt attcggtcat gtcggcgccg   2940
cggcgcgtga cggtgtactg atagttctcc tgcagcaggc cgaccgcctt gtcgatcacg   3000
tcctgccggc gtgccgacag ctcctcccag ccgaccggat ggctcgtgtg actgatgctc   3060
gttagcagtc ggaactcggt ctgcagcgac tgcccggaga acatcgtgaa ggcgagcgat   3120
cgctcgagtc gcttgatgag cgtcgactta ccggcgccct tgttcgcctg atcgtgata    3180
tgcggccaga agccgagcag cgccttcagg tggccgccga gcgcccatac gagcgggatc   3240
```

```
gttgcggcgt tttgcttgaa cgtcgtctga tacgcggcga tgacgcggcg cgcgtcgcca    3300
atcgggccgc tcgggaacgt caggttgtga tacggacact gcttgtcggc ttcggtgaag    3360
tagcagtccg ggccttcgtt gacgatcagc cgaccgtcgc gccacgcgag cccaacaaag    3420
ttcgccgctt ggcgcgcgcc gaggtcggcg ccgcgctcga ggatgttgac catgcgcttg    3480
aacggtgccg gcgcccagat cgggccgaac ttgcccact  ggtcgacgtt gtgcagctgg    3540
tcgtcgagca tgacgcgacg gatgagctgc gcgccgtggc gcggcgcttg caccgacacg    3600
gcgaaataca cggtcggcgc ctggtcggcg tcgcccgtca tcgtcgacgt cgcgctcgcc    3660
acggacacgc ggctgatgcc ggcgatgcgg aagccgcaca ggtccgtcat gacgggcgtc    3720
tcgacgccgc tttcctcgtt cttgtccatc ttcgtgatgt agctggtgaa gtcgggccgg    3780
acgcggaaac gccagtactg cgcgaagtca tgcgacggca ggaagatgcg tggccggccg    3840
cgacgcgtgg cgtcgccggc gaggccggcg atgagccagg gctccagctg gtcgagcgcg    3900
cgctgcagat cggccgggcc gcgcagttgc aggtagtcgt tgacgtcgtt gatgggcttc    3960
tgctgtttct cgccgtccgc gaggtcagcg agccaccccg cctggtcgac gagcacggcg    4020
ctgatgttca gcgccgtgag ccgctcgtac agcgcccacg cagcttcggg gccggggcgg    4080
tggccggcgc gcggatgacc gtcggcgaac ggctcgtcgt tgtccatgca gatcacaacc    4140
tgcttgccgc gcagcggcgt gaagtcgagc cgtcgacat  tgcccaagcc gcgcagcgcg    4200
agcgccgccg cgccgggtag cgtgcaggtg tcgatcgaca cgcgcgttgat cgcgcttttcg   4260
acgatgaaca cgcgcttcgc cttgtcgagc cggcgcggat ccgcagtcca gccgtagccg    4320
gctttgtcgc cctgcgtctg tgtcttgacg ccgccgttga gcgcgggatc cacgtagcgc    4380
atgtcgacgg cgacgacgcg gccgtcgctc ggcgcacgta cgatgaacgc ggcagccggc    4440
ccgccgtggc cgacttcgcc ggcggcaact ttcgagctcg tccaggtgtt gaacccgagc    4500
gtgcgtgcgg cgatcgccgc gtcgatcgcg gcggcggaaa tgccgcggcc gccgaggtat    4560
tcgcggacct gatcgcgctc ggcgaagcag cgatcggcga tgtattcgac ggtcgttttc    4620
tcgcggcgct cggccggtgc gggccggtcg agcggaatgc cgtaggcgtc gtgcaggtag    4680
cgcacggcgt ccgccacggt gccgccgcgt cgtgaatga  ccaggtcgat gcacgacccg    4740
ccgacgccgg cgctgtggtc tcgccagccg gtgccatgct tcgggtgatt cacgtagatg    4800
gacagggacg ggctcctgtc ctcgtgttgc ggcgaatggt agagcgcctt gtcgccgccg    4860
cggccgcgct tgagaccgag gcgatcggcg aggtcgtgca ggtcgatgcg ttgtttcagt    4920
tcgtcgatcg aagccatcgt tattgctgtt gctcagattg ctgctgggtg tggtcggccg    4980
ggttgttcgg cgtcgcggga gagaagacga gcgcgcgcag cgcatcggcg gactcgggaa    5040
agccgagcgc gaggcgatca ctcaatgccg cgacgaacag gccgagcgca cactggcgag    5100
cgacgctgcc ggggcggttg ttgaagtgca gaggatttgc ggccgcgacg atcgcggccc    5160
ggagcgtcgc atcgtgcgat gaagcatcga ggcggctcat gcggcttccc ccaggatcgc    5220
gagccgattg cgcgcgagct gataggtggc gaactgcaga tcggtgcggg ctgcagtcgc    5280
ctcgtcgagc atcgtgcgca gtcggggccg attgcgttcg acgttcgtcg tcgcgttttgt   5340
gatggctgcg gtgcgggatg tgcccgtccc ggcttcatg  cccgaggcca ggtgcgtgac    5400
gacccacttt tccggatggc catcggccag ataggctcg  gcgtggatgc cgaaagtcgc    5460
gccgacgtcg ttcggaatga cgacatgctc cccggtgacg gtgcggagac cggccgaggt    5520
tagcagctca tagcggatag cggattcgat cgtcatcaca tcaccccga  ggcggaacgg    5580
accatccgag cgcgacgacg agcgcaacca tcaccgcgac gccgccgacg aaggcgatcg    5640
```

```
ggcgtgcgta tcggacgtcg aataggcgca ggacgtcggt ggtgaggtag tacgcaccgg    5700
tgagggagag cgagagcatc agcagcacac tgatgccgaa aacgtagggt ttcatggttt    5760
ggctccaggt aagtgcgccg gcatcggcgc ggattcgtca ttcgtcgacg tcgtttgcgg    5820
cgcggcgctt cacgtcggaa gcgcgccgca accgggcctg ttctcggtcc tgcatcgcac    5880
gcgccgcaga ttccacgacc aggcgtacgg cgcgatggcg gatcgacgtg tcgaaatcac    5940
cgaccatgcg caggcgatgc catgccgcgc gcaggtcgac gtcggtgagc ggcgcgcgca    6000
tcggtcagtg catccaggcg agcagcggcg tgccgcgcgc gagatcccac gacacggcga    6060
aaccgagtgc gcgtgcggat gcgacgaata cgtcggcgcg gacgtcagtc gcgcagagct    6120
tctgcaggta ggcgacgcgc tggttgaagt cgagcgacga ggtgagggtg gtgacgtggg    6180
cgggagtcgg cgtttgcatg agtctctcca gaatttcagg caaaaggagt ccctcgcgcc    6240
cgcgctgggc gggtgcgatg ggtgcgaaac aaaaactgcg attacgggtt aggcgtcgat    6300
cagcgggagc tggcgcgggt cgcgcggtag ccggtcaacc ttgccgagag gcaggtagac    6360
ggccgggttc ggcgtcaggc tcggggcgat cgtatggacg gtggcgacgt gaatcttgta    6420
ggtcgtcgcg cactcgatgt tggtgcattg gcaatacgct tcgcgaacga gagcggacag    6480
cgtgcggctg gttcgaataa cggcgcggct gccgcagtga tggcacttca atttcattcg    6540
gggctcctac gggcggctgc attcgccgcg gccttggcgg gcgcactggc agaacatgcc    6600
gacttcgccc aaggtcgcga cagcgtcgag gtatttgcgg gtcacgcaga cgaagcccac    6660
ggcagcgaca agcgtgtcga tcttgtcgat gacgattccc ttgccgccgc tcaggaagcg    6720
gctgacctcg gagtcgtccc atccgagtgc agcttgtact tcgtgacgtt tggggccgtg    6780
cagcgcatgg cgcagcgcgg gttcgataag ggcgggcggc tgcatgactc aacgcccggc    6840
aaaagaactt gcgtgcagtt gagcggccgg gccggtaact ttggcgcggt atcgctcgac    6900
gccctcgagg tagaccagac gggcgacgct ggaggtggag cggttcagga gcgtggacag    6960
ctcttcgagc gcacggcgct cgtcgggcat cagccgcatg tatacgggct tgctggacag    7020
cacgccgcgt ggtgagcgcg tgacgggggc tttcttgcgg agcatgacgg tatacttccc    7080
ttcgttaacc ttgcacaacc ctgataatac acaccgatcg gtgcgtatgc aacaaaaaac    7140
aaaccgtatg gtaagtatcg gcgaccgact gcgcgatgaa cggaagcgca cgtctctgtc    7200
acaacgcgcg ttcgctgaac gcggtggtgt gacggagaag acgcaagtgc tctacgaaaa    7260
aggggagcgc gtgccggatg cgatctatct ggaaaagatt gcggccgcgg gcgtggacgt    7320
gcttttcgtt ttgacggggc accgcaactc agccgaactg tcgcccgatg aggaagtgct    7380
ggtcacgggt tatcggtccc tcgatgcgaa gggccgtgct ggcgtgctcg gcatgatcgc    7440
cgggatgacg caacagccga ccgagtctgc accggcgaaa gtggcgaagg tacgtcagaa    7500
cttcgaaggt gcgagcatcg gtcagcaggt cactggggat gtgaccgcgc cgttctccat    7560
caacatgggt agtgcgggc gaaagaagaa gcgcgaaggc tgattactgc gaaacgcaga    7620
ccacggcagg gccagccgta ggagaaaaaa gggaattcaa tgaatcagaa gttcgatgga    7680
gaaatcgggc aagtcgccgg cggggatgtg aagagcaaca gcgcgcagac tagcgtcaac    7740
gtgcacttcc acggtggcga gccgaaagcg gctgagacga agttcatcaa caacaagcag    7800
cgcgcagcga tcgcgcaccg ggtcttcaag atacaaaaac agaccggcac cgaggcgctg    7860
atggtgtacc gccgcctcaa aacggtgttc gattatgaga gtatcgaacg gatgccacgt    7920
agcaagtaca agccggcgat cagctatctg gatagctggc tccgaaacgg caatctcgga    7980
```

```
aaccctcccg gctcggccgc cctgcaaaag gtcaaacacc catctccggc tgcgcccacg    8040
gcacgccgtg agtcaccatc tccgcacgtt caattcgcgt cgccggccgc ggcgacattc    8100
agccctgctg cgcccatggc gacggctgtc cctgtccaac aaaatagcag ggcctcgcga    8160
cgaggcgcga tggcgctggt agggatcgcg gtgatagtcg ctgcggccac tgtgtacctc    8220
tatgtcgaga gacatcctgc cggcgttcgt caacaagtcg aagctgcgga gccgccgcag    8280
tgcgaatacg gcggcaaccg ctactctctg ggtggcgtag tgatgcaggc tgggattcgc    8340
cagcggtgcg tggccgacgc cgatcatggt gtgcggtggg agagagcgac aggcggccga    8400
cgttaattgc gacgtgcgat tcaataaatt tccaataggc attcatgcca tacgtccggg    8460
gaaccaatga agaaagtact caaagttacg ggatacgctt gtgctgcgct gtttgggctg    8520
atgctgctcg tcggaatatt cggcaacacg aagcataaag acgaagcaac tgcgccggca    8580
gtcagcgttg cgagtggagc atcgtctgaa gccgcagtgc agaaggaaag tgcgacagtt    8640
gaagcgcagg catcgaggaa gcaagacgcc gctcaggagc cagaggttgc cgacaatgat    8700
ttggacatca cgcccgatca gtatgcgaag gcgttcaatg cgatcatggt caacttgaag    8760
gaaccttttc gaatcaagcc gaggattgag aaaggtgagt ccgtcgacac ttttaagtct    8820
gcgctcaacg agaatttgta tgtgattggc tccgtcagca agaccactgg taagctgcgt    8880
agcatcgtat tcatgggcgc cggtgatggt acggtgacgt ctggagcgaa catcatcatt    8940
gtatccacgg ctgctctgac tgccgcggtt cctaaggaaa cactgatcaa ttcggcttgg    9000
cggtcatcgc tgacgaggcc aagggcgttg tagaaagaag ctcacggaac ggacccacga    9060
cgatgcagcg gcagatcggt tttgcggaag cggaaagtgc gggcaagaag cgggtgacca    9120
agcgtcaacg ctttctggcc gagatggaga aggtcgtccc ttggtcgcgg ctgctgtcgg    9180
tgatcgggcc gtattacccg aagggcgagc gtggccggcc gccgattggc ctggaacgga    9240
tgctgcggat ctacttgctg cagcagtggt acgggttgtc ggacgaaggg cttgaagatg    9300
cgctctacga cagcatcgcg atgcgcgcct tcgcgggcat cgacctggcg cgcgagaacg    9360
tgccggacgc caccacgctg ttgaaattcc ggcgcctgct ggtcgagcac gcactgacgc    9420
gaaagctgtt cgacgagatc ggcatcgagt tgtgcgagcg cgggctgatg atgaaggaag    9480
gcacgctggt ggatgcgacg atcttcgagg ctgcgccgtc cacgaagaac gccgggaaga    9540
gccgtgaccc ggagatgcat cagacgaaga agggcaacga ctggtatttc ggcatgaagg    9600
cccatgtcgg cgtcgacgcc gactcgggtc tggtgcatag cgtggtcacc acggcggcca    9660
acgagccgga cgtatcgcag gcccacgccc tgctgcacgg tcatgagcag gaagcgtttg    9720
gcgatgcggg ctacaccggc gtggacaagc gcgaggagat gaagggcaag acggtgaagt    9780
ggcacgtggc gctcaagcgc ggaaagatca gggcgatgca ggaaggtccg ctgaaggacc    9840
tcgtgatcgc ggtcgagcga accaaggcgc agatccgcgc ccgggtcgag catccgtttc    9900
atgtcgtgaa gaacctgttt cgtcatcgca aggtgcgcta caagggtcta gccaggaaca    9960
cggcacagct gttcagtctg ttcgcgctgg cgaacctggt gatcgcgaaa aatcagctgt    10020
tgtcgactca tgggagcaat ccgtcatgtg tgtgaaaaac gcgggaagtg aggcccgaat    10080
acgagcgaaa ctcacctcgc atgtcgtcaa attcctacgt caatctgaaa attgcaacct    10140
gcctcgtccg ttatgcggac gacaggctca ttgatcagcg tttccctaat gggacgacga    10200
agacggttgg cccgatcgtt gtgtcgttga tgagcgactt cgacgagaag tctggtaaat    10260
ctgcgtcgaa gattctcaac aatgtaaagc tgtggcacac ccgaagcgaa cagatgggcg    10320
catggttcgg ggcagagcct gcgtaagtcg cgacacgcct attctatgtc ggtcgaggtg    10380
```

```
tcgatctccg gcacctcgct cgccttgact tccagatcga ggtccgatgt aaatccgccg   10440
ttaccgtcga gcgtatgtgt aacgcgcgcg acgatccact tgcagtcgtc gatgacacgt   10500
ttataaccgc gcacggtgac aggcaattcg gtcatcagct ccggccggcc gagcgcgagc   10560
acgatgctga actccgcgac accgcgctgt agcttctccc attcagcctt cgccgcgcgc   10620
gtcgcgttgc tcttgttcgc gtaggtgtgc cgcagcacct tcacgttttc ggcggtgccg   10680
aacaacacgt cgccgctctt gtcgatcggc ttcttcttcg tagtgcggcg cctgcgccgc   10740
ttcacggtgg tcgactgctt cttcgcggtg cgcgtgttca ggtagaacgc ctgcacgccg   10800
gaatacgtgt cgcgatcggc gacgccgaac tcgtggcgat cgccaacgtc gcgcgtgatc   10860
gtgatggcgg gcaacggctt gccgctggcc gtcgtcgcct caccggcctt gatgaacagc   10920
agctttccgt tcttcactgt cgcgatcgca tcgaacattt tcgccaggcg cgacagcagg   10980
ttcgcgtccg actccgcggt ctggtcgatg tggtcgacga gctggccgtc gagcgccttg   11040
ctgatgcgcg cctccacctt gttctggctc gcgatcgcgc gcacgatcgc gccgacggtc   11100
tgacggtgcc acgatcgctc cttcttgatc gacaggcctg cacgcagatc gacgctgcgc   11160
gcgcgaatcg tgagcacgtc cggcgtgccg gtgtgccgca cctcgtcgac gacgaattcg   11220
cccttgtcga cgaggccgtt tgcggcaccg gcccaaccga tcgccacctt caatctcacg   11280
ccacggctcg gaatctcgag cgcgccgtcc gaatcgtcca ggctaatgtc gagctggtcg   11340
gcttcgaagc gcggttgtc ctgcagcgtc atcgagatca accggccgtc gaacttgtgc   11400
gagatgtcct ttccgttcag cgtaatcgag tagatcgcgc gcggcacacg atcgtcggcc   11460
aggacggttt tctgcaccag gtcggcgccc ggcaggtcgg cgaggttcat agcgagatcg   11520
cctccttgat cgcgtcggtc acgatgccga gcatgtcgat gtcgtcgttg cgcgtgagcg   11580
cgaccgtgaa atcgatgcgg cgcgcggcgc catccgggaa gaacagcgtg cgtgtcgtat   11640
cgatgttgtc gatcgtgaac atgccgtaga tgtggccggt gccctcgatt agcggccacg   11700
cggtgtgctg gtccgccatc gcctcgagca ccgacagcga cagatcgccg ccggtcagct   11760
cgggcagcag cacgccggac agcacgatcg tttcctcgtc ctcgccgacg tactgccgcg   11820
ccggcttccg gccgacacgg ttgttgctcg cgtagcgcca gccgcgccgg cgcttcagct   11880
cctgataggg cagcgtcgag aggctgaaca cgaacagccc gagcgccatc atcatgacaa   11940
tccctccttc aatcccgatc gcgcaggcgc gaccgatcgc gcgcggcctg cgcggcctgc   12000
tcttggcgca tcagctgcag caccttctgc gcgagcgcat tcgcgtccat gccgggcgac   12060
gcgtacacgt tgatcgtgat cggcgccggt gtcgacgctg gcgtgcgcgc aacggccgcg   12120
gcggtcaacg gcgggcggtt gtcgacggtg aggggtgcgc cgccggcgat ggccgcgccc   12180
gtgatgccga tgccggcgcc ggccgcgaca atccgcttgc cgagttcgcg cacggtcgca   12240
agcggcccgt cctggccgtt gcgcagcccc tgctcgagac cggccatcgt ccagccgccg   12300
agcgcggcga acacgcggct cggcgaatgg atgccgagcc gttccttgaa ccagccgacc   12360
acgctgtcgc cggcggactg gatcgcggtc ttcacggcgc ccaggccgtt cgtgatcccg   12420
ttgacgagcc ccgacatcag attcgagccg aactcggcga agcgtgcgga cgcctgcgcg   12480
aggccggcaa tgatgtcggc cagccacgtg ccgaaggcgc ggccggcgcc ggttgcggcg   12540
tcgaggctct tcttgctggc gtcgacgggg accagcagtc gtgtaagcca gtcccacacc   12600
cctttcaggg caccggtcag ccaatcggcc aggggtttga gcggcgcgaa cgcggcgccg   12660
agaatcgcga aggctcggct cacgagcggc gcgagcggct tcaggccgtc ggtgatccct   12720
```

```
tgccagaagc ctgagaaaaa cgccttgatc ggctcccaat atttgacgat gagcagcgcg    12780
gcgagcgcga tgccggcaat cacgaggccg atcggactca tcaatgcgac gcggccgacg    12840
agcagcagcg ttttgccgat ggcgccgagc gcgcgcacca ggacgccgcc ctggatgccg    12900
agcatcgaca tgctgaagcg cacgatcgcg agcggcccga ggatgccggc gagcgcgatc    12960
gtcaacgtgc cgagcacggc taacagcacg ccgagcccgg ccgcgccgat cgcgaccgcg    13020
cgcgtaaagt tgggatactg cttcgcgaag ccgagcagtc gctcgagcac ggtcgtcgtc    13080
agctcgagcg cgcggttgta cacgggcaat acctgctcgc cgatgacggt gcgcaggttg    13140
cgtaccttct ccaacgcgat cagctcgcgc ccttcggttt gcttctgccc gagcgcgtgc    13200
aactggtcga tcccgtacgc gccccggttc agcttctcgt ttttgtgaat ctgctcgcgc    13260
tgcatgtaca tcgtcgcgaa cagattcgcg ccgttgccgt tcgtcatgat cgtggagaat    13320
tcctccagaa tcttggcgtc cgacgtgatg cccttggctt tcagcttcgg cagcagcacc    13380
ttctccatcc attcgaacgg cgacgcgttg aacagctccc cctggatcag cgcaccgggc    13440
ttgatgcgct tcacgttacc gatggtgttg tattcgactg acttcttgtc gacgaggccc    13500
agctcgacca ggcgcttcgc ggcgcgcacg gtggtcttgc cttgcatcag gttgctgtac    13560
gccgcttgca caccggtgcc ggccgcatgc ccgcccattt cctgaatcag cggttccatc    13620
tggtagtaga acgcgtcctg gcgcatctgc tttgcagcga ccttgccggt ctggatgaag    13680
ttccgccatt cgtcgccgcc gacgcgtcca ccggtcgcgg tcagcacctg ctgaaccatg    13740
ttcgcttctt tgatgaacgc tgcctcggat ttcgtgccgc cgcgcagctc gatcaccttc    13800
agcatgttca tgaacttctc ttcgttttcg tgccctggc cggcgccgaa catcgcctcg    13860
ttcgcgaact tcatcttcgc gagcgtcggc atcaccatct gcgcgtgatg ctcgtccgcg    13920
aagatcgaca tcgcgtcgcg catcagcgtc atgttgtccg cgatcgcgac gcccggcgtt    13980
ttcattcccc gcacgtagcg ctcggcgtcc tgcgtcgcgt gatcgccgag accgagcccc    14040
tgaatgcggc cgcgctcgtt ctggattttc ttcgcctcgg ccagcggctc gcgcagatcg    14100
tcgaggatgt gctgaccggt cgagcgcgcg gcatatccgc caattgccat ctcggccgca    14160
gcgccacgca tggcgcccat cttcgtgcgc gcggccgcga tgcgctgctg acggtggttc    14220
agcgcgtcga cggcgcgt ctgcgcatcg atggcgtcgg tggttgcggc gatgtcgttc    14280
cgcagagtgc gctcgtgctg ggagagcttg ctcgtgtcga cgccggcgcg cacgagccga    14340 tgcgcagct cgtcaacgcc cgccgattgc ttcttgaacg cgataccgag cctcgacgac    14400
gcttgccgcg ccttcgccag ctcggcaatc atctgctgcg acggcggccc gtacgcatgc    14460
agcgacttcg cgagttcctt caccttcttc tgcgcatcgg cgagcttcgc cgatgtgttc    14520
gcgaggcccg tgcgcatctc gcggaactcg ccgatacgcc gctgcgtgtc gctcagctcc    14580
ttcaggcgcg cgcgggtgtc gcgcaggtct ttcaccagcg tgccggttgcg gccggtgatc    14640 tcgcgaatcg ggcggctcgc ctggtcgagc gccttcagta ccacttccag acgaagcgaa    14700
cggtcgctca ttcgtcgcct cgctcgtagc gctcgcgcgc gcgttcgcgc cagtccatca    14760
gctcagacaa cggcatggcg gccatcgcgt cgggcgacca gtggaacacg agcgcgatat    14820
cggccatcac gtcgtcgacg gttcgaggga ggcgtccgcc ttcgacgagt tcggcaccaa    14880
aaaaccggct acctcggtgc cgagctggac gaggtccgca gggtccaggc gtagcacgtc    14940
ctgcgtggtc agaacgggat cgctgatgcg cggcagcacc ttcgacaacg cgatcacgtc    15000
cagctgcagc acgtcggtga gcgcgacgcc gcgcagcgcg cccgcgagcg gcttgttcag    15060
cgtgacagcg gtgatttcct gctcgccgcg cttgatcggt gtgtcgagcg tgatgacggc    15120
```

```
ggattgcttc gattgcatcg tatggttcct ctgagggtag gggtaagggg ttacaggcca   15180
atggcgcggc gctgctgtgc gagacgatcg acgccgccga cgacctcgac gaagttcggg   15240
acgtcgatct cgattagcgt ctcgccgttg cagacgagcc ggtaatacga cagggacatc   15300
gtgccggtct ggtcggcgtt gtcgccggcc ttggccttgc cggggtcgat ttccttgtag   15360
cggccgcgca cgtacacttc gaccgcgtcg acttcctcgg tgtcgtcgcg ctgataggag   15420
ccagcgaaac gtacggtgac gccgtcgacc ttcgacgtgc cccatgtctt gaacatctcc   15480
ttcatgaagc cgcccatcgt caggccgagc tccatcttct ccatgccgag gtcgatgtcg   15540
atctcggcgt tcatgccgcc gccgcgatac gcttccatct tgcgcgtgag cttcggcaac   15600
tggatttcgg tgacttcccc gacgaacgag gtgccgtctt cgaagacgtt gaagttcttc   15660
agtttggatg gcagagccat tgcgtttccc tatggtgagt gtcgagcgat cagaccgcga   15720
tgctttgcgc gaacttgacc agatagcggt cggtgatgcg ctggcggaac gtcaggtctt   15780
cgagcggcgg ggcagggcag aagtcgtaat cgatgaagcc ctggccggcc ttgagcgaat   15840
ccttgtcgtt cgcgcccgga tcgaaccagc attcgccgtc gatcaggtag ccggcggtct   15900
tccacgcgcg gaacttcgca ttcacgccat cgacgatgtc gcgcatcagc gtgcggctca   15960
tcggctggtc gacggcccac atgtgcgcct cggccatcgt gtcggcgatc acctgcgcac   16020
tgcgcacata gttctcgaac gcccacagct tgtcctcgga acaggtgcgc gatcccata   16080
gacggtaacc gtccgcgttc accagcgtgg tcacttcgtg gctgttcagg tagcccgcgt   16140
cggtgttcgg gtcctgcagg tcccagaaca cgtcgcggct gatgcccgtg acgccgttga   16200
ccacgacgtt cgagatcgtc ttgtgccagc cgatctcttc gtcgatcttc gcgcgcatgc   16260
cgagcgcgcg cgccgttgcc cacgtgatgt cctcggcgtt ggtcgtggtg ttccagttca   16320
cgaaatccgg ccagatcgtc atcagctcac gctggccgaa gttcgcgcgg taggtggtcg   16380
cttcctcctt cgtctgtgcg ccgaacgcgc tgatgtagcc gaagccgcgc agcttctgcg   16440
cgatcgtcgc aagctcggac gcgacgggca gggtgtcgag gcctggacaa ccgagcacgc   16500
gcggcttcac gccgaggcgg ctcttcgcgg cgagcagcgc cttcataccg gtgtactgac   16560
cgtccgcggt ggtcgtgccg atcacgttgc tggtcgtggt atccggatcc ttgccggtcg   16620
gcacacgcac cgcgacgatc agcggggacg tctgcgcggc gatcgcatcg agcgaacgcg   16680
cgagcgtgcc cttcgtgcct gccttgccga tcgctgcctg cacgtcggtg atgagaacgg   16740
gacggttttc ggggaaggtg gccgcatcgg cgtcgtcggc cgtgctgacc aggccgatga   16800
cggccgtgct gaccgtgcgg atggggcgcg taccctcatt gatctcaatg acccgtacgc   16860
cgtggtggta atcagaaggc atgcaatctc ccggaagtga gcctcccgaa agattgccgc   16920
tcgcgcgcgc gcagatcacg cgcgcttggt tgtgcagcgg ccgggcacaa ccgaaaccgg   16980
cgcgaaacgt cgctacgccg cgacgcccag agtgtcgagc ccggccagcc gcgccgttgc   17040
gacctgatgt taggccggct cgagctcgca gccgatccag ttcaagccgc cctgtttcgc   17100
agcgtcgagg aacgtccegg atccggtgaa cgggtccagg acgacgcccc cggccggcgc   17160
caggcgcacg acttcgcgcg cgagctgcgc gggcttttcg gtcatgtgac gcttcgggtg   17220
cgcgaggcgt tcggagaaca cgccgggcag gtacacgtca gcgcggcgca cggcgccctt   17280
cgtcgcccag accaggaatt cggcctgctg cgcgaagccg ccggcgcgcg gccgtgtacg   17340
gccattcgtc ttatcccaca cagcgacgcc gcgccacgtg aagccggccg cctggattgc   17400
atcggtgagg ctcggcaact ggcgccagtc gacgaagcag acgaggtgtg cttcgttgcg   17460
```

```
actgacgcgg tagacctcgg cgagccacgt catgcaccag aacgtccacg accgttgatc    17520
cttgctgtcg tgctggaact cagggtagac ggtcttcacg tcgccgccga tgtacttgct    17580
cgacggcgtc tggctgcgcg acgcgctcgt cgtgccgccg gacgagtagg gcggatccgt    17640
gaaggtcagg tcgatacagc cgtcgggcag gcgcgcagc acgctcgtcg cgtcggccag     17700
gtgaatgcgg ttgatcaggt cagcggagat ggggtgttgc atgggcgat  tccctcgtat    17760 cggaggctcg gtggcctgcg ggtaaggggc gctcggccct caagacgttc atggcccgac    17820
agcgcgggca tttgatggta agccggatgt actcgccggc gccaagttt  cggttacagc    17880 ttgcgcaacg gatgtcctgc atcggtgat  tcctgcttgt gctaggatgc cggcgcctct    17940
cgagaggtgt cgcggccctg gccaatcctg caggcgtgct ctgcgggtgc ggggcgtgcg    18000
cgatgttgcc gcatcgcgca cgtcgccgcg tcctttcttc gagtcgcctt acgtggcgat    18060
ctccttctcg gcgcgtgtgg gcgcctcgcg cgactctcct gcaccggcag gcgcgttcga    18120
ttccggcgcc ggcggcgcca catacggcgc gggctcctgc ggccacacca cattcgggaa    18180
cgtttcgcga ttgagcgcat gcttgagatg ttcggcgtac gctgaccaca cgcgatagtt    18240
gtattgctct tcgtccgaca gctcgcctgc cgcgtaggcg tcggccttcc cgtcgaagaa    18300
gcgctttgcc ttcgccatcc gcgtctcgaa ttcagcgagc gccggcgtgc acgcgatttc    18360
gaaaggcaca ggatcctccg gccagcgcag cgcgtcggga aagccgtccg cctggatcgc    18420
gcgaaccaga tcgagctggt aagcggacca cgcgcggaag taatacgctt cttccaccga    18480
caacagcccc gccgcatacg catccgcctt gcccgcgttc atctgacgcg cacgcgccat    18540
gcgcgattcg aactcgatca tcgcggcctc ccgtgctcgt tgcgcgacgc gtgcgggatc    18600
gatgacccag ccgccgtcgc gccacacgtg ctcgggtgaa gggcgcggga tttctgtgag    18660
cccctgtgct tccggcgtcg tgcccgcggc aaggatttcg gccggctcgc cggtgtcttg    18720
tcgatacaga acttgcccgc ggtgatcggg caggagcttc cacgcgccgt tgcggtaaaa    18780
cggccaggtg cgtggcgagc gctccgggag cgggtcgagc gtgctgaacg ccggcacgag    18840
ccagcggtcg ggattttcg  ggtccacgtc ggcaagatgg ctggagatgt actgtccggt    18900
ttcggcgtcg tattgatgga tgagcatagg tgtgtctcag taagcgcgaa tcatggcgag    18960
catggcgatg ttccggggac gggcctcgtt gccgccgtcc ccgttcacgg taatggcatg    19020
cgcgtgtgcg ccggcgccgc cgattccgac gttatggctg tgcgttccgg acccttcggt    19080
attgaactcg tgtgcgtgat cgccggacca tgcgatgtcg gccgaatcgc ctgcaccgac    19140
cgcctgctcg gagccgctac cggcctggtc ggaaccggtt agcgaccac  cgtaaggcgg    19200 ccgcagtaag cggctgaaaa tcccgttgtt gtgattgtgt ccgccgccgc cgccggtcca    19260
gccgtggtga ccatgccagc cttgcgcgtc cgtccaggcg ccgtgcgtat ggtcgccgac    19320
ggctgccgac gatgccccgt gcgcatgcca tgcgttctgg aagctctgga aagtgccaat    19380
cccgcgcgca gaatccgcgc cgcggccgtc gtcccagcag cgcaagaatt cgccgcgcag    19440
ctccggcaga cggaacgtcg tcgcgccgtc gcccgtcgag aaacatcccc aattgttctg    19500
cccccacgcc gactcggcga cgagcgcgcc gctcgcctgt gcgtacgccc acagcgcggg    19560
atagtcgctg cggttgacga gcgcgccgtt caatttcaga aagccggcgc gcacgctggt    19620
gcgcggctcg aacacgatcg tgccgatgcc ggccgacgcg atcgctgcga caacccattc    19680
ggtcgttggc acgcgcttcg atcgtcgcc  cgatggaggc gtttgagccg tgatgaggcc    19740
gccgacgtca agcgtgccgc gaaagccggt attgccggtg cgcgtatcga accagtgaga    19800
aaactctgtt cgcggtacgg gcatgccgtc gatcgttggc gcgaacccga tgccatacca    19860
```

```
cgaacgcaac gcgacgttgg tcgtcgaggc ggatgcgcca tcgccgttgc cggcgccgag    19920
aatcgcgccg gtgccgccag gcgccgacgc gagatgcagg acgtcccgcg tgctgatgcg    19980
gcccgtgaag tcagcgccgg aaagattggc cttcgcgtcg agccgtggct tgagcgtagc    20040
cggcgtcacg gcgcgcgtcg cgtcagtgcc tgcggcgacc tcttccgtcg tcgcgagctc    20100
gacgacgccc ttgcggtcca tcgtcgccgg tgggttcagg aacgtggcgg ggccgaactg    20160
gagctgcgat gcgtcgatcg acttgaatac gatgtcgctc gcaagcagca tcatcgccgc    20220
cggagacttt tccagaatgg gcgtgtcctg aacgtagacg ccgaagagca caccgttgtc    20280
gaggtacaga ccgtacgcga acagcgaata ctgatcgtcg gtgtcgtcct ggatgacgac    20340
atgcactgta tcgggcgcga cgttttcgcc gccgaacgtg gtcacgcgtt tgcgctcggc    20400
gggcatggtt ttcatgccct tgtcgaaggt gaatgccgcg gtgccgagac cgacttcggt    20460
cacgcggcgg gcaaccgtgc cggtattgcc agctgcgacg agcgccgcgc gtccggcgtc    20520
ggtaatgttg atgaggtttc cagccatgtt caggtatccg agagggacag gcggtgatag    20580
accgcggcgc gggcgcctgc gccgagcagc tgcgtgccga tcgcgctgta gccctgcttg    20640
aagatgtaat gcgcggttcc ccgcttcgcc cgatcgactt cggcacgaac gtcagcgacg    20700
tactgcgcgg tggccggaac gccctcacgc gcgcccaccg tcatcacgat ttcgaacgtg    20760
cccggcacgc cgcgcggtgt catctcgaac cattcgcgca tcaccacgtt cgcgccgaac    20820
gacgcgcata cggcgcgcac ggcatcggcc gtgcccttt tgcgcgcgat gcggatggca    20880
gacttcacac gcgcgcgctt gacctgctcg ggccattcgt cgcgccacgt gtccacgccc    20940
atgtgccagg cgagccacgg caggaagcgc agcgggatcc gatccgggtc catcagcgtg    21000
tcgagctcga ccgggatgtc gcgtacgtcc gcattcgcct cggccaggcg ccgctcgagc    21060
gccgtcgcgt tcggcggtag cagtgagcgg ggcagcttac tcatcggcca ccccgccgtc    21120
gatcagttcg atgccggtgc agtacggtgc ttcgtcgatc gcgatcggca caccgttggc    21180
cggcgtgtcg agcagcacct tctggacacc ggccacgcgc attgatgcgt acaggccgtc    21240
cagcgtgatc tccgaacccg gacggtgcat cgcatcggcg aactgctgcg tgttcttgcg    21300
tgcggcggcg atcgcaacgg cgcgatcagg gccgttgaag aaccgcagcg tcgcgcgaat    21360
cccgtatcgc acgatcttcg cgctctgcac gatcacttcg tcagcctgcg ggcgtttctt    21420
ctccagcgcc ttcctgacga tgccgagaag ctcctcgctg gccgtgccat cgccttcgcg    21480
cgaaaggatc gtgacgatca tcacgcacgg cgaagggctg tacgcggtgg cggccttac    21540
gcggccgtca gcagcgcgcg cgtggaatac gtatgcgtcg tccggaccgg cgaccgaaaa    21600
gccgcgcggc gcgagctgga tgcgctcgcg caggctgtcg tcgtcctcgt agaccgggtc    21660
gacgccggtg tccgggtcgc cggccgagat cagcagacgc tcgacatcga acagcgcgcc    21720
gatgtgctcc agcgtcgtcc ccttcgcgta cgccagcagg atgccgcgtg ccttctcgtt    21780
gatgagcgcc agcagcagca ttttttcgta cgcgccttcc tgcagcagct tcaccatcgg    21840
ctcggattcg agctcgagcg cggcagcgat ttcgtcctgc tgttctttcg ggtacaggga    21900
aacgagccgg gccttcttct cggcgaggat ggtttcgtag tcgagctcct cgacgatgtc    21960
cggcgctgga agctgcgaca gatctatcgg ggtggttctc atgccgtgcc tcgaccggtg    22020
gcgcgaccgc ccatcgtcgg cagacgcatg gagaagggcg tgccggcgcg cgggccgtcc    22080
gtgcgctcgc cgtgcagctc aagcacggcg ccgccgtcga tgccggtgct tgcgaaatcc    22140
acttgattga cctgaatgcg cggttcccat cgggccagcg ccatgacgga tgcggccatc    22200
```

```
acgcgcatgc gcatgagcgg attgaccggg ccgtcgatca gctcgggaag cagcgacccg   22260
tagtcgcggc gcatgacgcg cgtgcccagc ggcgtgaaca gaatgtcggc ggcggattgt   22320
tcgatgtgcg cctgatttgc gaccgtgcgg ccggtgcgtg cgttcatgcc gatcatccgt   22380
gccccttcga cgtggtgccg cccatcgaat cgacgtgatc gtgttggtcg accgacacgc   22440
cgttcgaacg cagcgtgccg ccttcgtgcg tgatgttgcc gcgcaggaca gtgccgacgt   22500
cgccgccttc gcccgcgagg ccggccatgt acgacagcag cttcatgacg gtgcccgcgc   22560
cctcgatcgt cacgtcaccg gtgaagacga ccttcggcat gtcgaacgtg agcgtgccgc   22620
tgccctggac cgttgcggtc ttgatgccgg tcacagtcag atggccggtc ccagcgtcgt   22680
acgcgacacg ggcgccgtcc gcatagacgc gcacatgttc gttcgggttc gagctcggcg   22740
cgtcgtgacc gtcgcagtac acgccgggca ggaataggcc ggtcgtcggc tcgcccgacg   22800
ggcacagcag cagaccgggt tcgccgatcg atggcggatc ccattcgacg gtggcgccgg   22860
ttcgctgcgc gagccagcgg atccaatcgg tttgcaggcc gccggattcc acgcgcacgc   22920
ggcgggcatc atggtcgacg tcgatcacgg tgccctcgcg cagcaggctt cgaggcgac   22980 ggttcagatc agcaaaatca tccatgcggc aaggatgccg cgcgcgcggg agaggatcac   23040
gtggaaatgg ttgtgcacgg ccggttaaca acgcaaagcc tgccgcgcat cgcgatgccg   23100
cgatagcgat cgagatcgac tagaaggtga agttcggcgg ccacgcgaag cacggtcgga   23160
tcatcggggc gaatgtgttc gtcccgcgcg cgctttccat cgcgctctatg ttccacttgc   23220 cttcgcgagg atttgcttga gcatttccgg aactgttcct tttgcctcaa ccgtcgcagt   23280
gcgataggca tactgattct ttgcgagttg ataccggca gttgcctcaa ttgcctcaca   23340
cgatgtcctc caatcggtcc agttcgactc gaggtaggtc tcaaggtgat cactcagggt   23400
agctacctga gtgccgattt tctctggagg gaaatcgacc tcatcctcgc caaaatactt   23460
gagaagccgg cggttctcgg tggaaaactt cgtacggtca ctctctattg cagccggctt   23520
tttgccagca gctgtagctc gttcttcaaa gccagcatct ccgtcgaaaa gtacgtaggt   23580
tggtattccg agggaggtaa gaatggcatg agcaagggga atcccgcctt tgccaccagc   23640
ggaaacaatt gacagcccct tgtgattcgag acatccgacg cgtcccgat ctcctatgcc   23700 gtagaaaacg gccgcctcgg tatctccttc gacgagtagc acgcgtgttg cgaacaacgc   23760
gattgaaaga cgacttgtaa cgacgccgtc gagttggcgg gcgacttggt cggcatcaac   23820 cgttccttg agtttcgtct tcacgtcgtc gaccgtggcg cgatgcacgg tgacggcggg   23880
gatttcgtca gacgatcgcg tgagccggcg tatctgatgg aaatggcgtg cttcaagaaa   23940
gtacgggcta tgagtggcat acgtgacctg aatgcgctta ctggcgtctt cggccagtga   24000
ccgtagaact ttcgcaaacg tctgcgcttg gatcgggtgc tgaaaaagct ctggttcctc   24060
gatcgcgagg cagatcaccc cctctgccga tgcagctccc gactgcgcca agagctggag   24120
agccgaaatt agaagcgtgc gctggaaccc gtgcccctgt cgctccactg ccgtctcggt   24180
tgtgccatcg agcactgcca cctcgaaggt ggttcgaggt gccttgagct ctacttctgc   24240
cggagatacc gtgacagcgc ggcctgggga atatgaagag acgacatcgt tcagctgagc   24300
ggtcatttcc tcaagctgcg ctttgaactt ctccgcatag acactctgct gcttcgcgcg   24360
tgattcctcg acaatctttg caatttcttc atccgcagca gcacgatcca cggaacgctc   24420
aaggatccga ccgatgatgc tcgatttccc gtcgagcgat tcttcgctcg cccgaaggtc   24480
ggcagtgacc aagacgaagt caaaaagacc gctcatcttg ccgccactgt tgaagccgaa   24540
gaaattggtt tgcagagatt cggggggcgtc gataagttga tcggtgtgat tggcctccca   24600
```

```
cgtcgtcatg gcttggttcg cggcatcgac gctgctccag ggcgggaggc ctagcgaagg    24660
atcggactcc cgcaaccggt tgtactcgac cttcttgtcg ccggccgatc ccttgctgcg    24720
aatgtcgttg aatggcgggt aactcttaga gtttgcagat atgctttcag cgccatcttt    24780
gcttcggcgc ttccatgcgg tgaacgtcgt agtgccctcg ggggcatatt tgccaagctc    24840
agctcggtcc ttttccgtga ggtcgtcgaa tgtgacctga acttcgatgt cttcgtcgga    24900
cgcgccgaag aacagtccc tctcggtgag caaacccggc cgcccgttaa aaaaccagtc    24960
gagtgcgcgg agcaccgtgg atttgccggt gccgtttggc ccaatcagcg tcgtgacgga    25020
atcaaaagga atcgccacgt ctttcagtgt gcggaagttc ttgatgcgaa cggattggat    25080
tttcatagtt ggtccccact tcttttttgtc tatggcacga acaccggctt gctgccccga    25140
aacagcgacg ttatttaacc agcaggcgcc agtattaaag caggctttcg cgagaagcga    25200
tattccgtcc gagttatgtc ccatgtccgc ctaacctgga acgagggaat ggctggacgt    25260
ggttttggct attgcgataa agattcgagg acgatttccg cgatccgatc gacatcgaca    25320
tcggcaaggc cgagcaattc tcgcgtggga tactgcacga ttggaccgtc gcgccgcacc    25380
cgatcgcgca ggccatcttg atggacgcgc gcgatgcgct cgacgtcgcg cgtgaaatgc    25440
agcaccgacg cgtcggcgct cgaggtggtc ttgaggaagc gggcggtgcg cagcttcgcg    25500
aacatcgcgc gccggatgcg gccttttcttg cgccgcgcct gcggcttgcg cggcgcatag    25560
cggctgccgt ccgggttgcg cgcttcggcg atgcggcgcg actggcgccg gcgcagctcc    25620
gccgcaagct ctttcgccaa gcgcgcacgc tgcgcgctcg tgagctggcc gagcaggccc    25680
gaggcccatt cctcgacgcg ggacaggcga tcggccatca cgtccccgcg atcggcggct    25740
cgccgaagtg ccgaatctcg tagccgtccg gccgctcggt aacaccgacg cgctcggtca    25800
gcttcagcag gatctcgacg tccgatttcc cgttgtcgag cagctctgcc tggaacttga    25860
atccgtcgcg gcacagatcc cgattcagca gcagctcggg ctggtgaacc ttcagccagg    25920
cgatgatcgg tacgatcaga tgatccgaat ggcccgcgta gtccgttacg acgatgtcga    25980
gcgtatacgc atactcgaac gaaagcgatt gcgctgcggt gacggcgatc gacccgtgtt    26040
cgatgaagag gtgcagccga tccgggttgc gcgcgaactc gggcagggcg gccgtgagcg    26100
ccgcgcgcag gctgttcggt ttgttcacgg cgcctcctgc tcgacgtcgc gcacgcgcgc    26160
ctgcagcgcg atcagctgct cggcgttttc gtggcaggtg gtgtagttgc cggcgacggt    26220
tgcggcgacg gcagagagcg taacgcccgc ggcggccgca tcagcgcttc cgggatcgcc    26280
caccggcacg ttggcggctg ctgcgtcgtg cacgcgcaca aagccgacag gaacaacgca    26340
ggcacgatcc gcttcgcggt ccacataaac cggaacctcc ttgacgatgg tgtcgcccttt   26400 ctcgcggacg acctggacac gatcaacgta ctgcgtgacg accttgacat cgcggcgcgc    26460
cgcgtcgcgc tcggccgtcc gattacgcac gtcgcgttcg agcgcgttga cgcgctggct    26520
cgcgccgacc aggcgggcat gctggattgc gatgacggcg gccgcgccgg cgagcgcgat    26580
cgcgccggcc acgaagaggc gggtactgat ggtcatgcgg ccacccggct gtagcgatcg    26640
aacgcccgtt cgagcttcac gtcgtacagg ttctctgcgt aagcctcgcc gttgtacagc    26700
tcggcgaact tcgcccactt ccggccacgc agcgcggcga gtagcgcctt gtcgccgagg    26760
atgaagcgca cgaacgcctc gagctgctca gcttcgctga tcttcatcgc gtcgacgaac    26820
gcgaacacgt ccgggtagcc gagcgcgttc cagtgaaagc ccatgatctg gaacgcgccc    26880
cagctcgcgg cctcgagcgc gcacgcggca gaaatctgcg acgcgcttgc caggcgcgca    26940
```

```
tattccgccg cgcctccggc atagccgccg cgcttcggat tgacgacgcc cggatacttt    27000
gccgcgagcg cgtctgcgtc caggccggcg gccgcgagct ggcgatacat cacgtgacgt    27060
tcgaacagga tcacgggccg gccgtcgggg aggaagccag caccgcgcga ctcgacttcg    27120
ttcacggcgc gcacggccgc gaggtcggcc tgcagtcgat cggccgcgca ctgcaggtcg    27180
gcatcggtga gatggcgtgg atcgcgccgg ccggccgcga gcgcggccca cgtcttcggg    27240
ccggcgatgc cgtcggcgac caagccgtgc gacgcctgaa acgcgaccac ggcaccgcgc    27300
gtcgcgctgc cgtagatcgc gtcggcgtcg atgcgcgcgc cggcggcgac gagctgacgc    27360
tgcaggtagg cgacatccgc gccgcggtcg ccgaggtgaa gggtcttata catggcgccc    27420
ccgcggtttg aactgcagca cgcgcgcgat cagcgagtcg cgcggattgc cgcggtggaa    27480
cagttcgacg acgttgccgc gtacgccgta cacggccagg cacaggacgc cgacgaggac    27540
ggtgtccgcc agatccgccg gcggcagcac gccgaacgcg gcgcgaatcg gcgcggcgcc    27600
ggcggctacc gccagtgcgt aggccaggca cgaagcgagc ggtcggtgag cgctcccgcg    27660
ccggcgaaag atcactagac gcagcgcaag gcgggcgcac agcagcacgt agacggccgt    27720
gagcatcact tgtccctccc cttgaacacg ttcaacagcc ggtcgggcgc gtcggcctgg    27780
gcgatcagcc acagcagcag cttcacgacg agcgccgagg cgatcagcgc gccgatgccg    27840
gcgtggacct cgatgcgcgc gggcagcacg gcgtcgaggc cggccgcgaa gagctcggcc    27900
gtcaggcacc cggcgacgaa cgagatcacg aagaaggcga cgcgcttcgg aatcgacgga    27960
tcggccgatg tcatcacgaa cagcagcgag ccggcgaacg cgcccatgac gacgttggcg    28020
tcgacgccgg gaaacagcga cagcgtcgcg acgccgagcg ccgccaccgt cgcggacgac    28080
gtggaaatag gttcagccat tctcagtccc ataactggag ccgctcggcg ccggattgcg    28140
ccgctcgcgg tacttcatca ggcagctcga caagcagccc gtgaggcagg atcgggccgt    28200
actgcgcgag atcccggttg aggtcgagca ccgcttcgac gacgccgcgc gtgcggccga    28260
gcgcacgcca gcacagcgcg tcgacggttt caccctgaag cgcgcgcacc cacatcagga    28320
cagctccctg ccgttggcgt cgtaacgtgc gacgagcagc ggcttcagtg atgccagacg    28380
gcgtgcgcgc gctgcgctgt gcagcatcag ggaagcggtc tcgcggtttc ggcacacggc    28440
gatttctcgc cagaacagcc acgcgacgcg gcgctgaacc tgaaacggcg cggcgatgcg    28500
tcggccgtcg acgacgcggt cctgcgcgag gcgacggatt cggaacattg ctcgcatcag    28560
atgagctcca cggtcacacg cggccgaccg acgatgtcgc tgatcgccca gcgtgcgtcg    28620
cgacgcagct cgtcgctctg cggttcgagc tcgtcggcgc ggcgtgcgcc gtcgccggtc    28680
gtgtcgtagt cgcgataccg ctcgatcagc gtcgccttcg ccaggcagta cacggcgcgc    28740
cggtagtgct gcagcagcac gctttcgccg tcgagctggt cggccggcac gtcagcgagc    28800
cgtgtgatgc cggcctcgcg ccacgccgag cgagcggcgc gcaggtcgtc gttgacgctg    28860
gcgatcgccg cgagcaactc gtgccgcagg gcgcgtcgg tcacggtgcc gtcgaggcgc    28920
atcgtgtcgc gtgcgtgctc cagcgacacg tccgggtaga acgcatcgtt cgtgattggc    28980
ggcgccggcg tttcggacgg ctgtgacagc ggcggggtcg agacaaagga catggtcggg    29040
ttcgtcacgt tgaaagggtg aggcggtgga cggggctttc gcgcggactg cgccggctac    29100
ggccccgtgc cgcctggtgc gcggggtacg ctcggtatca gccatcgggg ccgcgctggc    29160
ccccgctggc aaagttcttc agctcgcgct cgagccgctc gatgtccttc ttcacgccga    29220
cgttcgcgaa cagctgcagc gcgcggcgca ggtggtcgag tgcatttgct ggatgggacg    29280
ccgccagccc gtagccgatt gccttgtgca gcttcgcgcg cacctcgtcg ggcatgtccg    29340
```

```
ccaatgcggt gagctgctcg atgtccagca gcggctcaac ctgaatcggc tcgccggcgc    29400
gatgcgcgcg cagcgcggcc tcggcgaatt cctccacgag caggcacggc gtgctccgct    29460
tgtactggtc aggcagcgga aggtcgtgtc gcagcgcgta cgcgccgatc ttcagcgcac    29520
cgcggaagtc gccgacgtcg acgcgccaga ccatgatcgt cattagcacg tcgtcgggcg    29580
cgccggccgc accgtccagg acgccggcga cccacgcgtc gtacgccggc aggaactgcc    29640
gtttcaggtc ggccttgcgc tcgagcgact cgacggcctt cagcgcgcgg cggtgctcgt    29700
cgagctgcgc cagcatcagc gtgtacgccg agtcgtcgcg cagcccgccg acgctcgccg    29760
gcgtgccgcg cgcggccttg gccgcgacgg tgcgctggaa gtgttggcgg aacgggttcg    29820
tcatgcgcca cccgccggtg cgtccggcgc cggatcggtg tcgacgaagc ggatgtcctc    29880
gaccacgcag cccgcgccga attcctcgat cacgtacgca tcgttcgagc tttcgaagtt    29940
ctcgatgcga tcgcgcttcg ggttgtcgat gagcgcgcga cggcgcgcac cgatttgcca    30000
gtacagcgac aggttgtcca ggcgcgtgat catcagcgcg cgcggggggga agtacggcac    30060 gcgcacggcc ggcagattgc cgatgcgctt ctgcgccgtg atgacgtccg cggcgagcgc    30120
ttcggtcggc ggctgatcct tgttcacgac cgggaaatac ttgtcctgca gcagctcgcg    30180
gccgcagatc acgacgagat tcggatcctc gacgtaccac ggctcgagca gttcgttgtt    30240
cgcgagcgtg acgacggcgt caaggttctt gaattgctcc cccttgccga tcttcacgcc    30300
cgagaacacg cgttccttcg cgttgttgcg gtattgctgc agccagccga tgttcacgtc    30360
ctgcaacagc gggttcgccg cgagatcggt gtcggctgcc gcgcgcacgc cattccagcc    30420
gatcatgatc cgatcgagcg ccgcgcgtcg aatgatcgcg tcgcgcagac gagcctggaa    30480
gtccgggaac ttcgcccagg cgtcgaggcg ctgatacgtg atgtgcgtgt cgtagttcgt    30540
cttctcggcg cgatagcgtt ggctgtcgag cgtcgcgatg tcgcgcgttt cgcgctcacg    30600
cttgctcgtg tcggtgcggc tcggacggg ccccgaaacg ccgaggccga ccttctcgcc    30660
ttccatctcg gtcacgccga tcacgttgat gctgttcagg aaggcgctcg attcctgcgt    30720
cttggtttcg agcgtctgct gcacggtcgg atcgaccgaa aacttcacag tcgcatcgct    30780
gatgccattc agttcctgaa tgcgctggac gaagcgggaa tagagcgcgc gggtatcgtt    30840
ccgcatggat tctccgttta acgaaaatgg gtgatgaggg cgatcagcaa tcggtcagcg    30900
cggcgttgtc gccgccgtc gacatcggcc gttgctggcg gtcgctgtcg gtgcgcgaca    30960
gcttctgcac cagatcggaa tggcgcgctt cggcgtcttt cagcgcgcgc ttcacatcgg    31020
cgagctcgct gctgaactgc tcgacctggt cgagcacctg gctctggctt tcggcgaccg    31080
ccacgacgga ctgcgacagg tcggagaagc gctgatcgtc agacacttcc ttgcgattga    31140
gcaggctgcg gaccttggag aacagcgaac gcgcggcgtc acccgagcgc gtcggcgcgt    31200
cgtcctcgag ctcgatgtcg gcttcgatcg ccgcgctgaa gaggttgtcg gggcgcaact    31260
tgcgcgtgtc gaacgcgcgg ttcttcgcgc tgaaggcgag catctccgtg ccgaggctcg    31320 ccggttgtc ggtgacggcg aggccgacga ggtacgcctc gccggtgccg gcgaaatccg    31380
gatcgacttc catcgacgtg tagaccttct ggcgctgctc ggtcgtcatc gcaatcaggt    31440 cttcgtcgg cgagagctgc gcgaacaacc gcatctttcc gtcctgctct tcggccttca    31500
gcgcgatcac gtcgccgtac gcgcggaatg cgccatccgg atagagcccg cgaatgtgtt    31560
ccatgttgat gcgcgcgccg tataccgccg gtcgtacgt gcgcgccatc tgttcgagca    31620
tcgcgcgatc gatcgtgcgc ccgtccgttg tcgcgccttc ggtcgcgatc cggaaaaact    31680
```

```
tcgtcttctt cgtgtcctgt gccatgtgcg aaacctctga gagggcgggg tgctgtgttc    31740
agggattcca gtgtcggcag ttcgaagcgg tgtcgcaatg aacgttggtt gtgtgcacaa    31800
ccggtacaac cgaaggcagt agggctcgcg cgcgcgcgtc ggtagccttg ctgcatgact    31860
gcacttccca tcgattcatc cgacgttgat ccacgccgac gcgcacgtga cctgtactgg    31920
cagggctatc gaattgcgcg gattgccgaa atgctcggcg agaagccggc cacgctgtac    31980
agctggaagc ggcgcgatcg atgggacgac accgagccgg tcgatcgcgt cgcgctgtcg    32040
atggaagcgc agctgattcg gcttgtcgtg aaggagaaaa aggaggggcg cgacttcaag    32100
gagatcgacc tgctgacgcg tcagctggac cggttgcgcg cacggccggc gaacgatgcg    32160
aagttgagcg actccgggag tgcgggcggc tcgcgccgtt cgcgccgcgc ggacgagcgc    32220
aacgcgttca gcgatgagca gatcgagaag ctcaacgacg cgttcctcga atcgatcttc    32280
gactatcagc gcaactggta tcgcgccggc ttcaaggaac ggatccgcaa cgtcctgaag    32340
agccggcaga tcggcgcgac ctggtacttc gcgcgcgagg cgttgctcga cgcgctgaac    32400
acaggccgca atcaaatctt cctgtcgccc agcaaggcac aggcgcacgt gttccgccag    32460
tacatcgtgc agttcgcgaa agacgcggtc gacgtcgagc tgaagggcga cccgatcgtg    32520
ctgccgaacg gtgcgacgct gtacttcctc ggcaccaacg cgcgcactgc gcagagctac    32580
cacggcaacc tgtatttcga cgagtacttc tgggtgccgc gcttccagga gctgcgcaag    32640
gtcgcctccg gcatggcgat tcacgaccag tggcggcaga cgtatttctc gacgccgtcg    32700
agcctcgcgc acgacgctta tccgttctgg tcgggcaagc tgttcaaccg tggccgaccg    32760
aaagatcagc acgtatcgat cgacatttcg cacgcggcgc tggccgcggg ccgttcgtgt    32820
caggacggcc agtggcgcca gatcgtcacg gtcgaggacg ccgtgcgcgg cggttgcaac    32880
agcggggcgc ggccgctctt caatctcgac cggctacgac tggaatacag ccccgaggaa    32940
tacgcgaacc tgctgctgtg ccagttcatc gacgattcgc tgtcggtttt cccgctgacg    33000
gtgttgcagc cgtgcatggt cgatacctgg gaggtgtggg acgacttcaa gccactgtac    33060
ctgcgcccgt tcggcgacga ggaggtctgg atcggctacg acccgtcgca tacgggcgac    33120
agcgccggct gcgtggtgat tgcgccgccg aagcgtccgg gcgggaagtt ccgcgtgctc    33180
gagcggttcc agtggcacgg tttggacttc gaggcgcagg ccgcgcaaat cgaagcgctg    33240
acgcggcgct atcgcgtgac ctacatcggc attgacacga ccgggatcgg gcagggcgtg    33300
tatcagctcg tcacgaagtt ttttcccggcc gcgacgccgt tccactactc ggtggaaatc    33360
aagaccgcgc tggtgatgaa ggcgcagaac gtgatccgca agggtcggct cgagttcgac    33420
gccggctgga acgatctcgc cgcgtcattc atggcgatca agaaaaccat cacgcccagc    33480
ggcctgcagg tcacgtacaa ggcgagccgc tcggaagaag cgagccacgg cgatctcgcc    33540
tgggcgtgca tgcacgcgct ggcgaacgag ccgctcgaag gggcgactgc caccaatacc    33600
ggattcatgg agattttctg atgtcacgca agtatcgacg cggcgccggg cgccgcgcac    33660
acgatcgcac cgagccggtg gccgcatgca agtcggcctc ggccacgcgc gcggaagtgt    33720
tctcgttcgg cgacccgatc gccgtgctgg atcggcgcga gctgctcgac tacgtcgagt    33780
gcatgcgcat ggggaactgg tacgagccgc cgctgccgct cgacgggctc gcgcgttcgt    33840
tccgggccgc gccgcatcac agctcggcca tctacgtgaa gcgcaacatc ctggtgcagt    33900
cgtacatcga gcatccgctg ctgccgcgcg cggacttcag ccggttcgtg ctggagtacc    33960
tggtgttcgc gaatagctac ctcgagcggc gcacgaaccg gctcggccag ccgatggcgc    34020
tgaaatgctc gctcgcgaaa tacacgcggg tcggcgtcga gccggaccag tactggttcg    34080
```

```
tgacgaacgt gcgtgaaccg cacgcgtttc cggcgggcgc catctatcac ctgtacgagc    34140
cggacctgaa ccaggagatt tacgggctgc ccgaatacct gtcggcgctg aactcgacct    34200
ggttgaacga gagcgcgacg ctgtttcgtc ggcgctatta caagaacggc agccatgcgg    34260
gcttcatcct gtacatgacc gacccggccg acaagcagga ggacgtcgac aacctgcgcg    34320
cggcgctgaa gaacgcgaag gggccgggca acttccggaa cctgttcatg tacgcgccga    34380
agggcaagaa ggacgggatc cagctgctgc cgatcggcga ggtggcggcg aaggacgagt    34440
tctggaacat caagaaggtg acggtcgagg atcagctcgc ggcgcaccgc gtgccgccgc    34500
agttgatggg gatcatcccg tcgaacgcgg gcgggttcgg cgacgtgcac aaggccgccg    34560
aggtgttcaa cgagctcgag atcgagccgc tgaaggcgcg gctgcgggag gtgaacgact    34620
ggctcgggat cgaggtggtg cgcttcaggg acttcgagcc gacgaagggc tgacgcccaa    34680
ccgcgcgacc ggcagacgac aagccgccgg gcacttcggt gccggcggct tttttgcgtc    34740
tggcgccatg cgcgtccgcg gcggaatacg gcgcctcaga gccgccggcg cgccggcggg    34800
tggctcgagt cggccgagcc gcgggcgagc ccgtggtggc ccttgggccg cgccgcagac    34860
gcgttctcgg gtccggaccc gctcggagga tgctgcctgc gacccggcgc gcgcagttgt    34920
gaccccgccc cacctgcccg caaaaacgga cgggttttat gcactcatgc gcgagctgcg    34980
cagggccgcc cggcgtggct cgcgcggcga tcggcgctca gattcgtcta tgcaatttca    35040
tgcgctctga atatgcaggc tcgccattat ccatgtcagg gaggatgcgg ctacggacag    35100
agaagtaagg cggacgagcg cctccgcctc catgcgcgac gggttagccc gatgctttct    35160
tcacagcagt tttgcgacga cgtctcagca ttgcccgtcg tgattgggtc gcgcgctcgg    35220
taacgattcg attccacgca ttcgaatgtt gtcgcaagac agcgcgcttt atctcgccat    35280
aggttgcgac aaattgttga gcttcattca acttgccaac cagcttcgat aacgtgggat    35340
ctacctcctc aggtgaggta gtggccaatt ctgcttgtag cttccgtatg tcccgagccc    35400
tatcgtgcgg aagtgtgatg ccgtctcgta gcacaattac gcccgttact tttatgggca    35460
taccttgaga tgctttgaat ttgtgtgcaa caagaccggt tgcatcaatt ctattcctta    35520
tttccgccaa aagcagtttg tcagcatttg gacccgagac ggtaatgtcg tcaatgtaaa    35580
gggtcatagt gcaaccttg gcggcgcaaa gcgaatttat ctcgtcaaaa agatggctgt    35640
atgcccagta tgaaaggatc ggacttaaac tgctgccagt gggaagatga gtccgcccgc    35700
atgctgaaac tgtacaaatt ttcgttaaaa gtgtcgcgac atcttgtgag catttaagat    35760
tgttgaggaa aaaatgatat atggcaccga atgtaacgga cggataatat tctttaatgt    35820
ccagcttgat gatattttgg ccaccaatgt gagcttctgc attggtttta tatgagcggc    35880
cttttgtggc ggactgaaga aagtccggtg gtgagacgcg gcacagcaac tttgcgatgc    35940
gtttgtggac ccgtctaagt tcgccgattg gctcagtgat atatcgaccc gattcttgct    36000
cgaaaaacat cttgtaacgc tgattggacg gcaaccccgc cagttcttca agactcttta    36060
gggttgtcgc caataaggtc gctaacttcc ttctagattc gagtcgaaag aatggagatc    36120 tattttttcgt gtactgcttt cttgtcgttt gagatttcgc cattttcgga aatccattcg    36180
agaaccttta gcattttctt tgcgacgaag ctttttacct tgctaacgct ttgacttccg    36240
tccaatgtct ctgagaatgc gaggatggaa gaaaggggga cattgaaaac ggttgagtac    36300
ctatttaata tttctaatgt cggttccttt ttaccgcttt cgattctgaa aaggtatgaa    36360
tttgatatcc ccaaggtgtt tgcgagcgct ccttggcttt gattgtgaaa ctggcgcatc    36420
```

```
gctttaagtg cgcggcctaa catatgcaac tccttcaaaa acggaagggg ggcaaccaag    36480
ttatgagaag aacatgccga acagcttatc ggcccattcg ggaattttaa cgaccagcca    36540
atgaaacgtc cgctcgttaa gcagcttaga acatacgtac cgagtgatac cggaaacaac    36600
gccctgcact gcaaccttcc agaagggacg ttcgtcccct ttttcttgct tgcgcttcgg    36660
ccgctttata gatggtgtag ccatgcaaac tcccatagga aagaccgggt cgccccgggg    36720
atatgcaccg tgcacatccg cctcgtgttc ctacaggatg gagaaagcag ccgaaaaccc    36780
cttcatatcg ttagtgacgt ggccgccata gcctcgggcg gccaccttgg catacgtttt    36840
ccgccgtcgg ggggcggtga acgtaccaaa tgtttggcga acaacaactg ttcgccacgg    36900
gcctaagccc aacacaaccg aggtttctcc atgcacccat ctatgcgccc agtctagcac    36960
gtcgccgtac gcagtcaaca aatttttttc gctggtggcg aaaattggat gccgaacccg    37020
acatgtacct cagcagacgg gactgtggct catgcaggcc gatgcggctg cagatcgggc    37080
gggcttgcct tcggcggggc atggagaaat gtaaatcttc acatgtctaa cttgcttgca    37140
gatcgctact acaatcctcg cgcaatcagg agcggtattt ccgcgaaaag tttgaggaaa    37200
tgacggaagg cattgatttg atgtgatttt gtgtct                             37236

<210> SEQ ID NO 4
<211> LENGTH: 32317
<212> TYPE: DNA
<213> ORGANISM: Bacteriophage KS14

<400> SEQUENCE: 4
atgtcaagtt ttaacgcgat cgaatcaccg accatcacgc ccgaaacggc cccgccggcc      60
gacgagctga tcgtcgcaaa cgtcgcatgg tttccctcga tcgacctcgc gcacatgcgc     120
gaagccgtgc gcctcactgg caccgtcaca acggcgcgac tgcgcgatgc cgtgatcgcc     180
gcgatcgacg aagtaaatcg cgagctggcg agctggcgcg cgtcgcacga agcggccggc     240
gtcgcatcgc tcgccgagct gccggccgac tcgatcggcg gcgaaagcgt gcagctcgcg     300
cgctatcgcc gcgccgtcta tttcctcgcg cgtgcagacc tcaccgagaa gtatcgcgat     360
ttcgatagca cgaagtcggg cgcgaacgac gccgacgagc tggtgacgac gatcgacgcc     420
gatcgccgca acgcacgcca agcgatcaac gacatgcgcg cgtcgcgcg cacaacgatc     480 gagctgatct gatgcgcgtc tatgcacgac aaggcgatac ggtcgacgcc ctctgttttc     540
gctacctcgg ccgcacgaaa ggcgtcgtcg aaacgacgct cgaacagaat gccggcctcg     600
ccgattacgg ccccgtgctg cctcacggcc tcgcggtcga cttgcccgat ccgccgagcg     660
atcaaacaac gatccagctc gtcaaccttt tcgattaacc ggagtcgcca acatggccga     720
acctagcacc accaccgtcg ccgctatctc ggccggcatt ggcttgcaa gcctgttcc     780 cggcatcgac ggcaatgcgc tcatcggcgc tttcacgggc gcggcgctcg tcgtcgtgac     840
ctcgaaagac ctgacgcttg ccaagcgctt cgcctatctc gtgatttcgc tgatcgccgg     900
ctatctggcc gcgcccgatg ttgtgaatca cacgccgatc acgagcacgg gcgttgcggc     960
tttcttcgcc gctgcactgg cgatcactgt cactctgcaa ctgatcgagc gcatcaagtc    1020
tttcgacctg ctcgcgctgt ttcgaaaggg ctgacccatg cacaaccccc tcgcactgat    1080
cgcattgatc gcgtacagcg tcgcggcgct gcgcatcctg ttctatcgcc gcgacggcgc    1140
gcggcatcgt cgccatgtct cgtggttcg atggctgctg ctcgtcgcgc tcggcggctc    1200
ggcgatcgag ctggccgtgc atgcgaaatc ggtcggctat ttcgaagcgg ctcgcgccgt    1260
tcttttcatg gtcttagtgt tcggcgcacg cggcaacgtc gcgcgcctgt tgcggagtga    1320
```

```
atgacgatga ttctgagaaa gggcgatatc ggcgacgaag ttttgttgct gcaaaagcgg   1380
ctcacgcgcg ccggctttcc cgtggccgag acgcacgttt tcgaccatga caccgaatcc   1440
gcggttatga cgttgcagaa agcgcgcggc ctcgtgatcg acggcattgc cggcccgaaa   1500
acgatgattg ctttaccggg cgttgcactg cctcgacacc tgaccgacga cgacctcgtg   1560
aaagcggccg acacgctcgg cgtatcggtc gcgtcgattc gcgcggtcaa tgaagtcgaa   1620
tcgcgcggcg agggtttcat cgtcgacggc cggccggcga tccttttcga gcggcacgtt   1680
ttctacaagc gcctcaaggc gaaaggcctc gacgccgacg cgctcgcggc gaagtatccg   1740
aacatcgtat cgagcaccgc cggcggatat gctggcaagg ccgccgagta tgtgcgcctc   1800
gcgacggccg agcgcatcga caccgacgcc tcgcacgagt cggcgagctg gggcgcgttt   1860
caaatcatgg gctatcactg gcaagccctg gactattcga gcatcgccga tttcgtcgcg   1920
tgcatgcaga gaagcgaagc cgatcacctc gacgcgttcg tgcggtttat cgcggccgac   1980
acggccttgc tttccgcgct gaagggtagg aagtgggcgg cgttcgccaa gggctacaac   2040
ggcccggatt acgcgcgcaa tctgtacgac gcaaagctcg ctcaggcata cacgaaatat   2100
gccgagcgcg agaaggcggc cgcatgaatc cgatcgccgc acgcctcgcg ccgatcgcgc   2160
tgcgcgtcgc tgcgatcgcg ctcgtcgtgc tcgcgatcgc ggccggctgg ttttacgtgc   2220
gcgagctgcg cgccgagctg gcgcacgcgc aagacgacgc gcagctcgcg cacgagacgg   2280
tcggccggcg cgacgcgacg atcgccgaca tgcagaagaa agagcgcgag catgcgaagg   2340
cactcgcgca gctcgaagcg aagcacgacg gcatcgccgc gagcctcgcg cagtctgaaa   2400
ccgactttga ggcgttgaaa catgaaaacg aagcgttgcg cgcgtgggct gatggcgctt   2460
tgcctgatga tgttgtgcgc ctgtacaacc gccccgcgat caccggagcc gacgactacc   2520
ttgcaatgcg cgcccgtcgc gcgctgcacg ctgccggcga cggccccgcg cactaatgac   2580
gagctgcggc gcgcgctcga tatcaccgag gcggcatggg gcgaatgcgc ggcccgtgtc   2640
gatctgatcg tcgattgcca atcgaaagcc ctttctctca ccgcccccga ccatgaataa   2700
ggcgaacagt ctgcgcaaag cgctcaatgc ggccgtgccg tcgctctcga atgatcccga   2760
caagctgctc gtgttcatcg acgccggcaa catcatcgcg acgggcgcgg catcgggttc   2820
attcgattac gcctatacgc ttaacgtgat gctgctcgac ttcgccggcg atgccgatat   2880
cgtgttcgcc gcgctgatcg catggatcaa gcgcaatcaa tccgacttgc tcacgaacga   2940
cgatctgcgc aagaccggca tatcgttcga agccgaccaa ctcacgcaaa cgacggtcga   3000
cctgtcgatc aaactcaagc tcaccgaaag cgtcgtcgtc ggcaccgacg acaccggcgc   3060
gcagaccatc acgcacgtcg acgaacccgt gcccgaatgg gaagtaaccg gcctttacga   3120
tccggcggcg caatggacga actaagcgcg ctcgaatcgt gggcgggcgg gctgctgtcg   3180
cagctcacgc cggccgctcg tcgcgctgcg ctgcgcgata tcgggcgcga gctgacgcga   3240
agccaacgca cgcgtatcgc gcagcaacgc aacccggacg ggagcgcata cgagaagcgc   3300
aagccgcgcc cgaaacacct gcgcgacaag gccggccgca tcaagcgcgc ggcaatgttc   3360
gcgagactga ggcaagcgcg ctacctgcgc gccgagactg acgcgcaagg cctcgcgatc   3420
ggattcgccg gccgcgtcgc gcgcgtcgct cgcattcacc aattcggcgg caccgatcgc   3480
gtcgcaccgg gcggcccga atacacctac cctgcccgcg ttctgctcgg attcaccgac   3540
gccgaccgca aaatgatccg cgatttactg ctcaagcaca tcgcgcctta acaattcgtc   3600
gaccgaagtt tgtacccgac acgctaacaa acgcagcgtg tcgacgcgcg cgtgcgtgct   3660
```

```
cggcaacatg gaggcatgaa ctcaaacgaa tcctcacgcc aatctctgaa cggcatacgc   3720
aaaggcaccg ttgaatcggt tgaaggcgcg ctatgtcgcg tagtgagcgg cgatttacat   3780
accgactgga ttcaatggtt cagcccttc gctggtgagt cgatcgagtg gcatgcgccc    3840
tcgatcggca aaggggtgat gctgctttgc ccgagtggcg accctgcgca agccgtcgcg   3900
ctgcgcggtt acttttccga agatttcccc ccgccgagca ccgacccggc gaagcatatg   3960
cgcgtctatc gcgacggcgc atcgatcgaa tacgacatgg ccgcccatgt tctcaacgcc   4020
gttttccccg atggtggaac cgtcaacatc accgcccccg gcgcggtcaa cgtgacgacg   4080
caaaaggcga cggtaaaggc cgacgatgtg acgctcgacg cgaagcaaac gaccgtcacg   4140
ggcgcgatga ccgtcaaagg cccgtttgct ttcgagtcgg gcatgactgg ctcggccggc   4200
gcaagcggcg gctcgacgat gaagatcaac ggcgcggccg acttcacggg cgaagttaag   4260
tcgcaaggta tcagcctgcc gaagcacacg caccgcgaac agggcgacgg caatctcgtg   4320
agcgcaccgc aatgattgga atgaacgcct caaccggccg ccctacgcc ggcctcgcac     4380
acctgtatca atcgatcggg aaaattctga cgacgccgat cggctcgcgc atcgctcgcc   4440
gcgatttcgg ctctgagctg cccgatctgg tcgacgcgcc gaacaatggc gcaacgcgcg   4500
tgcgcctgta tgccgcgatc gcgaccgcgc tgatgcagtg ggaaccccgc ttgcgcctgt   4560
cgcgcgtgca gctctcgacc gagctgacgg ataccggcgc gggcgtgcaa gtcgtcgaca   4620
ttgaaggcac gactacagaa accggcgatc cggtatcgac gcgcgtgcag ctcacgaacg   4680
ggggtgcggc atgagcgcaa cgccgatcga tctgtcgcgc cttccatcgc ccgatatcgt   4740
cgaaacgatc gactatgaaa cgctgctcgc cgagcgcaag gcgtcgctcg tcgcgctcta   4800
tccggccgac aagcaagccg aagtctcggc ggctctcgcg ctcgaatccg agccgatgaa   4860
cattcatttg caggaaaacg cgtatcgcga agtcgtgttg cgccaacgcg tgaacgatgc   4920
cgcgcgcgcc gtgatgctcg cttacgcaca gaaaggcgac ctcgaacacc tcgcggcgct   4980
gttcggcgtt gaacgcctga cgatcacgcc ggccgacccc gagaacgata tcgacgccgt   5040
aacggaagac gacaccgact tgcgcgcgcg cacgcagctc gcaccgcaag gttttccgt    5100
cgccggcccc gagggggcat acatcaagca tgcgcgcgat gctgacggcc tcgtgctcga   5160
tgcctcggcc ataagccccg caccgtgcga agtgatcgtt acggttctct cgcgccaagg   5220
caacggcacg gccgacgaaa cgctcatcgg caaggtaaag gccgcgctat cggccgacga   5280
tgtgcgcccg atgaccgacc ttgttgccgt tcaaagcgcg accgtgaagc actacagcgt   5340
gcgcgcgacg ctcgtttttct tcgccggccc cgatcgctct gtcgcgctcg ccgaggcgaa   5400
caagcgcgtt cgccagtacg ccgacgacat gcacaaactc ggcatggcga tcacgctcga   5460
cggcgtttat gccgctgcgc gcgcccccgg cgtgcaaaag gtgattctcg ccgagccggc   5520
cgccgacatt ccggcgacga agcaagaggc gacgtattgc gattcgatcg agctggtcga   5580
cgggggcatt tacgaaaatg gctgatctgc tcccgccgaa ctcgacgacg cacgagcgca   5640
acctcgcgcg cacgaacgca cgcattagcg atattccgtc gccgctcgcc gtgctgatga   5700
accccgatgc gatcccgctg ccgctgctgc cgtggctcgc gtggcacctc ggcgtcgacg   5760
cgtggaaaga ctactggccc gaacaaacga agcgcgcccg cgtaaaggcc gccattccga   5820
tcgcacgcaa gaaaggcacg gccgctgccg tgcgtgaagt cgtcgccgcg ttcggcgcaa   5880
acgtcgcgat tcgcgaatgg tttgaacaaa cgccccgtgg cacgcctggc acattcgacg   5940
tagtgctcac ggttagctcg cgcaacgcg aagcccctac ggccgcgctc gtcgccgaca     6000
tcattgcgga aatcgaccgc gtgaaacccg taagccggca ttacaccttc acgcaaggtt   6060
```

```
tttccatgca gggcacgcag cgcgtcgcgg cggccgtgcg gcccgcgctg tatcgccgtc    6120
tttctttcac ggatatctga cctatggccg gaaccctcat caccatcacc gacgcggggc    6180
gcgctgcgct cgtcgcgccc ggaaacacgg gcacgaacgc gcatcaagtc gtaaagatcg    6240
gccttgcctc ggcccctttc gtcgccgaca agggcatgct cgccatgccg aacgaacgca    6300
agcgcatcac gaccttcgcc ggcaagaaca tcgcggccga caccgtgcat gtcacgctga    6360
aagacgacac cgacgatcaa ttcacgctgt acgggttcgg cctgtatctc gaaaacgatg    6420
tgctgctcgg cgtctatagc caagcaacgc cgatcatgga gaagtcgccg gccgcaatgt    6480
tgctgctgtc ggccgacatt caattcacga cgatcgacgc ggcggcgatc acgttcggcg    6540
aagcatcgtt cgcgaatccg ccggcgacga ccgaagtgca aggcgtgatc gagctggcga    6600
cgcaagccga agtcgatgcc ggcaccgaca ccgtgcgcgc gctcactccg aaaacggccg    6660
cgagccgata tgcagctctc acgggcgcga ctttcgccgg ccctgtacgg gcaacgaaac    6720
tgcaatcgga cggcgacgcg acgatcggca catcactcac catcgtcggc caacgcgggg    6780
cgctcatcac gaccggcaat tcgacggcc tttcgatcga agcctatgac accgccaacg    6840
tgacgacgaa aaaagctgtc gcgctcgcgc cgtatggcgg ccgcgtgctg atcggcaaga    6900
ctccggccga cgatgacctc gcatcgctgc tgcaagtcgc cggcatcgcg acggtcgcga    6960
caccgccggc cggcgacagc tcgaagaaag tcgccacgac tgaatgggtt atcgcgacgg    7020
tcgcgaccgc actcgtcggg caaatcgtta ttgaggcacg cacgagcgcc cgcgccggct    7080
ttctcaagct caacgcgcg gtattgaagc gcgccgacta tccggccttg tgggcctatg    7140
cacaggcgag cggggcattg ctcaccgatg cgcaatgggg ggcgaacaat tcggcgctt    7200 tctcgtcggg cgatggcgcg acgaccttc gcatacccga gctgcgcggc gaatacatgc    7260
gttttgggga tgacggccga ggcgtcgacg cggggcgcgg tatcggctca tggcaagaca    7320
gccagaaccg ctcacacgct cacgcgcgca gtgcggggc tgttggcgat cacgcacaca    7380
gcgcatggac cgatgtgcag ggctggcacg accacgcgca cccctggaaa cacgcgctca    7440
actcaggcac ggcgaacggc tcggacggcg cggaagcatc ggacgccggc ggcggctggc    7500
gcccgcgcac cgatgcgaac ggcaatcacg tccataacgt cggcatcggc gcggccggcg    7560
cgcactcgca cggcatcacc atcaacgcgg acggcggcgc agaagtgcgc gttagaagcc    7620
tcgcaatgct cgcgatgatc cgggcttact gactttgaag ggaaccgacc atgctcattc    7680
atcaatacga caaccagacc ggccaataca tttcaagccg actcgccgac gaagacccgc    7740
gcaatcccgg ccgctggctt atcccggcct tttcgactac tgacgagctg cccgtgcgcg    7800
agtcgctgac gtggccgttt tacgtcaatg gcgcatggtc gctgcggccc gactggcgcg    7860
gccgaatcct gtatcgccgc gacaacgcg aggcggccga aatcctgatc gccggcgtca    7920
cgccggaaga aagcggcctc accgagacgc cccgacccctc ggagaaacac atttggggcg    7980
atggcgcatg ggtgatcgat ccggctgccg tcgcggccga gacgcgcgcg gcggcaatgg    8040
ccgaattcga gcgccggctc gcgctcgcgc gttcgaagaa caccggcaag gccgacgcta    8100
tcgcggccgg cctgctcgat gacgagcaaa tctattactt caaggcatgg tcggcgtatc    8160
agatggcgct cgttagcgcg atcgagaaag acacgttccc cgatgccccc gaatggcccg    8220
ccgagccggc cccgtatgtg ccaccggcac cgaccgaacc cgcgccggaa accccggccg    8280
accccgcgta acgccgaaag cgtcgcgagc tgcaacccgc cctttcactg tcacttttaa    8340
acaggaattc agatgcctac tgactaccat cacggcgtgc gcgtactcga aattaacgaa    8400
```

```
ggcacgcgcc cgattcgcac cgtatcaacg gccgttgtcg gcctcgtcgc gaccgccctc    8460
gatgctgacg cctcgatgtt cccgctcgat acgcccgtgc tgctgacgaa cattcaatcg    8520
gcgatcggca aggccggcga caagggcacg ctcgcgcgca cgcttcaagc gatggccgca    8580
caggcgaagc ccgtcactgt cgtcgtgcgc gtcgctgaag cgtcgacga cgcggcgacg     8640 acgagcaacg tgatcggcaa acccgacgcc gtgacgggcg cttatacggg catgcaagcg    8700
ctactctcgg cgcaatcgaa actcggcatc aagccgcgca ttctcggcgc tcccggcctc    8760
gatacgcagc ctgtcgcggc ggccctcggc acgctcgcac aaaagctgcg cgggttcggc    8820
tatgtgtcgg cgaacggcgc ggcgaacaag gaagcggcga tggcctatcg ccagcaattc    8880
agccaacgcg agctgatggt gatgtggccg gatttcctcg gatgggacac gaccgcgaac    8940
gcctcgacga cgatcgacgc gaccgcgatc gcgctcggct tgcgcgccaa gatcgacgag    9000
gaaacgggct ggcacaagac gatttcgaat gtcggcatca atggcgttac gggtatcagc    9060
aaggatgttt tctgggactt gcaagacccc gcgaccgatg ccggctacct caacgagaac    9120
gatgtgacga cgctcatcaa ctcgacgggc tatcgcttct ggggttcgcg cacctgctcg    9180
gatgatccgc tgttcgcatt cgagaactac acgcgcaccg cgcaagtgct cgccgacacg    9240
atggcggaag cacacatggt ttatgtcgac aagccgatgc accgtcgat cgtgaaagac     9300 atgatcgaaa gcatcaacgc gaaattccgc gagctgatcg caaacggcta tctgctcggc    9360
ggctcggctt ggtacgacga cagcgcgaac cccgtcgaat cgctcaaggc cggcaagctg    9420
gcgatcgatt acgactacac gcccgttccg ccgatcgaaa acctgatgct gcgccaacgc    9480
atcaccgacc gttacctcgc cgatttcgcc gcgcgcgtca cggcataact agggagtaaa    9540
tgaacatggc attgccgaag aaactgaaga acttcaatct gttccagaac ggcgaaaact    9600
tcgccggaca gattgcagaa gtcgggctgc cgaagctctc gcgcaagatg gaagcatggc    9660
gcggcggcgg cacgaatggc ccgatcgata tcgatcaagg gcaagaggcg atcgctttcg    9720 aatgacggc cggcggcttt atcaagtcgg tactcgcgca atacggcacg ctcaagcatg     9780
acggcgtgca actgcgattc gccggcgcgt atcgagccga ggattcgacg aagcacgacg    9840
caatcgaaat cgtcgtgcgc ggccgtcaca aggaaatcga tttcggcaac gcgaagcccg    9900
gcgacgatac ggcgttcaag gtttcgacga cgtgcagcta ttacaagctc accgtaaacg    9960
gcgaaacgct cgtcgaaatc gacctcatca acatggtcga agtcgtgaac ggcgacgacc   10020
tgctcgccga cctgcgcagc gcgatcggac tgtaacgcgc gctcgagcgc gggcatgtcc   10080
ccttccccgc ctggtcaagc atcgggcggg gcatcaaatc cccaatctga acagagaaag   10140
aaatgaccga acaagccaag ccgaacacga tcaccctcga cgccccgatc aagcgcggcg   10200
aacaggaaat caccgaaatc accttgcgta agcggccgc cggcgagctg cgcggcacgt    10260
cgctcaatgc gctcgtgaat ctggacgtcg acgcgctcgg caaggtgttg ccgcgcatct   10320
cgtcgccgac cctcaccgaa ttcgacgtgc agcagctcga ccccgccgac ctcgtgcaat   10380
tgggggtggc gttcgcatct ttttgctgc gaagcgggc gagctagagc acggcatccc     10440
cgaccacgtt gaagaagcga tggccgatat cgcgacggtt tttcactgga caccgcgcga   10500
tatggacggc ctcacactgg ccgagctggc cgactggcgc gagcgtgcgc gcgtgcgctc   10560
gccgtatgga agcgaatgac gatggcaaac ggaaacgacc tcaaattgcg cgtgctgttc   10620
gatatggtcg acggcgcaac gaagccgctg cgcaacattc tcaacggcaa taaaggcctc   10680
gcgaagtcgc tgaaagagtc gcgcgacgaa ctcggcaagc tgcaacgcac gcaaaaggac   10740
gtggccgcgt ttcgcgaaat gcgtgtcggc ctgctcggcg caaagcgcga catgcagggc   10800
```

```
gcgcaatcgc gcgtcgccga gctggcccgc acgatcggct cgaccgactc gccgacgaaa   10860
gcgatggtcg cagagtttga gaaggcaaag cgctcggccg cgcagctcac ggccgcgcac   10920
gacaaacagg ccgacaaggt gcgcgagctg cgcacgcgcc tttcggccgc cggcatcgac   10980
acgcgcaatc tgtcgcagca tgagcgcgag ctgcgcgcga gcatgagcgc gacgatcggc   11040
gtgatgacga cgcagcaaaa caggctcgcc gaccttaccg cgcgcacgaa gcgactcgcc   11100
gaggcgcgcg agaagatgaa caggacgaag gagctgcccg gctcgatggc cggcaccggc   11160
gcgaagatga tggccggcgg cgcagttatc ggcgctgcaa cgcttgttcc tgtcgccgag   11220
tatgcgaagg ccgaggactc ggcgacgcag ctcgcgagcg cactgatgcg cgccggcggc   11280
gtcgtgcccc ctgaattcca gaagatcaac gcgctcgcgc tcaagctcgg cgaccggctc   11340
cccggcacga ccgcggattt tcaggacatg atgacgatgc tcacgcgcca aggtatcagc   11400
gcgcaagcaa tcctcggcgg catgggcgag gcaacggcat acctcggcgt gcagctcaag   11460
aaaacgccgg ccgaggcggc cgaattcacc gcgaagctac aggacgcgac gcgcacgacc   11520
gagaaagaca tgctctcgct gacggacgtg atccagaaag cgtttatgct cggcgtcgac   11580
gataacaaca tgctcaacgg gttcgcgaag ctcggccccg cgatggatac gatcaagcaa   11640
aaaggcctcg aaggggcgaa ggctctggcg ccgttgctgg tgatggccga tcaatcgggc   11700
atggaaggaa gcgcggccgg caacgcatac cgcaaggtgt ttcagctcgg catggatgcg   11760
aagaaagtcg cgaaggcaaa caagcaactc gcgccggcgc aacgcctcga cttcactgac   11820
ggcaagggcg aattcggcgg cctcgacaag atgttcgcgc agttcgaaaa gctcaagacg   11880
ctcaacacgc aaaagcgcct cggcgtgctg aaagaagttt cggcgacga cgccgagacg   11940 ttgcaggtta tctctttgat gatcgagaaa gggaaagccg gctatgacga agtgcaaggc   12000
aagatggccg cacaggcctc gatgcaggag cgcgtaaaca agcaactcgg cacgcttaaa   12060
aacttgtggg aagcggccgg cggcaccttc acgaatggcc tcgtcgcgtt cggcgaggcg   12120
atcgcaccgg aagtgaaagg cgttgtcgaa tggctcggcg atatgtcgca acgcatgggg   12180
caatgggcgc gcgataaccc gcgcctcgct aacggcatca tgaaaatcgc ggccgtgctc   12240
gccgtgctgc tcgcggccgg cggcggcatt ctggtcatgc tcgccggcgt gctcggcccg   12300
ctcgcggccg tttcgtttgc ctttacgacg ctcggcgtcg ccggcctcgg cgtgatcgct   12360
gcgatcgccg cgtcgtcgc tgtcgtggcc gcgctcgccg tcgcgatcta tacctattgg   12420
gagccgatca aggcattttt cggcggccta tggtctcaga ttcaacaggc gttcgccggc   12480
ggcatttcag gcatcggcgc gcttatcctc aactggtcgc cgatgggcct gttttactcg   12540
gctttcgcgg ccgtgctgca atggttcggc atcgatatgc cgtcgaagtt ttccgaattc   12600
ggctcgaaca tgatcgccgg cctcgtgaat ggcatcacta gcggcctcgg cgctgttcaa   12660
gcggcgatca cgaacgtcgc atcaagcacg gtcggatggt tcaaggaaaa gctcggcatt   12720
catagcccgt cgcgcgtatt cggcgagctg ggcgggttca tcacgcaagg cgcggcgatc   12780
ggcatggaag gcgagcaagg ccgcatcgcg aaagctgcgg tcggcctcgc gacgctcgcg   12840
gcgacttcat tcgctgcgca aggcgcacag gcggccggca cgccggccgg cggccccggc   12900
gtgacgtttg acacgcgccc cgccctgcaa gcccgccaag cggccggaaa cgcggccggc   12960
gcggcatcgg cggcggccgg cgatagctat gttttttcaca tcaccggcaa cgacccgaaa   13020
gagatcgcga accaagtgcg ccaagtgctc gccgatatcg agcgcaagaa ggcctcgcgc   13080
gttagctcgc gcctgtcgga ttaacggagg aaagaaacga tgatgatgtc gttagggcaa   13140
```

```
ttcgttttca gcctgtcgac gctggcttat caagagctgc aacggcgcac gagctggaag    13200
catccgagca cgtcgcgcgt cggcggccgt aacgcgcggc aattcaccgg cgcgggcgac    13260
gactcgatca cgctgtcggg atggttcgcg cccgatcaag gcatcggcaa gctcgcgtcg    13320
gttcgcgagc tgcgcgacat gggcgacgat ggcgaggcgt atgtgctcgt cgacggcgcg    13380
ggcaatgtgt acggcgcttt cgtgatcgaa ggcctcgacg aagggcaatc gctgcacgcg    13440
aaggacggca cgccgaggcg catcgaattc accttgaacc tgatgcgcgt cgacgatggc    13500
ctcgtgaaaa cgaagaccga ccccgcaaac gatcacctca aaaagaatg aagcaaccga     13560 cgccgatcta tcaaatcacg ctcgacggca aagacctcac gagcaagctg tcgccgctgc    13620
tcaatcacct ttcgctcgac gagtcgcgag gggaggaagc cgacaccctc atgctttcgc    13680
tcgacgactc gcaaggcaag ctcgcgctac ccaagcgcgg cgaagtgatc cgcgtatcga    13740
tcggatggga agacaccgga ctcgtcgaca agggctcatt cacgatcaac gaaatcgagc    13800
atgccggctc cccggatatg ctcaccattc aggcgcgatc ggcctcgatg acaaaaggcc    13860
tgggcgaacg aaaggaaaag agctggcacg gcagacgat cggcgcgatc gtgcgcaaga    13920
tcgccggcac gcacgggcta aagcctgcga tcgccgaagc gctcgcgaaa gtcgtgatcg    13980
cgcacatcga tcaaacgcac gagtcggata tgtcgtttct cacgcgcctc gcgaagcgtt    14040
acgacgccgt gatgaacgtg aaagactcgc acttgctttt catgccgatc ggacacggca    14100
cgagcgttac cggcaaagca ctcggccccg ttgagctgac ccgcaaggaa ggcgaccggc    14160
accgctatca cgtatccgag cgcgagaact atgccggcgt gcgtgcgtac tatcacgcga    14220
ccggtcgcgc aaagcgcaag gatgttgtcg tcggcggcga aaccaatcac aacatgaagg    14280
tattgccgga gacctacccg accgaagccg aggcacgcgc ggcggcaacg gccgagctga    14340
accgcacgca acgcagtcag gcaactatgt cgctcacgct ggcgctcggc cggcccgata    14400
tttacccgga agtgcccgtt tatctcaacg gctggaaacc ggatatcgac gccgaatcgt    14460
ggctcgtgaa gaaggtgcgg catgaaatga gcgacgccgg ctatacgtgc gacctcgacc    14520
tagagacgcg cgacgacccg acaagcgacc gacaccgctc gcactttcgc aagggcggaa    14580
aatgaagaaa gggccaaggt ttcgcagcct tggcccttt gctttactcg tctccggcga     14640
tcacttcacc cggccggcgc ggccgacact cggcccccgc gacgcaaacc catgtgtgcg    14700
catcgacata ctttcgcacc tctgcatcgc ccccgctcac gcccccagc tcggcgcatt     14760 cctttcggcc gcctcggaat gaatagccct gcgcgccgat cgcgttgcgc acctcgatac    14820
tgttgaccgt cgccgatccc caagccttgc gcgaagcggc ccatagcggc gagcacgcgc    14880
cgatcaatac gatgttggaa tacatcgccc gcgtcactgt cggcctgttc atcgtgattc    14940
tgagcgcacc gctctcgatc gtggccgagc tgatcgaata cggtttgaga ctcttttgca    15000
gagccggcgg caactccccc gcgtgagcgt tgaaagcgca gcagagcgcc gcgacgatcg    15060
ccggccgcgc ggccttgtcg aacagtttca ttgtcgaacc ctcgttgatg acccctcgca    15120
ttctaagcaa ggcggcaacg cggccgagct ggccggcgca cgcgtcaaac aaacgaccgt    15180
tttctttcct gttcggcttt ggggcgcgct gcgccccttt ttttcgccta tgtcgtaaag    15240
aaacgtcgta aaataatcaa agtaacgaaa acgcccgctc aacgggtttc ttaacgacta    15300
caggcgacca tgcaaaaaca cctcgtcatc atggcgtgct cggcgacgaa ggcctcgacg    15360
gccgcgccgg cgatcgacct ttaccaaggc gtgatgtatt cgacgtttcg agcgaatgcg    15420
ccggcgcgcg ggccggccgt tctcatcctg tcggcaaagc acggtttcat cgaagctgat    15480
cgcgtgatcg aaccatacga gcaacgcatg accgacgcgc gcgccgacga aatgctcgcc    15540
```

```
gatctgccgg cgttcgattc ggtcgcgtgg ccgtgggacg cgaaaacgat catgctcgtc   15600
ggcggcaaga catatcggcg cgtgatgcgc gctgcaatca cgagacgcat gcgcctcggc   15660
tcgatcgata cgcatgtaac tctgcgcgag acggccggcg gcattggcta ccaacgcgcg   15720
cagctcggcg cgtatctgcg cggcatgggg caactcaatc cgggcgacct cgtgcgctgc   15780
ggctcatgcg aaaacgtgac gccctacacc ccgccctatc gacccgatca atgcttgtgc   15840
gcggagtgtg agcgcgtcgt cggcgaaatg cgcgaggcgg gcgagctatg aaaggggaag   15900
catggtttaa cgtcgacgcc gagcgaatgc gccgcgacct gtacatcggc acattcgcac   15960
cgacgcctcg cacgcagctc gacgagctgg ctgccgagta tcacgagcga tgcgaggcat   16020
acgatcggct cgtctgtacc ggcccgatca ttcacggctc gatcatgccg gcgacggctc   16080
acgagctgcg ccttatcggc cgcaatgcgc gcgccgtatt gcgcgagctg gccgagcgcg   16140
cggcaatgct cggctattca tcaaggcaac tcacgaaggc gatacaagaa aatgcgtgat   16200
ccactcgaca agggcacact cgatatcgtc accggcggca tgcgcatcgg ctatgcgcgc   16260
gtgtcgacgg tcgatcaaaa cctagagctg caacacgacg cgctcgcgcg agctggttgc   16320
gtgcaggtgt acgaagaaaa ggcgagcgga aagtcgaagg acggacggcc cgagctggcg   16380
aacatgatgc gagcgttacg caagggcgac acgctgatcg tttggcggct cgatcgcctc   16440
ggccgctcgc tcgtcgacct cgtgcagctc gtcgacgagc tggccggccg tggcgtcgcg   16500
ttcgaaagcc tgtcggaaaa gatcgacacg agcaccgcgc aaggccgcat gttttttcggt   16560 ttcatcgcgg cgatggctca gtatcaacgc gacgtgataa gcgaaaacac cctcgccggc   16620
ctgaaagcgg ctcgcgcacg cggtcgcaac ggcggccggc ccgctgcgct cgacgatgcc   16680
gcgatcaagg aaatacgcgt gctgatgaaa agccctgata tctcgatggc gagcatcgcg   16740
aagcgctacg gcgttagcaa accgacgctt tacaactcac tcaaacgagc tgagaagaaa   16800
ggagccgaga agccatcacg caagcgcact agcgcaaatt cctcaagatc gcgaagcaat   16860
acccgatgaa ttcaacggcg tcgacctgtt cggcgctgat gatttcggac ttataggcgg   16920
gattgtctgt tagcaagtgc agctcgcccc cgtgcatgcg ctgcactcgc cgcaatctga   16980
tgctatcccc catacgcaac acataaacgc cgtcaacatc acgcgccgt cgatccacga   17040 gcaccacgtc gccattgttg attgttgtcg ccatgctgtt ccccggcacg cgcatcgcga   17100
tcgtttccat aggggcaaag ctcgaatcat tcactccctc gacgatgcct aacgcttctg   17160
gctcaagcca agcacgcggc aagcgtatcg tcgattgcgc cgtttccccc tcgatgaaag   17220
ccggcatttc aaaggccggc aactcgacgt aactgcccccc gccctctatg tcgggcatgg   17280
cgatcgggtt caagttttgt tcgggttcct ctatccccgg cgtgcccctg cctagcacca   17340
accagtcaag gcttaccccc tccttttccg cgagcgagac gcactcggcg agcggcatgc   17400
gatcgcgaat tttccacacg gcaggcgagc tgcgcgaagc accgatggcc tcggcgagat   17460
ccacatcgga tttcacgccg acaacctctt tcattctgtc gacgatgcct tgaattcgcg   17520
ccttcttttc tttcatattg ggccttaaaa attacaaata tatatgtgcg ttagccaaca   17580
gtaaggcgta caattacact tagtaacact aagcgacgac ctgttacata ctgaaaacac   17640
catgcgcacc atgacctctc gaacctcgcc ggcgaaacgc gtaccgatcc cacttagtgc   17700
cgagcaaatc gacaacctgc aacgcctcgc caagcaagag caacgcagcg aagcacagat   17760
ggctcggatt atctatctcg tcggactcga acagtattcg agcaaagtta aacgcgctg   17820 aacgatgctg caaccgtgaa ggatcaaggc cgggggcgga ttccttatct cgatcggagt   17880
```

```
aacacctatg cgattcacta tcgattgccc gcactgcaaa ggccgcgtta tcgctcgatc    17940
gtcgcgctat atgtcgatca cgttgcgaga atcgtgttc gtttgccgcg atccagaatg    18000
cgggcacacg ttcgtcgcga acctcgaagc cgtgcgaacg ctgtcgccaa gtgcaaagcc    18060
gaatgaggcg attcgattgc cgctttcgcc acacgtcaga gaacgcgtga tgaaacaact    18120
tcaattgctc gtcgactgaa cgggcgaacc tttgagggac cgaaccatgc tgaacaccga    18180
gccattgcat tacgctgcac atacgtttct cgccgctcac gaaggcgcac acctcgacca    18240
cgatcgcgcc gtgctgatcg atcgatgtgt cgctcacctg atcgataagg cgctcgtatc    18300
gaagcgcgag gcggaagtcg caacgctcca ggcatacggc gagcgcgagt cgcgccgctg    18360
caatgcctat gtcgacgtgt cgcttaccac gagccacacc gtattcattc gcgacgctcg    18420
gaacggcatg ctgcgcgttt tcacggtcgc cgagctgatc gaccttgtaa agacgccggc    18480
actggcgagc gtgcccgtgc cgagcacgcg cgcgatgctc gctaacggcc tcgacgacgc    18540
ggccggcact ctttagccct atccccacaa aacacccttt cctagccgcg ctcggcgagc    18600
tgcggccggg agaactcacg cccgcgattc tgaaaaatgg catcgatcac tgaactcaag    18660
cgccgcgtcg accttcacga gctggccgat cgactcggca tcaagaaagg caaaggcggc    18720
gaaaaggcga attaccactc gccacatacg accgacaaag tgccctcgct gtcgatcttt    18780
cccgcgctcc ccgagaaggg cgaaggctgg aaagatcact cgaccggcaa gggcggctcg    18840
tgcattgacc tcgtgatgta cgtgcaaggc tgcgacgtat ccgaggcaat gcgctatctg    18900
cacgaagcgt tcggcattcc gttcgatacg atcgataagc ccgccgaaca gacccgcacg    18960
aaaaccgcga tcgactacat cgccgagcgc tctattgagc accgcgagaa ggcgcgcgac    19020
tatctcaagt cgcgcggcat cgccgacgcg gcgatcgatc gggcgttcaa gtgcaagacg    19080
gccggcttta acgactggac aagccccaag cggccggccg cgaagtcgg gcacggcggc    19140 cccgctgccg ttttcctcgt gcatgccctt aacggctcgc agctcgtcgc ggctgacatg    19200
cgctatatcg acccggccct taacggcggc gtcaagacgc agacacaggg cgagaaggac    19260
gggcacggat ggacggccga cccgcgcaag ctgcacgcgg ctcaccgcgt cgtgatcgtt    19320
gaaagcgcaa tcaatgcgct gtctgtcgac tcgtgcggca tccccggcac ggccgcctat    19380
gcactgcgcg gcatcggcaa cgtcgacaac atcgacttta cgtttctgcg cggcaagcaa    19440
gtcgtgatct gtctcgataa cgatgatgtg atcgccgacg acaagccgcg cgccggcgag    19500
cgccccggcc ccgatgccgc atgcaagctg tatgagcgcc ttaccgcgct caacattgcg    19560
tgcatcctga tcgatcaagc cgaatgggtg aaagaccttg cggacggctc taacaagacc    19620
gaatcgatca acgatgtaaa cgactatctg caactgcgcg gcgctgacga gctgcgcaag    19680
gcgctcgaca cttacgagca atggcttatc cccggcatgg ccggcgacac gacccggaag    19740
ggaaagccac gcgtattcct gccctcgcac gacttcgcgc aatactggcg tttccgctcg    19800
cggctcgact tctcgacgta catcgccaag gccggcgaaa ccgaggacga tgcgccgacg    19860
cacatcgacc tcgccggctt tcgcgtcgca tcgtttagcc gcgtgtctgt cgcaagcgcc    19920
tcgtcgacca tgacgggcga tcccgacaac tcgccgaccg tctatttcgc cgtcaccgtg    19980 cagacccgc gacacggcgc ggacctcacg cgctctgtgc tcaacgacaa acagattcac    20040
aacctcacgg tatggaacca gttcggcccg atctgggagc cgaaacgttt ctcgcgcatg    20100
gtgacgattc ttgaacgcac ggcgcacctc ggcgcgcgca atgccgcgaa ctatgtcggc    20160
ctcgcatggc gcgacggccg gctcgtcgtc aatgaaggcc ccgactgcta tttcacgaac    20220
gccgaacagc aatgcccgta tcacaacctc acgtttccga gcggcacggc ctcggacgcg    20280
```

```
gcccgcgtga tcggcaagta tcaagagacg ttcaaagaca acgcggcggc tctcgcgctc    20340 gtatgggac taggcgggca ccttaaggcc ctgctcggat tctggccgca catgatgatg     20400
caagccgaca agagcgccgg taagtcgacg ctcatcaagg cgctcgaacg cacgatcggt    20460
ttcaccatgt tttcagggca atcgctgcaa accgagtttc gtttgctgac gagtatcagc    20520
cacacatcgc accctgtcgg atgggaagaa ctgagcgcgc gcaagcaaga cgtgatcgat    20580
aaagcggtcg gcctgttgca agagaactac aatacacga tcacgaaacg cggctcggaa     20640
atgaccgaat atgtgctctc tgcgcccgtg ctgctcgccg gcgaggatgt gcccgtgcga    20700
tcgctgcacg gaaagctcgt gcgcaccaac ctcaccggca agaaaggccc gatgctgccg    20760
cgcgatctgc cgcgctttcc cgtgcgtcaa tggctgcaat acctcgccga gctggaccgc    20820
gacaccgtgt cgacaagta tgacgagctg cgcgcgcact gccttaaaaa gagctgcgga    20880
agcggcgacg atgaaggcgg gaagcgcatg gcctcgaact atgccgcgct gctgctcgca    20940
tggtcctatc tgtgcgactt cgccggtatc ccgacgaacg ccggcgcgtt tggcgacgat    21000
gtgctcgccg aaatgaatcg ccatatcgcc gagacgagcg ccgatcgctc gccgtgggtc    21060
tggattctcg aaacggctct ctctgagatt gattcgggcg cgttcaagca cccgtataaa    21120 tcgacgacg tcgaaggcga agactgtttg ctcgtgcggc cggctcacat catggaccac    21180
attgccggct cgaacagtct gcgcgagaag tggaacgccc tgcccgtcaa acgccggcc    21240 gtgtttcgcc gccaattgct ctcggccggc gtcgcggtcg gcgacaagga aatcgaacgg    21300
actatccatc aaaagcgcgt gcaacaccTT accccgctct cgctcaagcg cctcgccggc    21360
tatggcctgt ctgtcgctcg caatctgaac cacgtacacg agaactgagg cgaggcatga    21420
gcgccgaaac ccgcatcgat accgtacagc tcgccggcat gctgccgcac gaccccacgt    21480
ttcgcgaatg ggtggcgatc tttacgcccc acatcgaaac cgtgaccgag cgcaagccg    21540 cgcaatttat ccgcctcgtc tgtgagattg aatcgcgcgc cgagctggcg accaaccaag    21600
aagccgcacg acgctttcac accatcttgc gacgcacctt tgtcgcctgg cgtgatgcgc    21660
gacaccggag gcgataggaa ggccgccggc gcgtcgccgg ccggccgccc tgacctaccc    21720
attacccgaa ccctgccggc cgctcgtgcg gcccgctaat cgaccggagt gatgtttatg    21780
aaataccgcg aggctttgaa aaagacggct ttgttatcc ccgtgtcgct gatggaccgc    21840
ggactatggc gagcgatcgg cgagcacgcc ggcgagctgc ttgtcgcgct cgtcgcgctc    21900
gtcggccggc tcggcgcgat cacgctctat cccgtggccg tgccgatcct cgccgcgctc    21960
gtcgtcgcgc ccgagcgtga gaacgagcgc gcgcacgagc gtttcatgcg cgagtttcgc    22020
gccgagtggg agccgcaccg atacgagccg cgcgagctgc gcgccggcga cacgacaagc    22080
ccatgaaaaa agccgctgac gctctggcgc cggcggcttg atgaattccc cctgcctgac    22140
cttttggccg cctcgtgcgg cctttttttc gacctatctc ggcgcgtatc cggccgagcg    22200
caaggccgct tgcaacttgg caacggcgtc gcgcatcaca taggcctcgt cgttgtcgac    22260
cgagcacgag cgaagatcgg aaaacgtgat gcgcttgcac aactgcgcga gcgcaacggc    22320
ctcggcctcg ctcatttccg aatagcccTC ggcggcgcg tcgtcggcga tcgcgatttt    22380
cagatgcgtc attcaattcc cctttTCACA cggttatcgt tcgagccaac cgatcgactc    22440
gacgcaaatc ttttcgtcgt cgatctggca cgtatcgctc gcgtcggcga tcactcccca    22500
agccgacgcg cacgcgattt caagcgccgc gaagatcaac accacggcgg cgactctcat    22560
gccccctctt tgctcttgag ccaatcggcg cacgcgtcgg cgatcgctgc cgctcggctc    22620
```

```
agacctcgcg cggcggccgc ctcatccatg cgggcaagga tcgccgcgtc aatggtcaag    22680
ctgatcggcg ttttttcgcgt gctcgatgcg acggcacgcg ccggcgcggc cggcgtcgga    22740
gctgcaaccg gagccggcgc ggccggcgct gcgacgccct gcccttcgc gtcgggtgcg     22800 ctgttgatga attttcgat cgccgctgga tcgacctttg ccggcgtcgg ccgttcgtg      22860 atacccattt tgctattacc tcgctatcaa ctcgatattt acttgatatt aacttaccgt    22920
cgacattgca gcgaagaacg ccccgcgaag ccgatcgatt tcggcgcatg cgcgctggtc    22980
gcgccgcttc atttcctcga cgtgcaagcc cgcgccgctc gcgttcgcaa aggccttgcg    23040
atcgctcacg cgcacatcaa gcaactcaag ccccggatac tcggcgaccg cctcggccgc    23100
ctcgcggtta tcggcgctct gagggtcggc ccgattcacg aacgcgaatg cgcgcaagtc    23160
ggcgaccgcg cgcgactcgt cgacgatctg cgcgatatcg gccaacgccc acacatcgaa    23220
cgaacgagga aggaaaggaa tgagcacggc gtcgctcacc gtgagcgcgg cccgcaacgc    23280
ggtcgaatca cggccgccgg cgtcgatcac gacatgatcg taattggcgc gctgctgcat    23340
tacctgagcg cgcagcgtcg cgccctcggc ataggccgac gcggcgatca tcggccggcc    23400
gctgtcggcg cgcgccgtga tcgcgctaag gcttgttcc tgccgatcgc cgtcgatcaa     23460
ccagacccgc tcccctcga tcgccaaccc tagcgcgagc tgcacggcac acgtcgactt     23520
acctaccccg cccttgctgt tcccgaccgt aaaaatcatt tcgcatgctc caataaggtt    23580
tgcattacct acatagcatg ttgatatcaa cttgctataa acgataacc aactgaatac     23640 cgattatata ttcatcgcaa cttgatatca acacaatatc aacatgatcg acggccggcg    23700
agggtagggc ggtcgcgatc gcgccgcgc ccgcgtcgcg cgcccgcgtc gaccgtgcgg     23760
ccgagtaggg aagggcggcc cctgccctcg atcgagctgc gcgcgcgacg cggccggcga    23820
tcgcagctcg tcgacgtgcg cctcgatgct cggccgccgg cgctggccgc ctcgatccga    23880
ccgcgcgcag ctcgtcgacg gccgccagaa agccggcgat cgagcgccgg ccgacgccgg    23940
cccgcgtcgt ttctcaagtc ggtacaggta tatccaaaaa cccgaggatt acggcccggt    24000
ttcgcgctaa gtctttgatt tttgagcaaa caccatcctc gaccgacccc gttttttcct    24060
cggatgcccc cgttttttcc tcggaccgt ttcaccggtt tctatactct ctctcttatt     24120
aagttattga aagaaagaa agaaataggc attgagaaga aaagcgcgc gcactcaacc      24180 cgaacccgga ttcactcggt ttccgcacct gcctattttt taatcctcgg attcctcacc    24240
cgaaaaaggg ctcatccgag gattgccgag gggggcgaaa tccttatgcg acaagggttt    24300
caggccgatc ccctcggcat cctcgtatcc tcgcgaaaat ctcccctacc ccccgacct     24360 gcgacgggaa gcccgctctt tcgtggctgt cgattcatcc ggccggcgcg cagctcaaaa    24420
cgcagctcac gcgcatcgaa tcgcatcacg ccggcggcct cgaaatcgcc gcgaaggcct    24480
tgccgcaagg cgctcggccg gccggcgctc gaccgcatca aaagggggcga cccaagaaca    24540 ggccaggcgc ggaggggtga ctgcgaaatt cgggcgaggg tcgaccgcgc gccggccccg    24600
taggccggcc ggctcccccg gcctcgccgg accccttgcc gacccattgc cggccccgtg    24660
gcggccctgc acgcgcctcg gcgaccccgt gccacgtcga cggcacggcg agcgctcaga    24720
agggccgatt gcaggatgaa acacggcgat gccgcgagct gcgccgatgc ttcacggcgt    24780
cgacggcccg cgagccgatc gagaagggcg acggctgaca ggatcacccc ctctctgctg    24840
aacattcggg cggtcgtgca tcacaggtgc atcggcatgg atcgcacgcg atccgacttg    24900
agcgggcgac gtggcgcgaa gcgacgcggc gggcgcgatt tatgtcggcc ttagcgctcg    24960
gcgcggcttt gccgcgtcgg gcggttaggc catagcccg catgcgttcg ccgcgcgata    25020
```

```
ggtttgtgag agagtcgcgt gcggctcgcc gagctggtcg tgagctgccg agggtagggc   25080
accacggccg cgccaacgtg cgcggccctc gttcgtctgg atatgggttt gatcgtcaag   25140
tgtcgcgccg taggcgcgca cttgttgccc ctcacggggc ggagcgcgaa gcgcgggggg   25200
gtggggttaa aaccggccgc gatcggcttt cctcgcgtgc ggtttcttag ttttacgttt   25260
ttaccgtttt aaaaacgttt taggcaccat cggagccttg ctgggcgggc gtttccgggc   25320
gctatggtgt acaaatcccc ggttctattg gggcaaaacc ccggttcaag gtgtacaaat   25380
ccccggttta tgggacaaaa ccccggttct atccacaggt gtacggcaaa atttgcttgc   25440
accaatacta ctattgggac acaatcagac gctgcaccaa tcacagggga agcgtcccaa   25500
tgaaagcacc tcgcgcggct gtcgctctga acccggatgc gatgctatcc gaccgtaacg   25560
tgaacatgag caacgcgctc acgcgcgcgt cgcacggcct cggcctcgca gaaaagcgcc   25620
tgatcgcctc gtgcatcgcg aaaaacgact cgatgccgat ggctgagatt catcgcaaag   25680
gcgcgtggac ggttcgcctg tcggcggccg agtatgccga gacgttcgaa atcggcctcg   25740
attccgcgta tgagcaattg cagcaagcgg ccgatagcct gttcaatcgg tacgtgcgca   25800
ccgtgcagga aacgccgaaa ggcccgaaag aaatcaaatt ccgatgggtc ggcaaggccg   25860
agtatcacaa gggcgaggga tgggtagagc tgcactggtg gcatgaagtc gtcccgcacc   25920
tgttcggact gcgccaacaa ttcacgtcat acaagctcaa gcaaacggcc gcgctgcgct   25980
cggcgtactc gtggcgcctg tatgagtgtt tcaagtcgtg ggcgggcaaa gggcgctaca   26040
cgccgagcat cgaagaattt caccgcgcga tggatgcgaa agagagtcac cgcgcgaact   26100
tcaaagagct gcgccggcgc gtgatcgagc cggccgtgac cgagctgatc gagaaaaacg   26160
gtttgttgat cgagtggact accgtgaacg ctggccgcaa agtcgtcggc ctcgacttca   26220
aattcagcgc gaacccgcaa acctctcttt tctgagctgg ttaaccgggc gtttgcccca   26280
ataacaaaat gctttcattc tgtaaccact tgtaagttga cgcgcgttct tggtgcaacg   26340
cctcggcatg tcttaccgtt tgtaagctgt acgtggcaat tttgtaataa gggccggggt   26400
taaccctcgg cctttctatt gggacaaatc cccggttact tcgccggcgc ggccgtcgcg   26460
acgctgtacg gcgtgaagcg cacaacctcg tcgccgatcc actcgttgag ctgttcaaag   26520
cgccgttgca ggggcgcgat ttcattcacg ccgaacacct cggcggcctt gtccgttgcg   26580
ccgaatccgc cggtattgct cggcacgatc cccatgagct gaggcgggat gcgatgcgcc   26640
gcgagcaagt cgtcgcgcgt gacattcttg atgttgaaga actcgtcttt cgccgtgacc   26700
tcggaaaccg gaatgagctg gatgccgtct ttcttgccgt tcggcgcgta catgaaaagg   26760
tttcggaaat tccccggccc cttgctgttc ttcaacgcct cgcgcatctt gtcgacatcg   26820
ctttgacttt gcgccgcatc ggtcatgtac aggatgaaac cggcgtgcga tccattctcg   26880
taatacttgc gacgaaagag cgtcgccgac tcgttcaacc atgccgagtg cagcgcgccg   26940
agatattcgg gcaagccgta cacctcttga ttaatgtcgg gttccatcaa gtgatgcacc   27000
gaacccggct cgaactcata ttcgatctgt tgatagccgt tgagctgcac gaagcgttgc   27060
aagtcggttc gacggcgcac gtatttcgac ggcgcgcgtt tgagcgcgag cgtattgccg   27120
atccttgcct ttcgccgctc gatgtaccca ttgccgaacg tgaggaaatc gagcgcccac   27180
ttgtcgaatt cttcgcgcgt gagcaacttg tgcgggatga acgtcgacga caacacattg   27240
cgtttgaagt agatcgccga cccgtgatgc acgccgcgc gaaacgtctt tgcaaggccc   27300
gcccatgaca ccggcggctc ataccaatcg ccgatcgcat acgcttgcac gtagtcaaga   27360
```

```
atttcggcgc gatccatcac cggcacagga tcgtcgaagg tgaaggcctc ggcgcgcgcc   27420
ggcgtcgacg tggccgccgg cgtcgtgctc gacgcgtgat agttgctgcg ctgcttacgc   27480
ttgctcatta agagaactcc ataaagccgg tattgtttgc ggtcgtgccc tctagcggct   27540
cgttatcgag cgcgtgcagg cacgcccacg ctagatcggc gtggccggtt tcctcgctgc   27600
ggctcgcctc gtatgtcacc tttcggccgc tcgccgtcat ggttttccga atggccatga   27660
aggattgcgc taggtctgtc caaccggcat cgaattcgag ccggcccttg ccgatcaccg   27720
acaagccctt aagcacgaga cgcccttga tttcgggcga atagttgagc gcgaccgcgc   27780
tcggatagaa ctgtttgacg agctgataaa caccctggcc gatgcccgtc gtatcgatcg   27840
acatatattc gacgttgtat tgctgagtga tctgtcgaat cgcctcggct tgcccctcga   27900
aatccatgcc gcgaaattgg cacttgtgca atacgcggaa cttgcccccc ggcaccgccg   27960
gcggggcgac gacgacaagg ccggccgagt cgccggaaag cgctggatcg tagccaaccc   28020
ataccggccg gaacccgaaa gggcggggcg cgagcggctt gaaatcgtcg gcccattctt   28080
cccacgagtc gaccatgcag cgttgcagct cggcgagcgg aaagatcgac gcggtatcgt   28140
cgataaactg acacatcaac agattcgcgt attcctgcgc gctgtattca aggcgcagct   28200
cgtcgatatc gaacaagtcg caaccgccgg cgacggcatc ctcgaccgtc acgatctggc   28260
gaaactgtcg atcctcgcag agccggccgc gagcgagcgc cgagtgcgaa atatcgagat   28320
gaatgtgatc ggccttttgcg cggcccctgt tgtagtgctc gccactccag aaggtgtaag   28380
cctcgtgcgt gatgctcgac ggcgttgaaa aatacgtctt tcgccatttc ttgtgcatcg   28440
ccatgcccga tgcaaccttg ttgagctggc gaaacccgct cacccaaaaa tactcgtcga   28500
aatagaaatt gccgtgatag ctctgcgccg ttcgcgaatt cgtgccgagg aaaatcaact   28560
ctgccatgtt cggcaaaatg atcgggtcgc cggtcaattc gacctcggcg gcctcggcgg   28620
caaactgccg aatgtacgac ttgaaaacgt gcgcctgcgc cttgctggcc gatagaaaaa   28680
tctgattgcg tgcagtctgc aaggcatcgt ctagcgcctc gcgtgcgaaa tagaacgtcg   28740
cgccgatctg ccgcgacttg agaatgttgc gcgtgcgctg atggccgttt cgataccaca   28800
cctttttgata accgaactgg caatcaagaa aggcctcgtg aagccgtgcg atctgctcgt   28860
cgctgaaatc gttgcgggcg gccttttctt tacggggcgc tttgttgcgc gcctcgatgt   28920
tcgggtttaa gtcgctctct ttccccgttt cgccgtactt gcgcacgcgt gcaagccgct   28980
cgacctgacg gccgagcaag tcgatttcct tgaagtcgct gcccgtcttt accggcttgg   29040
caatgagcac cgcgaggcgc gtttcaagcg acgactcgat cgctcgatc ggggcggcct   29100
tgtcccactc gtcgcgctgt ttccatgcct cgacggtcgc gcgtttgagc tgcaagtgct   29160
cggcgacgga cgtgatgcgc caaccctgcc agtagagcgc gcgcgcaatc cggcgagggt   29220
cggcattcga ttcgagtgcg ggggtgatat cggctgtttc gatcatgccg gcaagtttcg   29280
cgtgtcgcgc gcgcgcaagc acgcccgcct atgtgtaccc gacacgcgaa caaacgcgaa   29340
acgttgagcg cttgcggccg tgatcgcaag atatcaactc acgctgaacc ccctcgaac   29400
ctgttggaga cctaacaatg caatttcgca agctgtcgct catgtcgctc gccgtcgcgg   29460
cgatcgcgct cgctgtcacg atggacgcaa acgcggcgac gctcgccgca agcgccgttt   29520
tcaatcacgc cgatgcgctc tcgttctga gcgggcacgg catcgccggc gcggccggcc   29580
tcggcgctat ggcgatcggc tcgaccgctg ccccgacgc gacgaagctc gcgaaatcca   29640
agatgttccg catcgccgtc gaaggcgcga cgactgacgg ccgcgtgatc gagcgcgcat   29700
ggctcgaaca gattgccgcg aactactcgc cgacgaaata cggcgcacgc gtgaacctcg   29760
```

| | | | | | |
|---|---|---|---|---|---|
| aacactatcg | cggcatcgtg | cccgatggcc | cgttcaaggc | atacggcgac | gtgctcgcgg | 29820 |
| tcgaaacgca | agaactcacg | ggcgaattcg | ccggcaagct | cggactgttc | gcgcaaatcg | 29880 |
| agccgactgc | cgagctggtc | gcgatgacga | aggcgaagca | aaagatttac | acctcgtgcg | 29940 |
| aaatcgaccc | gtcattcgcc | gacacgaaac | aggcgtatct | catcggcctc | gccgtgaccg | 30000 |
| atagccccgc | gagcctcggc | accgaaatcc | tttctttcgc | agctcagaac | ccgaccgcct | 30060 |
| cgccgttctc | cggccgcaag | gtatcgccga | cgaacctttt | cacggtcgcc | gacgaaaccg | 30120 |
| tgatcgagtt | tgaagaagcg | gcacaaccgg | ccgtgctgcc | ggcgctgctg | tcccgcgtga | 30180 |
| aagagctgtt | gacaggcgca | agcaagaaac | aggcggccga | cgactcgcgt | ttcgctgacg | 30240 |
| tggcgcaagc | atgcgaagcg | ctcgcgacgc | acggcaacga | acaggccgca | acgatcgccg | 30300 |
| cactcacgaa | gcaagtcgcc | gaactgagcc | ccgcacgcga | agccgatcgc | aaggcattcg | 30360 |
| acgagctgca | agtgcagctc | tcgaaaaccg | agagcggcgt | gcaacgcccc | gcgtcgaccg | 30420 |
| gctcggccgg | cggcaccgta | acgaccgatt | gctaacccgg | caatcactcc | ctttcactgc | 30480 |
| cccggagaac | acaccacatg | cgcaacgaaa | cccggttcgc | tttcgatcaa | ttcctcgaag | 30540 |
| cgatcgccaa | gctcaacggc | atcccgaacg | cgacgaagaa | attcgccgtg | tcgccgagcg | 30600 |
| tgcaacaaaa | gctcgaaacc | cgcattcagg | aatcgagcga | ctttctgaaa | cgcatcaacg | 30660 |
| ttatcggcgt | gaccgacaag | gaaggcgcaa | agctcggcct | cggcgtcggc | tcgccgatcg | 30720 |
| cgagcacgac | cgacacgacg | cagaaggatc | gcgcaacggc | tgatgtgacc | gacctcgacg | 30780 |
| agaacggtta | caactgcacg | caaacgaatt | tcgactcgca | catcacgtat | gcgctgctcg | 30840 |
| acgcgtgggc | gaagtttccc | gacttccaga | cccgcattcg | cgacgtgatc | gtgcgccgtc | 30900 |
| aagcgctcga | ccgcatcgcg | atcggtttca | acggccgttc | gcgtgcggca | acgtccgacc | 30960 |
| gtgcagctaa | cccgctgttg | caggacgtca | ataagggctg | gttgcaacgc | atgcgcgacc | 31020 |
| aagccccgca | acgcgtgatg | gacgaaggcg | cgaagacggc | cggcaagatc | gtcgtcggcg | 31080 |
| cggccggcga | ttacgcgaac | ctcgatgcgc | tcgtcgccga | tctggtcgcg | agcatgatcg | 31140 |
| acccgtggca | ccaagacgac | acggctctcg | tcgtgatgtg | cggtcgcggc | ctgttgcacg | 31200 |
| acaagtattt | cccgctcgtc | aacaaggccc | aagcgccgac | cgaaatgatg | gccgctgacg | 31260 |
| tgatccagag | ccagaagcgc | atcggcaacc | tgccggccgt | gaccgtgcct | tcttcccgg | 31320 |
| ccaatgccgt | gatggtgacg | agtttcgaca | atctgtctct | gtactttcaa | gacagcgcac | 31380 |
| ggcgtcgcac | gatcgtcgac | aacgcgaagc | gcgaccgtat | cgagaactat | gaatcgtcga | 31440 |
| acgatgcgta | tgtcgtcgaa | gacctcggcc | gcgctgctgt | tgccgagaac | atcgaaatcg | 31500 |
| cgccggcggc | gtaacggagg | catgacgcga | tgactagccc | cgcacgacgc | cattttcagc | 31560 |
| gcgtatcggc | aagcctcgcg | tcggcctcgg | ccggcgcggg | cgaaacaatg | gtcggaagcg | 31620 |
| cttacgagct | gatgcttgcg | aaactcgcga | tcgatcggcg | acgactcaag | gaaatcaagt | 31680 |
| cgatcgcgcg | aaaaatcgaa | gtgaagcgcg | ccgagctgct | gcccgaatac | gtcgaatatg | 31740 |
| tcgccggcgc | gctgagtggc | gggcggggcg | ctcaagacga | tgtgctcacg | accgtaatga | 31800 |
| tctggcgcgt | cgacgtgggc | gacttcgccg | gcgcgctcga | tatcgcgcgt | tatgcgatcg | 31860 |
| cgcaccggat | gacgctgccc | gatcaatacg | accgcacgct | tgcgactgcg | atcgccgagg | 31920 |
| aattcgccga | ggcgtcgctt | gcatcgttca | agaaagaagc | gatcgcgatt | cgcgtcgacg | 31980 |
| gcgcgcagct | cgccgaagtc | gcgcagctaa | ccgagtcgca | cgacatgcac | gaccaagtgc | 32040 |
| gtgccaagct | gcacaaggca | atcggttaca | cgtttgagcg | cgacggcgac | ttgccggccg | 32100 |
| cactcgaaca | cctgcgccgc | gcgctcgacc | tcgacgagcg | cgccggcgtg | aaacaggaca | 32160 |

-continued

```
ttgcccgcat tgagaaagcg agcaatgcgg ccggcaccaa cgccggccgc acgtaaagag  32220
cccaccccgg cctgggcggc gccggctgac gatcgcaaca cctgacggta acgcgatccg  32280
acgccggccc accgcccacc ttttcagagc tgaaacc                           32317
```